US010085999B1

(12) United States Patent
Gordon et al.

(10) Patent No.: US 10,085,999 B1
(45) Date of Patent: Oct. 2, 2018

(54) BETA-LACTAMASE INHIBITORS AND USES THEREOF

(71) Applicant: ARIXA PHARMACEUTICALS, INC., Palo Alto, CA (US)

(72) Inventors: Eric M. Gordon, Palo Alto, CA (US); John Freund, Atherton, CA (US); Mark A. Gallop, San Francisco, CA (US); Matthew Alexander James Duncton, Palo Alto, CA (US)

(73) Assignee: ARIXA PHARMACEUTICALS, INC., Palo Alto, CA (US)

( * ) Notice: Subject to any disclaimer, the term of this patent is extended or adjusted under 35 U.S.C. 154(b) by 0 days.

(21) Appl. No.: 15/934,497

(22) Filed: Mar. 23, 2018

Related U.S. Application Data

(60) Provisional application No. 62/551,043, filed on Aug. 28, 2017, provisional application No. 62/504,523, filed on May 10, 2017.

(51) Int. Cl.
  *A61K 31/551* (2006.01)
  *A61P 31/04* (2006.01)
  *A61K 45/06* (2006.01)

(52) U.S. Cl.
  CPC ............ *A61K 31/551* (2013.01); *A61K 45/06* (2013.01); *A61P 31/04* (2018.01)

(58) Field of Classification Search
  CPC .................................................. A61K 31/551
  See application file for complete search history.

(56) References Cited

U.S. PATENT DOCUMENTS

| | | | |
|---|---|---|---|
| 3,658,849 A | 4/1972 | Leffingwell | |
| 4,522,811 A | 6/1985 | Eppstein et al. | |
| 5,674,533 A | 10/1997 | Santus et al. | |
| 7,112,592 B2 | 9/2006 | Lampilas et al. | |
| 7,994,218 B2 | 8/2011 | Jandeleit et al. | |
| 8,168,617 B2 | 5/2012 | Jandeleit et al. | |
| 8,772,490 B2 | 7/2014 | Abe et al. | |
| 9,035,062 B2 | 5/2015 | Abe et al. | |
| 9,284,273 B2 | 3/2016 | Abe et al. | |
| 9,340,493 B2 | 5/2016 | Brown et al. | |
| 9,393,239 B2 | 7/2016 | Maiti et al. | |
| 2009/0099253 A1 | 4/2009 | Li et al. | |
| 2014/0045943 A1 | 2/2014 | Khan et al. | |
| 2015/0196559 A1 | 7/2015 | Wang et al. | |
| 2015/0225335 A1 | 8/2015 | Takashima et al. | |
| 2017/0165371 A1 | 6/2017 | Goldberg | |
| 2017/0290918 A1 | 10/2017 | Honda et al. | |
| 2017/0296503 A1 | 10/2017 | Eto et al. | |

FOREIGN PATENT DOCUMENTS

| | | |
|---|---|---|
| DE | 3045373 | 7/1982 |
| WO | 2007/116922 | 10/2007 |
| WO | 2009/033054 | 3/2009 |
| WO | 2009/033079 | 3/2009 |
| WO | 2009/092606 | 7/2009 |
| WO | 2011/046771 | 4/2011 |
| WO | 2011/150380 | 12/2011 |
| WO | 2012/086241 | 6/2012 |
| WO | 2012/165648 | 12/2012 |
| WO | 2016/116788 | 7/2016 |

OTHER PUBLICATIONS

Beaudoin et al., "Bioanalytical method validation for the simultaneous determination of ceftazidime and avibactam in rat plasma," Bioanalysis, 2016, vol. 8, No. 2, p. 111-122.
Beaudoin et al., "Preparation of Unsymmetrical Sulfonyureas from N,N-Sulfuryldiimidazoles," the Journal of Organic Chemistry, 2003, vol. 68, No. 1, p. 115-119.
Boyd et al., "NMR spectroscopic studies of intermediary metabolites of cyclophosphamide. 2. Direct observation, characterization, and reactivity studies of iminocyclophosphamide and related species," The Journal of Medicinal Chemistry, 1987, vol. 30, No. 2, p. 366-374.
DeBergh et al., "Synthesis of Aryl Sulfonamides via Palladium-Catalyzed Chlorosulfonylation of Arylboronic Acids," Journal of the American Chemical Society, 2013, vol. 135, No. 29, p. 10638-10641.
Hecker et al., "Discovery of a Cyclic Boronic Acid β-Lactamase Inhibitor (RPX7009) with Utility vs Class A Serine Carbapenemases," Journal of Medicinal Chemistry, 2015, vol. 58, p. 3682-3692.
Illa et al., "Practical and Highly Selective Sulfur Ylide-Mediated Asymmetric Expoxidations and Aziridinations Using a Cheap and Readily Available Chiral Sulfide: Extensive Studies to Map Out Scope, Limitations, and Rationalization of Diastereo- and Enantioselectivities," Journal of the American Chemical Society, 2013, vol. 135, No. 32, p. 11951-11966.
King et al., "Structural and Kinetic Characterization of Diazabicyclooctanes as Dual Inhibitors of Both Seratin-B-Lactamase and Penicillin-Binding Proteins," ACS Chemical Biology, 2016, vol. 11, No. 4, p. 864-868.
Oger et al., "Lipase-Catalyzed Regioselective Monoacetylation of Unsymmetrical 1,5-Primary Diols," The Journal of Organic Chemistry, 2010, vol. 75, No. 6, p. 1892-1897.
Levasseur et al., "In vitro antibacterial activity of the ceftazidime-avibactam combination against enterobacteriaceae, including strains with well-characterized β-lactamases," Antimicrobial Agents Chemotherapy, 2015, vol. 59, No. 4, p. 1931-1634.
Livermore et al., "Activity of OP0595/β-lactam combinations against Gram-negative bacteria with extended-spectrum, AmpC and carapenem—hydrolysing β-lactamases," Journal of Antimicrobial Chemotherapy, 2015, vol. 70, Issue 11, p. 3032-3041.
Rusha et al., "Design and application of esterase-labile sulfonate protecting groups," Chemical Communications, 2011, vol. 47, p. 2038-2040.

(Continued)

*Primary Examiner* — Rebecca L Anderson
*Assistant Examiner* — Karen Cheng

(57) ABSTRACT

β-Lactamase inhibiting compounds, therapeutic methods of using the β-lactamase inhibiting compounds, particularly in combination with β-lactam antibiotics and pharmaceutical compositions thereof are disclosed. The β-lactamase inhibiting compounds are suitable for oral administration.

30 Claims, No Drawings

(56) References Cited

OTHER PUBLICATIONS

Shi et al., "The Rhodium-Catalyzed Carbene Cyclization Cycloaddition Cascade Reaction of Vinylsulfonates," Advanced Synthesis and Catalysis, 2009, vol. 351, p. 3128-3132.
Simpson et al., "A Comprehensive Approach to the Synthesis of Sulfate Esters," Journal of the American Chemical Society, 2006, vol. 128, No. 5, p. 1605-1610.
Soengas et al., "Convenient Procedure for the Indium-Mediated Hydroxymethylation of Active Bromo Compounds: Transformation of Ketones into a-Hydroxymethyl Nitroalkanes," Synlett, 2010, vol. 17, p. 2625-2627.
Zasowski et al., "The β-Lactams Strike Back: Ceftazidime-Avibactam," Pharmacotherapy, 2015, vol. 35, Issue 8, p. 755-770.
Zhang et al., "Enhanced Photoresponsive Ultrathin Graphitic-Phase C3N4 Nanosheets for Bioimaging," Journal of the American Chemical Society, 2013, vol. 135, No. 1, p. 18-21.

BETA-LACTAMASE INHIBITORS AND USES THEREOF

This application claims the benefit under 35 U.S. § 119(e) to U.S. Provisional Application No. 62/551,043, filed on Aug. 28, 2017, and U.S. Provisional Application No. 62/504,523, filed on May 10, 2017, each of which is incorporated by reference in its entirety.

FIELD

The present disclosure relates to β-lactamase inhibitors and pharmaceutical compositions thereof and the use of the β-lactamase inhibitors to treat bacterial infections.

BACKGROUND

Overuse, incorrect use, and agricultural use of antibiotics has led to the emergence of resistant bacteria that are refractory to eradication by conventional anti-infective agents, such as those based on β-lactams or fluoroquinolone architectures. Alarmingly, many of these resistant bacteria are responsible for common infections including, for example, pneumonia, sepsis, etc.

Development of resistance to commonly used β-lactam anti-infectives is related to expression of β-lactamases by the targeted bacteria. β-Lactamases typically hydrolyze the β-lactam ring, thus rendering the antibiotic ineffective against bacteria. Accordingly, inhibition of β-lactamases by a suitable substrate can prevent degradation of the β-lactam antibiotic, thereby increasing the effectiveness of the administered antibiotic and mitigating the emergence of resistance.

Avibactam is a known β-lactamase inhibitor that is currently marketed in combination with ceftazidime to treat gram negative bacterial infections. Avibactam must be administered intravenously, which limits use to expensive clinical settings.

SUMMARY

According to the present invention, compounds have the structure of Formula (1):

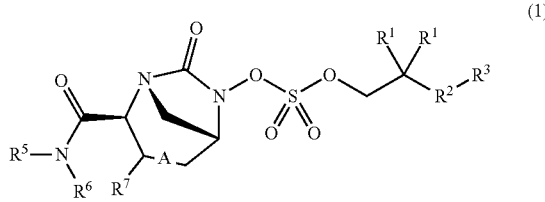

(1)

or a pharmaceutically acceptable salt thereof, wherein,
each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heteerocycloalkyl, substituted $C_{5-6}$ aryl, substituted $C_{5-6}$ heteroaryl, and —CH=C($R^4$)$_2$; wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (=) and $R^7$ is $C_{1-3}$ alkyl.

According to the present invention, pharmaceutical compositions comprise the compound according to the present invention and a pharmaceutically acceptable vehicle.

According to the present invention, methods of treating a bacterial infection in a patient comprise administering to a patient in need of such treatment a therapeutically effective amount of the compound according to the present invention.

According to the present invention, methods of treating a bacterial infection in a patient comprise administering to a patient in need of such treatment a therapeutically effective amount of the pharmaceutical composition according to the present invention.

According to the present invention, methods of inhibiting a β-lactamase in a patient comprise administering to the patient an effective amount of the compound according to the present invention.

According to the present invention, methods of inhibiting a β-lactamase in a patient comprise administering to the patient an effective amount of the pharmaceutical composition according to the present invention.

Reference is now made to certain compounds and methods. The disclosed embodiments are not intended to be limiting of the claims. To the contrary, the claims are intended to cover all alternatives, modifications, and equivalents.

DETAILED DESCRIPTION

A dash ("-") that is not between two letters or symbols is used to indicate a point of attachment for a moiety or substituent. For example, —CONH$_2$ is attached through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" is specifically intended to include groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy, or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. An aryl group can be $C_{6-10}$ aryl, $C_{6-9}$ aryl, $C_{6-8}$ aryl, or phenyl. Aryl, however, does not encompass or overlap in any way with heteroaryl, separately defined herein.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-16}$ arylalkyl, such as the alkanyl, alkenyl or alkynyl moiety of the arylalkyl group is $C_{1-6}$ and the aryl moiety is $C_{6-10}$. An arylalkyl group can be $C_{7-9}$ arylalkyl, wherein the alkyl moiety is $C_{1-3}$ alkyl and the aryl moiety is phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of the fraction absorbed, the fraction escaping gut-wall elimination, and the fraction escaping hepatic elimination; and the factors that influence bioavailability can be divided into physiological, physicochemical, and biopharmaceutical factors.

"Compounds" and moieties disclosed herein include any specific compounds within these formulae. Compounds may be identified either by their chemical structure and/or chemical name. Compounds are named using the ChemBioDraw Ultra Version 14.0.0.117 (CambridgeSoft, Cambridge, Mass.) nomenclature/structure program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing "Cycloalkyl" refers to a saturated or partially unsaturated cyclic alkyl radical. A cycloalkyl group can be $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, and cyclohexyl.

"Cycloalkylalkyl" refers to an acyclic alkyl radical in which one of the hydrogen atoms bonded to a carbon atom is replaced with a cycloalkyl group as defined herein. Where specific alkyl moieties are intended, the nomenclature cycloalkylalkyl, cycloalkylalkenyl, or cycloalkylalkynyl is used. A cycloalkylalkyl group can be $C_{4-30}$ cycloalkylalkyl, for example, the alkanyl, alkenyl, or alkynyl moiety of the cycloalkylalkyl group is $C_{1-10}$ and the cycloalkyl moiety of the cycloalkylalkyl moiety is $C_{3-20}$. A cycloalkylalkyl group can be $C_{4-20}$ cycloalkylalkyl for example, the alkanyl, alkenyl, or alkynyl moiety of the cycloalkylalkyl group is $C_{1-8}$ and the cycloalkyl moiety of the cycloalkylalkyl group is $C_{3-12}$. A cycloalkylalkyl can be $C_{4-9}$ cycloalkylalkyl, wherein the alkyl moiety of the cycloalkylalkyl group is $C_{1-3}$ alkyl, and the cycloalkyl moiety of the cycloalkylalkyl group is $C_{3-6}$ cycloalkyl. A cycloalkylalkyl group can be $C_{4-12}$ cycloalkylalkyl, $C_{4-10}$ cycloalkylalkyl, $C_{4-8}$ cycloalkylalkyl, and $C_{4-6}$ cycloalkylalkyl. A cycloalkylalkyl group can be cyclopropylmethyl (—CH$_2$-cyclo-C$_3$H$_5$), cyclopentylmethyl (—CH$_2$-cyclo-C$_5$H$_9$), or cyclohexylmethyl (—CH$_2$-cyclo-C$_6$H$_{11}$). A cycloalkylalkyl group can be cyclopropylethenyl (—CH=CH-cyclo-C$_3$H$_5$), or cyclopentylethynyl (—C≡C-cyclo-C$_5$H$_9$).

"Cycloalkylheteroalkyl" by itself or as part of another substituent refers to a heteroalkyl group in which one or more of the carbon atoms (and certain associated hydrogen atoms) of an alkyl group are independently replaced with the same or different heteroatomic group or groups and in which one of the hydrogen atoms bonded to a carbon atom is replaced with a cycloalkyl group. Where specific alkyl moieties are intended, the nomenclature cycloalkylheteroalkanyl, cycloalkylheteroalkenyl, and cycloalkylheteroalkynyl is used. In a cycloalkylheteroalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group is —O— or —NH—.

"Cycloalkyloxy" refers to a radical —OR where R is cycloalkyl as defined herein. Examples of cycloalkyloxy groups include cyclopropyloxy, cyclobutyloxy, cyclopentyloxy, and cyclohexyloxy. A cycloalkyloxy group can be $C_{3-6}$ cycloalkyloxy, $C_{3-5}$ cycloalkyloxy, $C_{5-6}$ cycloalkyloxy, cyclopropyloxy, cyclobutyloxy, cyclopentyloxy, or cyclohexyloxy.

"Disease" refers to a disease, disorder, condition, or symptom of any of the foregoing.

"Fluoroalkyl" refers to an alkyl group as defined herein in which one or more of the hydrogen atoms is replaced with a fluoro. A fluoroalkyl group can be $C_{1-6}$ fluoroalkyl, $C_{1-5}$ fluoroalkyl, $C_{1-4}$ fluoroalkyl, or $C_{1-3}$ fluoroalkyl. A fluoroalkyl group can be pentafluoroethyl (—CF$_2$CF$_3$), or trifluoromethyl (—CF$_3$).

"Fluoroalkoxy" refers to an alkoxy group as defined herein in which one or more of the hydrogen atoms is replaced with a fluoro. A fluoroalkoxy group can be $C_{1-6}$ fluoroalkoxy, $C_{1-5}$ fluoroalkoxy, $C_{1-4}$ fluoroalkoxy $C_{1-3}$, fluoroalkoxy, —OCF$_2$CF$_3$ or —OCF$_3$.

"Halogen" refers to a fluoro, chloro, bromo, or iodo group.

"Heteroalkoxy" refers to an alkoxy group in which one or more of the carbon atoms are replaced with a heteroatom. A heteroalkoxy group can be $C_{1-6}$ heteroalkoxy, $C_{1-5}$ heteroalkoxy, $C_{1-4}$ heteroalkoxy, or $C_{1-3}$ heteroalkoxy. In a heteroalkoxy, the heteroatomic group can be selected from —O—, —S—, —NH—, —NR—, —SO$_2$—, and —SO$_2$—, or the heteroatomic group can be selected from —O— and —NH—, or the heteroatomic group is —O— and —NH—. A heteroalkoxy group can be $C_{1-6}$ heteroalkoxy, $C_{1-5}$ heteroalkoxy, $C_{1-4}$ heteroalkoxy, or $C_{1-3}$ heteroalkoxy.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —NH—, —NR—, —O—O—, —S—S—, =N—N=, —N=N—, —N=N—NR—, —PR—, —P(O)OR—, —P(O)R—, —POR—, —SO—, —SO$_2$—, —Sn(R)$_2$—, and the like, where each R is independently selected from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, and substituted $C_{7-18}$ heteroarylalkyl. Each R can be independently selected from hydrogen and $C_{1-3}$ alkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example, $C_{1-6}$ heteroalkyl includes groups having five carbon atoms and one heteroatom, groups having four carbon atoms and two heteroatoms, etc. In a heteroalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—. A heteroalkyl group can be $C_{1-6}$ heteroalkyl, $C_{1-5}$ heteroalkyl, or $C_{1-4}$ heteroalkyl, or $C_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in the heteroaryl group is not more than two. In a heteroaryl, the heteroatomic group can be selected from —O—, —S—, —NH—, —N(—CH$_3$)—, —S(O)—, and —SO$_2$—, or the heteroatomic group can be selected from —O— and —NH—, or the heteroatomic group can be —O— or —NH—. A heteroaryl group can be selected from $C_{5-10}$ heteroaryl, $C_{5-9}$ heteroaryl, $C_{5-8}$ heteroaryl, $C_{5-7}$ heteroaryl, $C_{5-6}$ heteroaryl, $C_5$ heteroaryl or $C_6$ heteroaryl.

Examples of suitable heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. A heteroaryl group can be derived from thiophene, pyrrole, benzothiophene, benzofuran, indole, pyridine, quinoline, imidazole, oxazole, or pyrazine. For example, a heteroaryl can be $C_5$ heteroaryl and can be selected from furyl, thienyl, pyrrolyl, imidazolyl, pyrazolyl, isothiazolyl, or isoxazolyl. A heteroaryl can be $C_6$ heteroaryl, and can be selected from pyridinyl, pyrazinyl, pyrimidinyl, and pyridazinyl.

"Heteroarylalkyl" refers to an arylalkyl group in which one of the carbon atoms (and certain associated hydrogen atoms) is replaced with a heteroatom. A heteroarylalkyl group can be $C_{6-16}$ heteroarylalkyl, $C_{6-14}$ heteroarylalkyl, $C_{6-12}$ heteroarylalkyl, $C_{6-10}$ heteroarylalkyl, $C_{6-8}$ heteroarylalkyl, or $C_7$ heteroarylalkyl, or $C_6$ heteroarylalkyl. In a heteroarylalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, and Si. Examples of heterocycloalkyl groups include groups derived from epoxides, azirines, thiiranes, imidazolidine, morpholine, piperazine, piperidine, pyrazolidine, pyrrolidine, and quinuclidine. A heterocycloalkyl can be $C_5$ heterocycloalkyl and is selected from pyrrolidinyl, tetrahydrofuranyl, tetrahydrothiophenyl, imidazolidinyl, oxazolidinyl, thiazolidinyl, doxolanyl, and dithiolanyl. A heterocycloalkyl can be $C_6$ heterocycloalkyl and can be selected from piperidinyl, tetrahydropyranyl, piperizinyl, oxazinyl, dithianyl, and dioxanyl. A heterocycloalkyl group can be $C_{3-6}$ heterocycloalkyl, $C_{3-5}$ heterocycloalkyl, $C_{5-6}$ heterocycloalkyl, $C_5$ heterocycloalkyl or $C_6$ heterocycloalkyl. In a heterocycloalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Heterocycloalkylalkyl" refers to a cycloalkylalkyl group in which one or more carbon atoms (and certain associated hydrogen atoms) of the cycloalkyl ring are independently replaced with the same or different heteroatom. A heterocycloalkylalkyl can be $C_{4-12}$ heterocycloalkylalkyl, $C_{4-10}$ heterocycloalkylalkyl, $C_{4-8}$ heterocycloalkylalkyl, $C_{4-6}$ heterocycloalkylalkyl, $C_{6-7}$ heterocycloalkylalkyl, or $C_6$ heterocycloalkylalkyl or $C_7$ heterocycloalkylalkyl. In a heterocycloalkylalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Parent aromatic ring system" refers to an unsaturated cyclic or polycyclic ring system having a cyclic conjugated π (pi) electron system with 4n+2 electrons (Hückel rule). Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism.

"Metabolic intermediate" refers to a compound that is formed in vivo by metabolism of a parent compound and that further undergoes reaction in vivo to release an active agent. Compounds of Formula (1) are protected sulfonate nucleophile prodrugs of non-β-lactam β-lactamase inhibitors that are metabolized in vivo to provide the corresponding metabolic intermediates such as avibactam ([2S, 5R]-2-carbamoyl-7-oxo-1,6-diazabicyclo[3.2.1]octan-6-yl hydrogen sulfate). Metabolic intermediates undergo nucleophilic cyclization to release a non-β-lactam β-lactamase inhibitor such as avibactam and one or more reaction products. It is desirable that the reaction products or metabolites thereof not be toxic.

""Neopentyl" refers to a radical in which a methylene carbon is bonded to a carbon atom, which is bonded to three non-hydrogen substituents. Examples of non-hydrogen substituents include carbon, oxygen, nitrogen, and sulfur. Each of the three non-hydrogen substituents can be carbon. Two of the three non-hydrogen substituents can be carbon, and the third non-hydrogen substituent can be selected from oxygen and nitrogen. A neopentyl group can have the structure:

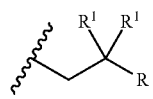

where each $R^1$ is defined as for Formula (1).

"Parent Aromatic Ring System" refers to an unsaturated cyclic or polycyclic ring system having a conjugated it electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous n-electron system characteristic of aromatic systems and a number of n-electrons corresponding to the Hückel rule (4n+2). Examples of heteroatoms to replace the carbon atoms include N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, and xanthene. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine.

"Patient" refers to a mammal, for example, a human. The term "patient" is used interchangeably with "subject."

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, such as an alkali metal ion, an alkaline earth ion, or an aluminum ion, or combinations thereof; or coordinates with an organic base such as ethanolamine, diethanolamine, triethanolamine, and N-methylglucamine. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt such as a hydrochloride salt, is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1) or a pharmaceutically acceptable salt thereof and at least one pharmaceutically acceptable vehicle, with which the compound of Formula (1) or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as prophylaxis. Compounds provided by the present disclosure can provide superior prophylaxis because of lower long-term side effects over long time periods.

"Prodrug" refers to a derivative of a drug molecule that requires a transformation within the body to release the active drug. Prodrugs are frequently, although not necessarily, pharmacologically inactive until converted to the parent drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. For example, for a compound of Formula (1), the promoiety can have the structure:

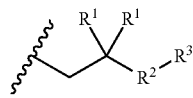

where $R^1$, $R^2$, and $R^3$ are defined as for Formula (1).

"Single bond" as in the expression "$R^2$ is selected from a single bond" refers to a moiety in which $R^2$ is a single bond. For example, in a moiety having the structure —C(R$^1$)$_2$—R$^2$—R$^3$, where $R^2$ is a single bond, —R$^2$— corresponds to a single bond, "—", and the moiety has the structure —C(R)$_2$—R$^3$.

Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Solvates" refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion. Solvates may also be formed, under certain circumstances, from other crystalline solvates or hydrates upon exposure to the solvent or upon suspension material in solvent. Solvates may crystallize in more than one form resulting in solvate polymorphism.

"Substituted" refers to a group in which one or more hydrogen atoms are independently replaced with the same or different substituent(s). Each substituent can be independently selected from deuterio, halogen, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl. Each substituent can be independently selected from deuterio, halogen, —NH$_2$, —OH, C$_{1-3}$ alkoxy, and C$_{1-3}$ alkyl, trifluoromethoxy, and trifluoromethyl. Each substituent can be independently selected from deuterio, —OH, methyl, ethyl, trifluoromethyl, methoxy, ethoxy, and trifluoromethoxy. Each substituent can be selected from deuterio, C$_{1-3}$ alkyl, =O, C$_{1-3}$ alkyl, C$_{1-3}$ alkoxy, and phenyl. Each substituent can be selected from deuterio, —OH, —NH$_2$, C$_{1-3}$ alkyl, and C$_{1-3}$ alkoxy.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or at least one or more symptoms thereof in a patient who may be exposed to or predisposed to a disease or disorder even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Therapeutically effective amount" means the amount of a compound that, when administered to a patient for treating a disease, is sufficient to affect such treatment for the disease. The "therapeutically effective amount" will vary depending, for example, on the compound, the disease and its severity and the age, weight, adsorption, distribution, metabolism and excretion, of the patient to be treated.

"Vehicle" refers to a diluent, excipient or carrier with which a compound is administered to a subject. In some embodiments, the vehicle is pharmaceutically acceptable.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds provided by the present disclosure are sulfonate ester prodrugs of non-β-lactam β-lactamase inhibitors. In the non-β-lactam β-lactamase inhibitor prodrugs a nucleophilic moiety is positioned proximate to the hydrogen sulfate group. In vivo, the nucleophilic moiety reacts to release the non-β-lactam β-lactamase inhibitor. Examples of non-β-lactam β-lactamase inhibitors include avibactam ([2S,5R]-2-carbamoyl-7-oxo-1,6-diazabicyclo[3.2.1]octan-6-yl hydrogen sulfate), relebactam ((1R,2S,5R)-7-oxo-2-(piperidin-4-ylcarbamoyl)-1,6-diazabicyclo[3.2.1]octan-6-yl hydrogen sulfate), and nacubactam (1R,2S,5R)-2-((2-aminoethoxy)carbamoyl)-7-oxo-1,6-diazabicyclo[3.2.1] octan-6-yl hydrogen sulfate, and derivatives and analogs of any of the foregoing. These compounds are inhibitors of class A, class C, and certain Class D β-lactamases and are useful in the treatment of bacterial infections when used in conjunction with β-lactam antibiotics.

Compounds provided by the present disclosure include compounds of Formula (1):

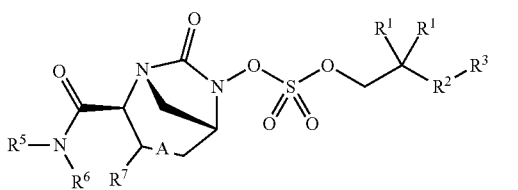

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—(O)—O—$R^4$, —NH—C(O)—O—$R^4$, —(O)—O—$R^4$, —C(O)—S—$R^4$, —C(O)—NH—$R^4$, —O—(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (=) and $R^7$ is $C_{1-3}$ alkyl. In compounds of Formula (1), each substituent can be independently selected from deuterio, —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R is independently selected from hydrogen and $C_{1-6}$ alkyl, such has methyl, ethyl, n-propyl, isopropyl, n-butyl, tert-butyl, or iso-butyl.

In compounds of Formula (1), a substituent group can be a nucleophilic group. Nucleophilic groups are functional group having a reactive pair of electrons and having the ability of forming a chemical bond by donating electrons. Examples of suitable nucleophilic groups include esters, carboxylates, sulfonates, substituted or unsubstituted amines, alcohols (hydroxyl), thiols, sulfides, hydroxylamines, and imines. Other examples of suitable nucleophilic groups include —OH, —CF$_3$, —O—CF$_3$, —NO$_2$, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), where each $R^4$ is independently selected from hydrogen, $C_{1-6}$ alkyl, $C_{1-6}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{6-8}$ heteroaryl, $C_{5-10}$ arylalkyl, $C_{5-10}$ heteroarylalkyl, substituted $C_{1-6}$ alkyl, substituted $C_{1-6}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{6-8}$ heteroaryl, substituted $C_{5-10}$ arylalkyl, and substituted $C_{5-10}$ heteroarylalkyl.

In compounds of Formula (1), each substituent can independently be selected from —OH, —CF$_3$, —O—CF$_3$, —NO$_2$, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), wherein each $R^4$ is selected from hydrogen, $C_{1-8}$ alkyl, and $C_{1-8}$ heteroalkyl.

In compounds of Formula (1), A can be a single bond (—) and $R^7$ can be hydrogen.

In compounds of Formula (1), A can be a double bond (=) and $R^7$ can be $C_{1-3}$ alkyl, such as methyl, ethyl, n-propyl, or iso-propyl.

In compounds of Formula (1), each of $R^5$ and $R^6$ can be hydrogen.

In compounds of Formula (1), A can be a single bond (—); $R^7$ can be hydrogen; and $R^5$ can be hydrogen.

In compounds of Formula (1), A can be a double bond (=) and $R^7$ can be $C_{1-3}$ alkyl, such as methyl, ethyl, n-propyl, or iso-propyl; and each of $R^5$ and $R^6$ can be hydrogen.

In compounds of Formula (1), the compound can have the structure of Formula (2):

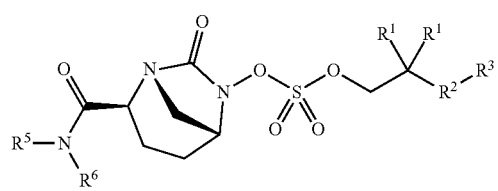

In compounds of Formula (1), the compound can have the structure of Formula (2a):

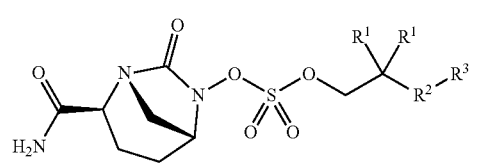

In compounds of Formula (1), the compound can have the structure of Formula (3):

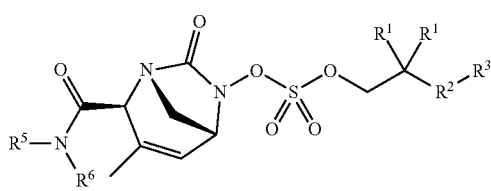

(3)

In compounds of Formula (1), the compound can have the structure of Formula (3a):

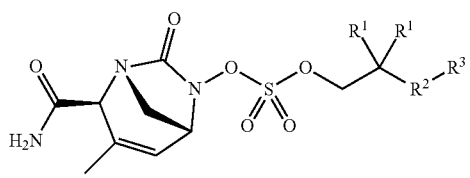

(3a)

In compounds of Formula (1), the compound can have the structure of Formula (4):

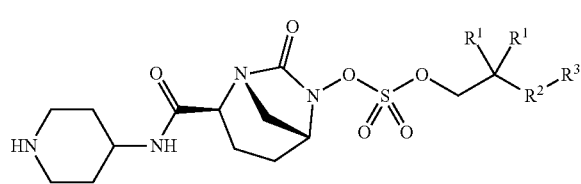

(4)

In compounds of Formula (1), the compound can have the structure of Formula (5):

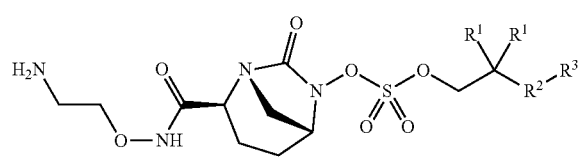

(5)

In compounds of Formula (1), $R^5$ can be $C_{2-6}$ heteroalkyl comprising a terminal amine group, and $R^6$ can be hydrogen. For example, $R^5$ can be $-O-(CH_2)_2-NH_2$, $-CH_2-O-CH_2-NH_2$, $-(CH_2)_2-O-CH_2-NH_2$, or $-CH_2-O-(CH_2)_2-NH_2$.

In compounds of Formula (1), A can be a single bond (—) and $R^7$ can be hydrogen, $R^5$ can be $-O-(CH_2)_2-NH_2$, and $R^6$ can be hydrogen.

In compounds of Formula (1), $R^5$ can be $C_{4-6}$ heterocycloalkyl comprising at least one —NH— moiety, and $R^6$ can be hydrogen. For example, $R^5$ can be 2-yl-piperidine, 3-yl-piperidine, or 4-yl-piperidine.

In compounds of Formula (1), A can be a single bond (—) and $R^7$ can be hydrogen, $R^5$ can be 4-yl-piperidine, and $R^6$ can be hydrogen.

In compounds of Formula (1)-(5), each $R^1$ can independently be $C_{1-6}$ alkyl.

In compounds of Formula (1)-(5), each $R^1$ can independently be methyl, ethyl, or n-propyl.

In compounds of Formula (1)-(5), each $R^1$ can be same and is methyl, ethyl, or n-propyl.

In compounds of Formula (1)-(5), each $R^1$ is methyl.

In compounds of Formula (1)-(5), each $R^1$ together with the geminal carbon atom to which they are bonded can form a $C_{3-6}$ cycloalkyl ring or a substituted $C_{3-6}$ cycloalkyl ring.

In compounds of Formula (1)-(5), each $R^1$ together with the geminal carbon atom to which they are bonded can form a $C_{3-6}$ cycloalkyl ring. For example, each $R^1$ together with the geminal carbon atom to which they are bonded can form a cyclopropyl ring, a cyclobutyl ring, a cyclopentyl ring, or a cyclohexyl ring.

compounds of Formula (1)-(5), each $R^1$ each $R^1$ together with the geminal carbon atom to which they are bonded can form a $C_{3-6}$ heterocycloalkyl ring or a substituted $C_{3-6}$ heterocycloalkyl ring.

In compounds of Formula (1)-(5), $R^2$ can be selected from a single bond, $C_{1-2}$ alkanediyl, and substituted $C_{1-2}$ alkanediyl.

In compounds of Formula (1)-(5), $R^2$ can be a single bond.

In compounds of Formula (1)-(5), $R^2$ can be a single bond; and $R^3$ can be $C_{1-6}$ alkyl.

In compounds of Formula (1)-(5), $R^2$ can be selected from $C_{1-2}$ alkanediyl and substituted $C_{1-2}$ alkanediyl.

In compounds of Formula (1)-(5), $R^2$ can be methanediyl, ethanediyl, substituted methanediyl, or substituted ethanediyl.

In compounds of Formula (1)-(5), $R^2$ can be substituted $C_{1-2}$ alkanediyl where the substituted group can be selected from —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R is independently selected from hydrogen and $C_{1-6}$ alkyl.

In compounds of Formula (1)-(5), $R^2$ can be substituted $C_{1-2}$ alkanediyl where the substituent group can be a nucleophilic group. For example, $R^2$ can be substituted $C_{1-2}$ alkanediyl where the substituent group can be selected from —OH, —CF$_3$, —O—CF$_3$, —NO$_2$, —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), where each $R^4$ is defined as for Formula (1), or each $R^4$ is selected from hydrogen and $C_{1-8}$ alkyl.

In compounds of Formula (1)-(5), $R^2$ can be substituted $C_{1-2}$ alkanediyl where the substituent group is selected from —OH, —O—C(O)—R$^4$, —S—C(O)—R$^4$, —NH—C(O)—R$^4$, —C(O)—O—R$^4$, —C(O)—S—R$^4$, —C(O)—NH—R$^4$, —S—S—R$^4$, —S—R$^4$, —NH—R$^4$, —CH(—NH$_2$)(—R$^4$), substituted $C_{5-6}$ aryl, —NHR$^4$, —CH(—NH$_2$)(—R$^4$); and $R^4$ is defined as for Formula (1), or each $R^4$ is selected from hydrogen and $C_{1-8}$ alkyl.

In compounds of Formula (1)-(5), where $R^2$ is substituted $C_{1-6}$ alkanediyl, substituted $C_{1-6}$ heteroalkanediyl, or substituted $C_{5-6}$ arenediyl, the stereochemistry of the carbon atom to which the substituent group is bonded can be of the (S) configuration.

In compounds of Formula (1)-(5), where $R^2$ is substituted $C_{1-6}$ alkanediyl, substituted $C_{1-6}$ heteroalkanediyl, or substituted $C_{5-6}$ arenediyl, the stereochemistry of the carbon atom to which the substituent group is bonded can be of the (R) configuration.

In compounds of Formula (1)-(5), $R^2$ is selected from $C_{5-6}$ cycloalkanediyl, $C_{5-6}$ heterocycloalkanediyl, $C_{5-6}$ arenediyl, and $C_{5-6}$ heterocycloalkanediyl.

In compounds of Formula (1)-(5), $R^2$ can be cyclopenta-1,3-diene-diyl, substituted cyclopenta-1,3-diene-diyl, benzene-diyl or substituted benzene-diyl. For example, $R^2$ can be 1,2-benzene-diyl or substituted 1,2-benzene-diyl.

In compounds of Formula (1)-(5), $R^3$ can be selected from —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$); where $R^4$ is defined as for Formula (1), or each $R^4$ is selected from hydrogen and $C_{1-8}$ alkyl.

In compounds of Formula (1)-(5), $R^3$ can be selected from —O—C(O)—$R^4$, —C(O)—O—$R^4$, —S—C(O)—$R^4$, —C(O)—S—$R^4$, —S—S—$R^4$, —NH—$R^4$, and —CH(—NH$_2$)(—$R^4$); where $R^4$ is defined as for Formula (1), or each $R^4$ is selected from hydrogen and $C_{1-8}$ alkyl.

In compounds of Formula (1)-(5), $R^3$ is —C(O)—O—$R^4$); where $R^4$ is defined as for Formula (1), or each $R^4$ is selected from hydrogen and $C_{1-8}$ alkyl.

In compounds of Formula (1)-(5), $R^4$ can be selected from hydrogen, $C_{1-3}$ alkyl, $C_{5-6}$ cycloalkyl, $C_{5-6}$ heterocycloalkyl, $C_{5-6}$ aryl, substituted $C_{1-3}$ alkyl, substituted $C_{5-6}$ cycloalkyl, substituted $C_{5-6}$ heterocycloalkyl, and substituted $C_{5-6}$ aryl.

In compounds of Formula (1)-(5), $R^4$ can be selected from methyl, ethyl, phenyl, and benzyl.

In compounds of Formula (1)-(5), $R^4$ can be selected from hydrogen and $C_{1-8}$ alkyl.

In compounds of Formula (1)-(5), $R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In compounds of Formula (1)-(5), $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1)-(5), $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1)-(5), $R^3$ can be —C(O)—O—$R^4$; and $R^4$ can be selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl, In compounds of Formula (1)-(5), $R^3$ can be —C(O)—O—$R^4$; and $R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In compounds of Formula (1)-(5), $R^3$ can be —C(O)—O—$R^4$; and $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1)-(5), $R^3$ can be selected from —O—C(O)—CH$_3$, —O—C(O)—CH$_2$—CH$_3$, —O—C(O)-phenyl, —O—C(O)—CH$_2$-phenyl, —S—C(O)—CH$_3$, —S—C(O)—CH$_2$—CH$_3$, —S—C(O)— phenyl, —S—C(O)—CH$_2$-phenyl, —NH—C(O)—CH$_3$, —NH—C(O)—CH$_2$—CH$_3$, —NH—C(O)-phenyl, —NH—C(O)—CH$_2$-phenyl, —O—C(O)—O—CH$_3$, —O—C(O)—O—CH$_2$—CH$_3$, —O—C(O)—O-phenyl, —O—C(O)—O—CH$_2$-phenyl, —S—C(O)—O—CH$_3$, —S—C(O)—O—CH$_2$— CH$_3$, —S—C(O)—O-phenyl, —S—C(O)—O—CH$_2$-phenyl, —NH—C(O)—O—CH$_3$, —NH—C(O)—O—CH$_2$—CH$_3$, —NH—C(O)—O-phenyl, —NH—C(O)—O—CH$_2$-phenyl, —C(O)—O—CH$_3$, —C(O)—O—CH$_2$—CH$_3$, —C(O)—O-phenyl, —C(O)—O—CH$_2$-phenyl, —C(O)—S—CH$_3$, —C(O)—S—CH$_2$—CH$_3$, —C(O)—S-phenyl, —C(O)—S—CH$_2$-phenyl, —C(O)—NH—CH$_3$, —C(O)—NH—CH$_2$—CH$_3$, —C(O)—NH-phenyl, —C(O)—NH—CH$_2$-phenyl, —O—C(O)—O—CH$_3$, —O—C(O)—O—CH$_2$—CH$_3$, —O—C(O)—O-phenyl, —O—C(O)—O—CH$_2$-phenyl, —O—C(O)—S—CH$_3$, —O—C(O)—S—CH$_2$—CH$_3$, —O—C(O)—S-phenyl, —O—C(O)—S—CH$_2$-phenyl, —O—C(O)—NH—CH$_3$, —O—C(O)—NH—CH$_2$—CH$_3$, —O—C(O)—NH-phenyl, —O—C(O)—NH—CH$_2$-phenyl, —S—SH, —S—S—CH$_3$, —S—S—CH$_2$—CH$_3$, —S—S-phenyl, —S—S—CH$_2$-phenyl, —SH, —S—CH$_3$, —S—CH$_2$—CH$_3$, —S-phenyl, —S—CH$_2$-phenyl, —NH$_2$, —NH—CH$_3$, —NH—CH$_2$—CH$_3$, —NH-phenyl, —NH—CH$_2$-phenyl, —CH(—NH$_2$)(—CH$_3$), —CH(—NH$_2$)(—CH$_2$—CH$_3$), —CH(—NH$_2$)(-phenyl), and —CH(—NH$_2$)(—CH$_2$-phenyl).

In compounds of Formula (1)-(5), $R^3$ can be selected from $C_{5-6}$ cycloalkyl, $C_{5-6}$ heterocycloalkyl, $C_{5-6}$ aryl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, comprising at least one nucleophilic group. For example, $R^3$ can have the structure of Formula (4a) or Formula (4b):

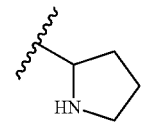

(4a)

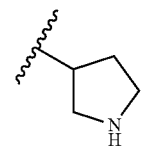

(4b)

In compounds of Formula (1)-(5), $R^4$ can be selected from $C_{1-3}$ alkyl, $C_{5-6}$ cycloalkyl, $C_{5-6}$ heterocycloalkyl, $C_{5-6}$ aryl, substituted $C_{1-3}$ alkyl, substituted $C_{5-6}$ cycloalkyl, substituted $C_{5-6}$ heterocycloalkyl, and substituted $C_{5-6}$ aryl.

In compounds of Formula (1)-(5), each $R^1$ together with the carbon atom to which they are bonded form a $C_{4-6}$ heterocycloalkyl ring comprising two adjacent S atoms or a substituted $C_{4-6}$ heterocycloalkyl ring comprising at least one heteroatom selected from O and S, and a carbonyl (=O) substituent group bonded to a carbon atom adjacent the at least one heteroatom.

In compounds of Formula (1)-(5), $R^2$ can be a bond; $R^3$ can be $C_{1-3}$ alkyl; and each $R^1$ together with the carbon atom to which they are bonded form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the heteroatom.

In compounds of Formula (1)-(5), the promoiety —CH$_2$—C($R^1$)$_2$—$R^3$—$R^4$ can have any of the following structures, where $R^3$ can be $C_{1-6}$ alkyl, such as $C_{1-4}$ alkyl, such as methyl or ethyl:

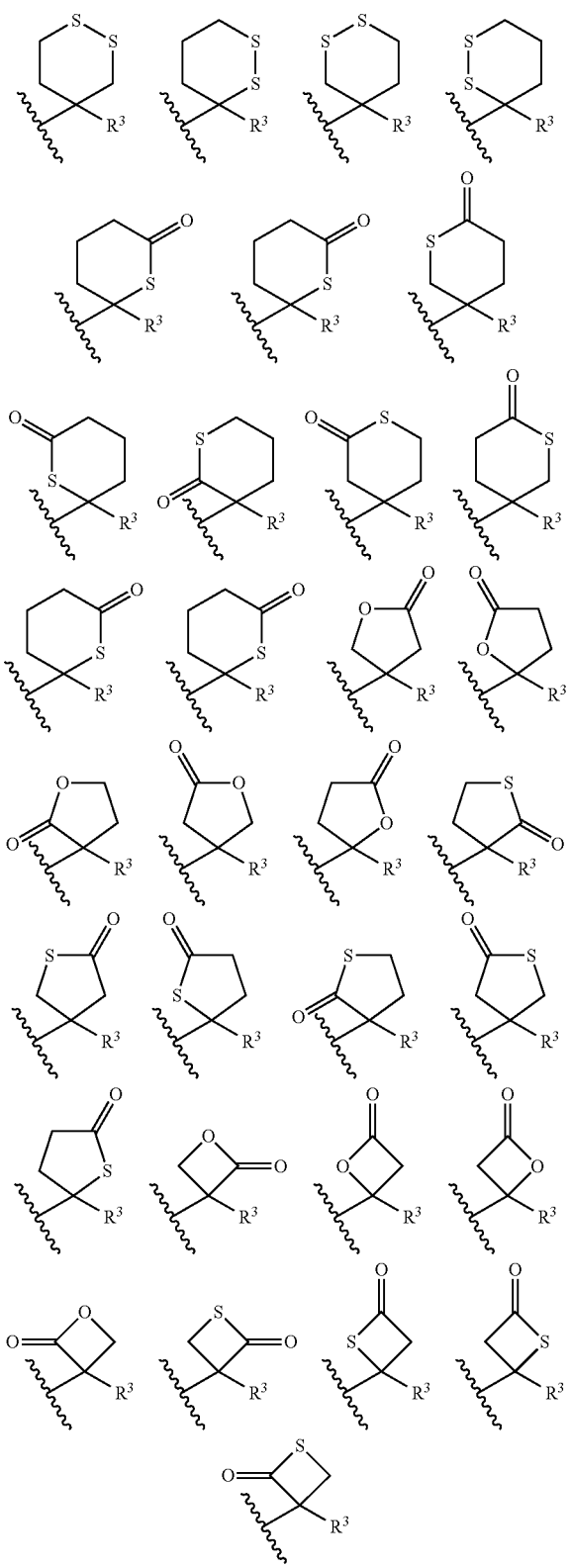

In compounds of Formula (1)-(5), $R^2$ can be a single bond; $R^3$ can be $C_{1-3}$ alkyl; and each $R^1$ together with the carbon atom to which they are bonded can form a $C_{4-6}$ heterocycloalkyl ring or a substituted $C_{4-6}$ heterocycloalkyl ring.

In compounds of Formula (1)-(5), $R^2$ can be a single bond; $R^3$ can be $C_{1-3}$ alkyl; and each $R^1$ together with the carbon atom to which they are bonded can form a $C_{4-6}$ heterocycloalkyl ring comprising two adjacent S atoms or a substituted $C_{4-6}$ heterocycloalkyl ring comprising at least one heteroatom selected from O and S, and a carbonyl (=O) substituent group bonded to a carbon atom adjacent the heteroatom.

In compounds of Formula (1)-(5), $R^2$ can be a single bond; $R^3$ can be $C_{1-3}$ alkyl; and each $R^1$ together with the carbon atom to which they are bonded can form a 1,2-dithiolane, 1,2-dithane ring, thietan-2-one ring, dihydrothiophen-2(3H)-one ring, tetrahydro-2H-thipyran-2-one ring, oxetan-2-one ring dihydrofuran-2(3H)-one ring, or tetrahydro-2H-pyran-2-one ring.

In compounds of Formula (1)-(5),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$), where $R^4$ can be selected from hydrogen, methyl, ethyl, cyclopentyl, cyclohexyl, phenyl, benzyl, and 2-pyrrolidinyl.

In compounds of Formula (1)-(5),
each $R^1$ and the geminal carbon to which they are bonded can form a $C_{3-6}$ cycloalkyl ring;
$R^2$ can be selected from a bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$), where $R^4$ can be selected from hydrogen, methyl, ethyl, cyclopentyl, cyclohexyl, phenyl, benzyl, and 2-pyrrolidinyl.

In compounds of Formula (1)-(5),
$R^2$ can be a bond;
$R^3$ be $C_{1-3}$ alkyl; and
each $R^1$ together with the carbon atom to which they are bonded can form a 1,2-dithiolante, 1,2-dithane ring, thietan-2-one ring, dihydrothiophen-2(3H)-one ring, tetrahydro-2H-thipyran-2-one ring, oxetan-2-one ring dihydrofuran-2(3H)-one ring, or tetrahydro-2H-pyran-2-one ring.

In compounds of Formula (1)-(5), each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$);
wherein $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1)-(5),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be —C(O)—O—$R^4$;
wherein $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1)-(5),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and R³ can be selected from —O—C(O)—R⁴, —C(O)—O—R⁴, —S—C(O)—R⁴, —C(O)—S—R⁴, —S—S—R⁴, —NHR⁴, and —CH(—NH₂)(—R⁴);
wherein R⁴ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1)-(5),
each R¹ can be methyl;
R² can be selected from a single bond, methanediyl, ethanediyl, —CH(—OH)—, —CH(—O—C(O)—CH₂CH₃)—, and 1,2-benzene-diyl; and
R³ can be —C(O)—O—R⁴;
wherein R⁴ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1)-(5),
each R¹ can be methyl;
R² can be a single bond; and
R³ can be —C(O)—O—R⁴;
wherein R⁴ can be selected from $C_{1-10}$ alkyl, $C_{1-10}$ heteroalkyl, $C_{7-10}$ alkylarene, and $C_{5-10}$ heteroalkylcycloalkyl.

In compounds of Formula (1)-(5),
each R¹ can be methyl;
R² can be a single bond;
R³ can be —C(O)—O—R⁴;
wherein R⁴ can be selected from $C_{1-10}$ alkyl, $C_{1-10}$ heteroalkyl, $C_{7-10}$ alkylarene, and $C_{5-10}$ heteroalkylcycloalkyl;
each of R⁵, R⁶, and R⁷ can be hydrogen; and
A is a single bond.

In compounds of Formula (1)-(5), A can be a single bond, and each of R⁵, R⁶, and R⁷ can be hydrogen.

In compounds of Formula (1)-(5), A can be a single bond; each R¹ can be independently $C_{1-3}$ alkyl; each R² can be a single bond; and each of R⁵, R⁶, and R⁷ can be hydrogen;

In compounds of Formula (1), the compound can be selected from:
3-(((((2S,5R)-2-carbamoyl-7-oxo-1,6-diazabicyclo[3.2.1]octan-6-yl)oxy)sulfonyl)oxy)-2,2-dimethylpropyl benzoate (2);
ethyl 3-(((((2S,5R)-2-carbamoyl-7-oxo-1,6-diazabicyclo[3.2.1]octan-6-yl)oxy)sulfonyl)oxy)-2,2-dimethylpropanoate (3);
benzyl 3-(((((2S,5R)-2-carbamoyl-7-oxo-1,6-diazabicyclo[3.2.1]octan-6-yl)oxy)sulfonyl)oxy)-2,2-dimethylpropanoate (4);
4-(((((2S,5R)-2-carbamoyl-7-oxo-1,6-diazabicyclo[3.2.1]octan-6-yl)oxy)sulfonyl)oxy)-3,3-dimethylbutyl benzoate (6);
4-(((((2S,5R)-2-carbamoyl-7-oxo-1,6-diazabicyclo[3.2.1]octan-6-yl)oxy)sulfonyl)oxy)-3,3-dimethylbutyl propionate (7);
benzyl (4-(((((2S,5R)-2-carbamoyl-7-oxo-1,6-diazabicyclo[3.2.1]octan-6-yl)oxy)sulfonyl)oxy)-3,3-dimethylbutyl) adipate (8);
6-(4-(((((2S,5R)-2-carbamoyl-7-oxo-1,6-diazabicyclo[3.2.1]octan-6-yl)oxy)sulfonyl)oxy)-3,3-dimethylbutoxy)-6-oxohexanoic acid (9);
methyl 3-(((((2S,5R)-2-carbamoyl-7-oxo-1,6-diazabicyclo[3.2.1]octan-6-yl)oxy)sulfonyl)oxy)-2,2-dimethylpropanoate (10);
isopropyl 3-(((((2S,5R)-2-carbamoyl-7-oxo-1,6-diazabicyclo[3.2.1]octan-6-yl)oxy)sulfonyl)oxy)-2,2-dimethylpropanoate (11);
hexyl 3-(((((2S,5R)-2-carbamoyl-7-oxo-1,6-diazabicyclo[3.2.1]octan-6-yl)oxy)sulfonyl)oxy)-2,2-dimethylpropanoate (12);
heptyl 3-(((((2S,5R)-2-carbamoyl-7-oxo-1,6-diazabicyclo[3.2.1]octan-6-yl)oxy)sulfonyl)oxy)-2,2-dimethylpropanoate (13);
tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14);
2-methoxyethyl 3-(((((2S,5R)-2-carbamoyl-7-oxo-1,6-diazabicyclo[3.2.1]octan-6-yl)oxy)sulfonyl)oxy)-2,2-dimethylpropanoate (15);
oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16);
ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17);
ethyl 1-((((((2S,5R)-2-carbamoyl-7-oxo-1,6-diazabicyclo[3.2.1]octan-6-yl)oxy)sulfonyl)oxy)methyl)cyclopropanecarboxylate (18);
ethyl 1-((((((2S,5R)-2-carbamoyl-7-oxo-1,6-diazabicyclo[3.2.1]octan-6-yl)oxy)sulfonyl)oxy)methyl)cyclobutanecarboxylate (19);
(2S,5R)-2-carbamoyl-7-oxo-1,6-diazabicyclo[3.2.1]octan-6-yl 1H-imidazole-1-sulfonate (34);
ethyl 5-(((((2S,5R)-2-carbamoyl-7-oxo-1,6-diazabicyclo[3.2.1]octan-6-yl)oxy)sulfonyl)oxy)-4,4-dimethylpentanoate (35);
hexyl 5-(((((2S,5R)-2-carbamoyl-7-oxo-1,6-diazabicyclo[3.2.1]octan-6-yl)oxy)sulfonyl)oxy)-4,4-dimethylpentanoate (36);
heptyl 5-(((((2S,5R)-2-carbamoyl-7-oxo-1,6-diazabicyclo[3.2.1]octan-6-yl)oxy)sulfonyl)oxy)-4,4-dimethylpentanoate (37);
2-methoxyethyl 5-(((((2S,5R)-2-carbamoyl-7-oxo-1,6-diazabicyclo[3.2.1]octan-6-yl)oxy)sulfonyl)oxy)-4,4-dimethylpentanoate (38);
5-(((((2S,5R)-2-carbamoyl-7-oxo-1,6-diazabicyclo[3.2.1]octan-6-yl)oxy)sulfonyl)oxy)-2,2,4,4-tetramethylpentyl propionate (39);
5-(((((2S,5R)-2-carbamoyl-7-oxo-1,6-diazabicyclo[3.2.1]octan-6-yl)oxy)sulfonyl)oxy)-2,2,4,4-tetramethylpentyl benzoate (40);
5-(((((2S,5R)-2-carbamoyl-7-oxo-1,6-diazabicyclo[3.2.1]octan-6-yl)oxy)sulfonyl)oxy)-2,2,4,4-tetramethylpentyl 2,6-dimethylbenzoate (41);
(2S,5R)-2-carbamoyl-7-oxo-1,6-diazabicyclo[3.2.1]octan-6-yl ((3-methyl-2-oxotetrahydrofuran-3-yl)methyl) sulfate (42);
3-(((((2S,5R)-2-carbamoyl-7-oxo-1,6-diazabicyclo[3.2.1]octan-6-yl)oxy)sulfonyl)oxy)-2,2-dimethylpropyl pivalate (43);
3-(((((2S,5R)-2-carbamoyl-7-oxo-1,6-diazabicyclo[3.2.1]octan-6-yl)oxy)sulfonyl)oxy)-2,2-dimethylpropyl 3-chloro-2,6-dimethoxybenzoate (44);
4-(((((2S,5R)-2-carbamoyl-7-oxo-1,6-diazabicyclo[3.2.1]octan-6-yl)oxy)sulfonyl)oxy)-2,2,3,3-tetramethylbutyl 2,6-dimethylbenzoate (45);
4-(((((2S,5R)-2-carbamoyl-7-oxo-1,6-diazabicyclo[3.2.1]octan-6-yl)oxy)sulfonyl)oxy)-2,2,3,3-tetramethylbutyl benzoate (46);
4-(((((2S,5R)-2-carbamoyl-7-oxo-1,6-diazabicyclo[3.2.1]octan-6-yl)oxy)sulfonyl)oxy)-2,2,3,3-tetramethylbutyl propionate (47);

(2S,5R)-2-carbamoyl-7-oxo-1,6-diazabicyclo[3.2.1]octan-6-yl ((3-methyl-2-oxotetrahydro-2H-pyran-3-yl)methyl) sulfate (48);

2-(3-(((((2S,5R)-2-carbamoyl-7-oxo-1,6-diazabicyclo[3.2.1]octan-6-yl)oxy)sulfonyl)oxy)-2,2-dimethylpropyl) phenyl acetate (49);

2-(3-(((((2S,5R)-2-carbamoyl-7-oxo-1,6-diazabicyclo[3.2.1]octan-6-yl)oxy)sulfonyl)oxy)-2,2-dimethylpropyl) phenyl pivalate (50);

S-(4-(((((2S,5R)-2-carbamoyl-7-oxo-1,6-diazabicyclo[3.2.1]octan-6-yl)oxy)sulfonyl)oxy)-3,3-dimethylbutyl) ethanethioate (51);

S-(5-(((((2S,5R)-2-carbamoyl-7-oxo-1,6-diazabicyclo[3.2.1]octan-6-yl)oxy)sulfonyl)oxy)-4,4-dimethylpentyl) ethanethioate (52);

S-(3-(((((2S,5R)-2-carbamoyl-7-oxo-1,6-diazabicyclo[3.2.1]octan-6-yl)oxy)sulfonyl)oxy)-2,2-dimethylpropyl) ethanethioate (53);

3-(((((2S,5R)-2-carbamoyl-7-oxo-1,6-diazabicyclo[3.2.1]octan-6-yl)oxy)sulfonyl)oxy)-2,2-dimethylpropyl 2,6-dimethylbenzoate (54);

3-(((((2S,5R)-2-carbamoyl-7-oxo-1,6-diazabicyclo[3.2.1]octan-6-yl)oxy)sulfonyl)oxy)-2,2-dimethylpropyl adamantane-1-carboxylate (55);

diethyl 2-((((((2S,5R)-2-carbamoyl-7-oxo-1,6-diazabicyclo[3.2.1]octan-6-yl)oxy)sulfonyl)oxy)methyl)-2-methylmalonate (56);

propyl 3-(((((2S,5R)-2-carbamoyl-7-oxo-1,6-diazabicyclo[3.2.1]octan-6-yl)oxy)sulfonyl)oxy)-2,2-dimethylpropanoate (57);

butyl 3-(((((2S,5R)-2-carbamoyl-7-oxo-1,6-diazabicyclo[3.2.1]octan-6-yl)oxy)sulfonyl)oxy)-2,2-dimethylpropanoate (58);

(5-methyl-2-oxo-1,3-dioxol-4-yl)methyl 3-(((((2S,5R)-2-carbamoyl-7-oxo-1,6-diazabicyclo[3.2.1]octan-6-yl)oxy)sulfonyl)oxy)-2,2-dimethylpropanoate (59);

4-(((((2S,5R)-2-carbamoyl-7-oxo-1,6-diazabicyclo[3.2.1]octan-6-yl)oxy)sulfonyl)oxy)-3,3-dimethylbutyl pivalate (60);

ethyl 2-((((((2S,5R)-2-carbamoyl-7-oxo-1,6-diazabicyclo[3.2.1]octan-6-yl)oxy)sulfonyl)oxy)methyl)-2-ethylbutanoate (61);

4-(((((2S,5R)-2-carbamoyl-7-oxo-1,6-diazabicyclo[3.2.1]octan-6-yl)oxy)sulfonyl)oxy)-3,3-dimethylbutyl 2,6-dimethylbenzoate (62);

4-(((((2S,5R)-2-carbamoyl-7-oxo-1,6-diazabicyclo[3.2.1]octan-6-yl)oxy)sulfonyl)oxy)-3,3-dimethylbutyl adamantane-1-carboxylate (63);

4-(((((2S,5R)-2-carbamoyl-7-oxo-1,6-diazabicyclo[3.2.1]octan-6-yl)oxy)sulfonyl)oxy)-3,3-dimethylbutyl 2,6-dimethoxybenzoate (64);

5-(((((2S,5R)-2-carbamoyl-7-oxo-1,6-diazabicyclo[3.2.1]octan-6-yl)oxy)sulfonyl)oxy)-4,4-dimethylpentyl benzoate (65);

5-(((((2S,5R)-2-carbamoyl-7-oxo-1,6-diazabicyclo[3.2.1]octan-6-yl)oxy)sulfonyl)oxy)-4,4-dimethylpentyl 2,6-dimethoxybenzoate (66);

5-(((((2S,5R)-2-carbamoyl-7-oxo-1,6-diazabicyclo[3.2.1]octan-6-yl)oxy)sulfonyl)oxy)-4,4-dimethylpentyl 2,6-dimethylbenzoate (67);

5-(((((2S,5R)-2-carbamoyl-7-oxo-1,6-diazabicyclo[3.2.1]octan-6-yl)oxy)sulfonyl)oxy)-4,4-dimethylpentyl 2-methylbenzoate (68);

4-(((((2S,5R)-2-carbamoyl-7-oxo-1,6-diazabicyclo[3.2.1]octan-6-yl)oxy)sulfonyl)oxy)-2,2,3,3-tetramethylbutyl 3-chloro-2,6-dimethoxybenzoate (69);

2-((((((2S,5R)-2-carbamoyl-7-oxo-1,6-diazabicyclo[3.2.1]octan-6-yl)oxy)sulfonyl)oxy)methyl)-2-methylpropane-1,3-diyl dibenzoate (70);

2-((((((2S,5R)-2-carbamoyl-7-oxo-1,6-diazabicyclo[3.2.1]octan-6-yl)oxy)sulfonyl)oxy)methyl)-2-methylpropane-1,3-diyl diacetate (71);

5-(((((2S,5R)-2-carbamoyl-7-oxo-1,6-diazabicyclo[3.2.1]octan-6-yl)oxy)sulfonyl)oxy)-2,2,4,4-tetramethylpentyl 2,6-dimethoxybenzoate (72);

ethyl 3-(((((2S,5R)-2-carbamoyl-7-oxo-1,6-diazabicyclo[3.2.1]octan-6-yl)oxy)sulfonyl)oxy)-2,2-dimethylbutanoate (73);

(2S,5R)-2-carbamoyl-7-oxo-1,6-diazabicyclo[3.2.1]octan-6-yl ((3,5,5-trimethyl-2-oxotetrahydrofuran-3-yl)methyl) sulfate (74);

a pharmaceutically acceptable salt of any of the foregoing; and a combination of any of the foregoing.

In compounds of Formula (1), the compound can be selected from:

ethyl 3-(((((2S,5R)-2-carbamoyl-7-oxo-1,6-diazabicyclo[3.2.1]octan-6-yl)oxy)sulfonyl)oxy)-2,2-dimethylpropanoate (3);

benzyl 3-(((((2S,5R)-2-carbamoyl-7-oxo-1,6-diazabicyclo[3.2.1]octan-6-yl)oxy)sulfonyl)oxy)-2,2-dimethylpropanoate (4);

methyl 3-(((((2S,5R)-2-carbamoyl-7-oxo-1,6-diazabicyclo[3.2.1]octan-6-yl)oxy)sulfonyl)oxy)-2,2-dimethylpropanoate (10);

isopropyl 3-(((((2S,5R)-2-carbamoyl-7-oxo-1,6-diazabicyclo[3.2.1]octan-6-yl)oxy)sulfonyl)oxy)-2,2-dimethylpropanoate (11);

hexyl 3-(((((2S,5R)-2-carbamoyl-7-oxo-1,6-diazabicyclo[3.2.1]octan-6-yl)oxy)sulfonyl)oxy)-2,2-dimethylpropanoate (12);

heptyl 3-(((((2S,5R)-2-carbamoyl-7-oxo-1,6-diazabicyclo[3.2.1]octan-6-yl)oxy)sulfonyl)oxy)-2,2-dimethylpropanoate (13);

tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14);

2-methoxyethyl 3-(((((2S,5R)-2-carbamoyl-7-oxo-1,6-diazabicyclo[3.2.1]octan-6-yl)oxy)sulfonyl)oxy)-2,2-dimethylpropanoate (15);

oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16);

ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17);

ethyl 1-((((((2S,5R)-2-carbamoyl-7-oxo-1,6-diazabicyclo[3.2.1]octan-6-yl)oxy)sulfonyl)oxy)methyl)cyclopropanecarboxylate (18);

ethyl 1-((((((2S,5R)-2-carbamoyl-7-oxo-1,6-diazabicyclo[3.2.1]octan-6-yl)oxy)sulfonyl)oxy)methyl)cyclobutanecarboxylate (19);

hexyl 5-(((((2S,5R)-2-carbamoyl-7-oxo-1,6-diazabicyclo[3.2.1]octan-6-yl)oxy)sulfonyl)oxy)-4,4-dimethylpentanoate (36);

heptyl 5-(((((2S,5R)-2-carbamoyl-7-oxo-1,6-diazabicyclo[3.2.1]octan-6-yl)oxy)sulfonyl)oxy)-4,4-dimethylpentanoate (37);

(2S,5R)-2-carbamoyl-7-oxo-1,6-diazabicyclo[3.2.1]octan-6-yl ((3-methyl-2-oxotetrahydrofuran-3-yl)methyl) sulfate (42);

S-(3-(((((2S,5R)-2-carbamoyl-7-oxo-1,6-diazabicyclo[3.2.1]octan-6-yl)oxy)sulfonyl)oxy)-2,2-dimethylpropyl) ethanethioate (53);
propyl 3-(((((2S,5R)-2-carbamoyl-7-oxo-1,6-diazabicyclo[3.2.1]octan-6-yl)oxy)sulfonyl)oxy)-2,2-dimethylpropanoate (57);
butyl 3-(((((2S,5R)-2-carbamoyl-7-oxo-1,6-diazabicyclo[3.2.1]octan-6-yl)oxy)sulfonyl)oxy)-2,2-dimethylpropanoate (58);
(5-methyl-2-oxo-1,3-dioxol-4-yl)methyl 3-(((((2S,5R)-2-carbamoyl-7-oxo-1,6-diazabicyclo[3.2.1]octan-6-yl)oxy)sulfonyl)oxy)-2,2-dimethylpropanoate (59);
a pharmaceutically acceptable salt of any of the foregoing; and
a combination of any of the foregoing.

In compounds of Formula (1), the compound can be selected from:
ethyl 3-(((((2S,5R)-2-carbamoyl-7-oxo-1,6-diazabicyclo[3.2.1]octan-6-yl)oxy)sulfonyl)oxy)-2,2-dimethylpropanoate (3);
benzyl 3-(((((2S,5R)-2-carbamoyl-7-oxo-1,6-diazabicyclo[3.2.1]octan-6-yl)oxy)sulfonyl)oxy)-2,2-dimethylpropanoate (4);
methyl 3-(((((2S,5R)-2-carbamoyl-7-oxo-1,6-diazabicyclo[3.2.1]octan-6-yl)oxy)sulfonyl)oxy)-2,2-dimethylpropanoate (10);
isopropyl 3-(((((2S,5R)-2-carbamoyl-7-oxo-1,6-diazabicyclo[3.2.1]octan-6-yl)oxy)sulfonyl)oxy)-2,2-dimethylpropanoate (11);
hexyl 3-(((((2S,5R)-2-carbamoyl-7-oxo-1,6-diazabicyclo[3.2.1]octan-6-yl)oxy)sulfonyl)oxy)-2,2-dimethylpropanoate (12);
heptyl 3-(((((2S,5R)-2-carbamoyl-7-oxo-1,6-diazabicyclo[3.2.1]octan-6-yl)oxy)sulfonyl)oxy)-2,2-dimethylpropanoate (13);
tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14);
2-methoxyethyl 3-(((((2S,5R)-2-carbamoyl-7-oxo-1,6-diazabicyclo[3.2.1]octan-6-yl)oxy)sulfonyl)oxy)-2,2-dimethylpropanoate (15);
oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16);
ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17);
ethyl 1-((((((2S,5R)-2-carbamoyl-7-oxo-1,6-diazabicyclo[3.2.1]octan-6-yl)oxy)sulfonyl)oxy)methyl)cyclopropanecarboxylate (18);
ethyl 1-((((((2S,5R)-2-carbamoyl-7-oxo-1,6-diazabicyclo[3.2.1]octan-6-yl)oxy)sulfonyl)oxy)methyl)cyclobutanecarboxylate (19);
a pharmaceutically acceptable salt of any of the foregoing; and
a combination of any of the foregoing.

In compounds of Formula (1), the compound can be selected from:
hexyl 5-(((((2S,5R)-2-carbamoyl-7-oxo-1,6-diazabicyclo[3.2.1]octan-6-yl)oxy)sulfonyl)oxy)-4,4-dimethylpentanoate (36);
heptyl 5-(((((2S,5R)-2-carbamoyl-7-oxo-1,6-diazabicyclo[3.2.1]octan-6-yl)oxy)sulfonyl)oxy)-4,4-dimethylpentanoate (37);
(2S,5R)-2-carbamoyl-7-oxo-1,6-diazabicyclo[3.2.1]octan-6-yl ((3-methyl-2-oxotetrahydrofuran-3-yl)methyl) sulfate (42);

S-(3-(((((2S,5R)-2-carbamoyl-7-oxo-1,6-diazabicyclo[3.2.1]octan-6-yl)oxy)sulfonyl)oxy)-2,2-dimethylpropyl) ethanethioate (53);
propyl 3-(((((2S,5R)-2-carbamoyl-7-oxo-1,6-diazabicyclo[3.2.1]octan-6-yl)oxy)sulfonyl)oxy)-2,2-dimethylpropanoate (57);
butyl 3-(((((2S,5R)-2-carbamoyl-7-oxo-1,6-diazabicyclo[3.2.1]octan-6-yl)oxy)sulfonyl)oxy)-2,2-dimethylpropanoate (58);
(5-methyl-2-oxo-1,3-dioxol-4-yl)methyl 3-(((((2S,5R)-2-carbamoyl-7-oxo-1,6-diazabicyclo[3.2.1]octan-6-yl)oxy)sulfonyl)oxy)-2,2-dimethylpropanoate (59);
a pharmaceutically acceptable salt of any of the foregoing; and
a combination of any of the foregoing.

In a compound of Formula (2a),
each $R^1$ can be independently selected from $C_{1-3}$ alkyl, or each $R^1$ together with the geminal carbon atom to which they are bonded form a $C_{3-6}$ cycloalkyl ring, a substituted $C_{3-6}$ cycloalkyl ring, a $C_{3-6}$ heterocycloalkyl ring, or a substituted $C_{3-6}$ heterocycloalkyl ring;
$R^2$ can be a single bond;
$R^3$ can be —C(O)—O—$R^4$; and
$R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In a compound of Formula (2a),
each $R^1$ can be independently selected from $C_{1-3}$ alkyl, or each $R^1$ together with the carbon atom to which they are bonded form a $C_{3-6}$ cycloalkyl ring;
$R^2$ can be selected from single bond, methane-diyl, and ethane-diyl; and
$R^3$ can be selected from —C(O)—O—$R^4$ and —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In a compound of Formula (2a),
each $R^1$ can be independently selected from $C_{1-3}$ alkyl, or each $R^1$ together with the carbon atom to which they are bonded form a $C_{3-6}$ cycloalkyl ring;
$R^2$ can be a single bond; and
$R^3$ can be —C(O)—O—$R^4$, where $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In a compound of Formula (2a),
each $R^1$ can be independently selected from $C_{1-3}$ alkyl, or each $R^1$ together with the carbon atom to which they are bonded form a $C_{3-6}$ cycloalkyl ring;
$R^2$ can be —(CH$_2$)$_2$—; and
$R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In a compound of Formula (2a),
each $R^1$ can be selected from $C_{1-3}$ alkyl, or each $R^1$ together with the carbon atom to which they are bonded form a $C_{3-6}$ cycloalkyl ring;
$R^2$ can be —CH$_2$—; and
$R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, substituted $C_{4-10}$ heterocycloalkylalkyl.

In a compound of Formula (2a),
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;

$R^2$ can be a single bond; and
$R^3$ can be $C_{1-3}$ alkyl.

In a compound of Formula (2a),
each $R^1$ can be independently selected from $C_{1-3}$ alkyl;
$R^2$ can be selected from a single bond and methanediyl; and
$R^3$ can be selected from —O—C(O)—$R^4$ and —C(O)—O—$R^4$, wherein $R^4$ can be selected from $C_{1-10}$ alkyl and substituted phenyl.

In a compound of Formula (2a),
each $R^1$ can be independently selected from $C_{1-3}$ alkyl;
$R^2$ can be a single bond;
$R^3$ can be —CH=C($R^4$)$_2$, wherein each $R^4$ can be —C(O)—O—$R^8$, or each $R^4$ together with the carbon atom to which they are bonded from a substituted heterocyclohexyl ring; and
each $R^8$ can be $C_{1-4}$ alkyl.

In a compound of Formula (2a),
each $R^1$ can be independently selected from $C_{1-3}$ alkyl;
$R^2$ can be selected from a single bond and methanediyl; and
$R^3$ can be substituted phenyl, wherein the one or more substituents can be independently selected from —CH$_2$—O—C(O)—$R^4$ and —O—C(O)—$R^4$, wherein $R^4$ can be selected from $C_{1-10}$ alkyl and phenyl.

In a compound of Formula (2a),
each $R^1$ can be independently selected from $C_{1-3}$ alkyl;
$R^2$ can be selected from —C($R^8$)$_2$— and —CH$_2$—C($R^8$)$_2$—, wherein each $R^8$ can be independently selected from $C_{1-3}$ alkyl; and
$R^3$ can be selected from —C(O)—O—$R^4$ and —O—C(O)—$R^4$, wherein $R^4$ can be selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one.

In a compound of Formula (2a),
each $R^1$ together with the carbon atom to which they are bonded form a substituted $C_{5-6}$ heterocyclic ring;
$R^2$ can be a single bond; and
$R^3$ can be $C_{1-3}$ alkyl.

A compound of Formula (1) can be a compound of sub-genus (1A), or a pharmaceutically acceptable salt thereof, wherein,

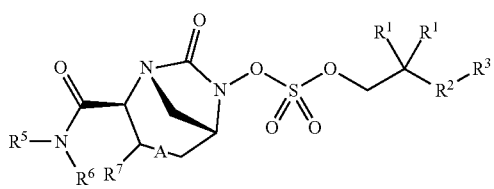

each of $R^5$, $R^6$, and $R^7$ can be hydrogen;
A can be a single bond;
each $R^1$ can be independently selected from $C_{1-3}$ alkyl, or each $R^1$ together with the carbon atom to which they are bonded form a $C_{3-6}$ cycloalkyl ring;
$R^2$ can be selected from single bond, methane-diyl, and ethane-diyl; and
$R^3$ can be selected from —C(O)—O—$R^4$ and —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of subgenus (1A), each $R^1$ can be independently selected from $C_{1-3}$ alkyl.

In compounds of subgenus (1A), each $R^1$ together with the carbon atom to which they are bonded form a $C_{3-6}$ cycloalkyl ring.

In compounds of subgenus (1A), $R^2$ a single bond.
In compounds of subgenus (1A), $R^2$ can be methane-diyl.
In compounds of subgenus (1A), $R^2$ can be ethane-diyl.
In compounds of subgenus (1A), $R^3$ can be —C(O)—O—$R^4$.
In compounds of subgenus (1A), $R^3$ can be —S—C(O)—$R^4$.
In compounds of subgenus (1A), $R^4$ can be $C_{1-10}$ alkyl.
In compounds of subgenus (1A), $R^4$ can be $C_{1-10}$ heteroalkyl.
In compounds of subgenus (1A), $R^4$ can be $C_{5-10}$ arylalkyl.
In compounds of subgenus (1A), $R^4$ can be $C_{3-6}$ heterocycloalkyl.
In compounds of subgenus (1A), $R^4$ can be substituted $C_{4-10}$ heterocycloalkylalkyl.

A compound of Formula (1) can be a compound of sub-genus (1B), or a pharmaceutically acceptable salt thereof, wherein,

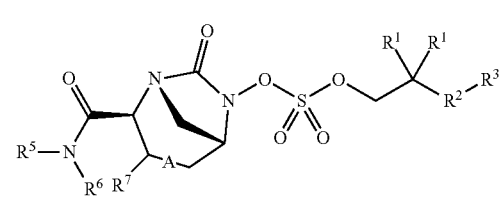

each of $R^5$, $R^6$, and $R^7$ can be hydrogen;
A can be a single bond;
each $R^1$ can be independently selected from $C_{1-3}$ alkyl, or each $R^1$ together with the carbon atom to which they are bonded form a $C_{3-6}$ cycloalkyl ring;
$R^2$ can be a single bond; and
$R^3$ can be —C(O)—O—$R^4$, where $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of subgenus (1B), each $R^1$ can be independently selected from $C_{1-3}$ alkyl.

In compounds of subgenus (1B), each $R^1$ together with the carbon atom to which they are bonded form a $C_{3-6}$ cycloalkyl ring.

In compounds of subgenus (1B), $R^4$ can be selected from $C_{1-7}$ alkyl, $C_{1-10}$ heteroalkyl wherein the one or more heteroatoms can be oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms can be oxygen, and —CH$_2$—$C_{3-6}$ substituted heterocycloalkyl, and —(CH$_2$)$_2$—$C_{3-6}$ substituted heterocycloalkyl.

In compounds of subgenus (1B), in the substituted $C_{3-6}$ heterocycloalkyl the one or more heteroatoms can be oxygen, and the one or more substituents can be independently selected from $C_{1-3}$ alkyl and =O.

In compounds of subgenus (1B), each $R^1$ can be methyl, or each $R^1$ together with the carbon atom to which they are bonded form a cyclohexyl ring or a cyclopentyl ring.

In compounds of subgenus (1B), $R^4$ can be selected from methyl, ethyl, n-propyl, iso-propyl, n-butyl, n-hexyl, n-heptyl, —CH$_2$—CH$_2$—O—CH$_3$, benzyl, 3-oxetanyl, and methyl-5-methyl-1,3-dioxol-2-one.

In compounds of subgenus (1B),
each of $R^5$, $R^6$, and $R^7$ can be hydrogen;
A can be a single bond;
each $R^1$ can be methyl, or each $R^1$ together with the carbon atom to which they are bonded form a cyclohexyl ring or a cyclopentyl ring;
$R^2$ can be a single bond; and
$R^3$ can be —C(O)—O—$R^4$, wherein $R^4$ can be selected from methyl, ethyl, n-propyl, iso-propyl, n-butyl, n-hexyl, n-heptyl, —CH$_2$—CH$_2$—O—CH$_3$, —CH$_2$-phenyl (benzyl), 3-oxetanyl, and methyl-5-methyl-1,3-dioxol-2-one.

A compound of Formula (1) can be a compound of sub-genus (1C), or a pharmaceutically acceptable salt thereof, wherein,

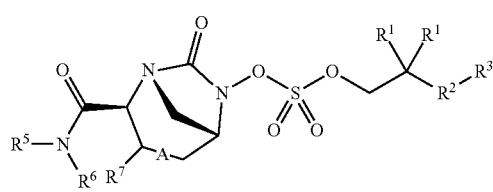

(1)

each of $R^5$, $R^6$, and $R^7$ can be hydrogen;
A can be a single bond;
each $R^1$ can be independently selected from $C_{1-3}$ alkyl, or each $R^1$ together with the carbon atom to which they are bonded form a $C_{3-6}$ cycloalkyl ring;
$R^2$ can be —(CH$_2$)$_2$—; and
$R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of subgenus (1C), each $R^1$ can be independently selected from $C_{1-3}$ alkyl.

In compounds of subgenus (1C), each $R^1$ together with the carbon atom to which they are bonded form a $C_{3-6}$ cycloalkyl ring.

In compounds of subgenus (1C), $R^4$ can be selected from $C_{1-7}$ alkyl, $C_{1-10}$ heteroalkyl wherein the one or more heteroatoms can be oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms can be oxygen, —CH$_2$—$C_{3-6}$ substituted heterocycloalkyl, and —(CH$_2$)$_2$—$C_{3-6}$ substituted heterocycloalkyl.

In compounds of subgenus (1C), in the substituted $C_{3-6}$ heterocycloalkyl the one or more heteroatoms can be oxygen, and the one or more substituents can be independently selected from $C_{1-3}$ alkyl and =O.

In compounds of subgenus (1C), $R^4$ can be $C_{1-10}$ alkyl.

In compounds of subgenus (1C),
each of $R^5$, $R^6$, and $R^7$ can be hydrogen;
A can be a single bond;
each $R^1$ can be methyl;
$R^2$ can be —(CH$_2$)$_2$—; and
$R^3$ can be —C(O)—O—$R^4$ wherein $R^4$ can be selected from n-hexyl and n-heptyl.

A compound of Formula (1) can be a compound of sub-genus (1D), or a pharmaceutically acceptable salt thereof, wherein,

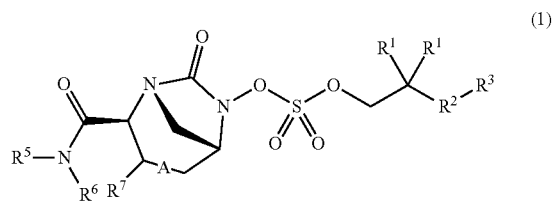

(1)

each of $R^5$, $R^6$, and $R^7$ can be hydrogen;
A can be a single bond;
each $R^1$ can be selected from $C_{1-3}$ alkyl, or each $R^1$ together with the carbon atom to which they are bonded form a $C_{3-6}$ cycloalkyl ring;
$R^2$ can be —CH$_2$—; and
$R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, substituted $C_{4-10}$ heterocycloalkylalkyl.

In compounds of subgenus (1D), each $R^1$ can be independently selected from $C_{1-3}$ alkyl.

In compounds of subgenus (1D), each $R^1$ together with the carbon atom to which they are bonded form a $C_{3-6}$ cycloalkyl ring.

In compounds of subgenus (1D), $R^4$ can be selected from $C_{1-7}$ alkyl, $C_{1-10}$ heteroalkyl wherein the one or more heteroatoms can be oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms can be oxygen, —CH$_2$—$C_{3-6}$ substituted heterocycloalkyl, —(CH$_2$)$_2$—$C_{3-6}$ substituted heterocycloalkyl.

In compounds of subgenus (1D), in the substituted $C_{3-6}$ heterocycloalkyl the one or more heteroatoms can be oxygen, and the one or more substituents can be independently selected from $C_{1-3}$ alkyl and =O.

In compounds of subgenus (1D), $R^4$ can be $C_{1-10}$ alkyl.

In compounds of subgenus (1D),
each of $R^5$, $R^6$, and $R^7$ can be hydrogen;
A can be a single bond;
each $R^1$ can be methyl;
$R^2$ can be —CH$_2$—; and
$R^3$ can be —S—C(O)—$R^4$, wherein $R^4$ can be methyl.

A compound of Formula (1) can be a compound of sub-genus (1E), or a pharmaceutically acceptable salt thereof, wherein,

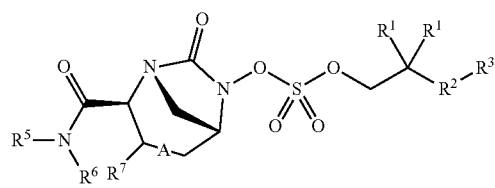

(1)

each of $R^5$, $R^6$, and $R^7$ can be hydrogen;
A can be a single bond;
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ can be a single bond; and
$R^3$ can be $C_{1-3}$ alkyl.

In compounds of subgenus (1E), each $R^1$ together with the carbon atom to which they are bonded form a $C_{3-6}$ heterocycloalkyl ring or a $C_{3-6}$ heterocycloalkyl ring;

In compounds of subgenus (1E), the one or more heteroatoms can be oxygen and the one or more substituents can be =O.

In compounds of subgenus (1E),
each $R^1$ together with the carbon atom to which they are bonded form a dihydrofuran-2(3H)-one ring;
$R^2$ can be a single bond; and
$R^3$ can be methyl.

A compound of Formula (1) can be a compound of sub-genus (1F), or a pharmaceutically acceptable salt thereof, wherein,

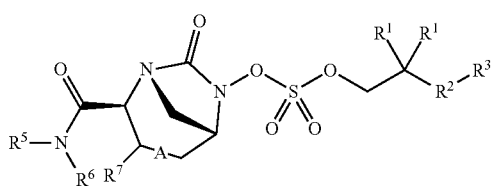
(1)

each of $R^5$, $R^6$, and $R^7$ can be hydrogen;
A can be a single bond;
each $R^1$ can be independently selected from $C_{1-3}$ alkyl;
$R^2$ can be selected from a single bond and methanediyl; and
$R^3$ can be selected from —O—C(O)—$R^4$ and —C(O)—O—$R^4$, wherein $R^4$ can be selected from $C_{1-10}$ alkyl and substituted phenyl.

In compounds of subgenus (1F), $R^2$ can be a single bond.
In compounds of subgenus (1F), $R^2$ can be methanediyl.
In compounds of subgenus (1F), $R^3$ can be —O—C(O)—$R^4$.
In compounds of subgenus (1F), $R^2$ can be methanediyl; and $R^3$ can be —O—C(O)—$R^4$.
In compounds of subgenus (1F), $R^3$ can be —C(O)—O—$R^4$.
In compounds of subgenus (1F), $R^2$ can be a single bond; and $R^3$ can be —C(O)—O—$R^4$.
In compounds of subgenus (1E), $R^2$ can be a single bond; $R^3$ can be —C(O)—O—$R^4$; and $R^4$ can be $C_{1-3}$ alkyl.
In compounds of subgenus (1F), $R^4$ can be $C_{1-10}$ alkyl.
In compounds of subgenus (1F), $R^4$ can be $C_{1-4}$ alkyl.
In compounds of subgenus (1F), $R^4$ can be substituted phenyl.
In compounds of subgenus (1F), $R^2$ can be methanediyl; $R^3$ can be —O—C(O)—$R^4$; and $R^4$ can be substituted phenyl.
In compounds of subgenus (1F), the one or more substituents can be independently selected from halogen, $C_{1-3}$ alkyl, and $C_{1-3}$ alkoxy.
In compounds of subgenus (1F), the substituted phenyl can be 2,6-substituted phenyl.
In compounds of subgenus (1F), each of the substituents can be selected from $C_{1-3}$ alkyl and $Ca-3$ alkoxy.
In compounds of subgenus (1F), the substituted phenyl can be 2,5,6-substituted phenyl.
In compounds of subgenus (1F), each of the substituents at the 2 and 6 positions can be independently selected from $C_{1-3}$ alkyl and $C_{1-3}$ alkoxy; and the substituent at the 5 position can be halogen.

A compound of Formula (1) can be a compound of sub-genus (1G), or a pharmaceutically acceptable salt thereof, wherein,

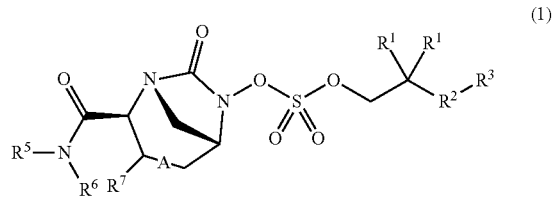
(1)

each of $R^5$, $R^6$, and $R^7$ can be hydrogen;
A can be a single bond;
each $R^1$ can be independently selected from $C_{1-3}$ alkyl;
$R^2$ can be a single bond; and
$R^3$ can be —CH=C($R^4$)$_2$, wherein each $R^4$ can be —C(O)—O—$R^8$, or each $R^4$ together with the carbon atom to which they are bonded from a substituted heterocyclohexyl ring; and
each $R^8$ can be $C_{1-4}$ alkyl.

In compounds of subgenus (1G), each $R^4$ can be —C(O)—O—$R^8$.
In compounds of subgenus (1G), each $R^4$ can be —C(O)—O—$R^8$, or each $R^4$ together with the carbon atom to which they are bonded from a substituted heterocyclohexyl ring.
In compounds of subgenus (1G), in the substituted heterocyclohexyl ring, the one or more heteroatoms can be oxygen.
In compounds of subgenus (1G), in the substituted heterocyclohexyl ring, the one or more substituents can be independently selected from $C_{1-3}$ alkyl and =O.
In compounds of subgenus (1G), the substituted heterocycloalkyl ring can be 2,2-dimethyl-5-yl-1,3-dioxane-4,6-dione.

A compound of Formula (1) can be a compound of sub-genus (1H), or a pharmaceutically acceptable salt thereof, wherein,

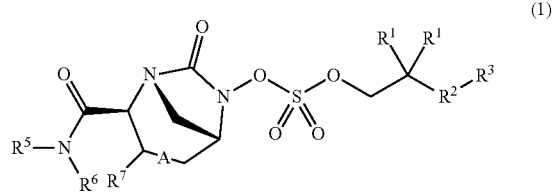
(1)

each of $R^5$, $R^6$, and $R^7$ can be hydrogen;
A can be a single bond;
each $R^1$ can be independently selected from $C_{1-3}$ alkyl;
$R^2$ can be selected from a single bond and methanediyl; and
$R^3$ can be substituted phenyl, wherein the one or more substituents can be independently selected from —CH$_2$—O—C(O)—$R^4$ and —O—C(O)—$R^4$, wherein $R^4$ can be selected from $C_{1-10}$ alkyl and phenyl.

In compounds of subgenus (1H), $R^2$ can be a single bond.
In compounds of subgenus (1H), $R^2$ can be 2-substituted phenyl.
In compounds of subgenus (1H), the one or more substituents can be —CH$_2$—O—C(O)—$R^4$.
In compounds of subgenus (1H), the one or more substituents can be —O—C(O)—$R^4$.
In compounds of subgenus (1H), $R^4$ can be $C_{1-10}$ alkyl.
In compounds of subgenus (1H), $R^4$ can be selected from methyl, ethyl, iso-propyl, pivalolyl, and phenyl.

A compound of Formula (1) can be a compound of sub-genus (11), or a pharmaceutically acceptable salt thereof, wherein,

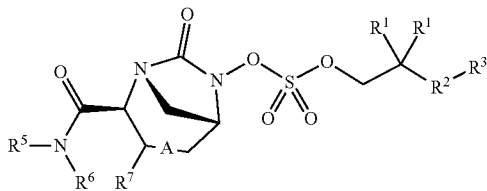

each of $R^5$, $R^6$, and $R^7$ can be hydrogen;
A can be a single bond;
each $R^1$ can be independently selected from $C_{1-3}$ alkyl;
$R^2$ can be selected from —C($R^8$)$_2$— and —CH$_2$—C(R)$_2$—, wherein each $R^8$ can be independently selected from $C_{1-3}$ alkyl; and
$R^3$ can be selected from —C(O)—O—$R^4$ and —O—C(O)—$R^4$, wherein $R^4$ can be selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one.

In compounds of subgenus (11), each $R^1$ can be methyl.
In compounds of subgenus (11), $R^2$ can be —C($R^8$)$_2$—.
In compounds of subgenus (11), $R^2$ can be —CH$_2$—C(R)$_2$—.
In compounds of subgenus (11), each $R^8$ can be methyl.
In compounds of subgenus (11), each $R^1$ can be methyl; and each $R^8$ can be methyl.
In compounds of subgenus (11), $R^3$ can be —C(O)—O—$R^4$.
In compounds of subgenus (11), $R^3$ can be —O—C(O)—$R^4$.

A compound of Formula (1) can be a compound of sub-genus (1J), or a pharmaceutically acceptable salt thereof, wherein,

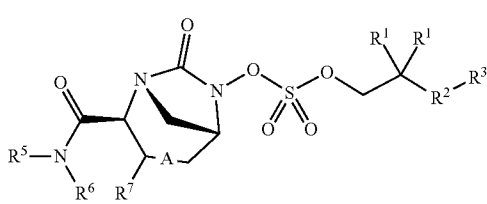

each of $R^5$, $R^6$, and $R^7$ can be hydrogen;
A can be a single bond;
each $R^1$ together with the carbon atom to which they are bonded form a substituted $C_{5-6}$ heterocyclic ring;
$R^2$ can be a single bond; and
$R^3$ can be $C_{1-3}$ alkyl.

In compounds of subgenus (1J), in the substituted $C_{5-6}$ heterocyclic ring, the one or more heteroatoms can be oxygen; and the one or more substituents can be independently selected from $C_{1-3}$ alkyl and =O.
In compounds of subgenus (1J), each $R^1$ together with the carbon atom to which they are bonded form a tetrahydro-2H-pyran-2-one ring.
In compounds of subgenus (1J),
each of $R^5$, $R^6$, and $R^7$ can be hydrogen;
A can be a single bond;
each $R^1$ can be independently selected from $C_{1-3}$ alkyl;
$R^2$ can be selected from $C_{2-4}$ alkanediyl; and
$R^3$ can be substituted $C_{5-6}$ heterocycloalkyl, wherein the one or more heteroatoms can be independently selected from N and O; and the one or more substituents can be independently selected from $C_{1-3}$ alkyl and =O.

In compounds of subgenus (1J), $R^3$ can have the structure of Formula (6):

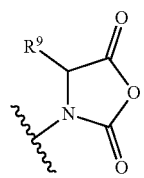

wherein $R^9$ can be selected from hydrogen, $C_{1-6}$ alkyl, $C_{4-6}$ cycloalkyl, $C_{1-6}$ heteroalkyl, $C_{4-6}$ heterocycloalkyl, substituted $C_{1-6}$ alkyl, substituted $C_{4-6}$ cycloalkyl, substituted $C_{1-6}$ heteroalkyl, and substituted $C_{4-6}$ heterocycloalkyl.

In compounds of subgenus (1J), $R^9$ can be selected from hydrogen and $C_{1-6}$ alkyl such as $C_{1-4}$ alkyl such as methyl or ethyl.

A compound of Formula (4) can be a compound of sub-genus (4A), or a pharmaceutically acceptable salt thereof, wherein,

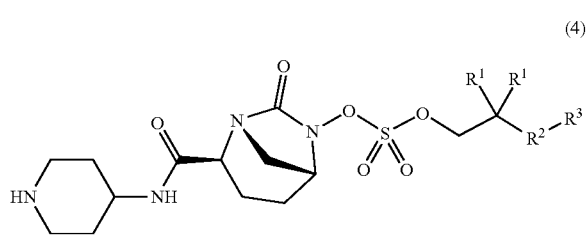

each of $R^5$, $R^6$, and $R^7$ can be hydrogen;
A can be a single bond;
each $R^1$ can be independently selected from $C_{1-3}$ alkyl, or each $R^1$ together with the carbon atom to which they are bonded form a $C_{3-6}$ cycloalkyl ring;
$R^2$ can be a single bond; and
$R^3$ can be —C(O)—O—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of sub-genus (4A), each $R^1$ can be independently selected from $C_{1-3}$ alkyl.
In compounds of sub-genus (4A), each $R^1$ together with the carbon atom to which they are bonded form a $C_{3-6}$ cycloalkyl ring.
In compounds of sub-genus (4A), $R^4$ can be selected from $C_{1-7}$ alkyl, $C_{1-10}$ heteroalkyl wherein the one or more heteroatoms can be oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms can be oxygen, —CH$_2$—$C_{3-6}$ substituted heterocycloalkyl, and —(CH$_2$)$_2$—$C_{3-6}$ substituted heterocycloalkyl.
In compounds of sub-genus (4A), in the substituted $C_{3-6}$ heterocycloalkyl the one or more heteroatoms can be oxygen, and the one or more substituents can be independently selected from $C_{1-3}$ alkyl and =O.

In compounds of sub-genus (4A), each $R^1$ can be methyl, or each $R^1$ together with the carbon atom to which they are bonded form a cyclohexyl ring or a cyclopentyl ring.

In compounds of sub-genus (4A), $R^4$ can be selected from methyl, ethyl, n-propyl, iso-propyl, n-butyl, n-hexyl, n-heptyl, —$CH_2$—$CH_2$—O—$CH_3$, benzyl, 3-oxetanyl, and methyl-5-methyl-1,3-dioxol-2-one.

In compounds of sub-genus (4A),
each of $R^5$, $R^6$, and $R^7$ can be hydrogen;
A can be a single bond;
$R^2$ can be a single bond; and
$R^3$ can be —C(O)—O—$R^4$, wherein $R^4$ can be $C_{1-10}$ alkyl.

A compound of Formula (4) can be selected from:
ethyl2,2-dimethyl-3-(((((2S,5R)-7-oxo-2-(piperidin-4-yl-carbamoyl)-1,6-diazabicyclo[3.2.1]octan-6-yl)oxy)sulfonyl)oxy)propanoate (20);
2-methoxyethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (21);
4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (22);
4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (23);
4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidin-1-ium 2,2,2-trifluoroacetate (24);
(5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (25);
a pharmaceutically acceptable salt of any of the foregoing; and
a combination of any of the foregoing.

A compound of Formula (4) can be selected from:
ethyl2,2-dimethyl-3-(((((2S,5R)-7-oxo-2-(piperidin-4-yl-carbamoyl)-1,6-diazabicyclo[3.2.1]octan-6-yl)oxy)sulfonyl)oxy)propanoate (20);
4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (22);
4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (23);
(5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (25);
a pharmaceutically acceptable salt of any of the foregoing; and
a combination of any of the foregoing.

A compound of Formula (5) can be selected from:
ethyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate (27);
2-methoxyethyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate (28);
(5-methyl-2-oxo-1,3-dioxol-4-yl)methyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (29);
hexyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (30);
heptyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (31);
ethyl 1-(((((2S,5R)-2-((2-aminoethoxy)carbamoyl)-7-oxo-1,6-diazabicyclo[3.2.1]octan-6-yl)oxy)sulfonyl)oxy)methyl)cyclohexanecarboxylate TFA salt (32);
a pharmaceutically acceptable salt of any of the foregoing; and
a combination of any of the foregoing.

A compound of Formula (1)-(5) can be a solvate, a pharmaceutically acceptable salt, or a combination thereof.

In compounds of Formula (1)-(5), a pharmaceutically acceptable salt can be the hydrochloride salt.

In compounds of Formula (1)-(5), a pharmaceutically acceptable salt can be the dihydrochloride salt.

A compound of Formula (1)-(5) can be a pharmaceutically acceptable salt of a compound of Formula (1)-(5), a hydrate thereof, or a solvate of any of the foregoing.

The compound described herein may be synthesized using methods known in the art. The synthesis of the various diazabicyclo[3.2.1]octane structures described herein are conventional and are well known to those of skill in the art (Tandiparthi et al., PCT International Application Publication No. WO 2016/116788; Lampilas et al., U.S. Pat. No. 7,112,592; King et al., *ACS Chemical Biology* 2016; 11, 864; and Bush et al., *Cold Spring Harb Perspect Med* 2016; 6:a025247). Formation of sulfate esters is also well-known in the art (Simpson et al., *J. Am. Chem. Soc.* 2006, 128, 1605; Li et al., U.S. Application Publication No. 2009/0099253; Jandeleit et al., PCT International Application Publication No. WO 2009/033054; Jandeleit et al., PCT International Application Publication No. WO 2009/033079; and Jandeleit et al., PCT International Application Publication No. WO 2011/150380).

Sulfate monoester analogs of sulfate-containing compounds can be prepared by reacting a hydroxyl-substituted sulfate-containing compound with a chlorosulfate monoester to provide the corresponding sulfate monoester analog. The methods can be useful in preparing prodrugs of sulfate-containing pharmaceutical compounds.

Prodrugs are derivatized forms of drugs that following administration are converted or metabolized to an active form of the parent drug in vivo. Prodrugs are used to modify one or more aspects of the pharmacokinetics of a drug in a manner that enhances the therapeutic efficacy of a parent drug. For example, prodrugs are often used to enhance the oral bioavailability of a drug. To be therapeutically effective, drugs exhibiting poor oral bioavailability may require frequent dosing, large administered doses, or may need to be administered by other than oral routes, such as intravenously. In particular, many drugs with sulfate groups exhibit poor oral bioavailability.

Intramolecular cyclization prodrug strategies have been used to modify the pharmacokinetics of drugs. Intramolecular cyclization release prodrug strategies have been applied to drugs containing sulfonic acid functional groups. For example, prodrugs comprising a substituted neopentyl sulfonate ester derivative in which the neopentyl group is removed in vivo by unmasking a nucleophilic heteroatom bonded to a substituted neopentyl moiety followed by intramolecular cyclization to generate the parent drug in the sulfonic acid or sulfonic salt form have been described, for example, in U.S. Pat. No. 7,994,218 and U.S. Pat. No. 8,168,617. In such prodrugs the nucleophilic heteroatom can be nitrogen or oxygen and the nitrogen or oxygen nucleophile can be masked with an amine or alcohol protecting group, respectively, capable of being deprotected in vivo.

Sulfate monoester analogs of a sulfate-containing compound can be prepared by reacting a hydroxyl-substituted analog of the sulfate-containing compound with a chlorosulfate monoester under basic conditions, to provide the corresponding sulfate monoester analog. A chlorosulfate monoester can be prepared by reacting sulfuryl chloride with an alcohol having the desired promoiety. Neopentyl alcohols having neopentyl promoieties can be prepared by standard synthetic methods such as those described in U.S. Pat. Nos. 7,994,218 and 8,168,617.

For example, sulfate monoester analogs of avibactam provided by the present disclosure can be synthesized by reacting (2S,5R)-6-hydroxy-7-oxo-1,6-diazabicyclo[3.2.1]octane-2-carboxamide with a chlorosulfate monoester having a desired promoiety to provide the corresponding (2S,5R)-2-carbamoyl-7-oxo-1,6-diazabicyclo[3.2.1]octan-6-yl sulfate monoester.

(2S,5R)-6-Hydroxy-7-oxo-1,6-diazabicyclo[3.2.1]octane-2-carboxamide can be prepared by hydrogenating (2S,5R)-6-(benzyloxy)-7-oxo-1,6-diazabicyclo[3.2.1]octane-2-carboxamide using the methods described, for example, in U.S. Pat. Nos. 8,772,490; 9,035,062; and 9,284,273.

(2S,5R)-6-Hydroxy-7-oxo-1,6-diazabicyclo[3.2.1]octane-2-carboxamide can be reacted with the chlorosulfate monoester in the presence of a base to provide the corresponding sulfate monoester analog of avibactam. Suitable methods are disclosed, for example, in J. Am. Chem. Soc. 2006, 128, 1605-1610.

Similar methods can be adapted to prepare sulfate monoester analogs of relebactam and nacubactam. For example, the tert-butyl carboxylate protected, 6-hydroxyl analog of relebactam can be reacted with a chlorosulfate monoester in the presence of a base to provide the corresponding tert-butyl carboxylate protected sulfate monoester analog of relebactam. The compound can then be deprotected in the presence of an acid to provide the sulfate monoester analog of relebactam. Methods similar to those used to prepare sulfate monoester analogs of relebactam can be used to prepare sulfate monoester analogs of nacubactam.

For example, a sulfate monoester analog of a sulfate monoester of Formula (80a) can be synthesized by reacting a cyclic hydroxamic acid of Formula (80b) with a chlorosulfonate monoester of Formula (80c) under basic conditions:

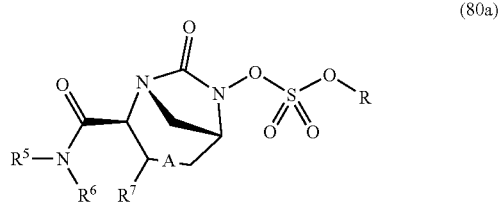
(80a)

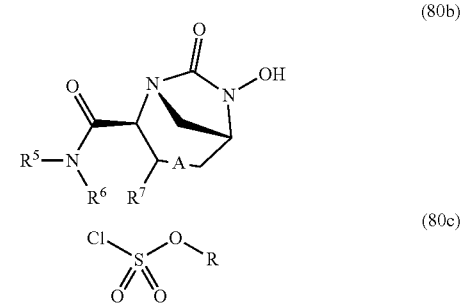
(80b)

(80c)

where,
R is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (=) and $R^7$ is $C_{1-3}$ alkyl.

The chlorosulfate monoester can comprise a chlorosulfate neopentyl ester, such as a chlorosulfate neopentyl ester of Formula (81):

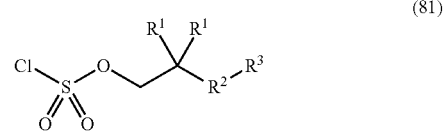
(81)

wherein,
each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

The chlorosulfate monoester can be synthesized by reacting an alcohol such as a neopentyl alcohol with sulfuryl chloride.

The method can be used to bond any suitable chlorosulfonate ester to a cyclic hydroxamic acid such as, for example, a chlorosulfonate ester of Formula (82) and a cyclic hydroxamic acid of Formula (83) to provide the corresponding sulfate monoester analog of Formula (84):

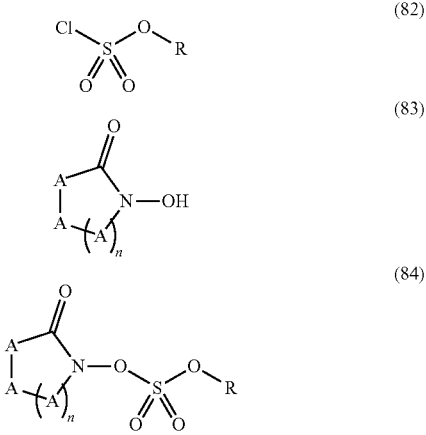

where,

R can be selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

n can be an integer from 1 to 6;

each A can be independently selected from —(CH$_2$)—, —(CHR)—, —(CR$_2$)—, —NH—, —NR—, O, and S, where R is independently elected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; or one A is bonded to another A through a group -L-, where L is selected from $C_{1-8}$ alkyl, $C_{1-8}$ heteroalkyl, substituted $C_{1-8}$ alkyl, and substituted $C_{1-8}$ heteroalkyl.

R can further include any of the promoieties disclosed herein, such as a promoiety having the structure:

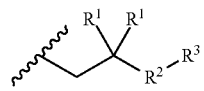

where $R^1$, $R^2$, and $R^3$ are defined as in Formula (1).

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration. In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethyl sulfoxide (DMSO), using surfactants or surface modifiers, such as TWEEN®, complexing agents such as cyclodextrin or dissolution by enhanced ionization (i.e. dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

Compositions can be lactose-free compositions containing excipients that are well known in the art and are listed, for example, in the U.S. Pharmacopeia (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Formulations can be solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water-soluble FD and C dyes, mixtures thereof; and water insoluble FD and C dyes suspended on alumina hydrate and advanced coloring or anti-forgery color/opalescent additives known to those skilled in the art.

Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least 0.01% w/w up to 90% w/w or more, such as more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

An agent may be administered using intravenous infusion, an implantable osmotic pump, a transdermal patch, liposomes, or other modes of administration. In some embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release, vol. 2*, pp. 115-138 (1984)). In some embodiments, a controlled release device is introduced into a subject in proximity of the site of inappropriate immune activation or a tumor. Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose, and other suitable agents. The solvent may contain a buffer, such as citrate, sodium or potassium phosphate or other such buffer known to those of skill in the art at, at neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step (e.g., PCT International Publication No. WO 2005/025506). A controlled particle size for the microcrystals can be selected to ensure that a significant fraction of the compounds or derivatives is deposited in the lung. In some embodiments, these particles have a mass median aerodynamic diameter of 0.1 microns to 10 microns, in other embodiments, 1 micron to 5 microns and still other embodiments, 1.2 microns to 3 microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as from 0.01% to 10% isotonic solutions, pH 5 to 7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is 2 gm to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then re-suspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

For use to treat or prevent infectious disease, the compounds or compositions described herein, or pharmaceutical compositions thereof, can be administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from 1 microgram per kilogram to 50 milligrams per kilogram, from 10 micrograms per kilogram to 30 milligrams per kilogram, from 100 micrograms per kilogram to 10 milligrams per kilogram, or from 100 micrograms per kilogram to 5 milligrams per kilogram).

In some embodiments, a therapeutically effective dosage should produce a serum concentration of active ingredient of from 0.001 ng/mL to 50 µg/mL to 200 µg/mL. The compositions, in other embodiments, should provide a dosage of from 0.0001 mg to 70 mg of compound per kilogram of body weight per day. Dosage unit forms are prepared to provide from 0.01 mg to 0.1 mg, form 1 mg to 500 mg, or from 1,000 mg 5,000 mg, and in some embodiments from 10 mg to 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), the MIC as determined in cell culture (i.e., the minimal inhibitory concentration for growth) or the $IC_{100}$ as determined in cell culture (i.e., the concentration of antimicrobial sulfonamide derivative that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known antimicrobial agents by comparing the $IC_{50}$, MIC and/or $I_{100}$ of the specific compound disclosed herein with that of a known antimicrobial agent, and adjusting the initial dosages accordingly. The optimal dosage may be obtained from these initial values by routine optimization In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, *In: The Pharmacological Basis of Therapeutics*, Ch.1, p.1).

The therapy may be repeated intermittently while infections are detectable, or even when they are not detectable. Administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

A compound of Formula (1) and/or pharmaceutical composition thereof can generally be used in an amount effective to achieve the intended purpose. For use to treat a disease such as a bacterial infection, a compound of Formula (1) and/or pharmaceutical compositions thereof, may be administered or applied in a therapeutically effective amount.

The amount of a compound of Formula (1) and/or pharmaceutical composition thereof that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of a compound of Formula (1) and/or pharmaceutical composition thereof administered will depend on, among other factors, the subject being treated, the weight of the subject, the severity of the affliction, the manner of administration and the judgment of the prescribing physician.

A compound of Formula (1) may be assayed in vitro and in vivo, for the desired therapeutic activity, prior to use in humans. For example, in vitro assays may be used to determine whether administration of a specific compound or a combination of compounds is preferred. The compounds may also be demonstrated to be effective and safe using animal model systems.

A therapeutically effective dose of a compound of Formula (1) and/or pharmaceutical composition thereof will provide therapeutic benefit without causing substantial toxicity. Toxicity of compounds of Formula (1) and/or pharmaceutical compositions thereof may be determined using standard pharmaceutical procedures and may be readily ascertained by the skilled artisan. The dose ratio between toxic and therapeutic effect is the therapeutic index. A compound of Formula (1) and/or pharmaceutical composition thereof exhibits a particularly high therapeutic index in treating disease and disorders. A dose of a compound of Formula (1) and/or pharmaceutical composition thereof will be within a range of circulating concentrations that include an effective dose with minimal toxicity.

A compound of Formula (1), a pharmaceutically acceptable salt thereof, or a pharmaceutical composition of any of the foregoing may be included in a kit that may be used to administer the compound to a patient for therapeutic purposes. A kit may include a pharmaceutical composition comprising a compound of Formula (1) suitable for administration to a patient and instructions for administering the pharmaceutical composition to the patient. A kit for use in treating a bacterial infection in a patient comprises a compound of Formula (1) or a pharmaceutically acceptable salt thereof, a pharmaceutically acceptable vehicle for administering the compound, and instructions for administering the compound to a patient. Instructions supplied with a kit may be printed and/or supplied, for example, as an electronic-readable medium, a video cassette, an audiotape, a flash memory device, or may be published on an internet web site or distributed to a patient and/or health care provider as an electronic communication.

The amount of a compound of Formula (1) that will be effective in the treatment of a bacterial infection will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of compound of Formula (1) administered may depend on, among other factors, the subject being treated, the weight of the subject, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound of Formula (1) and appropriate dosing intervals may be selected to maintain a sustained therapeutically effective concentration of the compound of Formula (1) in the blood of a patient, and in certain embodiments, without exceeding a minimum adverse concentration.

Pharmaceutical compositions comprising a compound of Formula (1) may be administered once per day, twice per day, or at intervals of more than once per day. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of compound of Formula (1) contained within each of the multiple dosage forms may be the same or different.

Suitable daily dosage ranges for administration may range from 2 µg to 20 mg of a compound of Formula (1) per kilogram body weight.

Suitable daily dosage ranges for administration may range from 1 µg to 50 mg of a compound of Formula (1) per square meter ($m^2$) of body surface.

A compound of Formula (1) may be administered to treat a bacterial infection in a patient in an amount from 1 mg to 2,000 mg per day, from 100 µg to 1,500 mg per day, from 20 µg to 1,000 mg per day, or in any other appropriate daily dose.

A pharmaceutical composition comprising a compound of Formula (1) may be administered to treat a bacterial infection in a subject to provide a therapeutically effective concentration of a compound of Formula (1) in the blood or plasma of the subject. A therapeutically effective concentration of a compound of Formula (1) in the blood or plasma of a subject is from 1 µg/mL to 60 µg/mL, from 2 µg/mL to 50 µg/mL, from 5 µg/mL to 40 µg/mL, from 5 µg/mL to 20 µg/mL, or from 5 µg/mL to 10 µg/mL. A therapeutically effective concentration of a compound of Formula (1) in the blood or plasma of a subject is at least 2 µg/mL, at least 5 µg/mL, at least 10 µg/mL, at least 15 µg/mL, at least 25 µg/mL, or at least 30 µg/mL. A therapeutically effective concentration of a compound of Formula (1) in the blood or plasma of a subject is less than an amount that causes unacceptable adverse effects including adverse effects to homeostasis. A therapeutically effective concentration of a compound of Formula (1) in the blood or plasma of a subject is an amount sufficient to restore and/or maintain homeostasis in the subject.

A pharmaceutical composition comprising a compound of Formula (1) may be administered to treat a bacterial infection in a patient so as to provide a therapeutically effective concentration of a compound of Formula (1) in the blood or plasma of a subject for an extended period of time such as, for example, for at least 4 hours, for at least 6 hours, for at least 8 hours, for at least 10 hours, or for at least 12 hours.

The amount of a compound of Formula (1) administered may vary during a treatment regimen.

Pharmaceutical compositions provided by the present disclosure may further comprise one or more pharmaceutically active compounds in addition to a compound of Formula (1). Such compounds may be provided to treat the bacterial infection being treated with the compound of Formula (1) or to treat a disease, disorder, or condition other than a bacterial infection being treated with the compound of Formula (1).

The compounds and compositions described herein can be used in a wide variety of applications to treat infectious diseases in a subject. The methods generally involve administering a therapeutically effective amount of a compound of Formula (1) or a pharmaceutical composition thereof to the subject, or administering a therapeutically effective amount of a compound of Formula (1) and an antibiotic, or a pharmaceutical composition thereof to the subject.

Compounds provided by the present disclosure are prodrugs of β-lactamase inhibitors. Compounds and compositions provided by the present disclosure can be used to treat a disease in which the etiology of the disease is associated with the expression of β-lactamases. For example, certain bacterial infections are resistant to β-lactamase antibiotics because β-lactamases produced by the bacteria hydrolyze the β-lactam ring of the β-lactam antibiotic.

Compounds and compositions provided by the present disclosure can be used to treat a bacterial disease in a patient.

Compounds and compositions provided by the present disclosure can be used to treat a bacterial infection. For example, compounds and composition provided by the present disclosure can be used to treat a bacterial infection associated with bacteria such as obligate aerobic bacteria, obligate anaerobic bacteria, facultitive anaerobic bacteria, and microaerophilic bacteria.

Examples of obligate aerobic bacteria include gram-negative cocci such as *Moraxella catarrhalis, Neisseria gonorrhoeae*, and *N. meningitidi*; gram-positive bacilli such as *Corynebacterium jeikeium*; acid-fast bacilli such as *Mycobacterium avium* complex, *M. kansasii, M. leprae, M. tuberculosis*, and *Nocardia* sp; nonfermentative, non-enterobacteriaceae such as *Acinetobacter calcoaceticus, Elizabethkingia meningoseptica* (previously *Flavobacterium meningosepticum*), *Pseudomonas aeruginosa, P. alcaligenes*, other *Pseudomonas* sp, and *Stenotrophomonas maltophilia*; fastidious gram-negative coccobacilli and bacilli such as *Brucella, Bordetella, Francisella,* and *Legionella* spp; and treponemataceae (spiral bacteria) such as *Leptospira* sp.

Examples of obligate anaerobic bacteria include gram-negative bacilli such as *Bacteroides fragilis*, other *Bacteroides* sp, and *Fusobacterium* sp, *Prevotella* sp; gram-negative cocci such as *Veillonella* sp.; gram-positive cocci such as *Peptococcus niger*, and *Peptostreptococcus* sp.; non-spore-forming gram-positive bacilli such as *Clostridium botulinum, C. perfringens, C. tetani*, other *Clostridium* sp; and endospore-forming gram-positive bacilli such as *Clostridium botulinum, C. perfringens, C. tetani*, and other *Clostridium* sp.

Examples of facultative anaerobic bacteria include gram-positive cocci, catalase-positive such as *Staphylococcus aureus* (coagulase-positive), *S. epidermidis* (coagulase-negative), and other coagulase-negative staphylococci; gram-positive cocci, catalase-negative such as *Enterococcus faecalis, E. faecium, Streptococcus agalactiae* (group B streptococcus), *S. bovis, S. pneumoniae, S. pyogenes* (group A streptococcus), viridans group streptococci (*S. mutans, S. mitis, S. salivarius, S. sanguis*), *S. anginosus* group (*S. anginosus, S. milleri, S. constellatus*), and *Gemella morbillorum*; gram-positive bacilli such as *Bacillus anthracis, Erysipelothrix rhusiopathiae*, and *Gardnerella vaginalis* (gram-variable); gram-negative bacilli such as Enterobacteriaceae (*Citrobacter* sp, *Enterobacter aerogenes, Escherichia coli, Klebsiella* sp, *Morganella morganii, Proteus* sp, *Plesiomonas shigelloides, Providencia rettgeri, Salmonella typhi*, other *Salmonella* sp, *Serratia marcescens*, and *Shigella* sp, *Yersinia enterocolitica, Y. pestis*); fermentative, non-Enterobacteriaceae such as *Aeromonas hydrophila, Chromobacterium violaceum*, and *Pasteurella multocida*; fastidious gram-negative coccobacilli and bacilli such as *Actinobacillus actinomycetemcomitans, Bartonella bacilliformis, B. henselae, B. quintana, Eikenella corrodens, Haemophilus influenzae*, and other *Haemophilus* sp; mycoplasma such as *Mycoplasma pneumoniae*; and treponemataceae (spiral bacteria) such as *Borrelia burgdorferi*, and *Treponema pallidum*.

Examples of microaerophilic bacteria include curved bacilli such as *Campylobacter jejuni, Helicobacter pylori, Vibrio cholerae*, and *V. vulnificus*; obligate intracellular parasitic; chlamydiaceae such as *Chlamydia trachomatis, Chlamydophila pneumoniae*, and *C. psittaci*; coxiellaceae such as *Coxiella burnetii*; and rickettsiales such as *Rickettsia prowazekii, R. rickettsii, R. typhi, R. tsutsugamushi, Ehrlichia chaffeensis*, and *Anaplasma phagocytophilum*.

Compounds and compositions provided by the present disclosure can be used to treat a bacterial disease in which the bacteria produce a β-lactamase. Examples of bacteria that produce a β-lactamase include *Mycobacterium tuberculosis*, methicillin-resistant *Staphylococcus aureus, Staphyloccus*, Enterobacteriaceae, *Pseudomonas aeruginosa, Haemophilus influenzae, Klebsiella pneumoniae, Citrobacter*, and *Morganella*.

Compounds and compositions provided by the present disclosure can be used to treat a bacterial disease in which a β-lactamase inhibitor is effective in treating the bacterial disease such as a bacterial infection.

An infectious disease can be a bacterial infection. A bacterial infection can be an infection of a gram-positive bacteria. A bacterial infection can be an infection of a gram-negative bacteria. Examples of gram-negative bacteria include *Acinetobacter, Aeromonas, Bacteroides, Burkholderia, Citrobacter, Enterobacter, Escherichia, Fusobacterium, Haemophilus, Klebsiella, Moraxella, Morganella, Mycoplasma, Neisseria, Pantoea, Pasteurella, Plesiomonas, Porphyromonas, Prevotella, Proteus, Providencia, Pseudomonas, Salmonella, Serratia, Shigella, Spirillum, Stenotrophomonas, Streptobacillus, Treponema*, or *Yersinia*.

Examples of gram-negative bacteria include *Acinetobacter baumannii, Aeromonas hydrophila, Arizona hinshawii, Bacteroides fragilis, Branhamella catarrhalis, Burkholderia cepacia, Citrobacter diversus, Citrobacter freundii, Enterobacter aerogenes, Enterobacter cloacae, Escherichia coli, Fusobacterium nucleatum, Haemophilus influenzae, Haemophilus parainfluenzae, Klebsiella oxytoca, Klebsiella pneumoniae, Moraxella catarrhalis, Morganella morganii, Neisseria gonorrhoeae, Neisseria meningitidis, Pantoea agglomerans, Pasteurella multocida, Plesiomonas shigelloides, Prevotella melaninogenica, Proteus mirabilis, Proteus rettgeri, Proteus vulgaris, Pseudomonas aeruginosa, Pseudomonas diminuta, Pseudomonas fluorescens, Pseudomonas stutzeri, Salmonella enterica, Salmonella enteritidis, Salmonella typhi, Serratia marcescens, Spirillum minus, Stenotrophomonas maltophilia, Streptobacillus moniliformis, Treponema pallidum*, or *Yersinia enterocolitica*.

The development of antibiotic resistance continues to grow as a problem facing patients and clinicians. Accordingly, the U.S. Food and Drug Administration has identified the following pathogens as presenting a potentially serious threat to public health: *Acinetobacter* species, *Aspergillus* species, *Burkholderia cepacia* complex, *Campylobacter* species, *Candida* species, *Clostridium difficile, Coccidioides* species, *Cryptococcus* species, Enterobacteriaceae (e.g., *Klebsiella pneumoniae*), *Enterococcus* species, *Helicobacter pylori, Mycobacterium tuberculosis* complex, *Neisseria gonorrhoeae, N. meningitidis*, non-tuberculous mycobacteria species, *Pseudomonas* species, *Staphylococcus aureus, Streptococcus agalactiae, S. pneumoniae, S. pyogenes*, and *Vibrio cholerae*. The FDA has designated these organisms "qualifying pathogens" for purposes of the Generating Antibiotic Incentives Now (GAIN) Act, intended to encourage development of new antibacterial and antifungal drugs for the treatment of serious or life-threatening infections. Other types of bacteria can be added or subtract from the list of "qualifying pathogens" and the methods provided by the present disclosure encompass any newly added bacteria. The compounds, compositions, methods, and kits, disclosed herein are useful for the treatment of diseases, infections, etc. caused by many of these organisms as well.

The compounds and compositions described herein may be used treat or prevent various diseases caused by the above bacteria. These include, but are not limited to, venereal disease, pneumonia, complicated urinary tract infections, urinary tract infections, complicated intra-abdominal infections and intra-abdominal infections.

Methods provided by the present disclosure can also be administered to a patient to inhibit a β-lactamase. Compounds and compositions provided by the present disclosure can be administered to a patient to inhibit any suitable type of β-lactamase. Examples of types of β-lactamases include extended-spectrum β-lactamases such as TEM β-lactamases (Class A), SHV β-lactamases (Class A), CTX-M β-lactamases (Class A), OXA β-lactamases (Class D), and other extended spectrum β-lactamases such as PER, VEB, GES, and IBC β-lactamases; inhibitor-resistant β-lactamases; AmpC-type-β lactamases (Class C); carbapenemases such as IMP-type carbapenemases (metallo-β-lactamases) (Class B), VIM (verona integron-encoded metallo-β-lactamase (Class B), OXA (oxcillinase) group β-lactamases (Class D), KPC (*K. pneumoniae* carbapenemase) (Class A), CMY (Class C), SME, IMI, NMC, and CcrA, and NDM-1 (New Delhi metallo-β-lactamase) (Class B).

Examples of types of β-lactamases include cephalosporinases, penicillinases, cephalosporinases, broad-spectrum β-lactamases, extended-spectrum β-lactamases, inhibitor-resistant β-lactamases, carbenicillinase, cloxicillinases, oxacillinases, carbapenemases, and metalloenzymes.

Types of β-lactamases include Class A, Class B, Class C, and Class D β-lactamases.

Compounds and compositions provided by the present disclosure can be administered orally.

Compounds provided by the present disclosure, when orally administered, provide an enhanced oral bioavailability of the β-lactamase inhibitor compared to the oral bioavailability of the parent B-lactamase inhibitor. For example, compounds of Formula (1) can exhibit an oral bioavailability (% F) of at least 10%, at least 20%, at least 30%, at least 40%, at least 50%, or at least 60%.

Pharmaceutical compositions provided by the present disclosure may further comprise one or more pharmaceutically active compounds in addition to a compound of Formula (1). Such compounds may be provided to treat a bacterial infection being treated with the compound of Formula (1) or to treat a disease, disorder, or condition other than the bacterial infection being treated with the compound of Formula (1).

A compound of Formula (1) may be used in combination with at least one other therapeutic agent. A compound of Formula (1) may be administered to a patient together with another compound for treating a bacterial infection in the patient. The at least one other therapeutic agent may be a different compound of Formula (1). A compound of Formula (1) and the at least one other therapeutic agent may act additively or synergistically. The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating a bacterial infection or a different disease, disorder or condition than a bacterial infection. Methods provided by the present disclosure include administration of a compound of Formula (1) and one or more other therapeutic agents provided that the combined administration does not inhibit the therapeutic efficacy of a compound of Formula (1) and/or does not produce adverse combination effects.

Pharmaceutical compositions comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain embodiments of combination therapy, the combination therapy may comprise alternating between administering a compound of Formula (1) and a composition comprising another therapeutic agent, e.g., to minimize adverse drug effects associated with a particular drug. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising a compound of Formula (1) may be administered with one or more substances to enhance, modulate and/or control release, bioavailability, therapeutic efficacy, therapeutic potency, stability, and the like of a compound of Formula (1). For example, to enhance the therapeutic efficacy of a compound of Formula (1), a compound of Formula (1) or a pharmaceutical composition comprising a compound of Formula (1) may be co-administered with one or more active agents to increase the absorption or diffusion of the compound of Formula (1) from the gastrointestinal tract to the systemic circulation, or to inhibit degradation of the compound of Formula (1) in the blood of a subject. A pharmaceutical composition comprising a compound of Formula (1) may be co-administered with an active agent having pharmacological effects that enhance the therapeutic efficacy of the compound of Formula (1).

A compound of Formula (1) may be administered together with another therapeutic compound, where the compound of Formula (1) enhances the efficacy of the other therapeutic compound. For example, the other therapeutic compound can be an antibiotic such as a β-lactam antibiotic, and the compound of Formula (1), which provides a systemic β-lactamase inhibitor, can enhance the efficacy for the β-lactam antibiotic by inhibiting the hydrolysis of the β-lactam ring by β-lactamases.

Compounds and compositions provided by the present disclosure can be administered in combination with an antibiotic such as a β-lactam antibiotic.

Antibiotics include, for example, aminoglycosides such as amikacin, gentamicin, neomycin, streptomycin, and tobramycin; β-lactams (cephalosporins, first generation) such as cefadroxil, cefazolin, cephalexin; β-lactams (cephalosporins, second generation) such as cefaclor, cefotetan, cefoxitin, cefprozil, and cefuroxime; β-lactams (cephalosporins, third generation) such as cefotaxime, cefpodoxime, ceftazidime, ceftibuten, and ceftriaxone; β-lactams (cephalosporins, sixth generation) such as cefepime; β-lactams (cephalosporins, fifth generation) such as ceftaroline; β-lactams (penicillins) such as amoxicillin, ampicillin, dicloxacillin, nafcillin, and oxacillin, penicillin G, penicillin G benzathine, penicillin G procaine, piperacillin, and ticarcillin; β-lactam monobactams such as aztreonam; β-lactam carbapenems such as ertapenem, imipenem, meropenem, and doripenem; fluoroquiniolones such as ciprofloxacin, gemifloxacin, levofloxacin, moxifloxacin, norfloxacin, and ofloxacin; macrolides such as azithromycin, clarithromycin, erythromycin, fidaxomicin, lactobionate, gluceptate, and telithromycin; sulfonamides such as sulfisoxazole, sulfamethizole, sulfamethoxazole, and trimethoprim; tetracyclines such as doxycycline, minocycline, tetracycline, and tigecycline; and other antibiotics such as clindamycin, chlorramphenicol, colistin (poloymyxin E), dalbavancin, daptomycin, fosfomycin, linezolid, metronidazole, nitrofurantoin, oritavancin, quinupristin, dalfoprisin, rifampin, rifapentine, tedizolid, telavancin, and vancomycin. The antibiotic can be ceftazidime.

Other examples of antibiotics include penicillins such as aminopenicillins including amoxicillin and ampicillin, antipseudomonal penicillins including carbenicillin, peperacillin, and ticarcillin, β-lactamase inhibitors including amoxicillin, ampicillin, piperacillin, and clavulanate, natural penicillins including penicillin g benzathine, penicillin v potassium, and procaine penicillin, and penicillinase resistant penicillin including oxacillin, dicloxacillin, and nafcillin; tetracyclines; cephalosporins such as avibactam, tazobactam, cefadroxil, defazolin, cephalexin, and cefazolin;

quinolones such as lomefloxacin, ofloxacin, norfloxacin, gatifloxacin, ciprofloxacin, moxifloxacin, levofloxacin, gemifloxacin, delafoxacin, cinoxacin, nalidixic acid, trovafloxacin, and sparfloxacin; lincomycins such as lincomycin and clindamycin; macrolides such as detolides including telithromycin and macrolides such as erythromycin, azithromycin, clarithromycin, and fidaxomicin; sulfonamides such as sulfamethoxazole/trimethoprim, sulfisoxazole; glycopeptides; aminoglycosides such as paromomycin, tobramycin, gentamycin, amikacin, kanamycin, and neomycin; and carbapenems such as doripenem, meropenem, ertapenem, and cilastatin/imipenem. Examples of suitable β-lactam antibiotics include penams such as β-lactamase-sensitive penams such as benzathine penicillin, benzylpenicillin, phenoxymethyl pencillin, and procain penicillin; β-lactamase-resistant penams such as cloxacillin, dicloxacillin, flucloxacillin, methicillin, nafcillin, oxacillin, and temocillin; broad spectrum penams such as amoxicillin and ampicillin; extended-spectrum penams such as mecillanam; carboxypenicillins such as carbenicillin and ticarcillin, and ureidopenicillins such as azlocillin, mezlocillin, and peperacillin.

Examples of suitable β-lactam antibiotics include cephams such as first generation cephams including cefazolin, cephalexin, cephalosporin C, cephalothin; second generation cephams such as cefaclor, cefamoandole, cefuroxime, cefotetan, and cefoxitin; third generation cephams such as cefixime, cefotaxime, cefpodoxime, ceflazidime, and ceftriaxone; fourth generation cephams such as cefipime and cefpirome; and fifth generation cephams such as ceftaroline.

Examples of suitable β-lactam antibiotics include carbapenems and penems such as biapenem, doripenem, ertapenem, faropenem, imipenem, meropenem, panipernem, razupenem, tebipenem, and thienamycin.

Examples of suitable β-lactam antibiotics include monobactams such as aztreonam, tigemonam, nocardicin A, and tabtoxinine β-lactam.

Compounds and pharmaceutical compositions provided by the present disclosure can be administered with β-lactamase inhibitors and/or carbapenemase inhibitors or pharmaceutical compositions thereof. Examples of suitable β-lactamase inhibitors and/or carbapenemase inhibitors include clavulanic acid, sulbactam, avibactam, tazobactam, relebactam, vaborbactam, ETX 2514, RG6068 (i.e., OP0565) (Livermore et al., *J AntiMicrob Chemother* 2015, 70: 3032) and RPX7009 (Hecker et al., *J Med Chem* 2015 58: 3682-3692).

Compounds and compositions provided by the present disclosure be used in combination with one or more other active ingredients. A compound may be administered in combination, or sequentially, with another therapeutic agent. Such other therapeutic agents include those known for treatment, prevention, or amelioration of infectious disease.

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided by the present disclosure are administered prior to or subsequent to the one or more additional active ingredients.

ASPECTS OF THE INVENTION

Aspect 1. A compound of Formula (1):

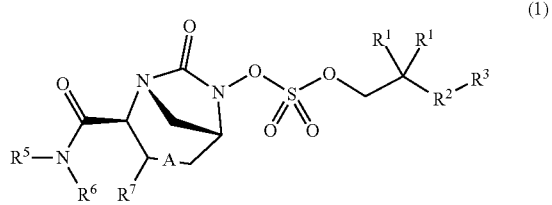

wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—(O)—O—$R^4$, —O—C(O)—S—$R^4$, —O—C(O)—NH—$R^4$, —S—S—$R^4$, —S—$R^4$, —NH—$R^4$, —CH(—$NH_2$)(—$R^4$), $C_{5-6}$ heterocycloalkyl, $C_{5-6}$ heteroaryl, substituted $C_{5-6}$ cycloalkyl, substituted $C_{5-6}$ heteerocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (=) and $R^7$ is $C_{1-3}$ alkyl.

Aspect 2. The compound of aspect 1, wherein each substituent is independently selected from —OH, —CN, —$CF_3$, —$OCF_3$, =O, —$NO_2$, $C_{1-6}$ alkoxy, $C_{1-6}$ alkyl, —COOR, —$NR_2$, and —$CONR_2$; wherein each R is independently selected from hydrogen and $C_{1-6}$ alkyl.

Aspect 3. The compound of any one of aspects 1 to 2, wherein each substituent is independently selected from —OH, —CF₃, —O—CF₃, —NO₂, —O—C(O)—R⁴, —S—C(O)—R⁴, —NH—C(O)—R⁴, —O—C(O)—O—R⁴, —S—C(O)—O—R⁴, —NH—C(O)—O—R⁴, —C(O)—O—R⁴, —C(O)—S—R⁴, —C(O)—NH—R⁴, —O—C(O)—O—R⁴, —O—C(O)—S—R⁴, —O—C(O)—NH—R⁴, —S—S—R⁴, —S—R⁴, —NH—R⁴, —CH(—NH₂)(—R⁴), wherein each R⁴ is selected from hydrogen, $C_{1-8}$ alkyl, and $C_{1-8}$ heteroalkyl.

Aspect 4. The compound of any one of aspects 1 to 3, wherein A is a single bond (—) and R⁷ is hydrogen.

Aspect 5. The compound of any one of aspects 1 to 4, wherein A is a double bond (═) and R⁷ is $C_{1-3}$ alkyl.

Aspect 6. The compound of any one of aspects 1 to 5, wherein the compound has the structure of Formula (2):

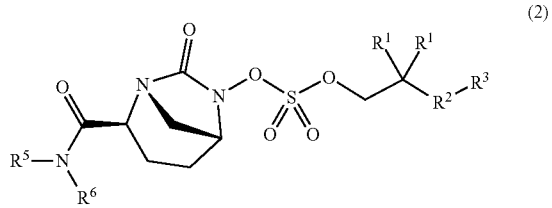

(2)

Aspect 7. The compound of any one of aspects 1 to 5, wherein the compound has the structure of Formula (2a):

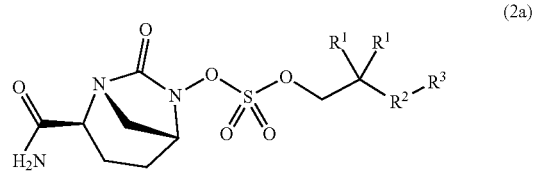

(2a)

Aspect 8. The compound of any one of aspects 1 to 5, wherein the compound has the structure of Formula (3):

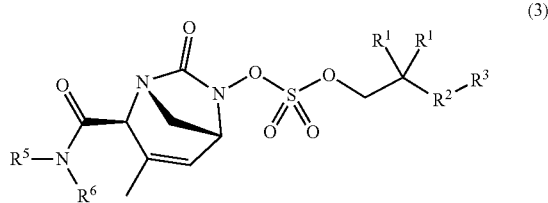

(3)

Aspect 9. The compound of any one of aspects 1 to 5, wherein the compound has the structure of Formula (3a):

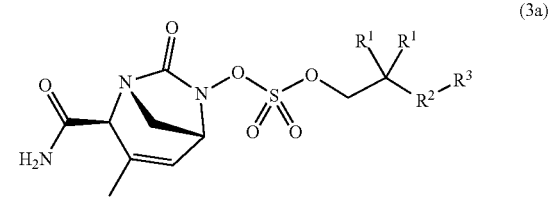

(3a)

Aspect 10. The compound of any one of aspects 1 to 5, wherein the compound has the structure of Formula (4):

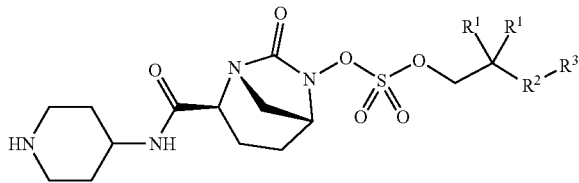

(4)

Aspect 11. The compound of any one of aspects 1 to 5, wherein the compound has the structure of Formula (5):

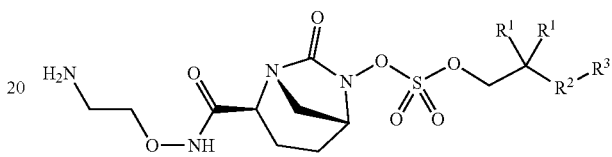

(5)

Aspect 12. The compound of any one of aspects 1 to 11, wherein, R⁵ is hydrogen; and R⁶ is hydrogen.

Aspect 13. The compound of any one of aspects 1 to 12, wherein, R⁵ is $C_{2-6}$ heteroalkyl comprising a terminal amine group; and R⁶ is hydrogen.

Aspect 14. The compound of any one of aspects 1 to 13, wherein, R⁵ is —O—(CH₂)₂—NH₂; and R⁶ is hydrogen.

Aspect 15. The compound of any one of aspects 1 to 14, wherein, R⁵ is $C_{4-6}$ heterocycloalkyl comprising at least one —NH— moiety; and R⁶ is hydrogen.

Aspect 16. The compound of any one of aspects 1 to 15, wherein, R⁵ is 4-yl-piperidine; and R⁶ is hydrogen.

Aspect 17. The compound of any one of aspects 1 to 16, wherein, A is a single bond; R⁵ is selected from hydrogen, —O—(CH₂)₂—NH₂, and 4-yl-piperidine; R⁶ is hydrogen; and R⁷ is hydrogen.

Aspect 18. The compound of any one of aspects 1 to 17, wherein each R¹ is independently $C_{1-6}$ alkyl.

Aspect 19. The compound of any one of aspects 1 to 18, wherein each R¹ is methyl.

Aspect 20. The compound of any one of aspects 1 to 19, wherein each R¹ together with the geminal carbon atom to which they are bonded form a $C_{3-6}$ cycloalkyl ring or a substituted $C_{3-6}$ cycloalkyl ring.

Aspect 21. The compound of any one of aspects 1 to 20, wherein each R¹ together with the geminal carbon atom to which they are bonded form a $C_{3-6}$ cycloalkyl ring.

Aspect 22. The compound of any one of aspects 1 to 21, wherein each R¹ together with the geminal carbon atom to which they are bonded form a cyclopropyl ring, a cyclobutyl ring, a cyclopentyl ring, or a cyclohexyl ring.

Aspect 23. The compound of any one of aspects 1 to 22, wherein each R¹ together with the geminal carbon atom to which they are bonded form a $C_{3-6}$ heterocycloalkyl ring or a substituted $C_{3-6}$ heterocycloalkyl ring.

Aspect 24. The compound of any one of aspects 1 to 23, wherein R² is a single bond.

Aspect 25. The compound of any one of aspects 1 to 24, wherein R² is a single bond; and R³ is $C_{1-6}$ alkyl.

Aspect 26. The compound of any one of aspects 1 to 25, wherein R² is selected from $C_{1-2}$ alkanediyl and substituted $C_{1-2}$ alkanediyl.

Aspect 27. The compound of aspect 26, wherein the substituent group is selected from —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl.

Aspect 28. The compound of aspect 26, wherein the substituent group is selected from —OH, —O—C(O)—R$^4$, —S—C(O)—R$^4$, —NH—C(O)—R$^4$, —C(O)—O—R$^4$, —(O)—S—R$^4$, —C(O)—NH—R$^4$, —S—S—R$^4$, —S—R$^4$, —NH—R$^4$, —CH(—NH$_2$)(—R$^4$), and —CH(—NH$_2$)(—R$^4$); and R$^4$ is selected from hydrogen and C$_{1-6}$ alkyl.

Aspect 29. The compound of any one of aspects 26-28, wherein, R$^2$ is substituted C$_{1-2}$ alkanediyl; and the stereochemistry of the carbon atom to which the substituent group is bonded is of the (S) configuration.

Aspect 30. The compound of any one of aspects 26-28, wherein, R$^2$ is substituted C$_{1-2}$ alkanediyl; and the stereochemistry of the carbon atom to which the substituent group is bonded is of the (R) configuration.

Aspect 31. The compound of any one of aspects 1 to 30, wherein R$^2$ is selected from C$_{5-6}$ cycloalkanediyl, C$_{5-6}$ heterocycloalkanediyl, C$_6$ arenediyl, and C$_{5-6}$ heterocycloalkanediyl.

Aspect 32. The compound of any one of aspects 1 to 31, wherein R$^3$ is selected from —O—C(O)—R$^4$, —C(O)—O—R$^4$, —S—C(O)—R$^4$, —C(O)—S—R$^4$, —S—S—R$^4$, —NH—R$^4$, and —CH(—NH$_2$)(—R$^4$).

Aspect 33. The compound of any one of aspects 1 to 32, wherein R$^3$ is —C(O)—O—R$^4$.

Aspect 34. The compound of any one of aspects 1 to 33, wherein R$^4$ is selected from C$_{1-8}$ alkyl, C$_{1-8}$ heteroalkyl, C$_{5-7}$ cycloalkyl, C$_{5-7}$ heterocycloalkyl, C$_6$ aryl, C$_{7-9}$ arylalkyl, substituted C$_{1-8}$ alkyl, substituted C$_{1-8}$ heteroalkyl, substituted C$_{5-6}$ cycloalkyl, substituted C$_{5-6}$ heterocycloalkyl, substituted C$_6$ aryl, and C$_{7-9}$ arylalkyl.

Aspect 35. The compound of any one of aspects 1 to 34, wherein R$^4$ is selected from C$_{1-8}$ alkyl, C$_{1-8}$ heteroalkyl, C$_{7-9}$ arylalkyl, C$_{5-7}$ heterocycloalkyl, substituted C$_{1-8}$ alkyl, substituted C$_{1-8}$ heteroalkyl, substituted C$_{7-9}$ arylalkyl, and substituted C$_{5-7}$ heterocycloalkyl.

Aspect 36. The compound of any one of aspects 1 to 35, wherein R$^4$ is selected from C$_{1-8}$ alkyl, C$_{1-8}$ heteroalkyl, C$_{7-9}$ arylalkyl, and C$_{5-7}$ heterocycloalkyl.

Aspect 37. The compound of any one of aspects 1 to 36, wherein R$^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 38. The compound of any one of aspects 1 to 37, wherein, R$^3$ is —C(O)—O—R$^4$; and R$^4$ is selected from C$_{1-8}$ alkyl, C$_{1-8}$ heteroalkyl, C$_{5-7}$ cycloalkyl, C$_{5-7}$ heterocycloalkyl, C$_6$ aryl, C$_{7-9}$ arylalkyl, substituted C$_{1-8}$ alkyl, substituted C$_{1-8}$ heteroalkyl, substituted C$_{5-6}$ cycloalkyl, substituted C$_{5-6}$ heterocycloalkyl, substituted C$_6$ aryl, and C$_{7-9}$ arylalkyl.

Aspect 39. The compound of any one of aspects 1 to 38, wherein, R$^3$ is —C(O)—O—R$^4$; and R$^4$ is selected from C$_{1-8}$ alkyl, C$_{1-8}$ heteroalkyl, C$_{7-9}$ arylalkyl, C$_{5-7}$ heterocycloalkyl, substituted C$_{1-8}$ alkyl, substituted C$_{1-8}$ heteroalkyl, substituted C$_{7-9}$ arylalkyl, and substituted C$_{5-7}$ heterocycloalkyl.

Aspect 40. The compound of any one of aspects 1 to 39, wherein, R$^3$ is —C(O)—O—R$^4$; and R$^4$ is selected from C$_{1-8}$ alkyl, C$_{1-8}$ heteroalkyl, C$_{7-9}$ arylalkyl, and C$_{5-7}$ heterocycloalkyl.

Aspect 41. The compound of any one of aspects 1 to 40, wherein each R$^1$ together with the carbon atom to which they are bonded form a C$_{4-6}$ heterocycloalkyl ring comprising two adjacent S atoms or a substituted C$_{4-6}$ heterocycloalkyl ring comprising at least one heteroatom selected from O and S, and a =O substituent group bonded to a carbon atom adjacent the at least one heteroatom.

Aspect 42. The compound of any one of aspects 1 to 41, wherein, R$^2$ is a single bond; R$^3$ is C$_{1-3}$ alkyl; and each R$^1$ together with the carbon atom to which they are bonded form a C$_{4-6}$ heterocycloalkyl ring or a substituted C$_{4-6}$ heterocycloalkyl ring.

Aspect 43. The compound of any one of aspects 1 to 42, wherein, R$^2$ is a single bond; R$^3$ is C$_{1-3}$ alkyl; and each R$^1$ together with the carbon atom to which they are bonded form a C$_{4-6}$ heterocycloalkyl ring comprising two adjacent S atoms or a substituted C$_{4-6}$ heterocycloalkyl ring comprising at least one heteroatom selected from O and S, and a=O substituent group bonded to a carbon atom adjacent the heteroatom.

Aspect 44. The compound of any one of aspects 1 to 43, wherein, R$^2$ is a single bond; R$^3$ is C$_{1-3}$ alkyl; and each R$^1$ together with the carbon atom to which they are bonded form a 1,2-dithiolante, 1,2-dithane ring, thietan-2-one ring, dihydrothiophen-2(3H)-one ring, tetrahydro-2H-thipyran-2-one ring, oxetan-2-one ring dihydrofuran-2(3H)-one ring, or tetrahydro-2H-pyran-2-one ring.

Aspect 45. The compound of any one of aspects 1 to 44, wherein, each R$^1$ is methyl; R$^2$ is selected from a single bond, methanediyl, ethanediyl, —CH(—OH)—, —CH(—O—C(O)—CH$_2$CH$_3$)—, and 1,2-benzene-diyl; and R$^3$ is selected from —O—C(O)—R$^4$, —C(O)—O—R$^4$, —S—C(O)—R$^4$, —C(O)—S—R$^4$, —S—S—R$^4$, —NHR$^4$, and —CH(—NH$_2$)(—R$^4$); wherein R$^4$ is selected from C$_{1-8}$ alkyl, C$_{1-8}$ heteroalkyl, C$_{7-9}$ arylalkyl, and C$_{5-7}$ heterocycloalkyl.

Aspect 46. The compound of any one of aspects 1 to 45, wherein, each R$^1$ is methyl; R$^2$ is selected from a single bond, methanediyl, ethanediyl, —CH(—OH)—, —CH(—O—C(O)—CH$_2$CH$_3$)—, and 1,2-benzene-diyl; and R$^3$ is selected from —C(O)—O—R$^4$; wherein R$^4$ is selected from C$_{1-8}$ alkyl, C$_{1-8}$ heteroalkyl, C$_{7-9}$ arylalkyl, and C$_{5-7}$ heterocycloalkyl.

Aspect 47. The compound of any one of aspects 1 to 46, wherein, each R$^1$ is methyl; R$^2$ is selected from a single bond, methanediyl, ethanediyl, —CH(—OH)—, —CH(—O—C(O)—CH$_2$CH$_3$)—, and 1,2-benzene-diyl; and R$^3$ is selected from —O—C(O)—R$^4$, —C(O)—O—R$^4$, —S—C(O)—R$^4$, —C(O)—S—R$^4$, —S—S—R$^4$, —NHR$^4$, and —CH(—NH$_2$)(—R$^4$); wherein R$^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 48. The compound of any one of aspects 1 to 47, wherein, each R$^1$ is methyl; R$^2$ is selected from a single bond, methanediyl, ethanediyl, —CH(—OH)—, —CH(—O—C(O)—CH$_2$CH$_3$)—, and 1,2-benzene-diyl; and R$^3$ is selected from —C(O)—O—R$^4$; wherein R$^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 49. The compound of any one of aspects 1 to 48, wherein A is a single bond, and each of R$^5$, R$^6$, and R$^7$ is hydrogen.

Aspect 50. The compound of any one of aspects 1 to 49, wherein, A is a single bond; each R$^1$ is independently C$_{1-3}$ alkyl; each R$^2$ is a single bond; and each of R$^5$, R$^6$, and R$^7$ is hydrogen.

Aspect 51. The compound of any one of aspects 1 to 50, wherein, each $R^1$ is methyl; $R^2$ is a single bond; and $R^3$ can be —C(O)—O—$R^4$; wherein $R^4$ is selected from $C_{1-10}$ alkyl, $C_{1-10}$ heteroalkyl, $C_{7-10}$ alkylarene, and $C_{5-10}$ heteroalkylcycloalkyl.

Aspect 52. The compound of any one of aspects 1 to 51, wherein, each $R^1$ is methyl; $R^2$ is a single bond; $R^3$ can be —C(O)—O—$R^4$; wherein $R^4$ is selected from $C_{1-10}$ alkyl, $C_{1-10}$ heteroalkyl, $C_{7-10}$ alkylarene, and $C_{5-10}$ heteroalkylcycloalkyl; each of $R^5$, $R^6$, and $R^7$ is hydrogen; and A is a single bond.

Aspect 53. The compound of aspect 1, wherein the compound is selected from:

3-(((((2S,5R)-2-carbamoyl-7-oxo-1,6-diazabicyclo[3.2.1]octan-6-yl)oxy)sulfonyl)oxy)-2,2-dimethylpropyl benzoate (2);

ethyl 3-(((((2S,5R)-2-carbamoyl-7-oxo-1,6-diazabicyclo[3.2.1]octan-6-yl)oxy)sulfonyl)oxy)-2,2-dimethylpropanoate (3);

benzyl 3-(((((2S,5R)-2-carbamoyl-7-oxo-1,6-diazabicyclo[3.2.1]octan-6-yl)oxy)sulfonyl)oxy)-2,2-dimethylpropanoate (4);

4-(((((2S,5R)-2-carbamoyl-7-oxo-1,6-diazabicyclo[3.2.1]octan-6-yl)oxy)sulfonyl)oxy)-3,3-dimethylbutyl benzoate (6);

4-(((((2S,5R)-2-carbamoyl-7-oxo-1,6-diazabicyclo[3.2.1]octan-6-yl)oxy)sulfonyl)oxy)-3,3-dimethylbutyl propionate (7);

benzyl (4-(((((2S,5R)-2-carbamoyl-7-oxo-1,6-diazabicyclo[3.2.1]octan-6-yl)oxy)sulfonyl)oxy)-3,3-dimethylbutyl) adipate (8);

6-(4-(((((2S,5R)-2-carbamoyl-7-oxo-1,6-diazabicyclo[3.2.1]octan-6-yl)oxy)sulfonyl)oxy)-3,3-dimethylbutoxy)-6-oxohexanoic acid (9);

methyl 3-(((((2S,5R)-2-carbamoyl-7-oxo-1,6-diazabicyclo[3.2.1]octan-6-yl)oxy)sulfonyl)oxy)-2,2-dimethylpropanoate (10);

isopropyl 3-(((((2S,5R)-2-carbamoyl-7-oxo-1,6-diazabicyclo[3.2.1]octan-6-yl)oxy)sulfonyl)oxy)-2,2-dimethylpropanoate (11);

hexyl 3-(((((2S,5R)-2-carbamoyl-7-oxo-1,6-diazabicyclo[3.2.1]octan-6-yl)oxy)sulfonyl)oxy)-2,2-dimethylpropanoate (12);

heptyl 3-(((((2S,5R)-2-carbamoyl-7-oxo-1,6-diazabicyclo[3.2.1]octan-6-yl)oxy)sulfonyl)oxy)-2,2-dimethylpropanoate (13);

tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14);

2-methoxyethyl 3-(((((2S,5R)-2-carbamoyl-7-oxo-1,6-diazabicyclo[3.2.1]octan-6-yl)oxy)sulfonyl)oxy)-2,2-dimethylpropanoate (15);

oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16);

ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17);

ethyl 1-((((((2S,5R)-2-carbamoyl-7-oxo-1,6-diazabicyclo[3.2.1]octan-6-yl)oxy)sulfonyl)oxy)methyl)cyclopropanecarboxylate (18);

ethyl 1-((((((2S,5R)-2-carbamoyl-7-oxo-1,6-diazabicyclo[3.2.1]octan-6-yl)oxy)sulfonyl)oxy)methyl)cyclobutanecarboxylate (19);

(2S,5R)-2-carbamoyl-7-oxo-1,6-diazabicyclo[3.2.1]octan-6-yl 1H-imidazole-1-sulfonate (34);

ethyl 5-(((((2S,5R)-2-carbamoyl-7-oxo-1,6-diazabicyclo[3.2.1]octan-6-yl)oxy)sulfonyl)oxy)-4,4-dimethylpentanoate (35);

hexyl 5-(((((2S,5R)-2-carbamoyl-7-oxo-1,6-diazabicyclo[3.2.1]octan-6-yl)oxy)sulfonyl)oxy)-4,4-dimethylpentanoate (36);

heptyl 5-(((((2S,5R)-2-carbamoyl-7-oxo-1,6-diazabicyclo[3.2.1]octan-6-yl)oxy)sulfonyl)oxy)-4,4-dimethylpentanoate (37);

2-methoxyethyl 5-(((((2S,5R)-2-carbamoyl-7-oxo-1,6-diazabicyclo[3.2.1]octan-6-yl)oxy)sulfonyl)oxy)-4,4-dimethylpentanoate (38);

5-(((((2S,5R)-2-carbamoyl-7-oxo-1,6-diazabicyclo[3.2.1]octan-6-yl)oxy)sulfonyl)oxy)-2,2,4,4-tetramethylpentyl propionate (39);

5-(((((2S,5R)-2-carbamoyl-7-oxo-1,6-diazabicyclo[3.2.1]octan-6-yl)oxy)sulfonyl)oxy)-2,2,4,4-tetramethylpentyl benzoate (40);

5-(((((2S,5R)-2-carbamoyl-7-oxo-1,6-diazabicyclo[3.2.1]octan-6-yl)oxy)sulfonyl)oxy)-2,2,4,4-tetramethylpentyl 2,6-dimethylbenzoate (41);

(2S,5R)-2-carbamoyl-7-oxo-1,6-diazabicyclo[3.2.1]octan-6-yl ((3-methyl-2-oxotetrahydrofuran-3-yl)methyl) sulfate (42);

3-(((((2S,5R)-2-carbamoyl-7-oxo-1,6-diazabicyclo[3.2.1]octan-6-yl)oxy)sulfonyl)oxy)-2,2-dimethylpropyl pivalate (43);

3-(((((2S,5R)-2-carbamoyl-7-oxo-1,6-diazabicyclo[3.2.1]octan-6-yl)oxy)sulfonyl)oxy)-2,2-dimethylpropyl 3-chloro-2,6-dimethoxybenzoate (44);

4-(((((2S,5R)-2-carbamoyl-7-oxo-1,6-diazabicyclo[3.2.1]octan-6-yl)oxy)sulfonyl)oxy)-2,2,3,3-tetramethylbutyl 2,6-dimethylbenzoate (45);

4-(((((2S,5R)-2-carbamoyl-7-oxo-1,6-diazabicyclo[3.2.1]octan-6-yl)oxy)sulfonyl)oxy)-2,2,3,3-tetramethylbutyl benzoate (46);

4-(((((2S,5R)-2-carbamoyl-7-oxo-1,6-diazabicyclo[3.2.1]octan-6-yl)oxy)sulfonyl)oxy)-2,2,3,3-tetramethylbutyl propionate (47);

(2S,5R)-2-carbamoyl-7-oxo-1,6-diazabicyclo[3.2.1]octan-6-yl ((3-methyl-2-oxotetrahydro-2H-pyran-3-yl)methyl) sulfate (48);

2-(3-(((((2S,5R)-2-carbamoyl-7-oxo-1,6-diazabicyclo[3.2.1]octan-6-yl)oxy)sulfonyl)oxy)-2,2-dimethylpropyl)phenyl acetate (49);

2-(3-(((((2S,5R)-2-carbamoyl-7-oxo-1,6-diazabicyclo[3.2.1]octan-6-yl)oxy)sulfonyl)oxy)-2,2-dimethylpropyl)phenyl pivalate (50);

S-(4-(((((2S,5R)-2-carbamoyl-7-oxo-1,6-diazabicyclo[3.2.1]octan-6-yl)oxy)sulfonyl)oxy)-3,3-dimethylbutyl) ethanethioate (51);

S-(5-(((((2S,5R)-2-carbamoyl-7-oxo-1,6-diazabicyclo[3.2.1]octan-6-yl)oxy)sulfonyl)oxy)-4,4-dimethylpentyl) ethanethioate (52);

S-(3-(((((2S,5R)-2-carbamoyl-7-oxo-1,6-diazabicyclo[3.2.1]octan-6-yl)oxy)sulfonyl)oxy)-2,2-dimethylpropyl) ethanethioate (53);

3-(((((2S,5R)-2-carbamoyl-7-oxo-1,6-diazabicyclo[3.2.1]octan-6-yl)oxy)sulfonyl)oxy)-2,2-dimethylpropyl 2,6-dimethylbenzoate (54);

3-(((((2S,5R)-2-carbamoyl-7-oxo-1,6-diazabicyclo[3.2.1]octan-6-yl)oxy)sulfonyl)oxy)-2,2-dimethylpropyl adamantane-1-carboxylate (55);

diethyl 2-((((((2S,5R)-2-carbamoyl-7-oxo-1,6-diazabicyclo[3.2.1]octan-6-yl)oxy)sulfonyl)oxy)methyl)-2-methylmalonate (56);

propyl 3-(((((2S,5R)-2-carbamoyl-7-oxo-1,6-diazabicyclo[3.2.1]octan-6-yl)oxy)sulfonyl)oxy)-2,2-dimethylpropanoate (57);
butyl 3-(((((2S,5R)-2-carbamoyl-7-oxo-1,6-diazabicyclo[3.2.1]octan-6-yl)oxy)sulfonyl)oxy)-2,2-dimethylpropanoate (58);
(5-methyl-2-oxo-1,3-dioxol-4-yl)methyl 3-(((((2S,5R)-2-carbamoyl-7-oxo-1,6-diazabicyclo[3.2.1]octan-6-yl)oxy)sulfonyl)oxy)-2,2-dimethylpropanoate (59);
4-(((((2S,5R)-2-carbamoyl-7-oxo-1,6-diazabicyclo[3.2.1]octan-6-yl)oxy)sulfonyl)oxy)-3,3-dimethylbutyl pivalate (60);
ethyl 2-((((((2S,5R)-2-carbamoyl-7-oxo-1,6-diazabicyclo[3.2.1]octan-6-yl)oxy)sulfonyl)oxy)methyl)-2-ethylbutanoate (61);
4-(((((2S,5R)-2-carbamoyl-7-oxo-1,6-diazabicyclo[3.2.1]octan-6-yl)oxy)sulfonyl)oxy)-3,3-dimethylbutyl 2,6-dimethylbenzoate (62);
4-(((((2S,5R)-2-carbamoyl-7-oxo-1,6-diazabicyclo[3.2.1]octan-6-yl)oxy)sulfonyl)oxy)-3,3-dimethylbutyl adamantane-1-carboxylate (63);
4-(((((2S,5R)-2-carbamoyl-7-oxo-1,6-diazabicyclo[3.2.1]octan-6-yl)oxy)sulfonyl)oxy)-3,3-dimethylbutyl 2,6-dimethoxybenzoate (64);
5-(((((2S,5R)-2-carbamoyl-7-oxo-1,6-diazabicyclo[3.2.1]octan-6-yl)oxy)sulfonyl)oxy)-4,4-dimethylpentyl benzoate (65);
5-(((((2S,5R)-2-carbamoyl-7-oxo-1,6-diazabicyclo[3.2.1]octan-6-yl)oxy)sulfonyl)oxy)-4,4-dimethylpentyl 2,6-dimethoxybenzoate (66);
5-(((((2S,5R)-2-carbamoyl-7-oxo-1,6-diazabicyclo[3.2.1]octan-6-yl)oxy)sulfonyl)oxy)-4,4-dimethylpentyl 2,6-dimethylbenzoate (67);
5-(((((2S,5R)-2-carbamoyl-7-oxo-1,6-diazabicyclo[3.2.1]octan-6-yl)oxy)sulfonyl)oxy)-4,4-dimethylpentyl 2-methylbenzoate (68);
4-(((((2S,5R)-2-carbamoyl-7-oxo-1,6-diazabicyclo[3.2.1]octan-6-yl)oxy)sulfonyl)oxy)-2,2,3,3-tetramethylbutyl 3-chloro-2,6-dimethoxybenzoate (69);
2-((((((2S,5R)-2-carbamoyl-7-oxo-1,6-diazabicyclo[3.2.1]octan-6-yl)oxy)sulfonyl)oxy)methyl)-2-methylpropane-1,3-diyl dibenzoate (70);
2-((((((2S,5R)-2-carbamoyl-7-oxo-1,6-diazabicyclo[3.2.1]octan-6-yl)oxy)sulfonyl)oxy)methyl)-2-methylpropane-1,3-diyl diacetate (71);
5-(((((2S,5R)-2-carbamoyl-7-oxo-1,6-diazabicyclo[3.2.1]octan-6-yl)oxy)sulfonyl)oxy)-2,2,4,4-tetramethylpentyl 2,6-dimethoxybenzoate (72);
ethyl 3-(((((2S,5R)-2-carbamoyl-7-oxo-1,6-diazabicyclo[3.2.1]octan-6-yl)oxy)sulfonyl)oxy)-2,2-dimethylbutanoate (73);
(2S,5R)-2-carbamoyl-7-oxo-1,6-diazabicyclo[3.2.1]octan-6-yl ((3,5,5-trimethyl-2-oxotetrahydrofuran-3-yl)methyl) sulfate (74); a pharmaceutically acceptable salt of any of the foregoing; and
a combination of any of the foregoing.

Aspect 54. A pharmaceutical composition comprising the compound of any one of aspects 1 to 53 and a pharmaceutically acceptable vehicle.

Aspect 55. The pharmaceutical composition of aspect 54, further comprising an antibiotic.

Aspect 56. The pharmaceutical composition of aspect 55, wherein the antibiotic comprises a β-lactam antibiotic.

Aspect 57. The pharmaceutical composition of any one of aspects 54 to 56, wherein the pharmaceutical composition comprises an oral dosage formulation.

Aspect 58. The pharmaceutical composition of any one of aspects 54 to 57, wherein the pharmaceutical composition comprises an oral dosage form.

Aspect 59. The pharmaceutical composition of any one of aspects 54 to 58, comprising an amount of the compound of claim 1 effective for treating a bacterial infection in a patient.

Aspect 60. A method of treating a bacterial infection in a patient comprising administering to a patient in need of such treatment a therapeutically effective amount of the compound of any one of aspects 1 to 53.

Aspect 61. The method of aspect 60, wherein administering comprises orally administering.

Aspect 62. The method of any one of aspects 60 to 61, wherein administering comprises administering an oral dosage form.

Aspect 63. The method of any one of aspects 60 to 62, further comprising administering an antibiotic to the patient.

Aspect 64. The method of any one of aspects 60 to 63, wherein the antibiotic comprises a β-lactam antibiotic.

Aspect 65. A method of treating a bacterial infection in a patient comprising administering to a patient in need of such treatment a therapeutically effective amount of the pharmaceutical composition of any one of aspects 54 to 59.

Aspect 66. The method of aspect 65, wherein administering comprises orally administering.

Aspect 67. The method of any one of aspects 65 to 66, wherein administering comprises administering an oral dosage form.

Aspect 68. The method of any one of aspects 65 to 67, further comprising administering an antibiotic to the patient.

Aspect 69. The method of aspect 66, wherein the antibiotic comprises a β-lactam antibiotic.

Aspect 70. A method of inhibiting a β-lactamase in a patient comprising administering to the patient an effective amount of the compound of any one of aspects 1 to 53.

Aspect 71. The method of aspect 70, wherein administering comprises orally administering.

Aspect 72. The of any one of aspects 70 to 71, wherein administering comprises administering an oral dosage form.

Aspect 73 A method of inhibiting a β-lactamase in a patient comprising administering to the patient an effective amount of the pharmaceutical composition of any one of aspects 54 to 59.

Aspect 74. The method of aspect 73, wherein administering comprises orally administering.

Aspect 75. The method of any one of aspects 73 to 74, wherein administering comprises administering an oral dosage form.

Aspect 76. A compound of Formula (1):

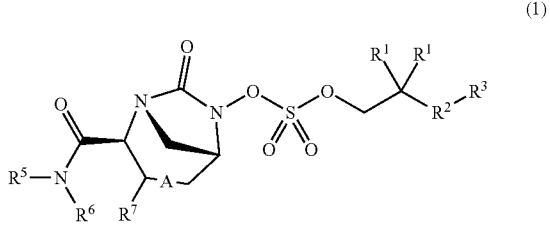

(1)

or a pharmaceutically acceptable salt thereof, wherein,
each of $R^5$, $R^6$, and $R^7$ is hydrogen;
A is a single bond;
each $R^1$ is independently selected from $C_{1-3}$ alkyl, or each $R^1$ together with the carbon atom to which they are bonded form a $C_{3-6}$ cycloalkyl ring;

$R^2$ is selected from single bond, methane-diyl, and ethane-diyl; and $R^3$ is selected from —C(O)—O—$R^4$ and —S—C(O)—$R^4$, wherein $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

Aspect 77. The compound of aspect 76, wherein each $R^1$ is independently selected from $C_{1-3}$ alkyl.

Aspect 78. The compound of aspect 76, wherein each $R^1$ together with the carbon atom to which they are bonded form a $C_{3-6}$ cycloalkyl ring.

Aspect 79. The compound of aspect 76, wherein $R^2$ a single bond.

Aspect 80. The compound of any one of aspects 76 to 79, wherein $R^2$ is methane-diyl.

Aspect 81. The compound of any one of aspects 76 to 79, wherein $R^2$ is ethane-diyl.

Aspect 82. The compound of any one of aspects 76 to 81, wherein $R^3$ is —C(O)—O—$R^4$.

Aspect 83. The compound of any one of aspects 76 to 81, wherein $R^3$ is —S—C(O)—$R^4$.

Aspect 84. The compound of any one of aspects 76 to 83, wherein $R^4$ is $C_{1-10}$ alkyl.

Aspect 85. The compound of any one of aspects 76 to 83, wherein $R^4$ is $C_{1-10}$ heteroalkyl.

Aspect 86. The compound of any one of aspects 76 to 83, wherein $R^4$ is $C_{5-10}$ arylalkyl.

Aspect 87. The compound of any one of aspects 76 to 83, wherein $R^4$ is $C_{3-6}$ heterocycloalkyl.

Aspect 88. The compound of any one of aspects 76 to 83, wherein $R^4$ is substituted $C_{4-10}$ heterocycloalkylalkyl.

Aspect 89. A compound of Formula (1):

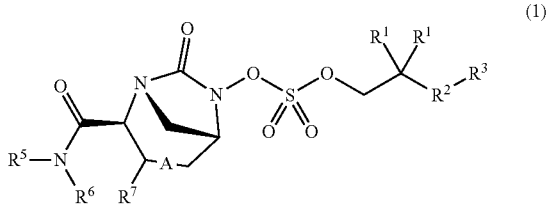

(1)

or a pharmaceutically acceptable salt thereof, wherein,
each of $R^5$, $R^6$, and $R^7$ is hydrogen;
A is a single bond;
each $R^1$ is independently selected from $C_{1-3}$ alkyl, or each $R^1$ together with the carbon atom to which they are bonded form a $C_{3-6}$ cycloalkyl ring;
$R^2$ is a single bond; and
$R^3$ is —C(O)—O—$R^4$, where $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

Aspect 90. The compound of aspect 89, wherein each $R^1$ is independently selected from $C_{1-3}$ alkyl.

Aspect 91. The compound of aspect 89, wherein each $R^1$ together with the carbon atom to which they are bonded form a $C_{3-6}$ cycloalkyl ring.

Aspect 92. The compound of any one of aspects 89 to 91, wherein $R^4$ is selected from $C_{1-7}$ alkyl, $C_{1-10}$ heteroalkyl wherein the one or more heteroatoms is oxygen, —$CH_2$—$C_{4-6}$ cycloalkyl, —$(CH_2)_2$—$C_{4-6}$ cycloalkyl, $C_{3-6}$ heterocycloalkyl wherein the one or more heteroatoms is oxygen, and —$CH_2$—$C_{3-6}$ substituted heterocycloalkyl, and —$(CH_2)_2$—$C_{3-6}$ substituted heterocycloalkyl.

Aspect 93. The compound of aspect 92, wherein in the substituted $C_{3-6}$ heterocycloalkyl the one or more heteroatoms is oxygen, and the one or more substituents is independently selected from $C_{1-3}$ alkyl and =O.

Aspect 94. The compound of any one of aspects 89 to 94, wherein each $R^1$ is methyl, or each $R^1$ together with the carbon atom to which they are bonded form a cyclohexyl ring or a cyclopentyl ring.

Aspect 95. The compound of any one of aspects 89 to 95, wherein $R^4$ is selected from methyl, ethyl, n-propyl, iso-propyl, n-butyl, n-hexyl, n-heptyl, —$CH_2$—$CH_2$—O—$CH_3$, benzyl, 3-oxetanyl, and methyl-5-methyl-1,3-dioxol-2-one.

Aspect 96. The compound of aspect 89, wherein
each of $R^5$, $R^6$, and $R^7$ is hydrogen;
A is a single bond;
each $R^1$ is methyl, or each $R^1$ together with the carbon atom to which they are bonded form a cyclohexyl ring or a cyclopentyl ring;
$R^2$ is a single bond; and
$R^3$ is —C(O)—O—$R^4$, wherein $R^4$ is selected from methyl, ethyl, n-propyl, iso-propyl, n-butyl, n-hexyl, n-heptyl, —$CH_2$—$CH_2$—O—$CH_3$, —$CH_2$-phenyl (benzyl), 3-oxetanyl, and methyl-5-methyl-1,3-dioxol-2-one.

Aspect 97. A compound of Formula (1):

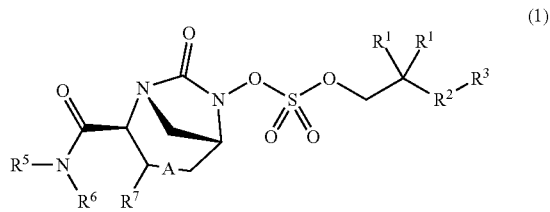

(1)

or a pharmaceutically acceptable salt thereof, wherein,
each of $R^5$, $R^6$, and $R^7$ is hydrogen;
A is a single bond;
each $R^1$ is independently selected from $C_{1-3}$ alkyl, or each $R^1$ together with the carbon atom to which they are bonded form a $C_{3-6}$ cycloalkyl ring;
$R^2$ is —$(CH_2)_2$—; and
$R^3$ is —C(O)—O—$R^4$ wherein $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

Aspect 98. The compound of aspect 97, wherein each $R^1$ is independently selected from $C_{1-3}$ alkyl.

Aspect 99. The compound of aspect 97, wherein each $R^1$ together with the carbon atom to which they are bonded form a $C_{3-6}$ cycloalkyl ring.

Aspect 100. The compound of any one of aspects 97 to 99, wherein $R^4$ is selected from $C_{1-7}$ alkyl, $C_{1-10}$ heteroalkyl wherein the one or more heteroatoms is oxygen, —$CH_2$—$C_{4-6}$ cycloalkyl, —$(CH_2)_2$—$C_{4-6}$ cycloalkyl, $C_{3-6}$ heterocycloalkyl wherein the one or more heteroatoms is oxygen, —$CH_2$—$C_{3-6}$ substituted heterocycloalkyl, and —$(CH_2)_2$—$C_{3-6}$ substituted heterocycloalkyl.

Aspect 101. The compound of aspect 100, wherein in the substituted $C_{3-6}$ heterocycloalkyl the one or more heteroatoms is oxygen, and the one or more substituents is independently selected from $C_{1-3}$ alkyl and =O.

Aspect 102. The compound of any one of aspects 97 to 99, wherein $R^4$ is $C_{1-10}$ alkyl.

Aspect 103. The compound of aspect 97, wherein,
each of $R^5$, $R^6$, and $R^7$ is hydrogen;
A is a single bond;
each $R^1$ is methyl;
$R^2$ is —(CH$_2$)$_2$—; and
$R^3$ is —C(O)—O—$R^4$ where $R^4$ is selected from n-hexyl and n-heptyl.

Aspect 104. A compound of Formula (1):

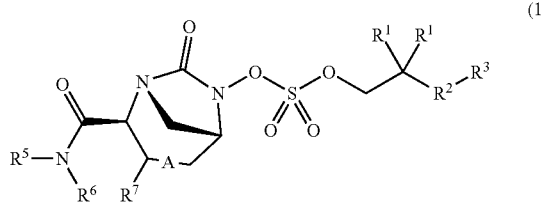

(1)

or a pharmaceutically acceptable salt thereof, wherein,
each of $R^5$, $R^6$, and $R^7$ is hydrogen;
A is a single bond;
each $R^1$ is selected from $C_{1-3}$ alkyl, or each $R^1$ together with the carbon atom to which they are bonded form a $C_{3-6}$ cycloalkyl ring;
$R^2$ is —CH$_2$—; and
$R^3$ is —S—C(O)—$R^4$, wherein $R^4$ is selected from $C_{1-10}$ alkyl, $C_{1-10}$ heteroalkyl, $C_{5-10}$ arylalkyl, $C_{3-6}$ heterocycloalkyl, substituted $C_{4-10}$ heterocycloalkylalkyl.

Aspect 105. The compound of aspect 104, wherein each $R^1$ is independently selected from $C_{1-3}$ alkyl.

Aspect 106. The compound of aspect 104, wherein each $R^1$ together with the carbon atom to which they are bonded form a $C_{3-6}$ cycloalkyl ring.

Aspect 107. The compound of any one of aspects 104 to 106, wherein $R^4$ is selected from $C_{1-7}$ alkyl, $C_{1-10}$ heteroalkyl wherein the one or more heteroatoms is oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms is oxygen, —CH$_2$—$C_{3-6}$ substituted heterocycloalkyl, —(CH$_2$)$_2$—$C_{3-6}$ substituted heterocycloalkyl.

Aspect 108. The compound of aspect 107, wherein, in the substituted $C_{3-6}$ heterocycloalkyl the one or more heteroatoms is oxygen, and the one or more substituents is independently selected from $C_{1-3}$ alkyl and =O.

Aspect 109. The compound of any one of aspects 104 to 106, wherein $R^4$ is $C_{1-10}$ alkyl.

Aspect 110. The compound of aspect 104, wherein,
each of $R^5$, $R^6$, and $R^7$ is hydrogen;
A is a single bond;
each $R^1$ is methyl;
$R^2$ is —CH$_2$—; and
$R^3$ is —S—C(O)—$R^4$, wherein $R^4$ is methyl Aspect 111. A compound of Formula (1):

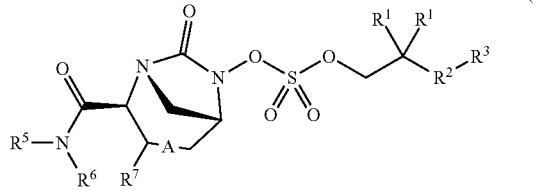

(1)

or a pharmaceutically acceptable salt thereof, wherein,
each of $R^5$, $R^6$, and $R^7$ is hydrogen;
A is a single bond;
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ is a single bond; and
$R^3$ is $C_{1-3}$ alkyl.

Aspect 112. The compound of aspect 111 wherein each $R^1$ together with the carbon atom to which they are bonded form a $C_{3-6}$ heterocycloalkyl ring or a $C_{3-6}$ heterocycloalkyl ring;

Aspect 113. The compound of aspect 112, wherein the one or more heteroatoms is oxygen and the one or more substituents is =O.

Aspect 114. The compound of aspect 111, wherein,
each $R^1$ together with the carbon atom to which they are bonded form a dihydrofuran-2(3H)-one ring;
$R^2$ is a single bond; and
$R^3$ is methyl.

Aspect 115. A compound of Formula (1):

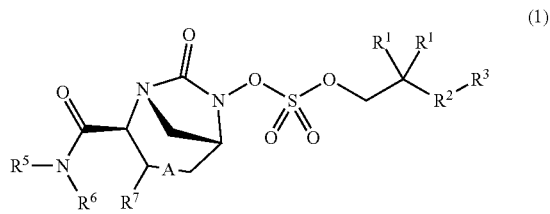

(1)

or a pharmaceutically acceptable salt thereof, wherein,
each of $R^5$, $R^6$, and $R^7$ is hydrogen;
A is a single bond;
each $R^1$ is independently selected from $C_{1-3}$ alkyl;
$R^2$ is selected from a single bond and methanediyl; and
$R^3$ is selected from —O—C(O)—$R^4$ and —C(O)—O—$R^4$, wherein $R^4$ is selected from $C_{1-10}$ alkyl and substituted phenyl.

Aspect 116. The compound of aspect 115, wherein $R^2$ is a single bond.

Aspect 117. The compound of aspect 115, wherein $R^2$ is methanediyl.

Aspect 118. The compound of any one of aspects 115 to 117, wherein $R^3$ is —O—C(O)—$R^4$.

Aspect 119. The compound of any one of aspects 115 to 117, wherein $R^2$ is methanediyl; and $R^3$ is —O—C(O)—$R^4$.

Aspect 120. The compound of any one of aspects 115 to 117, wherein $R^3$ is —C(O)—O—$R^4$.

Aspect 121. The compound of any one of aspects 115 to 117, wherein $R^2$ is a single bond; and $R^3$ is —C(O)—O—$R^4$.

Aspect 122. The compound of aspect 115, wherein $R^2$ is a single bond; $R^3$ is —C(O)—O—$R^4$; and $R^4$ is $C_{1-3}$ alkyl.

Aspect 123. The compound of any one of aspects 115 to 122, wherein $R^4$ is $C_{1-10}$ alkyl.

Aspect 124. The compound of any one of aspects 115 to 122, wherein $R^4$ is $C_{1-4}$ alkyl.

Aspect 125. The compound of any one of aspects 115 to 122, wherein $R^4$ is substituted phenyl.

Aspect 126. The compound of aspect 115, wherein $R^2$ is methanediyl; $R^3$ is —O—C(O)—$R^4$; and $R^4$ is substituted phenyl.

Aspect 127. The compound of aspect 126, wherein the one or more substituents is independently selected from halogen, $C_{1-3}$ alkyl, and $C_{1-3}$ alkoxy.

Aspect 128. The compound of aspect 126, wherein the substituted phenyl is 2,6-substituted phenyl.

Aspect 129. The compound of aspect 128, wherein each of the substituents is selected from $C_{1-3}$ alkyl and $C_{1-3}$ alkoxy.

Aspect 130. The compound of aspect 126, wherein the substituted phenyl is 2,5,6-substituted phenyl.

Aspect 131. The compound of aspect 130, wherein each of the substituents at the 2 and 6 positions is independently selected from $C_{1-3}$ alkyl and $C_{1-3}$ alkoxy; and the substituent at the 5 position is halogen.

Aspect 132. A compound of Formula (1):

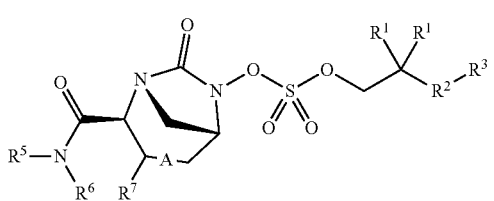

(1)

or a pharmaceutically acceptable salt thereof, wherein,
each of $R^5$, $R^6$, and $R^7$ is hydrogen;
A is a single bond;
each $R^1$ is independently selected from $C_{1-3}$ alkyl;
$R^2$ is a single bond; and
$R^3$ is —CH=C($R^4$)$_2$, wherein each $R^4$ is —C(O)—O—$R^8$, or each $R^4$ together with the
carbon atom to which they are bonded from a substituted heterocyclohexyl ring; and each $R^8$ is $C_{1-4}$ alkyl.

Aspect 133. The compound of aspect 132, each $R^4$ is —C(O)—O—$R^8$.

Aspect 134. The compound of aspect 132, each $R^4$ is —C(O)—O—$R^8$, or each $R^4$ together with the carbon atom to which they are bonded from a substituted heterocyclohexyl ring.

Aspect 135. The compound of aspect 133, wherein in the substituted heterocyclohexyl ring, the one or more heteroatoms is oxygen.

Aspect 136. The compound of any one of aspects 134 to 135, wherein in the substituted heterocyclohexyl ring, the one or more substituents is independently selected from $C_{1-3}$ alkyl and =O.

Aspect 137. The compound of aspect 134, wherein the substituted heterocycloalkyl ring is 2,2-dimethyl-5-yl-1,3-dioxane-4,6-dione.

Aspect 138. A compound of Formula (1):

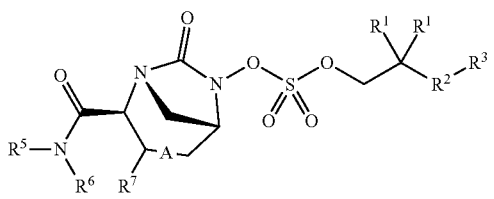

(1)

or a pharmaceutically acceptable salt thereof, wherein,
each of $R^5$, $R^6$, and $R^7$ is hydrogen;
A is a single bond;
each $R^1$ is independently selected from $C_{1-3}$ alkyl;
$R^2$ is selected from a single bond and methanediyl; and $R^3$ is substituted phenyl, wherein the one or more substituents is independently selected from —CH$_2$—O—C(O)—$R^4$ and —O—C(O)—$R^4$, wherein $R^4$ is selected from $C_{1-10}$ alkyl and phenyl.

Aspect 139. The compound of aspect 138, wherein $R^2$ is a single bond.

Aspect 140. The compound of aspect 138, wherein $R^2$ is methanediyl;

Aspect 141. The compound of aspect 138, wherein $R^2$ is 2-substituted phenyl.

Aspect 142. The compound of any one of aspects 138 to 141, wherein the one or more substituents is —CH$_2$—O—C(O)—$R^4$.

Aspect 143. The compound of any one of aspects 138 to 141, wherein the one or more substituents is —O—C(O)—$R^4$.

Aspect 144. The compound of any one of aspects 138 to 143, wherein $R^4$ is $C_{1-10}$ alkyl.

Aspect 145. The compound of any one of aspects 138 to 143, wherein $R^4$ is selected from methyl, ethyl, iso-propyl, pivalolyl, and phenyl.

Aspect 146. A compound of Formula (1):

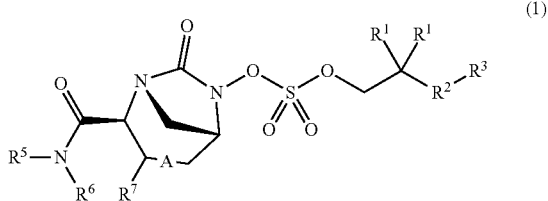

(1)

or a pharmaceutically acceptable salt thereof, wherein,
each of $R^5$, $R^6$, and $R^7$ is hydrogen;
A is a single bond;
each $R^1$ is independently selected from $C_{1-3}$ alkyl;
$R^2$ is selected from —C($R^8$)$_2$— and —CH$_2$—C(R)$_2$—, wherein each $R^8$ is independently selected from $C_{1-3}$ alkyl; and
$R^3$ is selected from —C(O)—O—$R^4$ and —O—C(O)—$R^4$, wherein $R^4$ is selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one.

Aspect 147. The compound of aspect 146, wherein each $R^1$ is methyl.

Aspect 148. The compound of any one of aspects 146 to 147, wherein $R^2$ is —C($R^8$)$_2$—.

Aspect 149. The compound of any one of aspects 146 to 147, wherein $R^2$ is —CH$_2$—C($R^8$)$_2$—

Aspect 150. The compound of any one of aspects 146 to 149, wherein each $R^8$ is methyl.

Aspect 151. The compound of any one of aspects 146 to 149, wherein each $R^1$ is methyl; and each $R^8$ is methyl.

Aspect 152. The compound of any one of aspects 146 to 151, wherein $R^3$ is —C(O)—O—$R^4$.

Aspect 153. The compound of any one of aspects 146 to 151, wherein $R^3$ is —O—C(O)—$R^4$.

Aspect 154. A compound of Formula (1):

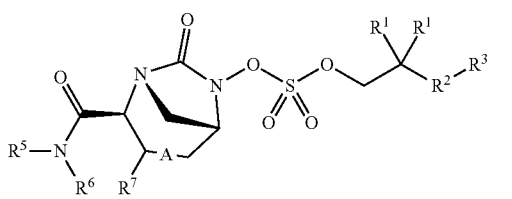

or a pharmaceutically acceptable salt thereof, wherein,
each of $R^5$, $R^6$, and $R^7$ is hydrogen;
A is a single bond;
each $R^1$ together with the carbon atom to which they are bonded form a substituted $C_{5-6}$ heterocyclic ring;
$R^2$ is a single bond; and
$R^3$ is $C_{1-3}$ alkyl.

Aspect 155. The compound of aspect 155, wherein in the substituted $C_{5-6}$ heterocyclic ring, the one or more heteroatoms is oxygen; and the one or more substituents is independently selected from $C_{1-3}$ alkyl and =O.

Aspect 156. The compound of aspect 155, wherein each $R^1$ together with the carbon atom to which they are bonded form a tetrahydro-2H-pyran-2-one ring.

Aspect 157. The compound of aspect 155, wherein,
each of $R^5$, $R^6$, and $R^7$ is hydrogen;
A is a single bond;
each $R^1$ is independently selected from $C_{1-3}$ alkyl;
$R^2$ is selected from $C_{2-4}$ alkanediyl; and
$R^3$ is substituted $C_{5-6}$ heterocycloalkyl, wherein the one or more heteroatoms is independently selected from N and O; and the one or more substituents is independently selected from $C_{1-3}$ alkyl and =O.

Aspect 158. The compound of aspect 157, wherein $R^4$ has the structure of Formula (6):

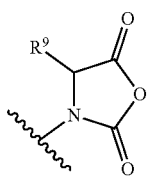

wherein $R^9$ is selected from hydrogen, $C_{1-6}$ alkyl, $C_{4-6}$ cycloalkyl, $C_{1-6}$ heteroalkyl, $C_{4-6}$ heterocycloalkyl, substituted $C_{1-6}$ alkyl, substituted $C_{4-6}$ cycloalkyl, substituted $C_{1-6}$ heteroalkyl, and substituted $C_{4-6}$ heterocycloalkyl.

Aspect 159. The compound of aspect 158, wherein $R^9$ is selected from hydrogen and $C_{1-6}$ alkyl.

Aspect 160. The compound of aspect 1, wherein the compound is selected from:
ethyl 3-(((((2S,5R)-2-carbamoyl-7-oxo-1,6-diazabicyclo[3.2.1]octan-6-yl)oxy)sulfonyl)oxy)-2,2-dimethylpropanoate (3);
benzyl 3-(((((2S,5R)-2-carbamoyl-7-oxo-1,6-diazabicyclo[3.2.1]octan-6-yl)oxy)sulfonyl)oxy)-2,2-dimethylpropanoate (4);
methyl 3-(((((2S,5R)-2-carbamoyl-7-oxo-1,6-diazabicyclo[3.2.1]octan-6-yl)oxy)sulfonyl)oxy)-2,2-dimethylpropanoate (10);
isopropyl 3-(((((2S,5R)-2-carbamoyl-7-oxo-1,6-diazabicyclo[3.2.1]octan-6-yl)oxy)sulfonyl)oxy)-2,2-dimethylpropanoate (11);
hexyl 3-(((((2S,5R)-2-carbamoyl-7-oxo-1,6-diazabicyclo[3.2.1]octan-6-yl)oxy)sulfonyl)oxy)-2,2-dimethylpropanoate (12);
heptyl 3-(((((2S,5R)-2-carbamoyl-7-oxo-1,6-diazabicyclo[3.2.1]octan-6-yl)oxy)sulfonyl)oxy)-2,2-dimethylpropanoate (13);
tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14);
2-methoxyethyl 3-(((((2S,5R)-2-carbamoyl-7-oxo-1,6-diazabicyclo[3.2.1]octan-6-yl)oxy)sulfonyl)oxy)-2,2-dimethylpropanoate (15);
oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16);
ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17);
ethyl 1-((((((2S,5R)-2-carbamoyl-7-oxo-1,6-diazabicyclo[3.2.1]octan-6-yl)oxy)sulfonyl)oxy)methyl)cyclopropanecarboxylate (18);
ethyl 1-((((((2S,5R)-2-carbamoyl-7-oxo-1,6-diazabicyclo[3.2.1]octan-6-yl)oxy)sulfonyl)oxy)methyl)cyclobutanecarboxylate (19);
hexyl 5-(((((2S,5R)-2-carbamoyl-7-oxo-1,6-diazabicyclo[3.2.1]octan-6-yl)oxy)sulfonyl)oxy)-4,4-dimethylpentanoate (36);
heptyl 5-(((((2S,5R)-2-carbamoyl-7-oxo-1,6-diazabicyclo[3.2.1]octan-6-yl)oxy)sulfonyl)oxy)-4,4-dimethylpentanoate (37);
(2S,5R)-2-carbamoyl-7-oxo-1,6-diazabicyclo[3.2.1]octan-6-yl ((3-methyl-2-oxotetrahydrofuran-3-yl)methyl) sulfate (42);
S-(3-(((((2S,5R)-2-carbamoyl-7-oxo-1,6-diazabicyclo[3.2.1]octan-6-yl)oxy)sulfonyl)oxy)-2,2-dimethylpropyl) ethanethioate (53);
propyl 3-(((((2S,5R)-2-carbamoyl-7-oxo-1,6-diazabicyclo[3.2.1]octan-6-yl)oxy)sulfonyl)oxy)-2,2-dimethylpropanoate (57);
butyl 3-(((((2S,5R)-2-carbamoyl-7-oxo-1,6-diazabicyclo[3.2.1]octan-6-yl)oxy)sulfonyl)oxy)-2,2-dimethylpropanoate (58);
(5-methyl-2-oxo-1,3-dioxol-4-yl)methyl 3-(((((2S,5R)-2-carbamoyl-7-oxo-1,6-diazabicyclo[3.2.1]octan-6-yl)oxy)sulfonyl)oxy)-2,2-dimethylpropanoate (59);
a pharmaceutically acceptable salt of any of the foregoing; and
a combination of any of the foregoing.

Aspect 161. A compound of Formula (4):

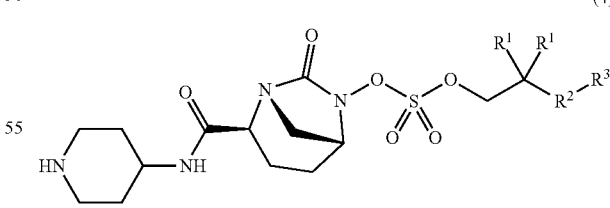

or a pharmaceutically acceptable salt thereof, wherein,
each $R^1$ is independently selected from $C_{1-3}$ alkyl, or each $R^1$ together with the carbon atom to which they are bonded form a $C_{3-6}$ cycloalkyl ring;
$R^2$ is a single bond; and
$R^3$ is —C(O)—O—$R^4$, wherein $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

Aspect 162. The compound of aspect 161, wherein each $R^1$ is independently selected from $C_{1-3}$ alkyl.

Aspect 163. The compound of aspect 161, wherein each $R^1$ together with the carbon atom to which they are bonded form a $C_{3-6}$ cycloalkyl ring.

Aspect 164. The compound of any one of aspects 161 to 163, wherein $R^4$ is selected from $C_1$-7 alkyl, $C_{1-10}$ heteroalkyl wherein the one or more heteroatoms is oxygen, —$CH_2$—$C_{4-6}$ cycloalkyl, —$(CH_2)_2$—$C_{4-6}$ cycloalkyl, $C_{3-6}$ heterocycloalkyl wherein the one or more heteroatoms is oxygen, —$CH_2$—$C_{3-6}$ substituted heterocycloalkyl, and —$(CH_2)_2$—$C_{3-6}$ substituted heterocycloalkyl.

Aspect 165. The compound of aspect 163, wherein in the substituted $C_{3-6}$ heterocycloalkyl the one or more heteroatoms is oxygen, and the one or more substituents is independently selected from $C_{1-3}$ alkyl and =O.

Aspect 166. The compound of aspect 161, wherein each $R^1$ is methyl, or each $R^1$ together with the carbon atom to which they are bonded form a cyclohexyl ring or a cyclopentyl ring.

Aspect 167. The compound of any one of aspects 161 to 166, wherein $R^4$ is selected from methyl, ethyl, n-propyl, iso-propyl, n-butyl, n-hexyl, n-heptyl, —$CH_2$—$CH_2$—O—$CH_3$, benzyl, 3-oxetanyl, and methyl-5-methyl-1,3-dioxol-2-one.

Aspect 168. The compound of aspect 161, wherein,
each of $R^5$, $R^6$, and $R^7$ is hydrogen;
A is a single bond;
$R^2$ is a single bond; and
$R^3$ is —C(O)—O—$R^4$, wherein $R^4$ is $C_{1-10}$ alkyl.

Aspect 169. A compound of Formula (4) is selected from:
ethyl2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (20);
2-methoxyethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (21);
4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (22);
4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (23);
4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidin-1-ium 2,2,2-trifluoroacetate (24);
(5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (25);
a pharmaceutically acceptable salt of any of the foregoing; and
a combination of any of the foregoing.

Aspect 170. A compound of Formula (4) is selected from:
ethyl2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (20);
4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (22);
4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (23);
(5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (25);
a pharmaceutically acceptable salt of any of the foregoing; and
a combination of any of the foregoing.

Aspect 171. A compound of Formula (5) is selected from:
ethyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate (27);
2-methoxyethyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate (28);
(5-methyl-2-oxo-1,3-dioxol-4-yl)methyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (29);
hexyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (30);
heptyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (31);
ethyl 1-(((((2S,5R)-2-((2-aminoethoxy)carbamoyl)-7-oxo-1,6-diazabicyclo[3.2.1]octan-6-yl)oxy)sulfonyl)oxy)methyl)cyclohexanecarboxylate TFA salt (32);
a pharmaceutically acceptable salt of any of the foregoing; and
a combination of any of the foregoing.

Aspect 172. A pharmaceutical composition comprising the compound of any one of aspects 76 to 171 and a pharmaceutically acceptable vehicle.

Aspect 173. The pharmaceutical composition of aspect 172, further comprising an antibiotic.

Aspect 174. The pharmaceutical composition of aspect 173, wherein the antibiotic comprises a β-lactam antibiotic.

Aspect 175. The pharmaceutical composition of any one of aspects 172 to 174, wherein the pharmaceutical composition comprises an oral dosage formulation.

Aspect 176. The pharmaceutical composition of any one of aspects 172 to 175, wherein the pharmaceutical composition comprises an oral dosage form.

Aspect 177. The pharmaceutical composition of any one of aspects 172 to 176, comprising an amount of the compound of any one of aspects 76 to 171 effective for treating a bacterial infection in a patient.

Aspect 178. A method of treating a bacterial infection in a patient comprising administering to a patient in need of such treatment a therapeutically effective amount of the compound of any one of aspects 76 to 171.

Aspect 179. The method of aspect 178, wherein administering comprises orally administering.

Aspect 180. The method of any one of aspects 178 to 179, wherein administering comprises administering an oral dosage form.

Aspect 181. The method of any one of aspects 178 to 180, further comprising administering an antibiotic to the patient.

Aspect 182. The method of any one of aspects 178 to 181, wherein the antibiotic comprises a β-lactam antibiotic.

Aspect 183. A method of treating a bacterial infection in a patient comprising administering to a patient in need of such treatment a therapeutically effective amount of the pharmaceutical composition of any one of aspects 172 to 177.

Aspect 184. The method of aspect 183, wherein administering comprises orally administering.

Aspect 185. The method of any one of aspects 183 to 184, wherein administering comprises administering an oral dosage form.

Aspect 186. The method of any one of aspects 183 to 185, further comprising administering an antibiotic to the patient.

Aspect 187. The method of aspect 184, wherein the antibiotic comprises a β-lactam antibiotic.

Aspect 188. A method of inhibiting a β-lactamase in a patient comprising administering to the patient an effective amount of the compound of any one of aspects 76 to 171.

Aspect 189. The method of aspect 188, wherein administering comprises orally administering.

Aspect 190. The of any one of aspects 188 to 189, wherein administering comprises administering an oral dosage form.

Aspect 191 A method of inhibiting a β-lactamase in a patient comprising administering to the patient an effective amount of the pharmaceutical composition of any one of aspects 172 to 177.

Aspect 192. The method of aspect 191, wherein administering comprises orally administering.

Aspect 193. The method of any one of aspects 191 to 192, wherein administering comprises administering an oral dosage form.

Aspect 194. A method of preparing a sulfate monoester analog of a cyclic hydroxamic acid comprising reacting the cyclic hydroxamic acid with a chlorosulfonate ester in the presence of a base to provide sulfate monoester analog.

Aspect 195. The method of aspect 194, wherein the cyclic hydroxamic acid has the structure of Formula (82) and the chlorosulfate ester has the structure of Formula (83):

(82)

(83)

where,

R is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

n is an integer from 1 to 6;

each A is independently selected from —(CH$_2$)—, —(CHR)—, —(CR$_2$)—, —NH—, —NR—, O, and S, where R is independently elected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; or one A is bonded to another A through a group -L-, where L is selected from $C_{1-8}$ alkyl, $C_{1-8}$ heteroalkyl, substituted $C_{1-8}$ alkyl, and substituted $C_{1-8}$ heteroalkyl.

Aspect 196. The method of aspect 194, wherein the sulfate monoester analog comprises a compound of Formula (80a) and the cyclic hydroxamic acid comprises a compound of Formula (80b):

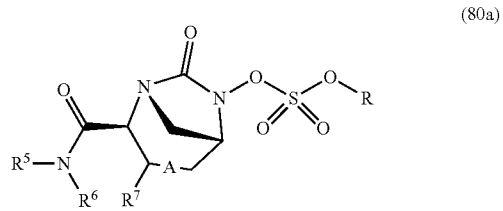

(80a)

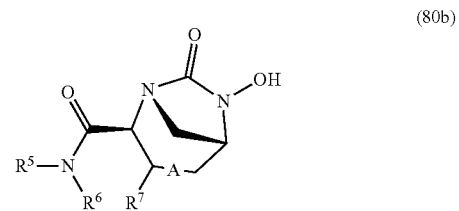

(80b)

wherein,

R is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_5$-10 heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (=) and $R^7$ is $C_{1-3}$ alkyl.

Aspect 197. The method of any one of aspects 194 to 196, wherein the chlorosulfonate monoester comprises a chlorosulfonate neopentyl ester.

Aspect 198. The method of any one of aspects 194 to 197, wherein the chlorosulfonate neopentyl ester has the structure of Formula (81):

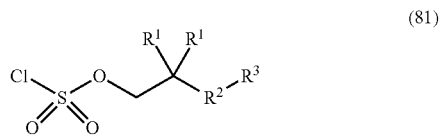

(81)

wherein,
each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and
$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—$NH_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein,
$R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 199. The method of any one of aspects 194 to 198, wherein the chlorosulfate monoester is prepared by reacting an alcohol with sulfuryl chloride.

Aspect 200. The method of aspect 199, wherein the alcohol comprises a neopentyl alcohol.

Aspect 201. The method of aspect 194, wherein the sulfate monoester analog has the structure of Formula (1):

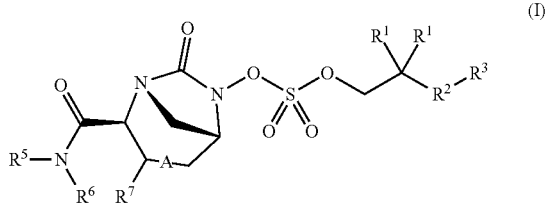

(I)

or a pharmaceutically acceptable salt thereof, wherein,
each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;
$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—$NH_2$)(—$R^4$), $C_{5-6}$ heterocycloalkyl, $C_{5-6}$ heteroaryl, substituted $C_{5-6}$ cycloalkyl, substituted $C_{5-6}$ heteeerocycloalkyl, substituted $C_{5-6}$ aryl, substituted $C_{5-6}$ heteroaryl, and —CH=C($R^4$)$_2$, wherein,
$R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;
$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;
$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and
A is a single bond (—) and $R^7$ is hydrogen, or A is a double bond (=) and $R^7$ is $C_{1-3}$ alkyl.

EXAMPLES

The following examples describe in detail the synthesis of compounds of Formula (1), characterization of compounds of Formula (1), and uses of compounds of Formula (1). It will be apparent to those skilled in the art that many modifications, both to materials and methods, may be practiced without departing from the scope of the disclosure.

Example 1

Synthesis of (2S,5R)-6-hydroxy-7-oxo-1,6-diazabicyclo[3.2.1]octane-2-carboxamide (1)

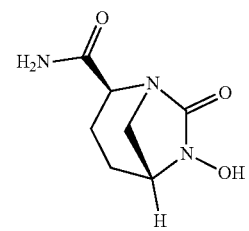 [SMILES: NC(=O)[C@@H]1CC[C@@H]2CN1C(=O)N2O]

Reference is made to International Application Publication No. WO 2012/086241 and International Application No. PCT/2012/016553, together with related procedures from the patent literature. A stirred mixture of (2S,5R)-6-(benzyloxy)-7-oxo-1,6-diazabicyclo[3.2.1]octane-2-carboxamide (550 mg, 2.0 mmol), palladium on carbon (10% by weight; 340 mg, 0.3 mmol) and MeOH (18 mL) was hydrogenated under 1 atm (balloon) until analysis by thin-layer chromatography (TLC) indicated completion of the reaction (approximately, 30 min; reaction monitored by TLC using MeOH/CH₂Cl₂ 5:95 as eluent). The mixture was filtered through a pad of Celite® and the pad was rinsed thoroughly with MeOH (ca. 20 mL). The filtrate was concentrated under vacuum (water bath temperature not exceeding 25° C.) to give the product as a clear and colorless oil. The oil was dried under vacuum for 1 h, and the residue was used immediately in the next step without further purification. Yield assumed quantitative. LC-MS: m/z=186.0 [M+H]⁺.

Example 2

Synthesis of 3-(((((2S,5R)-2-carbamoyl-7-oxo-1,6-diazabicyclo[3.2.1]octan-6-yl)oxy)sulfonyl)oxy)-2,2-dimethylpropyl benzoate (2)

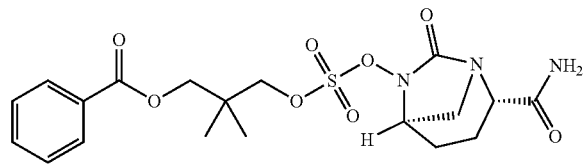 [SMILES: CC(C)(COC(=O)c1ccccc1)COS(=O)(=O)ON1C(=O)N2C[C@H]1CC[C@H]2C(N)=O]

Step 1: Synthesis of 3-hydroxy-2,2-dimethylpropyl benzoate (2a)

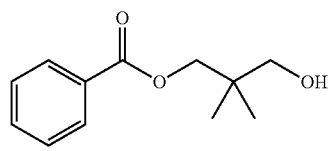

Benzoyl chloride (4.0 mL, 34.5 mmol) was added dropwise to a stirred solution of 2,2-dimethylpropane-1,3-diol (10.8 g, 103.4 mmol), pyridine (5.8 mL, 71.6 mmol) and N,N-4-dimethylaminopyridine (840 mg, 6.9 mmol) in dichloromethane (207 mL) at ca. 0° C. The mixture was stirred overnight with gradual warming to room temperature, quenched by addition of 1N HCl (100 mL) at 0° C. and extracted twice with dichloromethane. The combined organic extracts were washed with saturated aqueous NaHCO₃ (100 mL), brine (100 mL), dried (Na₂SO₄), filtered and the solvent concentrated under vacuum to leave a crude residue. The residue was split into two batches and purified by column chromatography on silica gel using EtOAc/hexanes (0:1 to 1:4) as eluent to give the product (5.95 g, 99%) as a colorless oil (note: oil dried under vacuum for 2 days). LC-MS: m/z=209.0 [M+H]⁺. ¹H NMR (300 MHz, CDCl₃): 8.05 (m, 2H), 7.58 (m, 1H), 7.45 (m, 2H), 4.19 (s, 2H), 3.38 (d, J=6.3 Hz, 2H), 2.29 (t, J=6.3 Hz, 1H), 1.02 (s, 6H).

Step 2: Synthesis of 3-((chlorosulfonyl)oxy)-2,2-dimethylpropyl benzoate (2b)

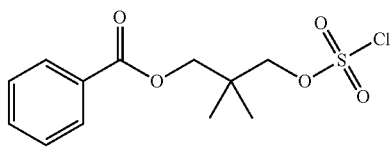 [SMILES: CC(C)(COC(=O)c1ccccc1)COS(=O)(=O)Cl]

Reference is made to *J. Am. Chem. Soc.* 2006, 128, 1605-1610. A solution of distilled sulfuryl chloride (1.2 mL, 15.8 mmol) in Et₂O (15 mL) was cooled to −78° C. under an atmosphere of argon. A solution of 3-hydroxy-2,2-dimethylpropyl benzoate (2a) (3.0 g, 14.4 mmol) and pyridine (1.2 mL, 14.4 mmol) in Et₂O (3.0 mL) was then added dropwise over 1 h via a syringe. The syringe was rinsed with Et₂O (3×1 mL), each rinse being added to the reaction mixture. The acetone/CO₂ bath was removed, and the mixture allowed to warm to room temperature, then stirred at room temperature for 4 h. TLC analysis (EtOAc/hexanes; 3:7) did not indicate complete reaction, so re-cooled to −78° C. and added more SO₂Cl₂ (0.1 mL), then allowed to warm to room temperature, and stirred for an additional 2 h. The mixture was filtered and the filtrate was concentrated under vacuum to give the product (3.97 g, 89%) as an oil. ¹H NMR (300 MHz, CDCl₃): 8.03 (m, 2H), 7.61-7.57 (m, 1H), 7.49-7.44 (m, 2H), 4.41 (s, 2H), 4.18 (s, 2H), 1.16 (s, 6H).

Step 3: Synthesis of 3-(((((2S,5R)-2-carbamoyl-7-oxo-1,6-diazabicyclo[3.2.1]octan-6-yl)oxy)sulfonyl)oxy)-2,2-dimethylpropyl benzoate (2)

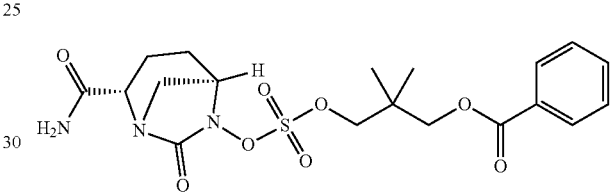

Reference is made to *J. Am. Chem. Soc.* 2006, 128, 1605-1610. (2S,5R)-6-Hydroxy-7-oxo-1,6-diazabicyclo[3.2.1]octane-2-carboxamide (1) (370 mg, 2.0 mmol) was dissolved in THF (7.0 mL) and 1,3-dimethyltetrahydropyrimidin-2(1H)-one (3.0 mL), and the resulting solution was cooled to −78° C. under an atmosphere of argon. A solution of NaHMDS in THF (1M; 2.2 mL, 2.2 mmol) was added dropwise, and the mixture was stirred at −78° C. for 10 min. 3-((Chlorosulfonyl)oxy)-2,2-dimethylpropyl benzoate (2b) (674 mg, 2.2 mmol) was then added quickly to the reaction mixture. After 10 min at −78° C., the reaction mixture was allowed to warm to room temperature and stirred at room temperature until judged complete by LC-MS and TLC analysis. EtOAc (20 mL) and saturated aqueous NaHCO₃ (20 mL) were added, and the organic and aqueous layers were partitioned. The organic layer was washed with water (3×20 mL), brine (20 mL), dried (Na₂SO₄), and concentrated under vacuum to leave a crude residue. The residue was purified by column chromatography on silica gel using EtOAc/hexanes (1:9 to 1:0) as eluent to give the product (400 mg, 43%) as a solid. After purification by column chromatography, the product appeared to degrade to a certain extent after drying the compound under vacuum over the weekend—one degradant was presumably avibactam by LC-MS, m/z=529.0 [2M−H]⁻. A portion of the material was subsequently re-purified by column chromatography on silica gel using the eluent system detailed above. The product was then stored at −20° C. immediately after isolation. LC-MS: m/z=456.2 [M+H]⁺. ¹H NMR (300 MHz, CDCl₃): δ 8.05 (d, J=6.9 Hz, 2H), 7.59-7.54 (m, 1H), 7.47-7.42 (m, 2H), 6.49 (s, 1H), 5.91 (s, 1H), 4.69 (d, J=9.3 Hz, 1H), 4.44 (d, J=9.3 Hz, 1H), 4.16-4.14 (m, 3H), 4.00 (d, J=7.5 Hz, 1H), 3.24-3.20 (m, 1H), 2.96 (d, J=11.7 Hz, 1H), 2.43-2.36 (m, 1H), 2.16-2.09 (m, 1H), 1.97-1.80 (m, 2H), 1.13 (s, 3H), 1.12 (s, 3H). $^{13}$C NMR (300 MHz, CDCl$_3$): δ 171.1, 167.1, 166.4, 133.3, 130.0, 129.8, 128.6, 80.7, 69.1, 62.0, 60.2, 47.1, 35.7, 21.5, 20.8, 17.6.

Example 3

Synthesis of ethyl 3-(((((2S,5R)-2-carbamoyl-7-oxo-1,6-diazabicyclo[3.2.1]octan-6-yl)oxy)sulfonyl)oxy)-2,2-dimethylpropanoate (3)

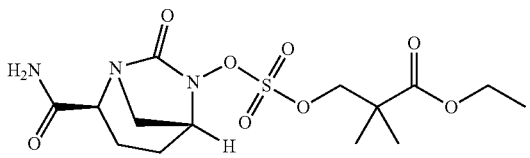 [SMILES: CCOC(=O)C(C)(C)COS(=O)(=O)ON1C(=O)N2C[C@H]1CC[C@H]2C(N)=O]

Step 1: Synthesis of ethyl 3-((chlorosulfonyl)oxy)-2,2-dimethylpropanoate (3a)

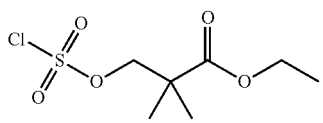

A solution of distilled sulfuryl chloride (0.55 mL, 7.5 mmol) in Et$_2$O (10 mL) was cooled to −78° C. under an atmosphere of argon. A solution of ethyl 3-hydroxy-2,2-dimethylpropanoate (2a) (1.0 g, 6.8 mmol) and pyridine (0.55 mL, 6.8 mmol) in Et$_2$O (1.0 mL) was then added dropwise over 1 h via a syringe. The syringe was rinsed with Et$_2$O (3×1 mL), each rinse being added to the reaction mixture. The acetone/CO$_2$ bath was removed, and the mixture was allowed to warm to room temperature, then stirred at room temperature for 4 h. TLC analysis (EtOAc/hexanes; 3:7) did not indicate that the reaction was complete. The mixture was re-cooled to −78° C. and more SO$_2$Cl$_2$ (0.11 mL) was added, and the mixture allowed to warm to room temperature and stirred for an additional 2 h. The mixture was filtered and the filtrate was concentrated under vacuum to give the product (yield assumed quantitative). $^1$H NMR (300 MHz, CDCl$_3$): δ 4.50 (s, 2H), 4.19 (q, J=6.9 Hz, 2H), 1.31 (s, 6H), 1.28 (t, J=6.9 Hz, 3H).

Step 2: Synthesis of ethyl 3-(((((2S,5R)-2-carbamoyl-7-oxo-1,6-diazabicyclo[3.2.1]octan-6-yl)oxy)sulfonyl)oxy)-2,2-dimethylpropanoate (3)

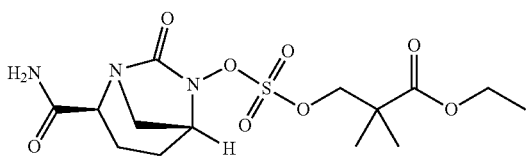 [SMILES: CCOC(=O)C(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (370 mg, 2.0 mmol) was dissolved in THF (7.0 mL) and 1,3-dimethyltetrahydropyrimidin-2(1H)-one (3.0 mL) and the resulting solution was cooled to −78° C. under an atmosphere of argon. A solution of NaHMDS in THF (1M; 2.2 mL, 2.2 mmol) was added dropwise, and the mixture was stirred at −78° C. for 10 min. A solution of ethyl 3-((chlorosulfonyl)oxy)-2,2-dimethylpropanoate (3a) (538 mg, 2.2 mmol) in THF (1 mL) was then added quickly to the reaction mixture via syringe. The syringe was rinsed with THF (3×0.5 mL), each rinse being added to the reaction mixture. After 10 min at −78° C., the reaction mixture was allowed to warm to room temperature and stirred at room temperature until judged complete by LC-MS and TLC analysis (ca. 2 h). EtOAc (20 mL) and saturated aqueous NaHCO$_3$ (20 mL) were added and the organic and aqueous layers were partitioned. The organic layer was washed with saturated NaHCO$_3$ (20 mL), water (3×20 mL), brine (20 mL), dried (Na$_2$SO$_4$) and concentrated under vacuum to leave a crude residue. The residue was purified by column chromatography on silica gel using EtOAc/hexanes (1:9 to 1:0) as eluent to give the product (318 mg, 39%) as a solid. LC-MS: m/z=394.1 [M+H]$^+$. $^1$H NMR (CDCl$_3$, 300 MHz): δ 6.50 (s, 1H), 5.78 (s, 1H), 4.71 (d, J=8.7 Hz, 1H), 4.59 (d, J=8.7 Hz, 1H), 4.22-4.12 (m, 3H), 4.05 (d, J=6.9 Hz, 1H), 3.34-3.30 (m, 1H), 3.01 (d, J=12.3 Hz, 1H), 2.46-2.40 (m, 1H), 2.18-2.12 (m, 1H), 2.00-1.79 (m, 2H), 1.28-1.24 (m, 9H). $^{13}$C NMR (300 MHz, CDCl$_3$): δ 174.2, 171.2, 167.1, 80.5, 61.9, 61.4, 60.2, 47.2, 42.8, 22.2, 21.7, 20.8, 17.5, 14.2.

Example 4

Synthesis of benzyl 3-(((((2S,5R)-2-carbamoyl-7-oxo-1,6-diazabicyclo[3.2.1]octan-6-yl)oxy)sulfonyl)oxy)-2,2-dimethylpropanoate (4)

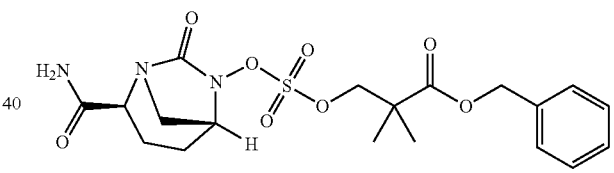

Step 1: Synthesis of benzyl 3-((chlorosulfonyl)oxy)-2,2-dimethylpropanoate (4a)

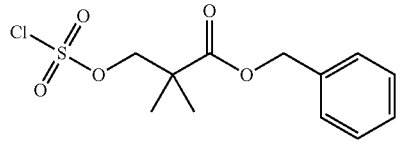 [SMILES: CC(C)(COS(=O)(=O)Cl)C(=O)OCc1ccccc1]

A solution of distilled sulfuryl chloride (0.77 mL, 10.6 mmol) in Et$_2$O (10 mL) was cooled to −78° C. under an atmosphere of argon. A solution of ethyl 3-hydroxy-2,2-dimethylpropanoate (2a) (Sigma-Aldrich; 2.0 g, 9.6 mmol) and pyridine (0.85 mL, 10.6 mmol) in Et$_2$O (2.0 mL) was then added dropwise over 1 h via a syringe. The syringe was rinsed with Et$_2$O with each rinse being added to the reaction mixture. The acetone/CO$_2$ bath was removed and the mixture allowed to warm to room temperature, then stirred at room temperature for 30 min. TLC analysis (EtOAc/hexanes; 3:7) did not indicate complete reaction, so re-cooled to −78° C. and added more SO$_2$Cl$_2$ (0.07 mL), then allowed to warm to room temperature and stirred for an additional 1 h. Et$_2$O (5 mL) was added and the mixture stirred for a few min, then filtered and the filtrate concentrated under vacuum to give the product (2.19 g, 75%). $^1$H NMR (300 MHz, CDCl$_3$): δ 7.41-7.32 (m, 4H), 5.18 (s, 2H), 4.52 (s, 2H), 1.34 (s, 6H).

Step 2: Synthesis of benzyl 3-(((((2S,5R)-2-carbamoyl-7-oxo-1,6-diazabicyclo[3.2.1]octan-6-yl)oxy)sulfonyl)oxy)-2,2-dimethylpropanoate (4)

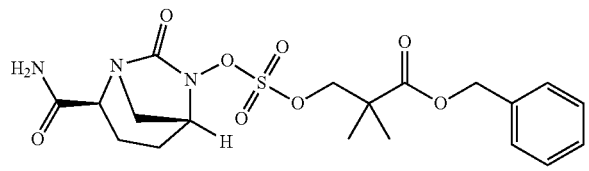 [SMILES: CC(C)(COS(=O)(=O)ON1C(=O)N2C[C@H]1CC[C@H]2C(N)=O)C(=O)OCc1ccccc1]

(2S,5R)-6-Hydroxy-7-oxo-1,6-diazabicyclo[3.2.1]octane-2-carboxamide (1) (370 mg, 2.0 mmol) was dissolved in THF (7.0 mL) and 1,3-dimethyltetrahydropyrimidin-2 (1H)-one (2.0 mL) was added, and the resulting solution was cooled to −78° C. under an atmosphere of argon. A solution of NaHMDS in THF (1M; 2.2 mL, 2.2 mmol) was added dropwise, and the mixture was stirred at −78° C. for 10 min. A solution of ethyl benzyl 3-((chlorosulfonyl)oxy)-2,2-dimethylpropanoate (4a) (674 mg, 2.2 mmol) in THF (1 mL) was then added quickly to the reaction mixture via syringe. The syringe was rinsed with THF (3×0.5 mL), each rinse being added to the reaction mixture. After 10 min at −78° C., the reaction mixture was allowed to warm to room temperature and stirred at room temperature until judged complete by LC-MS and TLC analysis. EtOAc (20 mL) and saturated aqueous NaHCO$_3$ (20 mL) were added, and the organic and aqueous layers were partitioned. The organic layer was washed with saturated NaHCO$_3$ (20 mL), water (3×20 mL), brine (20 mL), dried (Na$_2$SO$_4$) and concentrated under vacuum to leave a crude residue. The residue was purified by column chromatography on silica gel using EtOAc/hexanes (1:9 to 1:0) as eluent to give the product (244 mg, 26%) as a solid. LC-MS: m/z=456.2 [M+H]$^+$. $^1$H NMR (CDCl$_3$, 300 MHz): δ 7.39-7.28 (m, 4H), 6.49 (s, 1H), 5.84 (s, 1H), 5.20-5.11 (m, 2H), 4.74 (d, J=9.0 Hz, 1H), 4.61 (d, J=9.0 Hz, 1H), 4.15-4.14 (m, 1H), 4.04 (d, J=6.9 Hz, 1H), 3.29-3.25 (m, 1H), 2.99 (d, J=11.7 Hz, 1H), 2.45-2.38 (m, 1H), 2.17-2.10 (m, 1H), 1.99-1.78 (m, 2H), 1.30 (s, 3H), 1.29 (s, 3H). $^{13}$C NMR (CDCl$_3$, 75 MHz): δ 174.1, 171.1, 167.1, 135.7, 128.7, 128.4, 128.0, 80.3, 67.0, 62.0, 60.2, 47.2, 43.0, 22.2, 21.7, 20.8, 17.5.

Example 5

Synthesis of (2S,5R)-2-carbamoyl-7-oxo-1,6-diazabicyclo[3.2.1]octan-6-yl phenyl sulfate (5)

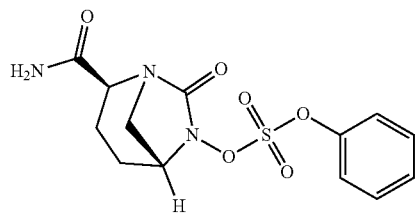 [SMILES: NC(=O)[C@@H]1CC[C@@H]2CN1C(=O)N2OS(=O)(=O)Oc1ccccc1]

Step 1: Synthesis of Phenyl Sulfochloridate (5a)

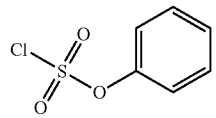 [SMILES: O=S(=O)(Cl)Oc1ccccc1]

Reference is made to *J. Am. Chem. Soc.* 2013, 135, 10638-10641. A solution of distilled sulfuryl chloride (2.6 mL, 35.1 mmol) in Et$_2$O (30 mL) was cooled to −78° C. under an atmosphere of argon. A solution of phenol (3.0 g, 31.9 mmol) in Et$_2$O (3.0 mL) and pyridine (2.6 mL, 31.9 mmol) were then added concurrently, but from different syringes, dropwise over 1 h. The syringes were each rinsed with Et$_2$O and each rinse was added to the reaction mixture. The mixture was allowed to warm to room temperature slowly, and stirred at room temperature overnight. The mixture was filtered, and the filtrate concentrated under vacuum to give the product (4.65 g), contaminated with other products and phenol starting material. The phenyl sulfochloridate product was not purified further and was used directly in the next step.

Step 2: Synthesis of (2S,5R)-2-carbamoyl-7-oxo-1, 6-diazabicyclo[3.2.1]octan-6-yl phenyl sulfate (5)

(2S,5R)-6-Hydroxy-7-oxo-1,6-diazabicyclo[3.2.1]octane-2-carboxamide (1) (370 mg, 2.0 mmol) was dissolved in THF (7.0 mL) and 1,3-dimethyltetrahydropyrimidin-2 (1H)-one (2.0 mL) and the resulting solution was cooled to −78° C. under an atmosphere of argon. A solution of NaHMDS in THF (1M; 2.2 mL, 2.2 mmol) was added dropwise and the mixture was stirred at −78° C. for 10 min. Neat phenyl sulfochloridate (5a) (423 mg, 2.2 mmol) was then added quickly to the reaction mixture via syringe. The syringe was rinsed with THF (3×0.5 mL), each rinse being added to the reaction mixture. After 10 min at −78° C., the reaction mixture was allowed to warm to room temperature and stirred at room temperature until judged complete by LC-MS and TLC analysis (ca. 1 h). EtOAc (20 mL) and saturated aqueous NaHCO$_3$ (20 mL) were added, and the organic and aqueous layers were partitioned. The organic layer was washed with saturated NaHCO$_3$ (20 mL), water (3×20 mL), brine (20 mL), dried (Na$_2$SO$_4$), and concentrated under vacuum to leave a crude residue. The residue was purified by column chromatography on silica gel using EtOAc/hexanes (1:9 to 1:0) as eluent to give the product (126 mg, 18%) as a solid. LC-MS: m/z=342.2 [M+H]$^+$. 1H NMR (300 MHz, CDCl3): δ 7.54-7.51 (m, 2H), 7.47-7.42 (m, 2H), 7.39-7.33 (m, 1H), 6.53 (s, 1H), 5.88 (s, 1H), 4.24 (fd, J=2.4 Hz, 1H), 4.09 (d, J=6.9 Hz, 1H), 3.34 (d, J=11.7 Hz, 1H), 3.05 (d, J=12.3 Hz, 1H), 2.46-2.39 (m, 1H), 2.19-2.11 (m, 1H), 2.02-1.81 (m, 2H). $^{13}$C NMR (75 MHz, CDCl$_3$): δ 171.2, 166.8, 150.9, 130.2, 128.1, 121.3, 62.1, 60.6, 47.0, 20.8, 17.6.

Example 6

Synthesis of 4-(((((2S,5R)-2-carbamoyl-7-oxo-1,6-diazabicyclo[3.2.1]octan-6-yl)oxy)sulfonyl)oxy)-3,3-dimethylbutyl benzoate (6)

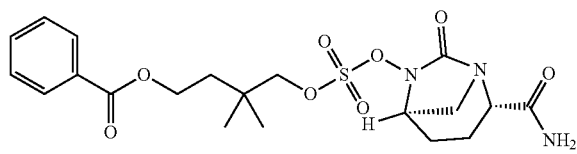 [SMILES: CC(C)(CCOC(=O)c1ccccc1)COS(=O)(=O)ON1C(=O)N2C[C@H]1CC[C@H]2C(N)=O]

Step 1: Synthesis of 2,2-dimethylbutane-1,4-diol (6a)

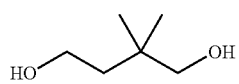

A solution of 2,2-dimethylsuccinic acid (10.0 g, 68.4 mmol) in THF (150 mL) was added dropwise to a suspension of lithium aluminum hydride (8.3 g, 219.0 mmol) in THF (80 mL) at 0° C. (ice bath). The mixture was warmed to room temperature over 20 min and then heated at reflux for 1.5 h. Upon completion (reaction monitored by TLC using MeOH/CH$_2$Cl$_2$ 5:95 as eluent) the reaction was quenched very carefully and dropwise by the addition of water (10 mL), 3 M NaOH (15 mL), and water (20 mL). The mixture was stirred at room temperature for 20 min, and the solids filtered over a pad of Celite®. The filter cake was rinsed thoroughly with THF. The filtrate was concentrated under vacuum giving a mixture of the title compound and unidentified by-products as a crude oil. The oil was purified by column chromatography on silica gel using MeOH/CH$_2$Cl$_2$ (0:1 to 1:9) as eluent to afford the product (4.649 g, 57%) as an oil. $^1$H-NMR (300 MHz, CDCl$_3$): δ 4.11 (s, 2H), 3.66 (t, J=5.9 Hz, 2H), 3.30 (s, 2H), 1.52 (t, J=5.6 Hz, 2H), 0.89 (s, 6H).

Step 2: Synthesis of 4-hydroxy-3,3-dimethylbutyl benzoate (6b)

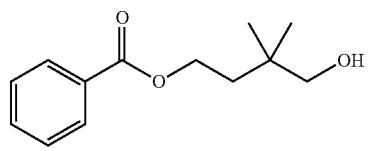 [SMILES: CC(C)(CO)CCOC(=O)c1ccccc1]

To a stirred solution of 2,2-dimethylbutane-1,4-diol (6a) (0.30 g, 2.5 mmol) in anhydrous dichloromethane (9 mL) was added benzoyl chloride (0.30 mL, 2.5 mmol), Et$_3$N (0.71 mL, 5.1 mmol), and a catalytic amount of N,N-4-dimethylaminopyridine at 0° C. (ice bath). The mixture was gradually warmed to room temperature and stirred overnight. After the starting material was completely consumed (reaction monitored by TLC using EtOAc/hexanes 2:8 as eluent), the reaction was quenched by the addition of 1N HCl (20 mL) at 0° C. (ice bath), and the mixture was extracted twice with dichloromethane. The combined organic layers were washed with saturated aqueous NaHCO$_3$, brine, dried (Na$_2$SO$_4$), filtered and the solvent concentrated to yield a mixture, of at least two products, as a clear and colorless oil. The oil was purified by column chromatography on silica gel using EtOAc/hexanes (0:1 to 4:6) as eluent to give the product (0.29 g, 51%) as an oil (which was dried under high vacuum for 2 d). $^1$H-NMR (300 MHz, CDCl$_3$): δ 8.04-8.01 (m, 2H), 7.58-7.53 (m, 1H), 7.46-7.41 (m, 2H), 4.41 (t, J=7.4 Hz, 2H), 3.41 (s, 2H), 1.78 (t, J=7.4 Hz, 2H), 1.70 (s, 1H), 0.99 (s, 6H).

Step 3: Synthesis of 4-((chlorosulfonyl)oxy)-3,3-dimethylbutyl benzoate (6c)

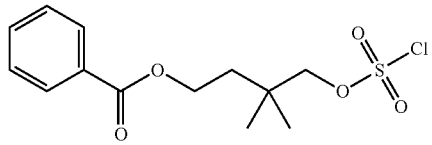 [SMILES: CC(C)(CCOC(=O)c1ccccc1)COS(=O)(=O)Cl]

A solution of freshly distilled sulfuryl chloride (0.11 mL, 1.5 mmol) in Et$_2$O (3 mL) was cooled to −78° C. under an atmosphere of Ar. A solution of 4-hydroxy-3,3-dimethylbutyl benzoate (6b) (0.28 g, 1.3 mmol) and pyridine (0.10 ml, 1.3 mmol) in Et$_2$O (2 mL) was added dropwise (over 1 h) to the cooled solution. The mixture was warmed to room temperature and stirred for 30 min (reaction was monitored by TLC using EtOAc/hexanes 2:8 as eluent). The mixture was re-cooled to −78° C. and sulfuryl chloride (0.02 mL) was added. The mixture was allowed to warm to room temperature, and stirred for 30 min. Et$_2$O (5 mL) was added and the mixture stirred for a few minutes. The mixture was filtered and the filtrate concentrated under vacuum to give the product (0.305 g, 75%). $^1$H-NMR (300 MHz, CDCl$_3$): δ 8.03 (d, J=8.1 Hz, 2H), 7.60-7.54 (m, 1H), 7.47-7.42 (m, 2H), 4.44-4.38 (m, 2H), 4.29 (s, 2H), 1.89-1.85 (m, 2H), 1.13 (s, 6H).

Step 4: Synthesis of 4-(((((2S,5R)-2-carbamoyl-7-oxo-1,6-diazabicyclo[3.2.1]octan-6-yl)oxy)sulfonyl)oxy)-3,3-dimethylbutyl benzoate (6)

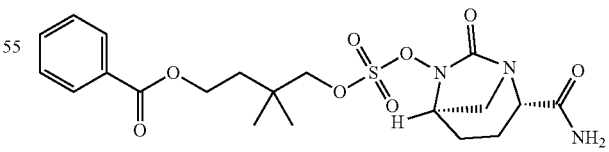

(2S,5R)-6-Hydroxy-7-oxo-1,6-diazabicyclo[3.2.1]octane-2-carboxamide (1) (176 mg, 1.0 mmol) was dissolved in THF (4 mL) and 1,3-dimethyltetrahydropyrimidin-2(1H)-one (1 mL) and the resulting solution was cooled to −78° C. under an atmosphere of Argon. NaHMDS (1.0 M in THF; 1.05 mL, 1.05 mmol) was added dropwise to the cooled solution and the mixture was stirred at −78° C. for 10 min.

4-((chlorosulfonyl)oxy)-3,3-dimethylbutyl benzoate (6c) (305 mg, 1.0 mmol) in THF (0.5 mL) was added quickly to the mixture. The syringe was rinsed with THF (3×0.5 mL) and this was also added to the mixture. After 10 min, the mixture was warmed to room temperature and stirred until judged complete by TLC analysis. EtOAc (10 mL) and saturated aqueous NaHCO₃ (10 mL) were added to the mixture and the organic and aqueous layers were partitioned. The organic layer was washed with saturated aqueous NaHCO₃ (10 mL), water (6×10 mL), brine (10 mL), dried (Na₂SO₄), filtered and concentrated under vacuum. Purification by column chromatography on silica gel using EtOAc/hexanes (1:9 to 1:0) as eluent gave the product (6) (215 mg, 18%) as a solid. LC-MS: 470.2 [M+H]⁺. 1H-NMR (300 MHz, CDCl3): δ 8.04-8.01 (m, 2H), 7.58-7.53 (m, 1H), 7.46-7.41 (m, 2H), 6.48 (s, 1H), 5.80 (s, 1H), 4.60 (d, J=9.3 Hz, 1H), 4.40 (t, J=6.9 Hz, 2H), 4.29 (d, J=9.3 Hz, 1H), 4.17-4.16 (m, 1H), 4.02 (d, J=7.8 Hz, 1H), 3.34-3.30 (m, 1H), 3.00 (d, J=12.3 Hz, 1H), 2.45-2.35 (m, 1H), 2.17-2.11 (m, 1H), 1.98-1.78 (m, 4H), 1.10 (s, 6H). ¹³C-NMR (75 MHz, CDCl3): δ 171.1, 167.1, 166.6, 133.1, 130.2, 129.7, 128.5, 83.7, 61.9, 61.5, 60.2, 47.2, 36.9, 34.1, 24.1, 23.8, 20.8, 17.5.

Example 7

Synthesis of 4-(((((2S,5R)-2-carbamoyl-7-oxo-1,6-diazabicyclo[3.2.1]octan-6-yl)oxy)sulfonyl)oxy)-3,3-dimethylbutyl propionate (7)

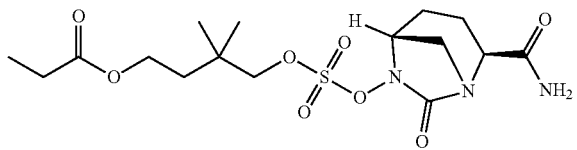 [SMILES: CCC(=O)OCCC(C)(C)COS(=O)(=O)ON1C(=O)N2C[C@H]1CC[C@H]2C(N)=O]

Step 1: Synthesis of 4-hydroxy-3,3-dimethylbutyl propionate (7a)

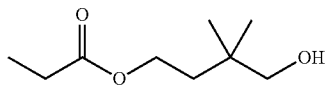

A solution of propionyl chloride (0.74 mL, 8.5 mmol) in anhydrous dichloromethane (5 mL) was added to a stirred solution of 2,2-dimethylbutane-1,4-diol (6a) (1.00 g, 8.5 mmol), Et₃N (2.4 mL, 16.9 mmol), and 4-N,N-dimethylaminopyridine (52 mg) in anhydrous dichloromethane (20 mL) at −78° C. under an atmosphere of argon. The mixture was stirred for 10 min and then allowed to warm to room temperature, stirred at room temperature for 1 h, then re-cooled to −78° C., and allowed to warm to room temperature slowly by allowing the mixture to stay in the cold bath and letting the dry ice sublime (recommended to allow warming to room temperature from −78° C. after addition of all the reagents). After the starting material was completely consumed (TLC 50% EtOAc/hexanes), the reaction was quenched by the addition of 0.5 N HCl (10 mL) at 0° C. The organic and aqueous layers were partitioned, and the aqueous layer was extracted with dichloromethane (2×20 mL). The combined organic layers were washed with saturated aqueous NaHCO₃ (20 mL), brine (20 mL), then dried (Na₂SO₄), filtered and the solvent concentrated under vacuum to leave a crude oil. The oil was purified by column chromatography on silica gel using EtOAc/hexanes (0:1 to 4:1) as eluent to give the product (7a) (463 mg, 22%) as an oil, contaminated with significant EtOAc solvent residues. ¹H-NMR (300 MHz, CDCl₃): δ 4.14 (t, J=7.4 Hz, 2H), 3.32 (s, 2H), 2.30 (q, J=7.6 Hz, 2H), 1.88 (s, 1H), 1.61 (t, J=7.7 Hz, 2H), 1.13 (t, J=7.5 Hz, 3H), 0.91 (fd, J=1.2 Hz, 6H).

Step 2: Synthesis of 4-((chlorosulfonyl)oxy)-3,3-dimethylbutyl propionate (7b)

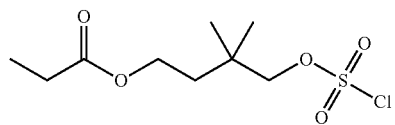 [SMILES: CCC(=O)OCCC(C)(C)COS(=O)(=O)Cl]

A solution of freshly distilled sulfuryl chloride (0.15 mL, 2.0 mmol) in Et₂O (3.5 mL) was cooled to −78° C. under an atmosphere of argon. A solution of 4-hydroxy-3,3-dimethylbutyl propionate (7a) (73% purity, the remainder being EtOAc; 441 mg, 1.8 mmol) and pyridine (0.15 mL, 1.8 mmol) in Et₂O (2.5 mL) was added dropwise over 1 h to the cooled solution. The mixture was allowed to warm to room temperature and was stirred for 30 min (monitored by TLC, 30% EtOAc/hexanes), re-cooled to −78° C. and sulfuryl chloride (0.03 mL) and pyridine (0.03 mL) was added, warmed to room temperature, and stirred for 30 min. Again, the mixture was re-cooled to −78° C. and another portion of sulfuryl chloride (0.15 mL) was added. The mixture was allowed to warm to room temperature, and stirred for 30 min. Et₂O (5 mL) was added and the mixture stirred for a few min. The mixture was filtered and the filtrate was concentrated under vacuum to give the product (7b) (401 mg, 79%). ¹H-NMR: (300 MHz, CDCl₃): 4.22 (s, 2H), 4.14 (t, J=6.8 Hz, 2H), 2.30 (q, J=7.6 Hz, 2H), 1.70 (t, J=6.8 Hz, 2H), 1.11 (t, J=7.7 Hz, 3H), 1.05 (s, 6H).

Step 3: Synthesis of 4-(((((2S,5R)-2-carbamoyl-7-oxo-1,6-diazabicyclo[3.2.1]octan-6-yl)oxy)sulfonyl)oxy)-3,3-dimethylbutyl propionate (7)

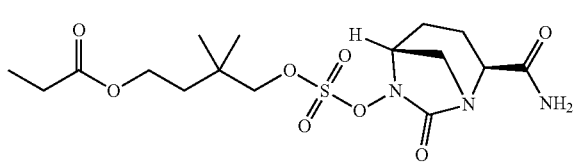 [SMILES: CCC(=O)OCCC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (185 mg, 1.0 mmol) was dissolved in THF (4 mL) and 1,3-dimethyltetrahydropyrimidin-2(1H)-one (1 mL) under an atmosphere of argon. The resulting solution was cooled to −78° C. NaHMDS (1.0 M in THF; 1.1 mL, 1.1 mmol) was added dropwise to the cooled solution and the mixture stirred for 10 min. 4-((chlorosulfonyl)oxy)-3,3-dimethylbutyl propionate (7b) (272 mg, 1.0 mmol) in THF (1 mL) was added quickly to the reaction mixture. The syringe was rinsed with THF (3×0.5 mL) and this was also added to the mixture. Further THF (3 mL) was added to the mixture to allow efficient stirring of the reaction. After 10 min, the mixture was allowed to warm to room temperature. Upon completion (1 h; TLC, 70% EtOAc/hexanes), EtOAc (10 mL) and saturated aqueous NaHCO$_3$ (10 mL) were added to the mixture. The aqueous and organic layers were partitioned, and the organic layer was washed with saturated aqueous NaHCO$_3$ (10 mL), water (6×10 mL), brine (10 mL), then dried (Na$_2$SO$_4$), filtered and the solvent concentrated under vacuum to leave a crude residue. The residue was purified by column chromatography on silica gel using EtOAc/hexanes (1:0 to 1:0) as eluent to give the product (7) (93 mg, 22%) as a solid. LC-MS: 422.1 [M+H]$^+$. $^1$H-NMR (300 MHz, CDCl$_3$): δ 6.51 (s, 1H), 5.76 (s, 1H), 4.54 (d, J=8.7 Hz, 1H), 4.25 (d, J=8.7 Hz, 1H), 4.17-4.12 (m, 3H), 4.04 (d, J=6.9 Hz, 1H), 3.36-3.32 (m, 1H), 3.02 (d, J=12.3 Hz, 1H), 2.47-2.40 (m, 1H), 2.32 (q, J=7.6 Hz, 2H), 2.18-2.15 (m, 1H), 2.00-1.79 (m, 2H), 1.75-1.61 (m, 2H), 1.13 (t, J=7.7 Hz, 3H), 1.03 (s, 6H). $^{13}$C-NMR (75 MHz, CDCl$_3$): δ 174.5, 171.0, 167.1, 83.6, 62.0, 60.8, 60.2, 47.2, 36.8, 34.0, 27.7, 24.1, 23.7, 20.8, 17.6, 9.2.

Example 8

Synthesis of benzyl (4-(((((2S,5R)-2-carbamoyl-7-oxo-1,6-diazabicyclo[3.2.1]octan-6-yl)oxy)sulfonyl)oxy)-3,3-dimethylbutyl) adipate (8)

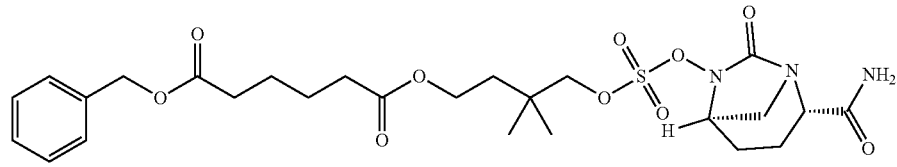 [SMILES: CC(C)(CCOC(=O)CCCCC(=O)OCc1ccccc1)COS(=O)(=O)ON1C(=O)N2C[C@H]1CC[C@H]2C(N)=O]

Step 1: Synthesis of benzyl (perfluorophenyl) adipate (8a)

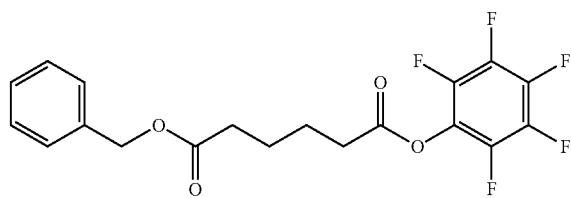 [SMILES: O=C(CCCCC(=O)Oc1c(F)c(F)c(F)c(F)c1F)OCc1ccccc1]

To a stirring solution of adipic acid monobenzyl ester (1.03 g, 4.3 mmol) and pentafluorophenol (0.87 g, 4.7 mmol) in EtOAc (18.7 mL) at 0° C. was added N,N'-dicyclohexylcarbodiimide (0.97 g, 4.7 mmol). The mixture was allowed to warm to room temperature and then stirred overnight. The resulting solid was removed by vacuum filtration through a pad of Celite®. The filter cake was washed with EtOAc. The filtrate was dry-loaded on to silica gel and purified by column chromatography on silica gel using EtOAc/hexanes (0:1 to 4:6) as eluent, to give the product (8a) (1.59 g, 93%) as a solid. $^1$H NMR (300 MHz, CDCl$_3$): δ 7.37-7.35 (m, 5H), 5.13 (s, 2H), 2.68 (t, J=6.8 Hz, 2H), 2.44 (t, J=6.5 Hz, 2H), 1.82-1.78 (m, 4H).

Step 2: Synthesis of benzyl (4-hydroxy-3,3-dimethylbutyl) adipate (8b)

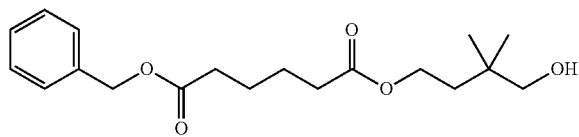 [SMILES: CC(C)(CO)CCOC(=O)CCCCC(=O)OCc1ccccc1]

To a stirred solution of 2,2-dimethylbutane-1,4-diol (6a) (0.22 g, 1.8 mmol) in anhydrous dichloromethane (4 mL) at ca. 0° C. (ice bath), under an atmosphere of argon, was added benzyl (perfluorophenyl) adipate (8a) (0.36 g, 0.9 mmol), Et$_3$N (0.25 mL, 1.8 mmol), and a catalytic amount of 4-N,N-dimethylaminopyridine (small unweighed amount). The mixture was gradually warmed to room temperature, and then at room temperature overnight. The mixture was dry-loaded on to silica gel and purified by column chromatography on silica gel using EtOAc/hexanes (0:1 to 3:7) as eluent to give the product contaminated with regio-isomeric product. This mixture was re-purified by column chromatography on silica gel using EtOAc/hexanes (0:1 to 3:7) as eluent to give pure product (8b) (113 mg 38%). $^1$H-NMR (300 MHz, CDCl$_3$): 7.36-7.34 (m, 5H), 5.11 (s, 2H), 4.14 (t, J=7.2 Hz, 2H), 3.34 (d, J=5.7 Hz, 2H), 2.38-2.31 (m, 4H), 1.68-1.59 (m, 6H), 0.92 (s, 6H). The reaction could be repeated to give larger amounts of material.

Step 3: Synthesis of benzyl (4-((chlorosulfonyl)oxy)-3,3-dimethylbutyl) adipate (8c)

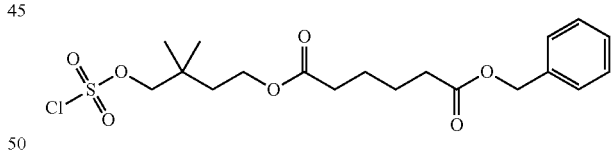

A solution of freshly distilled sulfuryl chloride (0.12 ml, 1.6 mmol) in Et$_2$O (5 mL) was cooled to −78° C. under an atmosphere of argon. A solution of benzyl (4-hydroxy-3,3-dimethylbutyl) adipate (8b) (446 mg, 1.3 mmol) and pyridine (0.11 mL, 1.3 mmol) in Et$_2$O (3.5 mL) was added dropwise over 1 h to the cooled solution. The mixture was allowed to warm to room temperature and was stirred for 30 min (monitored by TLC, 30% EA/hex). The reaction was not complete, so the mixture was recooled to −78° C., then sulfuryl chloride (0.05 mL) and pyridine (0.05 mL) were added. The mixture was allowed to warm to room temperature, and stirred for 30 min. Et$_2$O (5 mL) was added, and the mixture was stirred for a few mins. The mixture was filtered and the filtrate was concentrated under vacuum to give the product (8c) (446 mg, 77%). $^1$H-NMR (300 MHz, CDCl$_3$): δ 7.39-7.29 (m, 5H), 5.11 (s, 2H), 4.22 (s, 2H), 4.15 (t, J=6.8 Hz, 2H), 2.40-2.29 (m, 4H), 1.73-1.59 (m, 6H), 1.06 (s, 6H).

Step 4: Synthesis of benzyl (4-(((((2S,5R)-2-carbamoyl-7-oxo-1,6-diazabicyclo[3.2.1]octan-6-yl)oxy)sulfonyl)oxy)-3,3-dimethylbutyl) adipate (8)

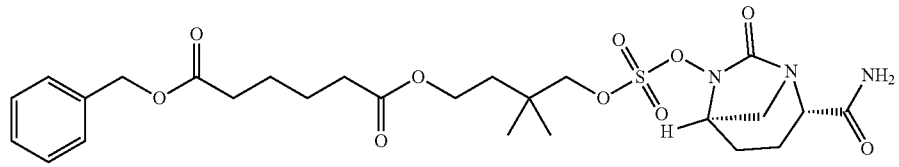 [SMILES: CC(C)(CCOC(=O)CCCCC(=O)OCc1ccccc1)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (185 mg, 1.0 mmol) was dissolved in THF (9 mL) and 1,3-dimethyltetrahydropyrimidin-2(1H)-one (1 mL), and the resulting solution was cooled to −78° C. under an atmosphere of argon. NaHMDS (1.0 M solution in THF; 1.1 mL, 1.1 mmol) was added dropwise to the cooled solution and stirred for 10 min. Benzyl (4-((chlorosulfonyl)oxy)-3,3-dimethylbutyl) adipate (8c) (435 mg, 1.0 mmol) in THF (1 mL) was added quickly to the mixture. The syringe was rinsed with THF (3×0.5 mL) and this was also added to the mixture. After 10 min, the mixture was allowed to warm to room temperature. Upon completion (30 min; TLC, 70% EtOAc/hexanes), EtOAc (10 mL) and saturated aqueous NaHCO$_3$ (10 mL) were added. The aqueous and organic layers were partitioned and the organic layer was washed with saturated aqueous NaHCO$_3$ (10 mL), water (3×10 mL), brine (10 mL), then dried (Na$_2$SO$_4$), filtered and concentrated under vacuum to leave a crude residue. The residue was purified by column chromatography on silica gel using EtOAc/hexanes (1:9 to 1:0) as eluent to give a solid. The solid was triturated with Et$_2$O (2×2 mL) to give the product (8) (43 mg, 7%) as a solid [together with less pure material (99 mg, 93% purity), which was used in the next step without further purification]. Data for the 43 mg of pure product is detailed below. LC-MS: 584.2 [M+H]$^+$. $^1$H-NMR (300 MHz, CDCl$_3$): δ 7.39-7.30 (m, 5H), 6.52 (s, 1H), 5.65 (s, 1H), 5.11 (s, 2H), 4.54 (d, J=9.6 Hz, 1H), 4.24 (d, J=8.7 Hz, 1H), 4.16-4.08 (m, 3H), 4.04 (d, J=7.2 Hz, 1H), 3.35-3.31 (m, 1H), 3.01 (d, J=12.3 Hz, 1H), 2.47-2.30 (m, 5H), 2.18-2.12 (m, 1H), 1.99-1.77 (m, 2H), 1.74-1.65 (m, 6H), 1.03 (s, 6H). $^{13}$C-NMR (75 MHz, CDCl$_3$): δ 173.34, 173.31, 171.0, 167.1, 136.1, 128.7, 128.4, 128.3, 83.5, 66.4, 62.0, 60.9, 60.2, 47.2, 36.8, 34.0, 24.5, 24.4, 24.2, 23.8, 20.8, 17.6.

Example 9

Synthesis of 6-(4-(((((2S,5R)-2-carbamoyl-7-oxo-1,6-diazabicyclo[3.2.1]octan-6-yl)oxy)sulfonyl)oxy)-3,3-dimethylbutoxy)-6-oxohexanoic acid (9)

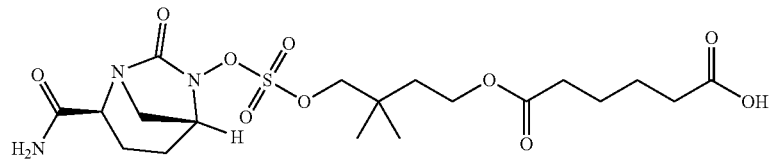 [SMILES: CC(C)(CCOC(=O)CCCCC(=O)O)COS(=O)(=O)ON1C(=O)N2C[C@H]1CC[C@H]2C(N)=O]

Palladium on carbon (10% by weight; 13 mg) was added to a Parr flask charged with benzyl (4-(((((2S,5R)-2-carbamoyl-7-oxo-1,6-diazabicyclo[3.2.1]octan-6-yl)oxy)sulfonyl) oxy)-3,3-dimethylbutyl) adipate (8) (93% purity; 50 mg, 0.1 mmol) in MeOH (14 mL). The mixture was hydrogenated at 1 atm of H$_2$ (balloon), at room temperature for 30 min (monitored by TLC, 100% EtOAc; PMA stain; LC-MS: product room temperature=4.66 min and m/z=494.2 [M+H]$^+$, starting material room temperature=5.48 min and m/z=584.3 [M+H]$^+$). The mixture was filtered through a pad of Celite®, and the filter cake was rinsed with MeOH (ca. 20 mL). The filtrate was concentrated under vacuum, then purified by column chromatography on silica gel using MeOH/CH$_2$Cl$_2$ (0:1 to 4:96) as eluent, to give the product (9) (12 mg) as a solid [ca. 73% purity by LC/MS]. LC-MS: 494.2 [M+H]$^+$.

Example 10

Synthesis of methyl 3-(((((2S,5R)-2-carbamoyl-7-oxo-1,6-diazabicyclo[3.2.1]octan-6-yl)oxy)sulfonyl)oxy)-2,2-dimethylpropanoate (10)

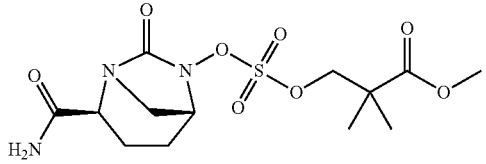

Step 1: Reaction to Produce methyl 3-((chlorosulfonyl)oxy)-2,2-dimethylpropanoate (10a)

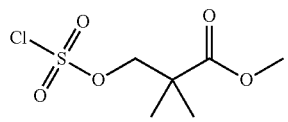

A solution of freshly distilled sulfuryl chloride (3.3 mL, 45.4 mmol) in Et$_2$O (45 mL) was cooled to −78° C. under an atmosphere of Ar. A solution of methyl 2,2-dimethyl-3- hydroxypropionate (3.0 g, 22.7 mmol) and pyridine (2.2 mL, 27.2 mmol) in Et$_2$O (20 mL) was added dropwise to the sulfuryl chloride solution over 30 min. The flask was rinsed with Et$_2$O (3×5 mL) and the rinse was added to the reaction mixture. The mixture was stirred at −78° C. until completion (monitored by TLC, 30% EA/hex, 30 min). The precipitate was filtered, and the filtrate was concentrated under vacuum to afford methyl 3-((chlorosulfonyl)oxy)-2,2-dimethylpropanoate (10a) (5.6 g, 70% yield). The mixture was stored at −78° C. and was used immediately for the next step without further purification. $^1$H-NMR (300 MHz, CDCl$_3$) δ 4.50 (s, 2H), 3.74 (s, 3H), 1.31 (s, 6H).

Step 2: Reaction to Produce methyl 3-(((((2S,5R)-2-carbamoyl-7-oxo-1,6-diazabicyclo[3.2.1]octan-6-yl)oxy)sulfonyl)oxy)-2,2-dimethylpropanoate (10)

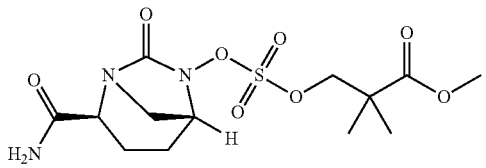 [SMILES: COC(=O)C(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (673 mg, 3.6 mmol) was dissolved in THF (35 mL) and 1,3-dimethyltetrahydropyrimidin-2 (1H)-one (5 mL), and the resulting solution was cooled to −78° C. under an atmosphere of Ar. A 1.0M solution of NaHMDS solution in THF (4.0 mL, 4.0 mmol) was added dropwise to the cooled solution. After complete addition, the mixture was stirred for 10 min. Neat methyl 3-((chlorosulfonyl)oxy)-2,2-dimethylpropanoate (10a) (1.27 g, 3.6 mmol, 1.0 equiv., 66% pure) was added quickly to the reaction mixture. The syringe was rinsed with THF (3×2.5 mL) and the rinse added to the mixture. After 10 min, the reaction mixture was allowed to warm to 23° C. Upon completion by TLC (30 min; 70% EtOAc/hexanes), EtOAc (50 mL) and saturated aqueous NaHCO$_3$ (50 mL) were added to the reaction mixture. The layers were partitioned and the organic layer washed with saturated aqueous NaHCO$_3$ (50 mL), water (3×50 mL), brine (50 mL), then dried (Na$_2$SO$_4$), and concentrated under vacuum to leave a crude residue. The residue was purified by column chromatography on silica gel using EtOAc/hexanes as eluent (1:9 to 1:0) to give the product (10) (98 mg, 7% yield). LC-MS: 380.2 [M+H]$^+$. $^1$H-NMR (300 MHz, CDCl$_3$): δ 6.47 (s, 1H), 5.61 (s, 1H), 4.72 (d, J=9.3 Hz, 1H), 4.58 (d, J=9.3 Hz, 1H), 4.18 (m, 1H), 4.05 (d, J=6.9 Hz, 1H), 3.72 (s, 3H), 3.35-3.31 (m, 1H), 3.02 (d, J=12.3 Hz, 1H), 2.47-2.41 (m, 1H), 2.19-2.13 (m, 1H), 2.01-1.79 (m, 2H), 1.29 (s, 3H), 1.28 (s, 3H). $^{13}$C-NMR (75 MHz, CDCl$_3$): δ 174.7, 171.1, 167.1, 80.4, 62.0, 60.2, 52.6, 47.2, 43.0, 22.2, 21.8, 20.9, 17.6

Example 11

Synthesis of isopropyl 3-(((((2S,5R)-2-carbamoyl-7-oxo-1,6-diazabicyclo[3.2.1]octan-6-yl)oxy)sulfonyl)oxy)-2,2-dimethylpropanoate (11)

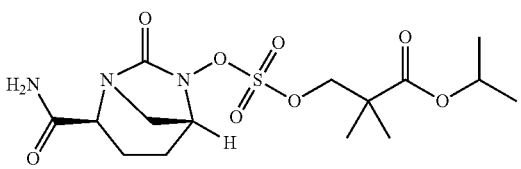 [SMILES: CC(C)OC(=O)C(C)(C)COS(=O)(=O)ON1C(=O)N2C[C@H]1CC[C@H]2C(N)=O]

Step 1: Reaction to Produce isopropyl 3-hydroxy-2,2-dimethylpropanoate (11a)

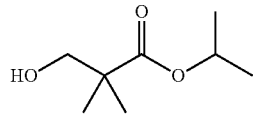

Reference is made to German Application Publication No. DE3045373. A mixture of 3-hydroxy-2,2-dimethylpropionic acid (4.7 g, 40 mmol), isopropanol (70 mL) and concentrated sulfuric acid (or fuming sulfuric acid; 1 mL) was heated to reflux and stirred overnight. After allowing to cool, the mixture was concentrated under vacuum and the residue partitioned between EtOAc (100 mL) and saturated aqueous NaHCO$_3$ (100 mL). The aqueous mixture was washed with H$_2$O (50 mL), saturated NaHCO$_3$ (50 mL) and brine (50 mL), then dried (Na$_2$SO$_4$), filtered and concentrated under vacuum to leave provide the product as an oil. The product (11a) was used directly in the next step without further purification. $^1$H-NMR (300 MHz, CDCl$_3$): δ 5.08-4.95 (m, 1H), 3.53 (fd, 3=1.8 Hz, 2H), 2.49 (s, 1H), 1.25 (fd, J=2.4 Hz, 3H), 1.22 (fd, J=2.4 Hz, 3H), 1.17 (s, 3H), 1.16 (s, 31-H).

Step 2: Reaction to Produce isopropyl 3-((chlorosulfonyl)oxy)-2,2-dimethylpropanoate (11b)

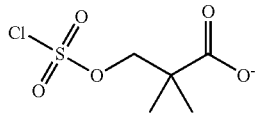

A solution of sulfuryl chloride (2.7 mL, 37.5 mmol) in Et$_2$O (45 mL) was cooled to −78° C. under an atmosphere of Ar. A solution of isopropyl 3-hydroxy-2,2-dimethylpropanoate (11a) (3.0 g, 18.7 mmol) and pyridine (1.82 mL, 22.5 mmol) in Et$_2$O (20 mL) was added dropwise to the sulfuryl chloride solution over the course of 30 min. The flask was rinsed with Et$_2$O (3×5 mL) and the rinse added to the reaction mixture. The mixture was stirred at −78° C. until completion by TLC (30 min; 30% EA/hex). The precipitate was filtered, and the filtrate was concentrated under vacuum to afford isopropyl 3-((chlorosulfonyl)oxy)-2,2-dimethylpropanoate (11b) (4.1 g, 85% yield). The mixture was stored at −78° C. and was used immediately for the next step without further purification. $^1$H-NMR (300 MHz, CDCl$_3$): δ 5.10-4.98 (m, 1H), 4.49 (s, 2H), 1.29 (s, 6H), 1.26 (s, 3H), 1.24 (s, 3H).

Step 3: Reaction to Produce isopropyl 3-(((((2S,5R)-2-carbamoyl-7-oxo-1,6-diazabicyclo[3.2.1]octan-6-yl)oxy)sulfonyl)oxy)-2,2-dimethylpropanoate (11)

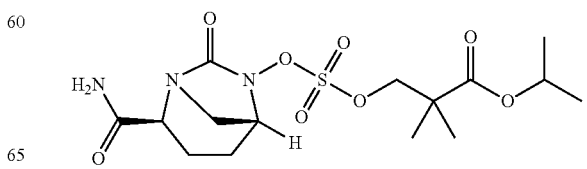

(2S,5R)-6-Hydroxy-7-oxo-1,6-diazabicyclo[3.2.1]octane-2-carboxamide (1) (673 mg, 3.6 mmol) was dissolved in THF (35 mL) and 1,3-dimethyltetrahydropyrimidin-2 (1H)-one (5 mL), and the resulting solution was cooled to −78° C. under an atmosphere of Ar. A 1.0M solution of NaHMDS in THF (4.0 mL, 4.0 mmol) was added dropwise to the cooled solution and stirred for 20 min. Neat isopropyl 3-((chlorosulfonyl)oxy)-2,2-dimethylpropanoate (11b) (0.94 g, 3.6 mmol) was added quickly to the reaction mixture. The syringe was rinsed with THF (3×3 mL) and the rinse was also added to the mixture. After 20 min, the mixture was allowed to warm to rt. Upon completion of the reaction by TLC (30 min; 70% EtOAc/hexanes), EtOAc (50 mL) and saturated aqueous NaHCO$_3$ (50 mL) were added to the reaction mixture. The aqueous and organic layers were separated, and the organic layer was washed with saturated aqueous NaHCO$_3$ (50 mL), water (3×50 mL), brine (50 mL), then dried (Na$_2$SO$_4$), and concentrated under vacuum to leave a crude residue. The residue was purified by column chromatography (40 g ISCO column) on silica gel using EtOAc/hexanes (1:9 to 1:0) as eluent to give the product (11) (63 mg, 4%) as a solid. LC-MS: 408.2 [M+H]$^+$. $^1$H-NMR (300 MHz, CDCl$_3$): δ 6.50 (s, 1H), 5.74 (s, 1H), 5.02 (quint, J=6.3 Hz, 1H), 4.70 (d, J=8.7 Hz, 1H), 4.60 (d, J=9.3 Hz, 1H), 4.17 (m, 1H), 4.05 (d, J=7.2 Hz, 1H), 3.34-3.30 (m, 1H), 3.02 (d, J=11.7 Hz, 1H), 2.47-2.40 (m, 1H), 2.19-2.12 (m, 1H), 2.04-1.66 (m, 2H), 1.26-1.23 (m, 12H). $^{13}$C-NMR (75 MHz, CDCl$_3$): δ 173.7, 171.1, 167.0, 80.6, 68.8, 62.0, 60.2, 47.2, 42.9, 22.2, 21.7, 21.6, 20.9, 17.5.

Example 12

Synthesis of hexyl 3-(((((2S,5R)-2-carbamoyl-7-oxo-1,6-diazabicyclo[3.2.1]octan-6-yl)oxy)sulfonyl)oxy)-2,2-dimethylpropanoate (12)

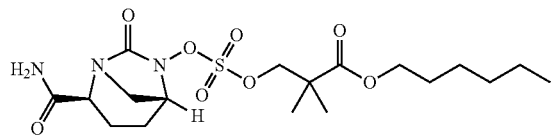 [SMILES: CCCCCCOC(=O)C(C)(C)COS(=O)(=O)ON1C(=O)N2C[C@H]1CC[C@H]2C(N)=O]

Step 1: Reaction to Produce hexyl 3-hydroxy-2,2-dimethylpropanoate (12a)

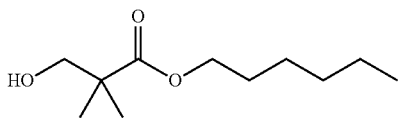

Reference is made to German Application Publication No. DE3045373. A mixture of 3-hydroxy-2,2-dimethylpropionic acid (4.7 g, 40 mmol), 1-hexanol (70 mL) and concentrated sulfuric acid (or fuming sulfuric acid; 1 mL) was heated to 80° C. and stirred overnight. After allowing to cool, the mixture was concentrated under vacuum (high vacuum pump required) and the residue partitioned between EtOAc (100 mL) and saturated aqueous NaHCO$_3$ (100 mL). The aqueous mixture was washed with H$_2$O (50 mL), saturated NaHCO$_3$ (50 mL) and brine (50 mL), then dried (Na$_2$SO$_4$), filtered and concentrated under vacuum to provide the product (12a) as an oil. The product was used directly in the next step without further purification. $^1$H-NMR (300 MHz, CDCl$_3$): δ 4.04-3.98 (m, 2H), 3.47-3.45 (m, 2H), 2.26 (s, 1H), 1.58-1.32 (m, 2H), 1.32-1.23 (m, 6l-), 1.12 (s, 3H), 1.11 (s, 3H).

Step 2: Reaction to Produce hexyl 3-((chlorosulfonyl)oxy)-2,2-dimethylpropanoate (12b)

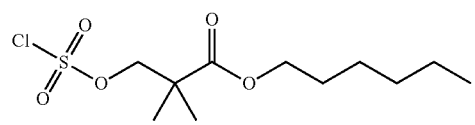 [SMILES: CCCCCCOC(=O)C(C)(C)COS(=O)(=O)Cl]

A solution of sulfuryl chloride (2.1 mL, 29.7 mmol) in Et$_2$O (40 mL) was cooled to −78° C. under an atmosphere of argon. A solution of hexyl 3-hydroxy-2,2-dimethylpropanoate (12a) (3.0 g, 14.8 mmol) and pyridine (1.4 mL, 17.8 mmol) in Et$_2$O (15 mL) was added dropwise to the sulfuryl chloride solution over the course of 30 min. The flask was rinsed with Et$_2$O (3×5 mL) and the rinse added to the reaction mixture. The mixture was stirred at −78° C. until completion by TLC (30 min; 30% EA/hex). The precipitate was filtered, and the filtrate was concentrated under vacuum to afford the product (12b) (3.7 g, 83% yield). The mixture was stored at −78° C. and was used immediately for the next step without further purification. $^1$H-NMR (300 MHz, CDCl$_3$): 4.50 (s, 2H), 4.13 (t, J=6.8 Hz, 2H), 1.69-1.60 (m, 2H), 1.40-1.27 (m, 12H), 0.91-0.87 (m, 3H).

Step 3: Reaction to Produce hexyl 3-(((((2S,5R)-2-carbamoyl-7-oxo-1,6-diazabicyclo[3.2.1]octan-6-yl)oxy)sulfonyl)oxy)-2,2-dimethylpropanoate (12)

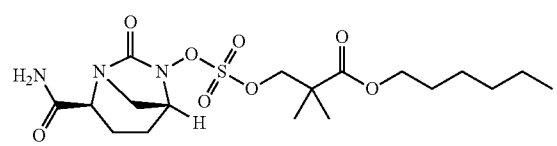 [SMILES: CCCCCCOC(=O)C(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (673 mg, 3.6 mmol) was dissolved in THF (35 mL) and 1,3-dimethyltetrahydropyrimidin-2 (1H)-one (5 mL), and the resulting solution was cooled to −78° C. under an atmosphere of Ar. A 1.0 M solution of NaHMDS in THF (4.0 mL, 4.0 mmol) was added dropwise to the cooled solution and stirred for 20 min. Neat hexyl 3-((chlorosulfonyl)oxy)-2,2-dimethylpropanoate (12b) (1.1 g, 3.6 mmol) was added quickly to the reaction mixture. The syringe was rinsed with THF (3×3 mL) and the rinse was also added to the mixture. After 10 min, the reaction mixture was warmed to 23° C. and stirred until the reaction was complete as determined by TLC and LC-MS. EtOAc (50 mL) and saturated aqueous NaHCO$_3$ (50 mL) were added to the mixture. The layers were partitioned, and the organic layer was washed with saturated aqueous NaHCO$_3$ (50 mL), water (3×50 mL), brine (50 mL), then dried (Na$_2$SO$_4$), filtered and concentrated under vacuum to leave a crude residue. The residue was purified by column chromatography on silica gel using EtOAc/hexanes (1:9 to 1:0) as eluent followed by high-performance liquid chromatography to give the product (12) (44 mg, 3%) as a solid. LC-MS: 450.1 [M+H]⁺. ¹H-NMR (300 MHz, CDCl₃): δ 6.49 (s, 1H), 5.71 (s, 1H), 4.71 (d, J=8.7 Hz, 1H), 4.60 (d, J=9.3 Hz, 1H), 4.17-4.04 (m, 4H), 3.34-3.30 (m, 1H), 3.04-3.00 (d, J=12.6 Hz, 1H), 2.47-2.40 (m, 1H), 2.18-2.13 (m, 1H), 2.01-1.79 (m, 2H), 1.66-1.59 (m, 2H), 1.37-1.27 (m, 12H), 0.91-0.86 (m, 3H). ¹³C-NMR (75 MHz, CDCl3): δ 174.3, 171.1, 167.0, 80.5, 65.6, 62.0, 60.2, 47.2, 43.0, 31.5, 28.6, 25.6, 22.6, 22.3, 21.8, 20.9, 17.6, 14.1.

Example 13

Synthesis of heptyl 3-(((((2S,5R)-2-carbamoyl-7-oxo-1,6-diazabicyclo[3.2.1]octan-6-yl)oxy)sulfonyl)oxy)-2,2-dimethylpropanoate (13)

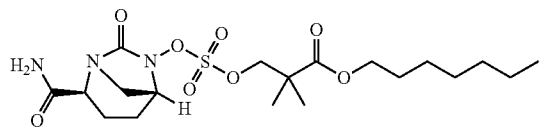 [SMILES: CCCCCCCOC(=O)C(C)(C)COS(=O)(=O)ON1C(=O)N2C[C@H]1CC[C@H]2C(N)=O]

Step 1: Reaction to Produce heptyl 3-hydroxy-2,2-dimethylpropanoate (13a)

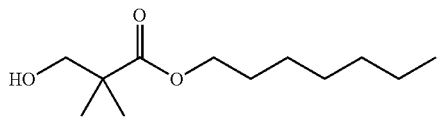

Reference is made to German Application Publication No. DE3045373. A mixture of 3-hydroxy-2,2-dimethylpropionic acid (4.7 g, 40 mmol), 1-heptanol (70 mL) and concentrated sulfuric acid (or fuming sulfuric acid; 1 mL) was heated to 80° C. and stirred overnight. After allowing the mixture to cool, the mixture was concentrated under vacuum (high vacuum pump required) and the residue partitioned between EtOAc (100 mL) and saturated aqueous NaHCO₃ (100 mL). The aqueous was washing with H₂O (50 mL), saturated NaHCO₃ (50 mL) and brine (50 mL), then dried (Na₂SO₄), filtered and concentrated under vacuum to provide the product (13a) as an oil. The product was used directly in the next step without further purification. ¹H-NMR (300 MHz, CDCl₃): δ 4.31 (t, J=6.5 Hz, 2H), 3.77 (s, 2H), 1.87-1.81 (m, 2H), 1.53-1.50 (m, 8H), 1.41 (s, 6H), 1.12-1.08 (m, 3H).

Step 2: Reaction to Produce heptyl 3-((chlorosulfonyl)oxy)-2,2-dimethylpropanoate (13b)

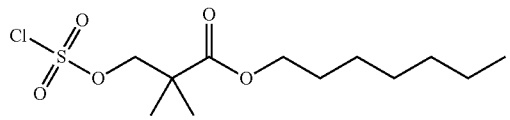 [SMILES: CCCCCCCOC(=O)C(C)(C)COS(=O)(=O)Cl]

A solution of sulfuryl chloride (2.0 mL, 27.7 mmol) in Et₂O (40 mL) was cooled to −78° C. under an atmosphere of argon. A solution of heptyl 3-hydroxy-2,2-dimethylpropanoate (13a) (3.0 g, 13.9 mmol) and pyridine (1.4 mL, 16.6 mmol) in Et₂O (15 mL) was added dropwise to the sulfuryl chloride solution over the course of 30 min. The flask was rinsed with Et₂O (3×5 mL) and the rinse added to the reaction mixture. The mixture was stirred at −78° C. until completion as monitored by TLC (30 min; 30% EA/hex). The precipitate was filtered, and the filtrate was concentrated under vacuum to afford heptyl 3-((chlorosulfonyl)oxy)-2,2-dimethylpropanoate (13b) (3.3 g, 75%). The mixture was stored at −78° C. and was used immediately for the next step without further purification. ¹H-NMR (300 MHz, CDCl₃): δ 4.46 (s, 2H), 4.11-4.00 (m, 2H), 1.64-1.55 (m, 2H), 1.26-1.24 (m, 8H), 0.85-0.81 (m, 3H).

Step 3: Reaction to Produce heptyl 3-(((((2S,5R)-2-carbamoyl-7-oxo-1,6-diazabicyclo[3.2.1]octan-6-yl)oxy)sulfonyl)oxy)-2,2-dimethylpropanoate (13)

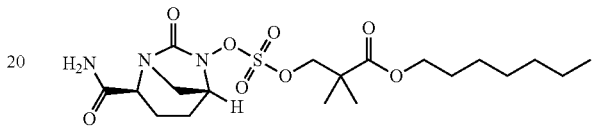

(2S,5R)-6-Hydroxy-7-oxo-1,6-diazabicyclo[3.2.1]octane-2-carboxamide (1) (673 mg) was dissolved in THF (35 mL) and 1,3-dimethyltetrahydropyrimidin-2(1H)-one (5 mL) and the resulting solution was cooled to −78° C. under an atmosphere of Ar. A 1.0 M solution of NaHMDS in THF (4.0 mL, 4.0 mmol) was added dropwise to the cooled solution and stirred for 20 min. Neat heptyl 3-((chlorosulfonyl)oxy)-2,2-dimethylpropanoate (13b) (1.3 g, 4.0 mmol) was added quickly to the reaction mixture. The syringe was rinsed with THF (3×3 mL) and the rinse was also added to the mixture. After 10 min, the reaction mixture was warmed to 23° C. and stirred until complete as determined by TLC and LC-MS. EtOAc (50 mL) and saturated aqueous NaHCO₃ (50 mL) were added to the mixture. The aqueous and organic layers were partitioned, and the organic layer was washed with saturated aqueous NaHCO₃ (50 mL), water (3×50 mL), brine (50 mL), then dried (Na₂SO₄), filtered and concentrated under vacuum to leave a crude residue. The residue was purified by column chromatography on silica gel using EtOAc/hexanes (1:9 to 1:0) as eluent, followed by purification using high-performance liquid chromatography to give the product (13) (65 mg, 4%) as a solid. LC-MS: 464.3 [M+H]⁺. ¹H-NMR (300 MHz, CDCl₃): δ 6.48 (s, 1H), 5.71 (s, 1H), 4.71 (d, J=9.6 Hz, 1H), 4.60 (d, J=9.3 Hz, 1H), 4.18-4.04 (m, 4H), 3.34-3.29 (m, 1H), 3.02 (d, J=11.7 Hz, 1H), 2.47-2.40 (m, 1H), 2.19-2.11 (m, 1H), 2.01-1.79 (m, 2H), 1.66-1.59 (m, 2H), 1.37-1.26 (m, 14H), 0.90-0.86 (m, 3H). ¹³C-NMR (75 MHz, CDCl₃): δ 174.3, 171.1, 167.0, 80.5, 65.6, 62.0, 60.2, 47.2, 43.0, 31.8, 29.0, 28.6, 25.9, 22.7, 22.2, 21.8, 20.9, 17.6, 14.2.

Example 14

Synthesis of tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14)

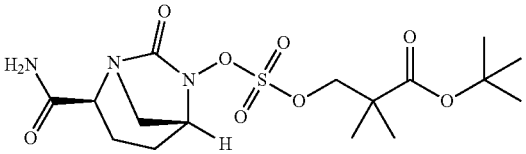 [SMILES: CC(C)(C)OC(=O)C(C)(C)COS(=O)(=O)ON1C(=O)N2C[C@H]1CC[C@H]2C(N)=O]

Step 1 and Step 2: Reaction to Produce tert-butyl 3-hydroxy-2,2-dimethylpropanoate (14a)

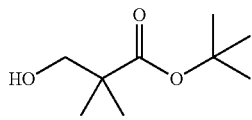

The compound was synthesized in accordance with PCT International Application Publication No. WO 2007116922. Sodium hydride (60% in mineral oil; 2.0 g) was added to a cooled solution of tert-butyl methyl malonate (4 g) in THF (100 mL) at 0° C. under an atmosphere of Ar. The mixture was stirred at 0° C. for 10 min. MeI (3.2 mL) was added to the mixture and the stirring was continued for 3 h (by this time the mixture was at room temperature). Brine and EtOAc were added to the mixture, and the organic layer was separated, dried ($Na_2SO_4$), filtered and concentrated under vacuum to give the product (ca. 4.5 g), which was used directly in the next step.

Solid lithium tri-tert-butoxy-aluminohydride (7.1 g, 28 mmol) was added portion-wise over 15 min to a solution of tert-butyl methyl 2,2-dimethyl-malonate (2.2 g) in THF (100 mL) under an atmosphere of Ar. The mixture was then heated to reflux and stirred overnight. After cooling to room temperature, a saturated solution of $NH_4Cl$ and EtOAc were added, and the aqueous and organic layers were separated. The organic layer was washed with $H_2O$ and brine, then dried ($Na_2SO_4$), filtered and concentrated under vacuum to provide a crude residue. The residue was purified by column chromatography on silica gel using EtOAc/hexanes (0:1 to 3:7) as eluent to give the product (14a) (900 mg) as an oil. $^1$H-NMR (300 MHz, $CDCl_3$): δ 3.50 (d, J=5.1 Hz, 2H), 2.53 (t, J=6.5 Hz, 1H), 1.45 (s, 9H), 1.14 (s, 6H)

Step 3: Reaction to Produce tert-butyl 3-((chlorosulfonyl)oxy)-2,2-dimethylpropanoate (14b)

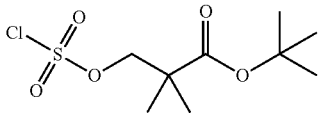 [SMILES: CC(C)(C)OC(=O)C(C)(C)COS(=O)(=O)Cl]

A solution of sulfuryl chloride (0.31 mL, 4.2 mmol) in $Et_2O$ (6 mL) was cooled to −78° C. under an atmosphere of Ar. A solution of tert-butyl 3-hydroxy-2,2-dimethylpropanoate (14a) (0.49 g, 2.8 mmol) and pyridine (0.25 ml, 3.1 mmol) in $Et_2O$ (6 mL) was added dropwise to the sulfuryl chloride solution over the course of 10 min. The mixture was stirred at −78° C. for 90 min and allowed to warm to 23° C. after TLC revealed that the reaction had not proceeded to completion (10% EtOAc/hexanes). The mixture was re-cooled to −78° C. and an additional 1 equivalent of sulfuryl chloride was added, stirred for 10 min, and the mixture allowed to warm to 23° C. (note: the mixture was allowed to stir for a total of 1 h after the addition and during the warming period). The precipitate was filtered, and the filtrate was concentrated under vacuum to give tert-butyl 3-((chlorosulfonyl)oxy)-2,2-dimethylpropanoate (14b) (961 mg, yield assumed quantitative) as a clear, oil. $^1$H-NMR (300 MHz, $CDCl_3$): δ 4.46 (fd, J=1.5 Hz, 2H), 1.47 (fd, J=1.2 Hz, 9H), 1.27 (s, 6H).

Step 4: Reaction to Produce tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14)

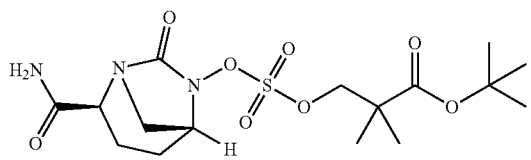 [SMILES: CC(C)(C)OC(=O)C(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (463 mg, 2.5 mmol) was dissolved in THF (25 mL) and 1,3-dimethyltetrahydropyrimidin-2(1H)-one (1.5 mL), and the resulting solution was cooled to −78° C. under an atmosphere of Ar. A 1.0 M NaHMDS solution in THF (2.8 mL, 2.8 mmol) was added dropwise to the cooled solution, and the mixture stirred for 10 min. Neat tert-butyl 3-((chlorosulfonyl)oxy)-2,2-dimethylpropanoate (14b) (0.75 g, 2.8 mmol) was added quickly to the reaction mixture. The syringe was rinsed with THF (3×3 mL) and these rinses were also added to the mixture quickly. After 20 min, the reaction mixture was allowed to warm to 23° C. After stirring for 70 min, the reaction was complete as determined by TLC (70% EA/hexanes). The mixture was cooled to 0° C., diluted with EtOAc (50 mL), and quenched with saturated aqueous $NaHCO_3$ (50 mL). The aqueous and organic layers were partitioned, and the organic layer was washed with saturated aqueous $NaHCO_3$ (50 mL), water (3×50 mL), and brine (50 mL), then dried ($Na_2SO_4$), and concentrated under vacuum to provide a crude residue. The residue was purified by column chromatography on silica gel using EtOAc/hexanes (1:9 to 1:0) as eluent to give the product (14) (368 mg, 35% yield) as a solid. LC-MS: 422.1 $[M+H]^+$. $^1$H-NMR (300 MHz, $CDCl_3$): δ 6.50 (s, 1H), 5.85 (s, 1H), 4.66 (d, J=9 Hz, 1H), 4.56 (d, J=8.7 Hz, 1H), 4.17 (s, 1H), 4.04 (d, J=6.9 Hz, 1H), 3.33-3.29 (m, 1H), 3.02 (d, J=12 Hz, 1H), 2.46-2.39 (m, 1H), 2.17-2.12 (m, 1H), 2.00-1.79 (m, 2H), 1.45 (s, 9H), 1.23 (s, 3H), 1.21 (s, 3H). $^{13}$C-NMR (75 MHz, $CDCl_3$): δ 173.3, 171.1, 167.0, 81.6, 80.9, 62.0, 60.2, 47.2, 43.4, 28.0, 22.2, 21.6, 20.8, 17.6.

Example 15

Synthesis of 2-methoxyethyl 3-(((((2S,5R)-2-carbamoyl-7-oxo-1,6-diazabicyclo[3.2.1]octan-6-yl)oxy)sulfonyl)oxy)-2,2-dimethylpropanoate (15)

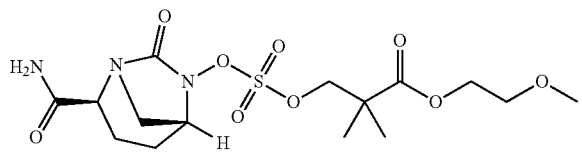 [SMILES: COCCOC(=O)C(C)(C)COS(=O)(=O)ON1C(=O)N2C[C@H]1CC[C@H]2C(N)=O]

105

Step 1: Reaction to Produce 2-methoxyethyl 3-hydroxy-2,2-dimethylpropanoate (15a)

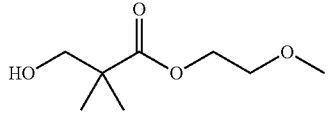

3-Hydroxy-2,2-dimethylpropanoic acid (1.2 g, 10.3 mmol) and Cs$_2$CO$_3$ (3.4 g, 10.4 mmol) were suspended in DMF (25 mL) at 23° C., then 2-bromoethyl methyl ether (1.0 mL, 10.4 mmol) was added. The resulting mixture was stirred at 70° C. overnight. After cooling, the mixture was filtered through a pad of Celite®. The filtrate was diluted with EtOAc (150 mL), and the mixture washed with water (3×100 mL) and brine, then dried (Na$_2$SO$_4$), filtered and concentrated to leave a crude residue. The residue was purified by column chromatography on silica gel using EtOAc/hexanes (1:4 to 4:1) as eluent to provide the product (15a) (1.3 g, crude weight) as an oil. $^1$H-NMR (300 MHz, CDCl$_3$): δ 4.28 (t, J=4.8 Hz, 2H), 3.62-3.55 (m, 4H), 3.38 (s, 3H), 2.65 (t, J=6.0 Hz, 1H), 1.21 (s, 6H).

Step 2: Reaction to Produce 2-methoxyethyl 3-((chlorosulfonyl)oxy)-2,2-dimethylpropanoate (15b)

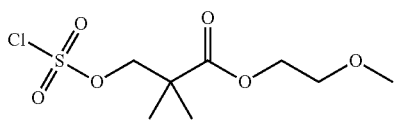 [SMILES: COCCOC(=O)C(C)(C)COS(=O)(=O)Cl]

A solution of freshly distilled sulfuryl chloride (0.2 mL, 2.8 mmol) in Et$_2$O (7.0 mL) was cooled to −78° C. under an atmosphere of Ar. A solution of 2-methoxyethyl 3-hydroxy-2,2-dimethylpropanoate (15a) (0.48 g, 2.7 mmol) and pyridine (0.24 mL, 3.0 mmol) in Et$_2$O (1 mL) was added dropwise to the sulfuryl chloride solution over the course of 11 min. The flask was rinsed with Et$_2$O (3×1 mL) which was also added to the reaction mixture. The mixture was stirred at −78° C. until completion (monitored by TLC, 30% EtOAc/hex, 30 min). The precipitate was filtered, and the filtrate was concentrated under vacuum to afford the product (15b) (0.5 g, 67%) as an oil, which was used directly in the next step without further purification [Note: $^1$HNMR indicated desired product with residue of pyridine and along with starting material].

Step 3: Reaction to Produce 2-methoxyethyl 3-(((((2S,5R)-2-carbamoyl-7-oxo-1,6-diazabicyclo [3.2.1]octan-6-yl)oxy)sulfonyl)oxy)-2,2-dimethyl-propanoate (15)

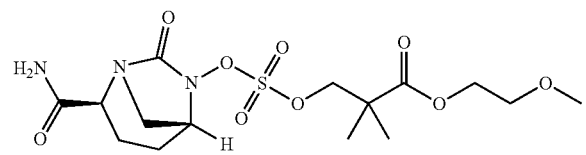 [SMILES: COCCOC(=O)C(C)(C)COS(=O)(=O)ON1C(=O)N2C[C@H]1CC[C@H]2C(N)=O]

106

(2S,5R)-6-Hydroxy-7-oxo-1,6-diazabicyclo[3.2.1]octane-2-carboxamide (1) (162 mg, 0.9 mmol) was dissolved in THF (2.5 mL) and 1,3-dimethyltetrahydropyrimidin-2 (1H)-one (0.3 mL), and the resulting solution was cooled to −78° C. under an atmosphere of Ar. A 1.0 M solution of NaHMDS in THF (1.0 mL, 1.0 mmol) was added dropwise to the cooled solution and the mixture stirred for 10 min. 2-Methoxyethyl 3-((chlorosulfonyl)oxy)-2,2-dimethylpropanoate (15b) (0.3 g, 1.1 mmol) in THF (2 mL) was added quickly to the reaction mixture. After 10 min at −78° C., the mixture was allowed to warm to 23° C. and stirred for 30 min. The mixture was diluted with EtOAc (40 mL) and water. The aqueous and organic layers were partitioned, and the organic layer was washed with water (3×20 mL), and brine (50 mL), then dried (Na$_2$SO$_4$), filtered and concentrated under vacuum to leave a crude residue. The crude residue was purified by column chromatography on silica gel (4 g column) using EtOAc/hexanes (3:7 to 1:0) as eluent to give an impure solid. The product was dissolved in Et$_2$O (20 mL) with the aid of sonication, and precipitated with hexanes. The resulting solid was filtered, and dried under vacuum to provide the product (15) (72 mg, 19.4%) as a solid. LCMS: m/z=424.3 [M+H]$^+$. $^1$H-NMR (300 MHz, CDCl$_3$): δ 6.48 (br. s, 1H), 5.56 (br. s, 1H), 4.62 (dd, J=28.8, 8.7 Hz, 2H), 4.33-4.22 (m, 2H), 4.17 (br. s, 1H), 4.05 (d, J=6.9 Hz, 1H), 3.60 (t, J=4.6 Hz, 2H), 3.38 (s, 3H), 3.33 (d, J=11.1 Hz, 1H), 3.02 (d, J=12.0 Hz, 1H), 2.46-2.41 (m, 1H), 2.18-2.13 (m, 1H), 1.98-1.84 (m, 2H), 1.31 (s, 3H), 1.29 (s, 3H). $^{13}$C-NMR (75 MHz, CDCl$_3$), δ 174.1, 170.8, 166.9, 80.2, 70.2, 64.1, 61.8, 60.0, 59.0, 47.1, 42.9, 22.1, 21.6, 20.7, 17.4.

Example 16

Synthesis of oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16)

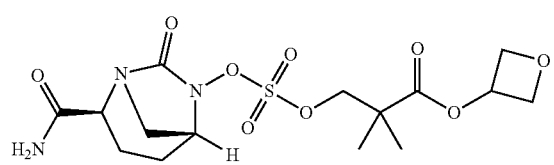 [SMILES: CC(C)(COS(=O)(=O)ON1C(=O)N2C[C@H]1CC[C@H]2C(N)=O)C(=O)OC1COC1]

Step 1: Reaction to Produce oxetan-3-yl 3-hydroxy-2,2-dimethylpropanoate (16a)

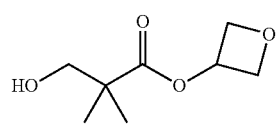

3-Hydroxy-2,2-dimethylpropanoic acid (4.7 g, 40 mmol) and Cs$_2$CO$_3$ (13.0 g, 40 mmol) were suspended in DMF (100 mL) at 23° C., then 3-iodooxetane (7.4 g, 40 mmol) was added. The resulting mixture was stirred at 70° C. overnight. After cooling, the mixture was diluted with EtOAc (150 mL), and the mixture washed with water (3×100 mL) and brine, then dried (Na$_2$SO$_4$), filtered and concentrated to provide a crude residue. The residue was purified by column chromatography on silica gel using EtOAc/hexanes as eluent to give the product (16a) (3.6 g, 51%) as an oil.

Step 2: Reaction to Produce oxetan-3-yl 3-((chlorosulfonyl)oxy)-2,2-dimethylpropanoate (16b)

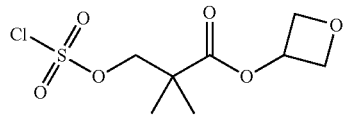 [SMILES: CC(C)(COS(=O)(=O)Cl)C(=O)OC1COC1]

A solution of freshly distilled sulfuryl chloride (0.2 mL, 2.7 mmol) in Et$_2$O (3 mL) was cooled to −78° C. under an atmosphere of Ar. A solution of oxetan-3-yl 3-hydroxy-2,2-dimethylpropanoate (16a) (0.46 g, 2.6 mmol) and pyridine (0.2 mL, 2.7 mmol) in Et$_2$O (2 mL) was added dropwise to the sulfuryl chloride solution over the course of 11 min. The flask was rinsed with Et$_2$O (3×1 mL) which was also added to the reaction mixture. The mixture was stirred at −78° C. until completion (monitored by TLC, 30% EtOAc/hex, 30 min). The precipitate was filtered, and the filtrate was concentrated under vacuum to afford the product (16b) (0.5 g, 69%) as an oil, which was used directly in the next step without further purification. $^1$H-NMR (300 MHz, CDCl$_3$): δ 5.50-5.46 (m, 1H), 4.94-4.89 (m, 2H), 4.65-4.60 (m, 2H), 4.52 (s, 2H), 1.72 (br. s, 1H), 1.36 (s, 6H).

Step 3: Reaction to Produce oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16)

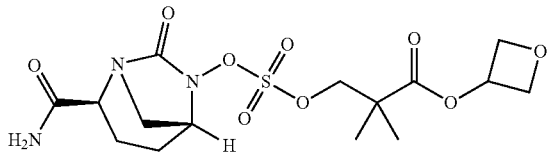 [SMILES: CC(C)(COS(=O)(=O)ON1C(=O)N2C[C@H]1CC[C@H]2C(N)=O)C(=O)OC1COC1]

(2S,5R)-6-Hydroxy-7-oxo-1,6-diazabicyclo[3.2.1]octane-2-carboxamide (1) (200 mg, 1.1 mmol) was dissolved in THF (3 mL) and 1,3-dimethyltetrahydropyrimidin-2(1H)-one (2 mL), DMPU was added, and the resulting solution was cooled to −78° C. under an atmosphere of Ar. A 1.0 M solution of NaHMDS in THF (1.2 mL, 1.2 mmol) was added dropwise to the cooled solution, and the mixture stirred for 10 min. A solution of oxetan-3-yl 3-((chlorosulfonyl)oxy)-2,2-dimethylpropanoate (16b) (0.37 g, 1.4 mmol) in THF (2 mL) was added quickly to the reaction mixture. After stirring at −78° C. for 10 min, the mixture was allowed to warm to 23° C. and stirred for a total of 1 h. The mixture was diluted with EtOAc (40 mL) and H$_2$O. The aqueous and organic layers were partitioned, and the organic layer washed with H$_2$O (3×20 mL), brine (50 mL), then dried (Na$_2$SO$_4$), filtered and concentrated under vacuum to give a crude residue. The crude residue was purified by column chromatography on silica gel (4 g column) using EtOAc/hexanes (3:7 to 1:0) as eluent to give an oil. The oil was triturated with Et$_2$O with the aid of sonication, and the filter cake was washed with Et$_2$O to provide the product (16) (170 mg, 37%) as a solid. LCMS: m/z=422.3 [M+H]$^+$. $^1$H-NMR (300 MHz, CDCl$_3$): δ 6.48 (br. s, 1H), 5.54 (br. s, 1H), 5.48-5.44 (m, 1H), 4.89 (t, J=7.4 Hz, 2H), 4.79 (d, J=8.7 Hz, 1H), 4.66-4.58 (m, 3H), 4.18 (br. s, 1H), 4.05 (d, J=6.9 Hz, 1H), 3.33 (d, J=12.3 Hz, 1H), 2.44-2.42 (m, 1H), 2.20-2.16 (m, 1H), 2.00-1.80 (m, 2H), 1.32 (s, 3H), 1.31 (s, 3H). 13C-NMR (75 MHz, CDCl$_3$): δ 173.4, 170.8, 167.0, 80.0, 68.6, 76.6, 61.9, 60.2, 47.1, 42.7, 21.9, 21.6, 20.7, 17.4.

Example 17

Synthesis of ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17)

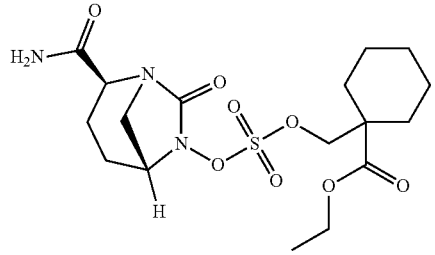 [SMILES: CCOC(=O)C1(COS(=O)(=O)ON2C(=O)N3C[C@H]2CC[C@H]3C(N)=O)CCCCC1]

Step 1: Reaction to Produce ethyl 1-(((chlorosulfonyl)oxy)methyl)cyclohexanecarboxylate (17a)

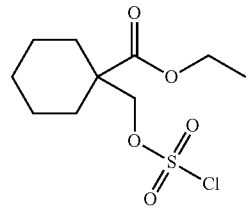 [SMILES: CCOC(=O)C1(COS(=O)(=O)Cl)CCCCC1]

A solution of freshly distilled sulfuryl chloride (77 μL, 1.1 mmol) in Et$_2$O (3 mL) was cooled to −78° C. under an atmosphere of Ar. A solution of ethyl 1-(hydroxymethyl)cyclohexanecarboxylate (0.2 g, 1.0 mmol) and pyridine (85 μL, 1.1 mmol) in Et$_2$O (2 mL) was added dropwise to the sulfuryl chloride solution over 11 min. The flask was rinsed with Et$_2$O (3×1 mL) and the rinse added to the reaction. The mixture was stirred at −78° C. until completion (ca. 30 min; monitored by TLC, 30% EtOAc/hex). The precipitate was filtered, and the filtrate was concentrated under vacuum to afford the title compound as an oil, which was used directly in the next step without purification. A second batch using 476 mg of the starting alcohol, afforded 600 mg of the product (17a) (approximately, 85% purity by $^1$H-NMR).

Step 2: Reaction to Produce ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17)

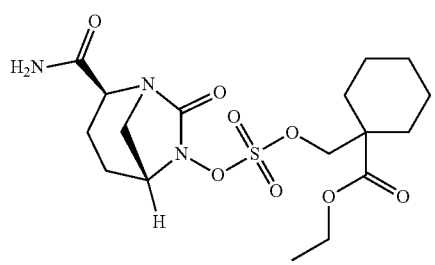 [SMILES: CCOC(=O)C1(COS(=O)(=O)ON2C(=O)N3C[C@H]2CC[C@H]3C(N)=O)CCCCC1]

(2S,5R)-6-Hydroxy-7-oxo-1,6-diazabicyclo[3.2.1]octane-2-carboxamide (1) (0.33 g, 1.8 mmol) was dissolved in THF (7 mL) and 1,3-dimethyltetrahydropyrimidin-2(1H)-one (3.5 mL), and the resulting solution was cooled to −78° C. under an atmosphere of Ar. A 1.0 M solution of NaHMDS in THF (1.8 mL, 1.8 mmol) was added dropwise over 20 min, and the mixture stirred for 10 min. Ethyl 1-(((chlorosulfonyl)oxy)methyl)cyclohexanecarboxylate (17a) (0.51 g, 1.8 mmol) in THF (2 mL) was added quickly to the reaction mixture. After 10 min stirring at −78° C. the mixture was allowed to warm to 23° C. and stirred for a total of 1 h. The reaction mixture was diluted with EtOAc (40 mL) and H$_2$O at −60° C. The aqueous and organic layers were partitioned, and the organic layer was washed with H$_2$O (3×20 mL), and brine (50 mL), then dried (Na$_2$SO$_4$), filtered and concentrated under vacuum to give the crude residue (330 mg). The oil was purified by column chromatography on silica gel (4 g column) using EtOAc/hexanes (3:7 to 1:0) as eluent, followed by purification using preparative HPLC (10-90% MeCN/H$_2$O over 20 min using UV detection at 254/220 nM) to give the product (17) (223 mg, 34%) as a solid. LCMS: m/z=434.3 [M+H]$^+$. $^1$H-NMR (300 MHz, CDCl$_3$): δ 6.50 (br. s, 1H), 5.80 (br.s, 1H), 4.66 (dd, J=48.6, 12.8 Hz, 2H), 4.21-4.15 (m, 3H), 4.04 (d, J=6.9 Hz, 1H), 3.31 (d, J=3.0 Hz, 1H), 3.01 (d, J=11.7 Hz, 1H), 2.44-2.39 (m, 1H), 2.16-1.78 (m, 5H), 1.57-1.39 (m, 8H), 1.27 (t, J=7.1 Hz, 3H). $^{13}$C-NMR (75 MHz, CDCl$_3$): δ 173.2, 171.0, 167.0, 80.2, 61.8, 61.1, 60.1, 47.1, 30.4, 30.0, 25.4, 22.2, 22.0, 20.7, 17.4, 14.1.

Example 18

Synthesis of ethyl 1-((((((2S,5R)-2-carbamoyl-7-oxo-1,6-diazabicyclo[3.2.1]octan-6-yl)oxy)sulfonyl)oxy)methyl)cyclopentane-1-carboxylate (18)

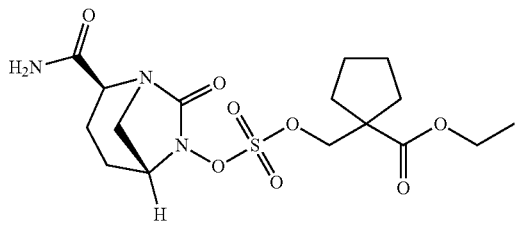 [SMILES: CCOC(=O)C1(COS(=O)(=O)ON2C(=O)N3C[C@H]2CC[C@H]3C(N)=O)CCCC1]

Step 1: Reaction to Produce ethyl 1-(((chlorosulfonyl)oxy)methyl)cyclopentane-1-carboxylate (18a)

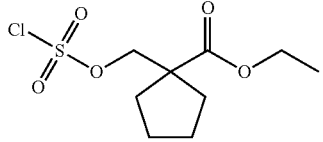 [SMILES: CCOC(=O)C1(COS(=O)(=O)Cl)CCCC1]

A solution of freshly distilled sulfuryl chloride (200 μL, 2.7 mmol) in Et$_2$O (3 mL) was cooled to −78° C. under an atmosphere of Ar. A solution of ethyl 1-(hydroxymethyl)cyclopentanecarboxylate (0.48 g, 2.7 mmol) and pyridine (222 μL, 2.7 mmol) in Et$_2$O (2 mL) was added dropwise to the sulfuryl chloride solution over 7 min. The flask was rinsed with Et$_2$O (2×1 mL) and both rinses were added to the reaction mixture. The mixture was stirred at −78° C. for 1.5 h. The precipitate was filtered, and the filter-cake washed with Et$_2$O (4 mL). The filtrate was concentrated under vacuum to afford the title compound (18a) as an oil, which was used directly in the next step without further purification.

Step 2: Reaction to Produce ethyl 1-((((((2S,5R)-2-carbamoyl-7-oxo-1,6-diazabicyclo[3.2.1]octan-6-yl)oxy)sulfonyl)oxy)methyl)cyclopentane-1-carboxylate (18)

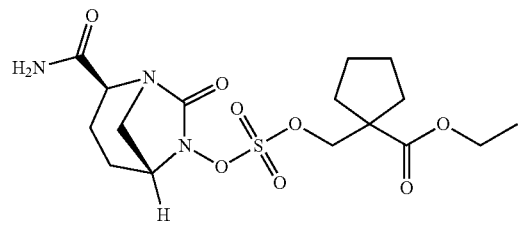 [SMILES: CCOC(=O)C1(COS(=O)(=O)ON2C(=O)N3C[C@H]2CC[C@H]3C(N)=O)CCCC1]

(2S,5R)-6-Hydroxy-7-oxo-1,6-diazabicyclo[3.2.1]octane-2-carboxamide (1) (200 mg, 1.1 mmol) was dissolved in THF (5 mL) and 1,3-dimethyltetrahydropyrimidin-2(1H)-one (2 mL), and the resulting solution was cooled to −78° C. under an atmosphere of Ar. A 1.0 M solution of NaHMDS in THF (1.3 mL, 1.3 mmol. Note: since the sulfonyl chloride contains about 20% starting alcohol, additional 0.2 eq NaHMDS was added) was added dropwise over 10 min. Note: the reaction mixture was immersed and lifted from the cooling bath, to get the solution to stir, otherwise it was a gel. Ethyl 1-(((chlorosulfonyl)oxy)methyl)cyclopentanecarboxylate (18a) (0.47 g, 1.7 mmol) in THF (2×1 mL) was added quickly to the reaction mixture. After 10 min, the mixture was allowed to warm to 23° C. and stirred for a total of 2 h. The reaction mixture was diluted with EtOAc (40 mL) and brine at −60° C. The aqueous and organic layers were partitioned, and the organic layer was dried (Na$_2$SO$_4$), filtered and concentrated under vacuum to leave a crude residue. The residue was purified by column chromatography on silica gel using EtOAc/hexanes (3:7 to 1:0) as eluent, followed-by reverse-phase preparative HPLC to afford the title compound (18) (62 mg, 14%) as a solid. LCMS: m/z=420.3 [M+H]$^+$. $^1$H-NMR (300 MHz, CDCl$_3$): δ 6.55 (br. s, 1H), 6.15 (br. s, 1H), 4.69 (dd, J=20.9, 9.3 Hz, 2H), 4.20-4.10 (m, 3H), 4.02 (d, J=6.6 Hz, 1H), 3.29 (d, J=12.3 Hz, 1H), 3.01 (d, J=11.7 Hz, 1H), 2.40-2.36 (m, 1H), 2.14-1.66 (m, 11H), 1.24 (t, J=7.4 Hz, 3H). $^{13}$C-NMR (75 Hz, CDCl$_3$): δ 174.4, 171.2, 167.0, 78.9, 61.8, 61.2, 60.1, 53.0, 47.0, 33.9, 32.9, 25.6, 25.5, 20.7, 17.5, 14.1.

Example 19

Synthesis of ethyl 1-((((((2S,5R)-2-carbamoyl-7-oxo-1,6-diazabicyclo[3.2.1]octan-6-yl)oxy)sulfonyl)oxy)methyl)cyclobutanecarboxylate (19)

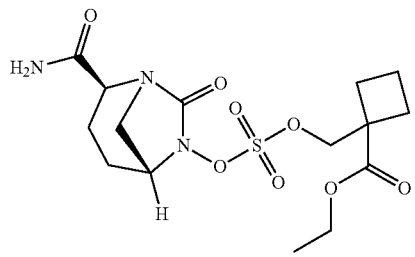

Step 1: Reaction to Produce ethyl 1-(((chlorosulfonyl)oxy)methyl)cyclobutanecarboxylate (19a)

A solution of freshly distilled sulfuryl chloride (451 µL, 6.2 mmol) in Et$_2$O (5 mL) was cooled to −78° C. under an atmosphere of Ar. A solution of ethyl 1-(hydroxymethyl)cyclobutanecarboxylate (1.0 g, 6.1 mmol) and pyridine (500 µL, 6.2 mmol) in Et$_2$O (10 mL) was added dropwise to the sulfuryl chloride solution over the course of 11 min. The flask was rinsed with Et$_2$O (3×1 mL), which was also added to the reaction mixture. The mixture was stirred at −78° C., which was allowed to warm to ambient temp. within 4 h. The precipitate was filtered, and the filtrate was concentrated under vacuum to afford the title compound (1.2 g, 76%) as an oil, which was used directly in the next step without further purification. Note: $^1$HNMR indicated desired product (19a), together with starting material.

Step 2: Reaction to Produce ethyl 1-(((((2S,5R)-2-carbamoyl-7-oxo-1,6-diazabicyclo[3.2.1]octan-6-yl)oxy)sulfonyl)oxy)methyl)cyclobutanecarboxylate (19)

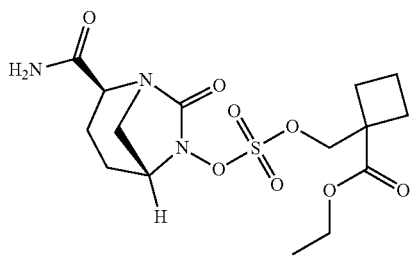 [SMILES: CCOC(=O)C1(COS(=O)(=O)ON2C(=O)N3C[C@H]2CC[C@H]3C(N)=O)CCC1]

(2S,5R)-6-Hydroxy-7-oxo-1,6-diazabicyclo[3.2.1]octane-2-carboxamide (1) (0.33 g, 1.8 mmol) was dissolved in THF (8 mL) and 1,3-dimethyltetrahydropyrimidin-2(1H)-one (2 mL), and the resulting solution was cooled to −78° C. under an atmosphere of argon. A 1.0 M solution of NaHMDS in THF (2 mL, 2.1 mmol. Note: since the sulfonyl chloride contains about 30% starting alcohol, an additional 0.3 eq NaHMDS was added.) was added dropwise over 10 min. Ethyl 1-(((chlorosulfonyl)oxy)methyl)cyclobutanecarboxylate (19a) (1.0 g, 3.9 mmol) in THF (2×1 mL) was added quickly to the reaction mixture. After 10 min, the mixture was allowed to warm to 23° C. and stirred for 1 h. The mixture was diluted with EtOAc (40 mL) and H$_2$O at −60° C. The aqueous and organic layers were partitioned, and the organic layer was washed with brine, dried (Na$_2$SO$_4$), filtered and concentrated under vacuum to give a crude residue. The oil was purified by preparative HPLC to give a solid (303 mg). The solid was dissolved in DCM and filtered through a filtered syringe, to give the product (19) (273 mg, 35%) as a solid. LCMS: m/z=406.1 [M+H]$^+$. $^1$H-NMR (300 MHz, CDCl$_3$): δ 6.57 (br. s, 1H), 6.28 (br. s, 1H), 4.85 (dd, J=63.9, 9.3 Hz, 2H), 4.30-4.13 (m, 3H), 4.01 (d, J=7.2 Hz, 1H), 3.27 (d, J=10.8 Hz, 1H), 3.01 (d, J=11.7 Hz, 1H), 2.50-2.35 (m, 3H), 2.13-1.76 (m, 8H), 1.24 (t, J=7.3 Hz, 3H). $^{13}$C-NMR (75 MHz, CDCl$_3$): δ173.1, 171.3, 167.2, 77.9, 61.8, 61.2, 60.7, 60.1, 47.0, 46.3, 27.1, 26.1, 20.7, 17.5, 15.6, 14.0.

Example 20

Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (20)

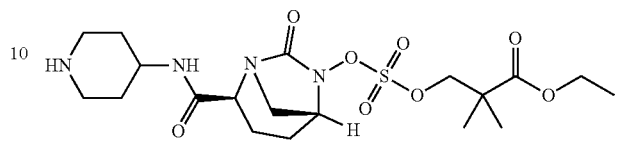

Step 1: Synthesis of (2S,5R)-6-(benzyloxy)-7-oxo-1,6-diazabicyclo[3.2.1]octane-2-carboxylic acid (20a)

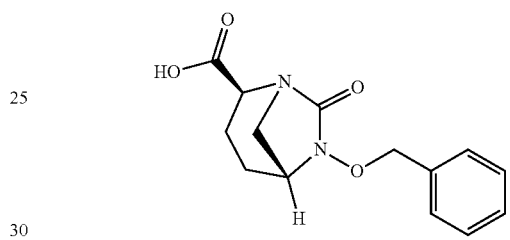

A solution of distilled sulfuryl chloride (0.61 mL, 7.5 mmol) in Et$_2$O (10 mL) was cooled to −78° C. under nitrogen. A solution of ethyl 3-hydroxy-2,2-dimethylpropanoate (2a) (1.0 g, 6.8 mmol) and pyridine (0.55 mL, 6.8 mmol) in Et$_2$O (2.0 mL) was then added dropwise over 1 h via a syringe. The reaction was stirred at −78° C. for 1 h, and the mixture was allowed to warm to room temperature and stirred for additional 2 h. After the mixture was filtered, the filtrate was concentrated under vacuum to give the product (20a) as a colorless liquid (1.46 g, yield 87%). $^1$H NMR (300 MHz, CDCl$_3$): δ 4.50 (s, 2H), 4.19 (q, J=6.9 Hz, 2H), 1.31 (s, 6H), 1.28 (t, J=6.9 Hz, 3H).

Step 2: Synthesis of tert-butyl 4-((2S,5R)-6-(benzyloxy)-7-oxo-1,6-diazabicyclo[3.2.1]octane-2-carboxamido)piperidine-1-carboxylate (20b)

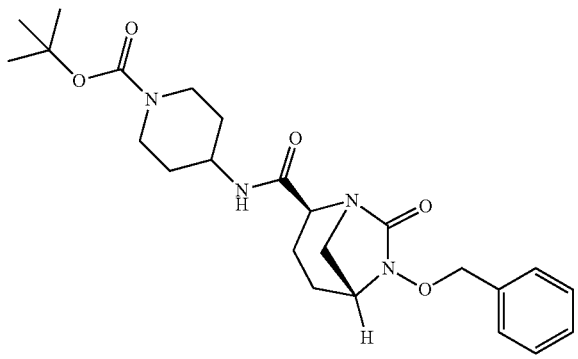 [SMILES: CC(C)(C)OC(=O)N1CCC(NC(=O)[C@@H]2CC[C@@H]3CN2C(=O)N3OCc2ccccc2)CC1]

To a mixture of (2S,5R)-6-(benzyloxy)-7-oxo-1,6-diazabicyclo[3.2.1]octane-2-carboxylic acid (20a) (10 g, 36.2 mmol), tert-butyl 4-aminopiperidine-1-carboxylate (7.26 g, 36.2 mmol) in DCM (200 mL) was added HATU (13.76 g, 36.2 mmol) and DIPEA (6.31 mL, 36.2 mmol). The reaction was stirred at room temperature overnight. The mixture was washed with saturated NH$_4$Cl solution, water and brine. The organic layer was dried with anhydrous Na$_2$SO$_4$, filtered, and concentrated under vacuum to give a crude residue. The residue was purified by silica gel column chromatography using EtOAc/hexane (1:1) as eluent to give the product (20b) (10.3 g, yield 62%) as a white solid. $^1$H NMR (300 MHz, CDCl$_3$): δ 7.36-7.44 (m, 5H), 6.55 (d, 1H, J=8.1 Hz), 5.05 (d, 1H, J=11.7 Hz), 4.90 (d, 1H, J=11.1 Hz), 4.02 (br, s, 1H), 3.87-3.99 (m, 2H), 3.29 (s, 1H), 3.01 (d, 1H), 2.85 (t, 2H), 2.64 (d, 1H), 2.37 (dd, 1H), 1.84-2.05 (m, 4H), 1.55-1.67 (m, 2H), 1.45 (s, 9H), 1.23-1.36 (m, 2H). MS (ESI) C$_{24}$H$_{34}$N$_4$O$_5$=459.1 (M+1)$^+$.

Step 3: Synthesis of tert-butyl 4-((2S,5R)-6-hydroxy-7-oxo-1,6-diazabicyclo[3.2.1]octane-2-carboxamido)piperidine-1-carboxylate (20c)

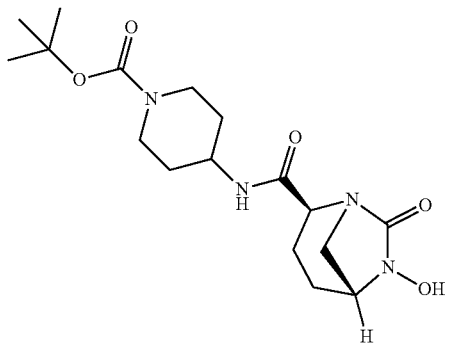 [SMILES: CC(C)(C)OC(=O)N1CCC(NC(=O)[C@@H]2CC[C@@H]3CN2C(=O)N3O)CC1]

To a solution of tert-butyl 4-((2S,5R)-6-(benzyloxy)-7-oxo-1,6-diazabicyclo[3.2.1]octane-2-carboxamido)piperidine-1-carboxylate (20b) (0.6 g, 1.31 mmol) in MeOH (6 mL) was added 10% palladium on carbon (0.2 g). The reaction mixture was stirred under 1 atm hydrogen pressure for 1 h. After the mixture was filtered through a pad of Celite®, the filtrate was concentrated under vacuum to give a crude product (20c) (0.48 g, yield 100%) that was used directly for the next step. $^1$H NMR (300 MHz, CDCl$_3$): δ 6.62 (d, 1H, J=7.8 Hz), 3.86-4.01 (m, 4H), 3.75 (s, 1H), 3.17 (d, 1H), 2.91 (t, 2H), 2.81 (d, 1H), 2.42 (m, 1H), 2.13 (m, 1H), 1.88 (m, 4H), 1.74 (m, 1H), 1.45 s, 9H), 1.31 (m, 2H).

Step 4: Synthesis of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (20d)

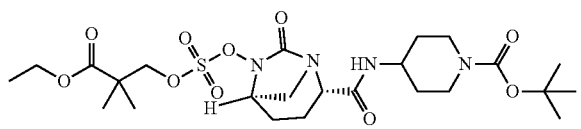 [SMILES: CCOC(=O)C(C)(C)COS(=O)(=O)ON1C(=O)N2C[C@H]1CC[C@H]2C(=O)NC1CCN(C(=O)OC(C)(C)C)CC1]

tert-Butyl 4-((2S,5R)-6-hydroxy-7-oxo-1,6-diazabicyclo[3.2.1]octane-2-carboxamido)piperidine-1-carboxylate (20c) (1.31 mmol) was dissolved in THF (7.0 mL) and 1,3-dimethyltetrahydropyrimidin-2(1H)-one (3 mL), and the resulting solution was cooled to −78° C. under a nitrogen atmosphere. A solution of NaHMDS in THF (1M, 1.31 mL, 1.31 mmol) was added dropwise, and the mixture was stirred at −78° C. for 10 min. A solution of ethyl 3-((chlorosulfonyl)oxy)-2,2-dimethylpropanoate (3a) (352 mg, 1.44 mmol) in THF (1 mL) was then added to the reaction mixture via syringe. After 10 min at −78° C., the reaction mixture was allowed to warm to room temperature and stirred overnight. The reaction mixture was diluted with EtOAc and washed with saturated NaHCO$_3$, water, and brine. The organic layer was dried with anhydrous Na$_2$SO$_4$, filtered, and concentrated under vacuum to give a crude residue. The residue was purified by silica gel column chromatography using EtOAc/hexane (1:1) as eluent to give the product (20d) (330 mg, yield 44%) as a white foam. $^1$H NMR (300 MHz, CDCl$_3$): δ 6.44 (d, 1H, J=8.1 Hz), 4.59-4.73 (dd, 2H, J=8.7 Hz), 3.89-4.23 (m, 7H), 3.28 (d, 1H), 2.83-2.92 (m, 3H), 2.42-2.49 (m, 1H), 2.14-2.17 (m, 1H), 1.80-1.97 (m, 4H), 1.46 (s, 9H), 1.58-1.23 (m, 11H). MS (ESI) C$_{24}$H$_{40}$N$_4$O$_{10}$S=577 (M+1)$^+$.

Step 5: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (TFA salt) (20)

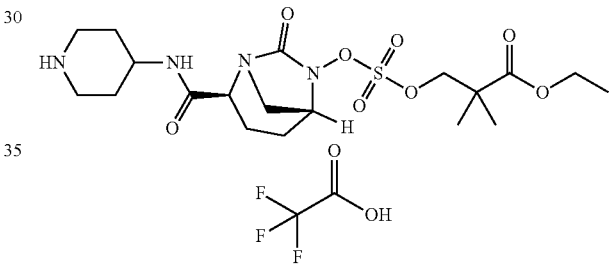

To a mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (20d) (240 mg, 0.42 mmol) in DCM (1.4 mL) was added trifluoroacetic acid (1.4 mL) at −10° C. The reaction was stirred at −10° C. for 30 min. LC/MS analysis indicated that the stating material was completely consumed. The mixture was concentrated under vacuum to give a crude residue. The residue was purified by prep-HPLC on C18 column eluting with MeCN/H$_2$O containing 0.1% TFA (5-100%) to give the title compound (20) (103 mg, yield 42%) as an off-white powder. $^1$H NMR (300 MHz, CDCl$_3$): δ 9.42 (br s, 1H), 9.06 (br s, 1H), 6.71 (d, 1H, J=7.8 Hz), 4.57-4.73 (dd, 2H, J=9.0 Hz), 3.99-4.19 (m, 5H), 3.48 (d, 2H), 3.26 (d, 1H), 3.00 (m, 2H), 2.88 (d, 1H), 1.82-2.39 (m, 7H), 1.23-1.30 (m, 9H). $^{13}$C NMR (75 MHz, CDCl$_3$): δ 174.5, 168.9, 167.3, 80.8, 62.0, 61.6, 60.4, 46.8, 44.9, 43.6, 43.3, 28.7, 22.3, 21.9, 20.9, 18.0, 14.4. $^{19}$F NMR (282 MHz, CDCl$_3$): δ −75.8. MS (ESI) C$_{19}$H$_{32}$N$_4$O$_8$S=477 (M+1)$^+$.

Analytical HPLC was performed on Agilent 1200 system using a Phenomenex® C18 column (150×4.6 mm i.d.). The mobile phase was a linear gradient of MeCN and water (0.1% TFA, 5% MeCN to 100% MeCN in 15 min). The flow rate was maintained at 1 mL/min and the eluent was monitored with UV detector at 220 and 254 nm. HPLC retention time: 7.31 min.

Example 21

Synthesis of 2-methoxyethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (21)

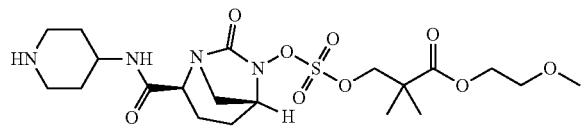 [SMILES: COCCOC(=O)C(C)(C)COS(=O)(=O)ON1C(=O)N2C[C@H]1CC[C@H]2C(=O)NC1CCNCC1]

Step 1: Synthesis of 2-methoxyethyl 3-((chlorosulfonyl)oxy)-2,2-dimethylpropanoate (21a)

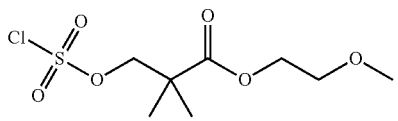 [SMILES: COCCOC(=O)C(C)(C)COS(=O)(=O)Cl]

A solution of distilled sulfuryl chloride (0.51 mL, 6.2 mmol) in Et$_2$O (10 mL) was cooled to −78° C. under nitrogen. A solution of 2-methoxyethyl 3-hydroxy-2,2-dimethylpropanoate (15a) (1.0 g, 5.68 mmol) and pyridine (0.46 mL, 5.68 mmol) in Et$_2$O (2.0 mL) was then added dropwise over 1 h via a syringe. The reaction was stirred at −78° C. for 1 h, and then the mixture was allowed to warm to room temperature and stirred for 2 h. After the mixture was filtered, the filtrate was concentrated under vacuum to give the product (21a) as a colorless liquid (1.5 g, yield 96%). $^1$H NMR (300 MHz, CDCl$_3$): δ 4.40 (s, 2H), 4.29 (t, 3H), 3.59 (t, 3H), 3.37 (s, 3H), 1.32 (s, 6H).

Step 2: Synthesis of tert-butyl 4-((2S,5R)-6-(((3-(2-methoxyethoxy)-2,2-dimethyl-3-oxopropoxy)sulfonyl)oxy)-7-oxo-1,6-diazabicyclo[3.2.1]octane-2-carboxamido)piperidine-1-carboxylate (21b)

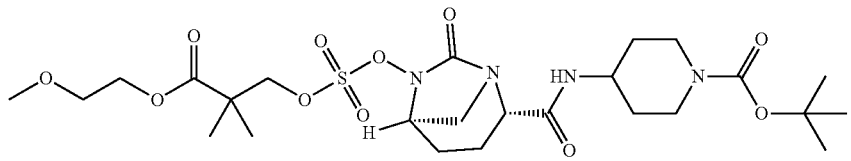 [SMILES: COCCOC(=O)C(C)(C)COS(=O)(=O)ON1C(=O)N2C[C@H]1CC[C@H]2C(=O)NC1CCN(C(=O)OC(C)(C)C)CC1]

tert-Butyl 4-((2S,5R)-6-hydroxy-7-oxo-1,6-diazabicyclo[3.2.1]octane-2-carboxamido)piperidine-1-carboxylate (20c) (3.26 mmol) was dissolved in THF (14 mL) and 1,3-dimethyltetrahydropyrimidin-2(1H)-one (6 mL), and the resulting solution was cooled to −78° C. under a nitrogen atmosphere. A solution of NaHMDS in THF (1M, 3.59 mL, 3.59 mmol) was added dropwise, and the mixture was stirred at −78° C. for 10 min. A solution of 2-methoxyethyl 3-((chlorosulfonyl)oxy)-2,2-dimethylpropanoate (21a) (878 mg, 3.59 mmol) in THF (2 mL) was then added to the reaction mixture via a syringe. After 10 min at −78° C., the reaction mixture was allowed to warm to room temperature and stirred overnight. The reaction mixture was diluted with EtOAc and washed with saturated NaHCO$_3$, water, and brine. The organic layer was dried with anhydrous Na$_2$SO$_4$, filtered, and concentrated under vacuum to give a crude residue. The residue was purified by silica gel column chromatography using EtOAc/hexane (1:1) as eluent to give the product (21b) (0.96 g, yield 48%) as a white foam. MS (ESI) C$_{25}$H$_{42}$N$_4$O$_{11}$S=607.0 (M+1)$^+$.

Step 3: Synthesis of 2-methoxyethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (TFA salt) (21)

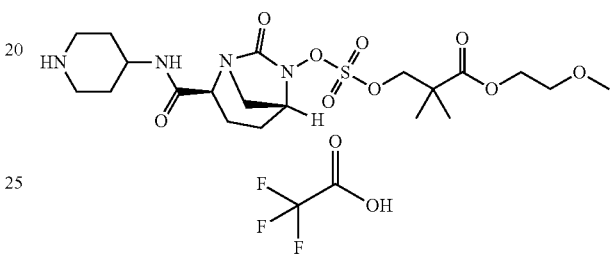

To a mixture of tert-butyl 4-((2S,5R)-6-(((3-(2-methoxyethoxy)-2,2-dimethyl-3-oxopropoxy)sulfonyl)oxy)-7-oxo-1,6-diazabicyclo[3.2.1]octane-2-carboxamido)piperidine-1-carboxylate (21b) (0.86 g, 1.42 mmol) in DCM (4.3 mL) was added trifluoroacetic acid (4.3 mL) at −10° C. The reaction mixture was stirred at −10° C. for 30 min. LC/MS analysis indicated that the stating material was completely consumed. The mixture was concentrated under vacuum to give a crude residue. The residue was purified by prep-HPLC on a C18 column eluting with MeCN/H$_2$O containing 0.1% TFA (5-75%) to give the title compound (21) (513 mg, yield 58%) as a yellow powder. $^1$H NMR (300 MHz, CDCl$_3$): δ 9.09 (br s, 1H), 8.75 (br s, 1H), 6.83 (d, 1H, J=7.8 Hz), 4.59-4.71 (dd, 2H, J=9.3 Hz), 3.99-4.36 (m, 5H), 3.60 (m, 2H), 3.50 (d, 2H), 3.39 (s, 3H), 3.30 (d, 1H), 3.02 (m, 2H), 2.89 (d, 1H), 1.87-2.40 (m, 7H), 1.25-1.30 (m, 9H). $^{13}$C NMR (75 MHz, CDCl$_3$): δ 174.4, 168.9, 167.4, 80.6, 70.6, 64.5, 62.0, 60.4, 59.3, 46.8, 44.9, 43.6, 43.2, 28.7, 22.4, 21.8, 20.9, 18.0. 19F NMR (282 MHz, CDCl$_3$): δ −75.8. MS (ESI) C$_{20}$H$_{34}$N$_4$O$_9$S=507 (M+1)$^+$. HPLC retention time (MeCN/H$_2$O in 0.1% TFA): 6.75 min.

Example 22

Synthesis of 4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (22)

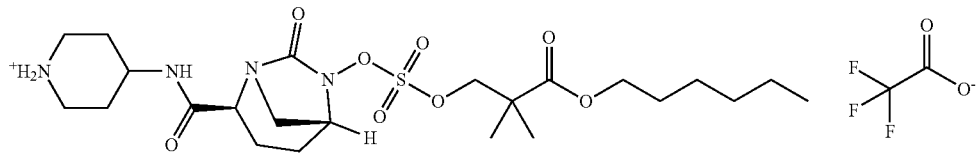 [SMILES: CCCCCCOC(=O)C(C)(C)COS(=O)(=O)ON1C(=O)N2C[C@H]1CC[C@H]2C(=O)NC1CC[NH2+]CC1 ; O=C([O-])C(F)(F)F]

Step 1: Synthesis of hexyl 3-hydroxy-2,2-dimethylpropanoate (22a)

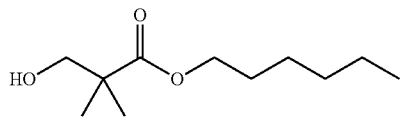

A mixture of 3-hydroxy-2,2-dimethylpropionic acid (4.7 g, 40 mmol), 1-hexanol (70 mL) and concentrated sulfuric acid (or fuming sulfuric acid, 1 mL) was heated to 80° C. and stirred overnight. After allowing to cool, the mixture was concentrated under vacuum (high vacuum pump required) and the residue was then partitioned between EtOAc (100 mL) and saturated aqueous NaHCO$_3$ (100 mL). The aqueous phase was washed with H$_2$O (50 mL), saturated NaHCO$_3$ (50 mL) and brine (50 mL), and then dried over anhydrous Na$_2$SO$_4$, filtered and concentrated under vacuum to provide the product as an oil. The product was difficult to purify using silica gel chromatography; and therefore the product was distilled under high vacuum at 47° C. to provide 4.92 g of the pure ester product (22a) (yield 61%). $^1$H NMR (300 MHz, CDCl$_3$) δ 4.10 (td, J=6.7, 1.3 Hz, 2H), 3.55 (d, J=5.1 Hz, 2H), 2.42 (s, 1H), 1.64 (s, 1H), 1.72-1.56 (m, 1H), 1.35 (s, 1H), 1.31 (s, 6H), 1.27-1.11 (m, 6H), 0.95-0.84 (m, 3H). MS (ESI) C$_{11}$H$_{22}$O$_3$=203 (M+1)$^+$.

Step 2: Synthesis of hexyl 3-((chlorosulfonyl)oxy)-2,2-dimethylpropanoate (22b)

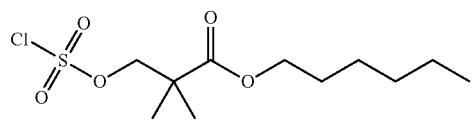 [SMILES: CCCCCCOC(=O)C(C)(C)COS(=O)(=O)Cl]

A solution of freshly distilled sulfuryl chloride (0.60 mL, 7.4 mmol) in Et$_2$O (10 mL) was cooled to −78° C. under an atmosphere of N$_2$. A solution of hexyl 3-hydroxy-2,2-dimethylpropanoate (22a) (1.0 g, 4.94 mmol) and pyridine (0.48 mL, 5.93 mmol) in Et$_2$O (5 mL) was added dropwise to the sulfuryl chloride solution over the course of 20 min. The flask was rinsed with Et$_2$O (3×1 mL) and the rinse added to the reaction mixture. The mixture was stirred at −78° C. until completion by TLC (30 min; 30% EA/hexane). The precipitate was filtered, and the filtrate was concentrated under vacuum to afford the crude product (22b) as a solid foam and was used in the next step without further purification. $^1$H-NMR (300 MHz, CDCl$_3$): δ 4.50 (s, 2H), 4.13 (t, J=6.8 Hz, 2H), 1.69-1.60 (m, 2H), 1.40-1.27 (m, 12H), 0.91-0.87 (m, 3H).

Step 3: Synthesis of tert-butyl 4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidine-1-carboxylate (22d)

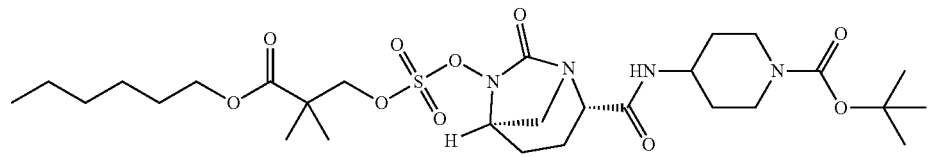 [SMILES: CCCCCCOC(=O)C(C)(C)COS(=O)(=O)ON1C(=O)N2C[C@H]1CC[C@H]2C(=O)NC1CCN(C(=O)OC(C)(C)C)CC1]

The hydroxamic acid (2.39 mmol) was dissolved in THF (12 mL) and 1,3-dimethyltetrahydropyrimidin-2(1H)-one (3.4 mL), and the resulting solution was cooled to −78° C. under an atmosphere of N$_2$. A solution of NaHMDS in THF (2.4 mL, 1.0 M, 2.4 mmol) was added dropwise to and the mixture stirred for 20 min. Neat hexyl 3-((chlorosulfonyl)oxy)-2,2-dimethylpropanoate (22b) (0.973 g, 2.64 mmol) was added quickly to the reaction mixture. The syringe was rinsed with THF (3×4 mL) and the rinse was also added to the mixture. After 10 min, the reaction mixture was warmed to room temperature and stirred until complete as determined by TLC and LC-MS. EtOAc (30 mL) and saturated aqueous NaHCO$_3$ (30 mL) were added to the mixture. The layers were partitioned, and the organic layer was washed with saturated aqueous NaHCO$_3$ (30 mL), water (3×20 mL), and brine (30 mL), and then dried (Na$_2$SO$_4$), filtered and concentrated under vacuum to leave a crude residue. The residue was purified by silica gel column chromatography using EtOAc/hexane (1:9 to 1:0) as eluent, followed by high-performance liquid chromatography to give the product (22d) (740 mg, yield 49% for 3 steps) as a solid foam. ¹H NMR (300 MHz, CDCl₃) δ 6.43 (d, J=8.2 Hz, 1H), 4.76-4.64 (m, 1H), 4.60 (d, J=9.0 Hz, 1H), 4.19-4.03 (m, 5H), 3.98 (d, J=7.5 Hz, 2H), 3.28 (d, J=12.0 Hz, 1H), 2.90 (d, J=12.0 Hz, 2H), 2.45 (dd, J=14.8, 6.2 Hz, 1H), 2.14 (s, 1H), 1.97-1.84 (m, 3H), 1.62 (q, J=7.0 Hz, 11H), 1.46 (s, 9H), 1.34-1.19 (m, 14H), 0.88 (d, J=7.0 Hz, 3H). MS (ESI) C₂₈H₄₈N₄O₁₀S=633 (M+1)⁺.

Step 4: Synthesis of 4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (22)

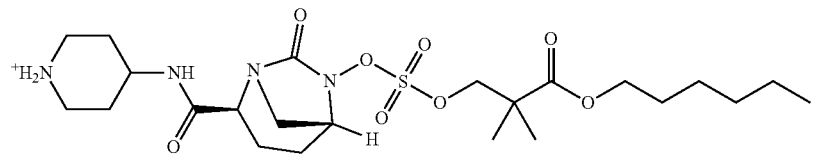

tert-Butyl 4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidine-1-carboxylate (22d) (300 mg, 0.474 mmol) was dissolved in DCM (2 mL) and cooled to −10° C. To the solution was added TFA (2 mL) dropwise. The reaction was monitored with LCMS or TLC until completion (ca. 10 min). The solvent was removed in vacuo and the residue was purified using prep-HPLC with MeCN/H₂O containing 0.1% TFA (20-100%) as an eluent to provide, after lyophilization, the title compound (22) (212.4 mg, yield 84%) as a foam. ¹H NMR (300 MHz, CDCl₃) δ 9.08 (s, 1H), 8.74 (s, 1H), 6.88 (d, J=7.9 Hz, 1H), 4.70-4.51 (m, 2H), 4.23-3.92 (m, 6H), 3.47 (d, J=12.6 Hz, 2H), 3.31-3.19 (m, 1H), 2.95 (dd, J=19.6, 11.0 Hz, 3H), 2.34 (dd, J=15.0, 6.2 Hz, 1H), 2.10 (s, 2H), 1.91 (ddd, J=15.8, 12.6, 8.0 Hz, 1H), 1.61 (ddd, J=12.5, 8.1, 6.3 Hz, 3H), 1.40-1.16 (m, 14H), 0.91-0.80 (m, 3H). ¹³C NMR (75 MHz, CDCl₃) δ 174.2, 168.6, 167.1, 80.4, 65.5, 61.7, 60.1, 46.6, 44.7, 43.3, 42.9, 42.9, 31.4, 31.4, 28.5, 25.6, 25.5, 22.2, 22.2, 21.6, 20.7, 17.8, 14.0. ¹⁹F NMR (282 MHz, CDCl₃) δ −75.6. MS (ESI) C₂₃H₄₀N₄O₈S=533 (M+1)⁺. HPLC retention time (MeCN/H₂O in 0.1% TFA): 8.18 min.

Example 23

Synthesis of 4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (23)

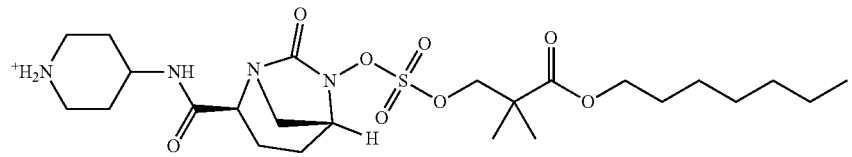

Step 1: Synthesis of heptyl 3-hydroxy-2,2-dimethylpropanoate (23a)

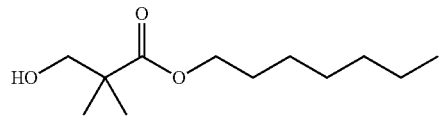

A mixture of 3-hydroxy-2,2-dimethylpropionic acid (4.7 g, 40 mmol), 1-heptanol (70 mL) and concentrated sulfuric acid (1 mL) was heated to 80° C. and stirred overnight. After allowing to cool, the mixture was concentrated under vacuum (high vacuum pump required) and the residue partitioned between EtOAc (100 mL) and saturated aqueous NaHCO₃ (100 mL). The aqueous phase was washed with H₂O (50 mL), saturated NaHCO₃ (50 mL) and brine (50 mL), and then dried (Na₂SO₄), filtered and concentrated under vacuum to provide the product as an oil. The product was distilled under high vacuum at 65° C. to provide the title compound (23a) as an oil (6.7 g, 77% yield). ¹H NMR (300 MHz, CDCl₃) δ 4.09 (td, J=6.7, 0.9 Hz, 2H), 3.55 (d, J=6.1 Hz, 2H), 2.43 (t, J=6.7 Hz, 1H), 1.60 (d, J=22.8 Hz, 4H), 1.3-1.58 (m, 6H), 1.27-1.14 (m, 6H), 0.92-0.83 (m, 3H).

Step 2: Synthesis of heptyl 3-((chlorosulfonyl)oxy)-2,2-dimethylpropanoate (23b)

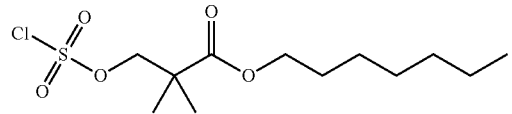 [SMILES: CCCCCCCOC(=O)C(C)(C)COS(=O)(=O)Cl]

A solution of sulfuryl chloride (0.6 mL, 7.4 mmol) in Et₂O (15 mL) was cooled to −78° C. under an atmosphere of N₂. A solution of heptyl 3-hydroxy-2,2-dimethylpropanoate (23a) (1.0 g, 4.94 mmol) and pyridine (479 μL, 5.93 mmol) in Et₂O (1 mL) was added dropwise to the sulfuryl chloride solution over the course of 30 min. The flask was rinsed with Et₂O (3×1 mL) and the rinse added to the reaction mixture. The mixture was stirred at −78° C. until completion as monitored by TLC (30 min; 30% EA/hexane). The precipitate was filtered, and the filtrate was concentrated under vacuum to afford heptyl 3-((chlorosulfonyl)oxy)-2,2-dimethylpropanoate (23b) (1.37 g, yield 92%). The mixture was stored at −78° C. and used in the next step without further purification. ¹H NMR (300 MHz, CDCl₃) δ 4.50 (s, 2H), 4.20-4.02 (m, 2H), 1.68 (m, 2H), 1.31 (d, J=3.1 Hz, 13H), 1.23 (s, 1H), 0.95-0.83 (m, 3H).

Step 3: Synthesis of tert-butyl 4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidine-1-carboxylate (23c)

tert-Butyl 4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidine-1-carboxylate (23c) (472.1 mg, 0.73 mmol) dissolved in DCM (5 mL) was cooled to −10° C., to which was added TFA (5 mL) dropwise. After completion, the solvent was evaporated in vacuo and the residue was purified with prep-HPLC using MeCN/H₂O containing 0.1% TFA (20-100%) to give the title compound (23) (390 mg, 81% yield) as a solid foam. ¹H NMR (300 MHz, CDCl₃) δ 8.93 (d, J=10.4 Hz, 1H), 8.62 (s, 1H), 6.90 (d, J=7.8 Hz, 1H), 4.70-4.51 (m, 2H), 4.18-3.92 (m, 6H), 3.48 (d, J=12.2 Hz, 2H), 3.26 (d, J=11.5 Hz, 1H), 2.98 (dt, J=24.4, 11.7 Hz, 3H), 2.34 (dd, J=15.1, 6.3 Hz, 1H), 2.10 (s, 2H), 1.60 (h, J=6.6 Hz, 3H), 1.24 (q, J=11.1, 9.8 Hz, 18H), 0.90-0.79 (m, 4H). ¹³C NMR (75 MHz, CDCl₃) δ 174.2, 168.6, 167.1, 80.3, 73.9, 65.4, 61.6, 60.1, 46.5, 44.6,

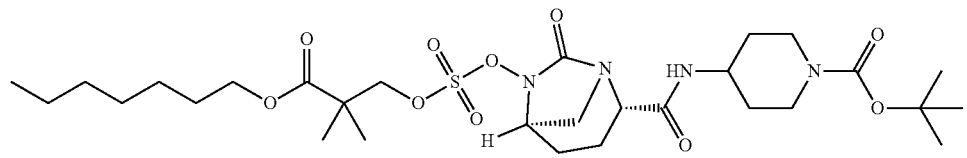 [SMILES: CCCCCCCOC(=O)C(C)(C)COS(=O)(=O)ON1C(=O)N2C[C@H]1CC[C@H]2C(=O)NC1CCN(C(=O)OC(C)(C)C)CC1]

Hydroxamic acid (1) (2.399 mmol, from hydrogenation, without further purification) was dissolved in THF (12 mL) and 1,3-dimethyltetrahydropyrimidin-2(1H)-one (3 mL) and the resulting solution was cooled to −78° C. under a nitrogen atmosphere. A 1.0 M solution of NaHMDS in THF (2.4 mL, 2.4 mmol) was added dropwise to the cooled solution and stirred for 20 min. Heptyl 3-((chlorosulfonyl)oxy)-2,2-dimethylpropanoate (23b) (0.79 g, 2.63 mmol) in THF (5 mL) was rapidly added to the reaction mixture. The syringe was rinsed with THF (3×2 mL) and the rinse was also added to the mixture. After 10 min, the reaction mixture was warmed to room temperature and stirred until completion as determined by TLC and LC-MS. EtOAc (50 mL) and saturated aqueous NaHCO₃ (50 mL) were added to the mixture. The aqueous and organic layers were partitioned, and the organic layer was washed with saturated aqueous NaHCO₃ (10 mL), water (3×10 mL), brine (20 mL), and then dried (Na₂SO₄), filtered and concentrated under vacuum to provide a crude residue. The residue was purified by silica gel column chromatography using EtOAc/hexane (5% to 95%) as eluent, to give 740.0 mg (49% yield) of the product (23c).

Step 4: Synthesis of 4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (23)

43.4, 42.8, 42.8, 31.6, 28.8, 28.4, 28.3, 25.8, 25.7, 22.5, 22.1, 22.1, 21.5, 20.6, 17.8, 14.0. ¹⁹F NMR (282 MHz, CDCl₃) δ −75.7. MS (ESI) C₂₄H₄₂N₄O₈S=547 (M+1)⁺. HPLC retention time (MeCN/H₂O in 0.1% TFA): 9.59 min.

Example 24

Synthesis of 4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidin-1-ium 2,2,2-trifluoroacetate (24)

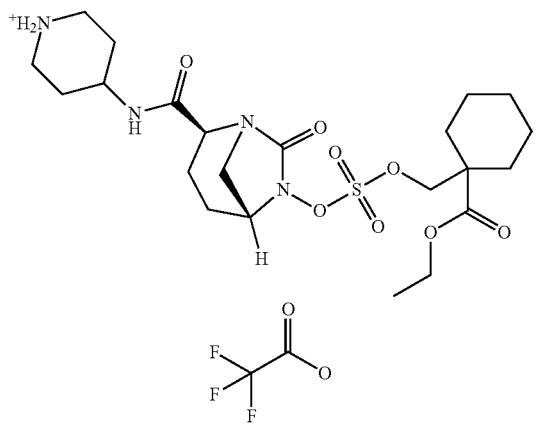

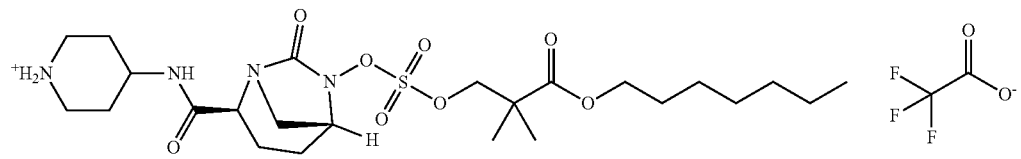 [SMILES: CCCCCCCOC(=O)C(C)(C)COS(=O)(=O)ON1C(=O)N2C[C@H]1CC[C@H]2C(=O)NC1CC[NH2+]CC1 ; O=C([O-])C(F)(F)F]

Step 1: Synthesis of ethyl 1-(hydroxymethyl)cyclohexanecarboxylate (24a)

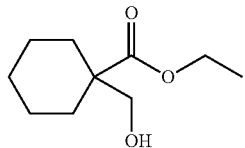

Diethyl cyclohexane-1,1-dicarboxylate (2.12 g, 9.29 mmol) was dissolved in THF (50 mL) and to which was added LiAl(OtBu)₃ (5.9 g, 23.2 mmol) in portions. The reaction mixture was stirred at reflux overnight. The reaction was cooled in an ice bath and treated carefully with 10% KHSO₄ aq. solution (30 mL) with stirring for 10 min. The precipitate formed was filtered out through a pad of Celite®. The filtrate was extracted with EtOAc (3×40 mL) and the organic phase was combined and washed with brine (50 mL), dried over NaSO₄, filtered and concentrated in vacuo. The residue was purified with CombiFlash (SiO₂) in 0-5% MeOH/DCM to obtain the desired product (24) as an oil (1.23 g, 71% yield). $^1$H NMR (300 MHz, CDCl₃) δ 4.19 (qd, J=7.1, 0.8 Hz, 2H), 3.62 (d, J=6.4 Hz, 2H), 3.46 (s, 1H), 2.00 (dt, J=11.5, 6.4 Hz, 4H), 1.57-1.22 (m, 9H).

Step 2: Synthesis of ethyl 1-(((chlorosulfonyl)oxy)methyl)cyclohexanecarboxylate (24b)

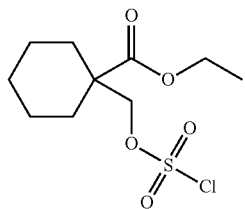 [SMILES: CCOC(=O)C1(COS(=O)(=O)Cl)CCCCC1]

A solution of freshly distilled sulfuryl chloride (294 μL, 3.63 mmol) in Et₂O (10 mL) was cooled to −78° C. under an atmosphere of nitrogen. A solution of ethyl 1-(hydroxymethyl)cyclohexanecarboxylate (24a) (0.615 g, 3.3 mmol) and pyridine (294 μL, 3.63 mmol) in Et₂O (6 mL) was added dropwise to the sulfuryl chloride solution during 15 min. The flask was rinsed with Et₂O (3×1 mL) and the rinse added to the reaction. The mixture was stirred at −78° C. until completion (ca. 30 min; monitored by TLC, 30% EtOAc/hexane). The precipitate was filtered, and the filtrate was concentrated under vacuum to afford the title compound (24b) as an oil, 0.94 g in quantitative yield, which was used directly in the next step without purification. $^1$H-NMR (300 MHz, CDCl₃): δ 4.52 (s, 2H), 4.21 (q, J=7.1 Hz, 2H), 2.04 (s, 2H), 1.53-1.39 (m, 8H), 1.39-1.21 (m, 3H).

Step 3: Synthesis of tert-Butyl 4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidine-1-carboxylate (24c)

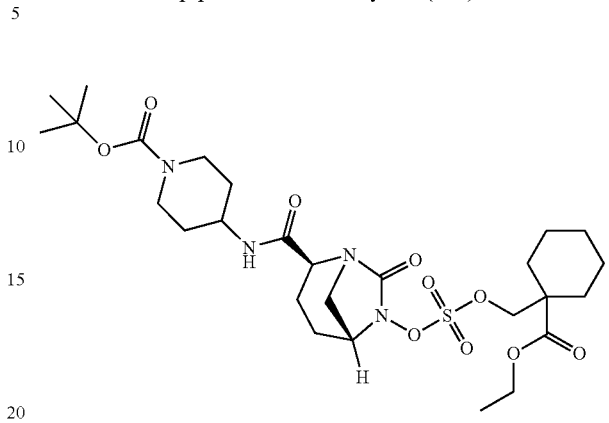

Hydroxamic acid (2.73 mmol) was dissolved in THF (14 mL) and 1,3-dimethyltetrahydropyrimidin-2(1H)-one (7 mL), and the resulting solution was cooled to −78° C. under an atmosphere of nitrogen. A 1.0 M solution of NaHMDS in THF (2.73 mL, 2.73 mmol) was added dropwise over 20 min, and the mixture stirred for 10 min. Ethyl 1-(((chlorosulfonyl)oxy)methyl)cyclohexanecarboxylate (24b) (0.94 g, 3.3 mmol) in THF (2 mL) was rapidly added to the reaction mixture. After 10 min stirring at −78° C., the mixture was allowed to warm to room temperature and stirred for 1 h. The reaction mixture was diluted with EtOAc (60 mL) and H₂O at −60° C. The aqueous and organic layers were partitioned, and the organic layer was washed with H₂O (3×30 mL), and brine (50 mL), then dried (Na₂SO₄), filtered and concentrated under vacuum to give the crude residue (330 mg). The oil was purified by silica gel column chromatography using EtOAc/hexane (3:7 to 1:0) as eluent to give the product (24c) (0.98 g, yield 59%) as a solid. $^1$H-NMR (300 MHz, CDCl₃): δ 6.43 (d, J=8.2 Hz, 1H), 4.75 (d, J=9.2 Hz, 1H), 4.59 (d, J=9.1 Hz, 1H), 4.28-4.05 (m, 5H), 4.04-3.90 (m, 3H), 2.87 (t, J=12.4 Hz, 3H), 2.45 (dd, J=15.0, 5.7 Hz, 1H), 2.08-1.84 (m, 4H), 1.56 (d, J=10.6 Hz, 3H), 1.46 (s, 9H), 1.46-1.34 (m, 5H), 1.37-1.20 (m, 8H). MS (ESI) C₂₇H₄₄N₄O₁₀S: 617 (M+H)⁺.

Step 4: 4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidin-1-ium 2,2,2-trifluoroacetate (24)

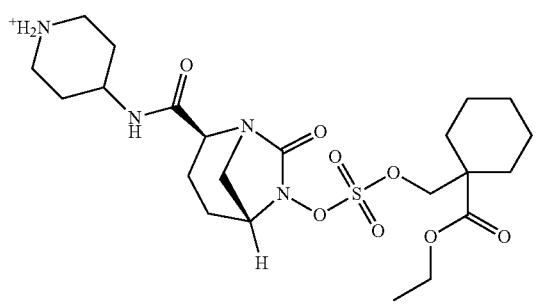

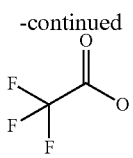

tert-Butyl 4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidine-1-carboxylate (24c) (403.3 mg, 0.65 mmol) dissolved in DCM (4 mL) was cooled to −10° C. (salt ice bath) to which was added TFA (4 mL) dropwise. The reaction monitored by LCMS. After 30 min, it was complete. The solvent was removed in vacuo and the residue was purified with prep-HPLC in MeCN/H2O containing 0.1% TFA (20-100%) to give the title compound (24) (263.7 mg, yield 78%) as a solid foam. $^1$H NMR (300 MHz, CDCl$_3$) δ 9.02 (d, J=10.6 Hz, 1H), 8.66 (s, 1H), 6.87 (d, J=7.8 Hz, 1H), 4.70 (d, J=9.1 Hz, 1H), 4.54 (d, J=9.0 Hz, 1H), 4.16 (dtd, J=12.9, 6.7, 6.3, 3.1 Hz, 4H), 4.00 (q, J=8.7, 7.2 Hz, 3H), 3.47 (d, J=12.3 Hz, 2H), 3.26 (d, J=11.5 Hz, 1H), 2.95 (dd, J=25.8, 11.9 Hz, 3H), 2.35 (dd, J=15.3, 6.3 Hz, 1H), 2.11 (t, J=10.3 Hz, 4H), 1.99 (s, 2H), 2.08-1.87 (m, 2H), 1.89-1.72 (m, 4H), 1.54 (d, J=8.0 Hz, 5H), 1.25 (dd, J=14.4, 3.8 Hz, 2H). $^{13}$C NMR (75 MHz, CDCl$_3$) δ 173.2, 168.5, 167.0, 80.2, 61.7, 61.1, 60.0, 47.0, 46.6, 44.6, 43.3, 30.4, 29.9, 28.3, 25.3, 22.4, 22.2, 22.0, 20.6, 17.7, 14.1. $^{19}$F NMR (282 MHz, CDCl$_3$) δ −75.7. MS (ESI) C$_{22}$H$_{36}$N$_4$O$_8$S=517 (M+1)$^+$. HPLC retention time (MeCN/H$_2$O in 0.1% TFA): 8.15 min.

Example 25

Synthesis of (5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (25)

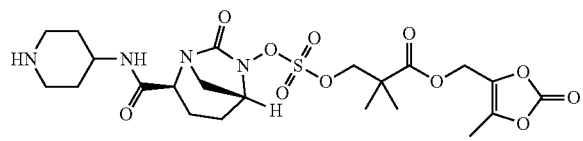 [SMILES: Cc1oc(=O)oc1COC(=O)C(C)(C)COS(=O)(=O)ON1C(=O)N2C[C@H]1CC[C@H]2C(=O)NC1CCNCC1]

Step 1: Synthesis of (5-methyl-2-oxo-1,3-dioxol-4-yl)methyl 3-hydroxy-2,2-dimethylpropanoate (25a)

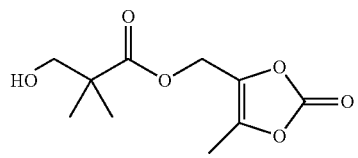 [SMILES: Cc1oc(=O)oc1COC(=O)C(C)(C)CO]

To a stirred solution of 3-hydroxy-2,2-dimethylpropanoic acid (4.0 g, 33.9 mmol) and potassium carbonate (4.68 g, 33.9 mmol) in DMF (45 mL) at 0° C. was added 4-(hydroxymethyl)-5-methyl-1,3-dioxol-2-one (5.03 g, 33.9 mmol) in DMF (5 mL) dropwise over 1 h. The reaction was stirred at room temperature overnight. The reaction mixture was diluted with EtOAc and washed with water and brine. The organic layer was dried with anhydrous Na$_2$SO$_4$, filtered, and concentrated under vacuum to give a crude residue. The residue was purified by silica gel column chromatography using EtOAc/hexane (1:4 to 2:3) as eluent to give the product (25a) as a yellow liquid (1.6 g, yield 21%). $^1$H NMR (300 MHz, CDCl$_3$): δ 4.86 (s, 2H), 3.58 (s, 2H), 2.18 (s, 3H), 1.20 (s, 6H).

Step 2: Synthesis of (5-methyl-2-oxo-1,3-dioxol-4-yl)methyl 3-((chlorosulfonyl)oxy)-2,2-dimethylpropanoate (25b)

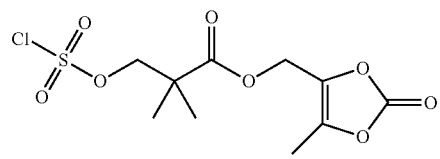 [SMILES: Cc1oc(=O)oc1COC(=O)C(C)(C)COS(=O)(=O)Cl]

A solution of distilled sulfuryl chloride (0.61 mL, 7.53 mmol) in Et$_2$O (15 mL) was cooled to −78° C. under nitrogen. A solution of (5-methyl-2-oxo-1,3-dioxol-4-yl)methyl 3-hydroxy-2,2-dimethylpropanoate (25a) (1.48 g, 6.43 mmol) in Et$_2$O (1 mL) was added. Subsequently, a solution of pyridine (0.55 mL, 6.86 mmol) in Et$_2$O (1 mL) was added over a period of 1 h. The reaction was stirred at −78° C. for 1 h. After the mixture was filtered, the filtrate was concentrated under vacuum to give the product (25b) as a yellow oil (1.6 g, yield 76%). $^1$H NMR (300 MHz, CDCl$_3$): δ 4.90 (s, 2H), 4.49 (s, 2H), 2.19 (s, 3H), 1.33 (s, 6H).

Step 3: Synthesis of tert-butyl 4-((2S,5R)-6-(((2,2-dimethyl-3-((5-methyl-2-oxo-1,3-dioxol-4-yl)methoxy)-3-oxopropoxy)sulfonyl)oxy)-7-oxo-1,6-diazabicyclo[3.2.1]octane-2-carboxamido)piperidine-1-carboxylate (25c)

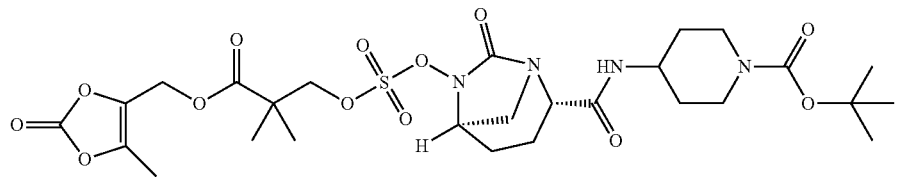 [SMILES: Cc1oc(=O)oc1COC(=O)C(C)(C)COS(=O)(=O)ON1C(=O)N2C[C@H]1CC[C@H]2C(=O)NC1CCN(C(=O)OC(C)(C)C)CC1]

tert-Butyl 4-((2S,5R)-6-hydroxy-7-oxo-1,6-diazabicyclo[3.2.1]octane-2-carboxamido)piperidine-1-carboxylate (20c) (2.18 mmol) was dissolved in THF (14 mL) and 1,3-dimethyltetrahydropyrimidin-2(1H)-one (6 mL), and the resulting solution was cooled to −78° C. under nitrogen. A solution of NaHMDS in THF (1M, 2.62 mL, 2.62 mmol) was added dropwise, and the mixture was stirred at −78° C. for 10 min. A solution of (5-methyl-2-oxo-1,3-dioxol-4-yl)methyl 3-((chlorosulfonyl)oxy)-2,2-dimethylpropanoate (25b) (106b) (0.86 g, 2.62 mmol) in THF (1 mL) was then added to the reaction mixture via a syringe. After stirring for 1 h at −78° C., the reaction mixture was diluted with EtOAc and washed with saturated NaHCO$_3$, water, and brine. The organic layer was dried with anhydrous Na$_2$SO$_4$, filtered, and concentrated under vacuum to give a crude residue. The residue was purified by silica gel column chromatography using EtOAc/hexane (1:3 to 1:1) as eluent to give the product (25c) as a yellow paste (0.44 g, yield 31%). $^1$H NMR (300 MHz, CDCl$_3$): δ 6.73 (d, 1H, J=8.1 Hz), 4.78-4.98 (m, 3H), 4.47 (d, 1H, J=8.7 Hz), 3.93-4.15 (m, 5H), 3.27 (d, 1H), 2.83-2.92 (m, 3H), 2.41-2.45 (m, 1H), 2.18 (s, 3H), 2.15 (m, 1H), 1.78-1.92 (m, 4H), 1.45 (s, 9H), 1.23-1.58 (m, 8H). MS (ESI) C$_{27}$H$_{40}$N$_4$O$_{13}$S=661 (M+1)$^+$.

Step 5: Synthesis of (5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (TFA salt) (25)

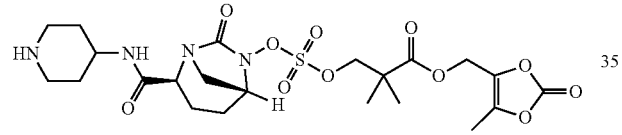

To a solution of tert-butyl 4-((2S,5R)-6-(((2,2-dimethyl-3-((5-methyl-2-oxo-1,3-dioxol-4-yl)methoxy)-3-oxopropoxy)sulfonyl)oxy)-7-oxo-1,6-diazabicyclo[3.2.1]octane-2-carboxamido)piperidine-1-carboxylate (25c) (100 mg, 0.15 mmol) in DCM (3 mL) was added trifluoroacetic acid (0.4 mL) at −10° C. The reaction was stirred at −10° C. for 1 h. LC/MS analysis indicated that the stating material was consumed. The mixture was concentrated under vacuum to give a crude residue. The residue was purified by prep-HPLC on a C18 column eluting using MeCN/H$_2$O containing 0.1% TFA (5-80%) to give the title compound (25) as off-white powder (55.2 mg, yield 55%). $^1$H NMR (300 MHz, CDCl$_3$): δ 9.43 (br s, 1H), 9.05 (br s, 1H), 7.14 (d, 1H, J=6.9 Hz), 4.99 (d, 1H, J=13.5 Hz), 4.95 (d, 1H, J=8.1 Hz), 4.78 (d, 1H, J=14.1 Hz), 4.41 (d, 1H, J=9.3 Hz), 4.14 (s, 1H), 4.06 (m, 1H), 3.98 (d, 1H, J=6.3 Hz), 3.47 (d, 2H), 3.29 (d, 1H), 3.04 (m, 2H), 2.86 (d, 1H), 1.82-2.40 (m, 11H), 1.29-1.33 (ds, 6H). $^{13}$C NMR (75 MHz, CDCl$_3$): δ 173.9, 169.1, 167.3, 152.9, 141.0, 133.7, 80.3, 62.0, 60.4, 54.8, 46.8, 44.7, 43.4, 43.3, 28.5, 22.3, 22.0, 20.8, 18.0, 9.6. $^{19}$F NMR (282 MHz, CDCl$_3$): δ −75.9. MS (ESI) C$_{22}$H$_{32}$N$_4$O$_{11}$S=561 (M+1)$^+$.

Analytical HPLC was performed on an Agilent 1200 system using a Phenomenex® C18 column (150×4.6 mm i.d.). The mobile phase was a linear gradient of MeCN and water (0.1% TFA, 5% MeCN to 100% MeCN in 15 min). The flow rate was maintained at 1 mL/min and the eluent was monitored with UV detector at 220 nm and 254 nm. HPLC retention time: 7.25 min.

Example 26

Synthesis of (2S,5R)-7-oxo-2-(piperidin-4-ylcarbamoyl)-1,6-diazabicyclo[3.2.1]octan-6-yl hydrogen sulfate (26)

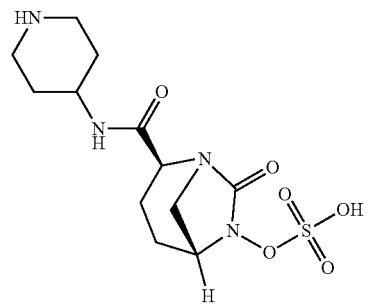 [SMILES: O=C(NC1CCNCC1)[C@@H]1CC[C@@H]2CN1C(=O)N2OS(=O)(=O)O]

Step 1: Synthesis of tetrabutylammonium (2S,5R)-2-((1-(tert-butoxycarbonyl)piperidin-4-yl)carbamoyl)-7-oxo-1,6-diazabicyclo[3.2.1]octan-6-yl sulfate (26a)

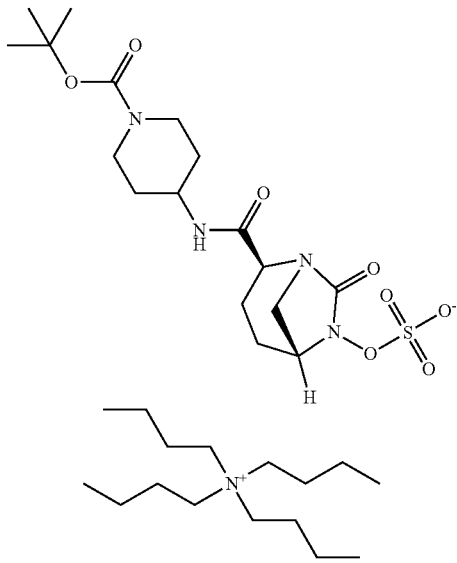

To a solution of tert-butyl 4-((2S,5R)-6-hydroxy-7-oxo-1,6-diazabicyclo[3.2.1]octane-2-carboxamido)piperidine-1-carboxylate (20c) (1.92 g, 5.21 mmol) in DCM (30 mL) was added triethylamine (3 mL) and pyridine-sulfur trioxide complex (3.34 g, 21.0 mmol). The reaction was stirred at 35° C. overnight. The mixture was concentrated under vacuum to give a crude residue. The residue was stirred with 0.5 N aqueous potassium dihydrogen phosphate solution (30 mL) for 1 h. The resulting solution was extracted three times with DCM. The combined organic layer was dried with anhydrous Na$_2$SO$_4$, filtered, and concentrated under vacuum to give triethylamine salt of (2S,5R)-2-((1-(tert-butoxycarbonyl)piperidin-4-yl)carbamoyl)-7-oxo-1,6-diazabicyclo[3.2.1]octan-6-yl sulfate (26a) (2.3 g, yield 80%).

To a solution of above product (26a) (2.2 g, 4.0 mmol) in DCM (30 mL) was added 0.5 N aqueous dipotassium hydrogen phosphate (12.4 mL) at 0° C. After stirred at 0° C. for 10 min, tetrabutyl ammonium hydrogen sulfate (1.49 g, 4.4 mmol) was added. The resulting solution was stirred at room temperature for 30 min. After the organic layer was separated, the aqueous layer was extracted three times with DCM. The combined organic layer was dried with anhydrous Na$_2$SO$_4$, filtered, and concentrated under vacuum to give a residue. The residue was purified by silica gel column chromatography using 10% MeOH in DCM as eluent to give the product (26a) (1.35 g, yield 49%) as a white solid. $^1$H NMR (300 MHz, CDCl$_3$): δ 6.55 (d, 1H, J=8.1 Hz), 4.33 (br s, 1H), 4.03 (m, 2H), 3.91-3.95 (m, 1H), 3.86 (d, 1H), 3.48 (m, 1H), 3.25-3.31 (m, 10H), 2.85 (m, 2H), 2.73 (d, 1H), 2.39 (dd, 1H), 2.13 (m, 1H), 1.81-1.92 (m, 4H), 1.60-1.71 (m, 11H), 1.29-1.50 (m, 14H), 1.00 (t, 12H). MS (ESI) C$_{17}$H$_{28}$N$_4$O$_8$S=446.9 (M−1)$^+$.

Step 2: Synthesis of (2S,5R)-7-oxo-2-(piperidin-4-ylcarbamoyl)-1,6-diazabicyclo[3.2.1]octan-6-yl hydrogen sulfate (26)

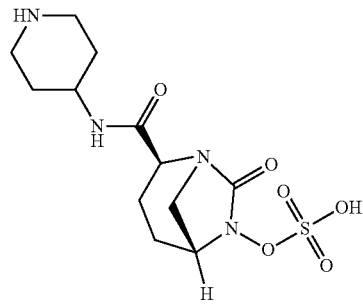 [SMILES: O=C(NC1CCNCC1)[C@@H]1CC[C@@H]2CN1C(=O)N2OS(=O)(=O)O]

To a solution of tetrabutylammonium (2S,5R)-2-((1-(tert-butoxycarbonyl)piperidin-4-yl)carbamoyl)-7-oxo-1,6-diazabicyclo[3.2.1]octan-6-yl sulfate (26a) (1.35 g, 1.96 mmol) in DCM (15 mL) at −10° C. was added TFA (15 mL). After the starting material was consumed as indicated by LC/MS, the mixture was concentrated under vacuum to give a crude residue. The residue was stirred with diethyl ether to provide a precipitate. The solid was filtered, and washed twice with acetone to provide the title compound (26) as off-white solid (0.56 g, yield 82%). $^1$H NMR (300 MHz, DMSO-d$_6$): δ 8.30 (br s, 2H), 8.21 (d, 1H, J=7.5 Hz), 3.97 (s, 1H), 3.86 (m, 1H), 3.71 (d, 1H), 3.25 (m, 2H), 2.97 (m, 4H), 2.06 (m, 1H), 1.83 (m, 3H), 1.64 (m, 4H). $^{13}$C NMR (75 MHz, DMSO-d$_6$): 169.5, 166.7, 59.6, 58.0, 46.7, 43.9, 42.5, 28.0, 20.6, 18.6. MS (ESI) C$_{12}$H$_{20}$N$_4$O$_6$S=346.9 (M+1)$^+$. HPLC retention time (MeCN/H$_2$O in 0.1% TFA): 1.60 min.

Example 27

Synthesis of ethyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate (27)

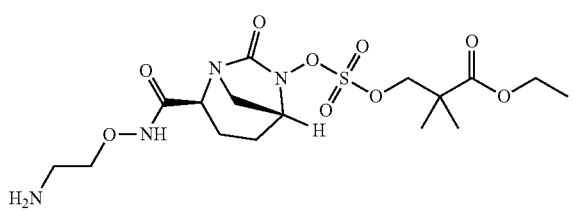 [SMILES: CCOC(=O)C(C)(C)COS(=O)(=O)ON1C(=O)N2C[C@H]1CC[C@H]2C(=O)NOCCN]

Step 1: Synthesis of N-(2-tert-Boc-aminoethoxy)phthalimide (27a)

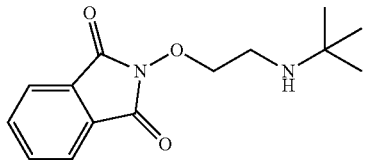 [SMILES: CC(C)(C)NCCON1C(=O)c2ccccc2C1=O]

To a mixture of tert-butyl (2-bromoethyl)carbamate (5.0 g, 22.3 mmol) and N-hydroxyphthalimide (3.64 g, 22.3 mmol) in acetonitrile (80 mL) at room temperature was added triethylamine (7.46 mL, 53.5 mmol). The reaction was stirred at 70° C. for 20 h and was then concentrated. The mixture was diluted with ethyl acetate, and washed extensively with 1 N HCl, saturated NaHCO$_3$, and water. The organic layer was dried with anhydrous Na$_2$SO$_4$, filtered, and concentrated under vacuum to give the crude product (27a) as an off-white solid (3.8 g, yield 56%). $^1$H NMR (300 MHz, CDCl$_3$): δ 7.76-7.87-4.90 (m, 4H), 5.65 (m, 1H), 4.25 (t, 3H), 3.44 (t, 3H), 1.46 (s, 9H).

Step 2: Synthesis of tert-butyl (2-(aminooxy)ethyl)carbamate (27b)

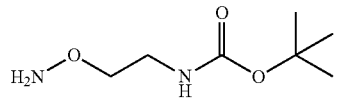

To a solution of N-(2-tert-Boc-aminoethoxy)phthalimide (27a) (3.8 g, 12.4 mmol) in EtOH (38 mL) at room temperature was added hydrazine monohydrate (0.63 mL, 13.0 mmol). The reaction was stirred at room temperature for 2 h. The mixture was filtered and washed with ethyl acetate. The filtrate was concentrated and a white solid was formed. The white solid was removed by filtration and washed with ethyl acetate. This process was repeated three additional times. The combined filtrate was then concentrated to give the product (27b) as a yellow paste (2.16 g, yield 99%). $^1$H NMR (300 MHz, CDCl$_3$): δ 5.46 (br s, 2H), 4.91 (br s, 1H), 3.70 (m, 2H), 3.35 (m, 2H), 1.44 (s, 9H).

Step 3: Synthesis of tert-butyl (2-(((2S,5R)-6-(benzyloxy)-7-oxo-1,6-diazabicyclo[3.2.1]octane-2-carboxamido)oxy)ethyl)carbamate (27c)

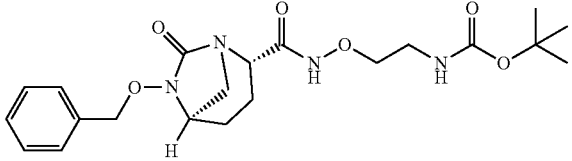 [SMILES: CC(C)(C)OC(=O)NCCONC(=O)[C@@H]1CC[C@@H]2CN1C(=O)N2OCc1ccccc1]

To a mixture of (2S,5R)-6-(benzyloxy)-7-oxo-1,6-diazabicyclo[3.2.1]octane-2-carboxylic acid (20a) (3.19 g, 11.6 mmol), tert-butyl (2-(aminooxy)ethyl)carbamate (27b) (2.06 g, 11.7 mmol) in DCM (20 mL) was added HATU (4.39 g, 11.6 mmol) and DIPEA (2.02 mL, 11.6 mmol). The reaction was stirred at room temperature overnight. The mixture was washed with saturated NH₄Cl solution, water and brine. The organic layer was dried with anhydrous Na₂SO₄, filtered, and concentrated under vacuum to give a crude residue. The residue was purified by silica gel column chromatography using EtOAc/hexane (1:1 to 3:1) as an eluent to give the product (27c) as a white paste (4.0 g, yield 79%). ¹H NMR (300 MHz, CDCl₃): δ 9.46 (br, s, 1H), 7.26-7.43 (m, 5H), 5.46 (t, 1H), 4.80-5.10 (dd, 2H, J=11.1 Hz), 2.75-3.97 (m, 8H), 1.61-2.33 (m, 4H), 1.43 (t, 9H). MS (ESI) C₂₁H₃₀N₄O₆=435 (M+1)⁺.

Step 4: Synthesis of tert-butyl (2-(((2S,5R)-6-hydroxy-7-oxo-1,6-diazabicyclo[3.2.1]octane-2-carboxamido)oxy)ethyl)carbamate (27d)

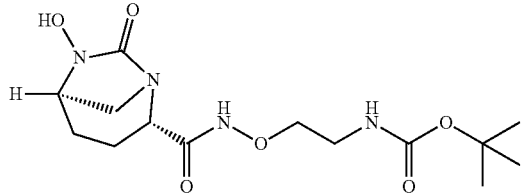 [SMILES: CC(C)(C)OC(=O)NCCONC(=O)[C@@H]1CC[C@@H]2CN1C(=O)N2O]

To a solution of tert-butyl (2-(((2S,5R)-6-(benzyloxy)-7-oxo-1,6-diazabicyclo[3.2.1]octane-2-carboxamido)oxy)ethyl)carbamate (27c) (1.0 g, 2.30 mmol) in MeOH (10 mL) was added 10% palladium on carbon (0.3 g). The reaction mixture was stirred under 1 atm hydrogen pressure for 1 h. After the mixture was filtered through a pad of Celite®, the filtrate was concentrated under vacuum to give a crude product (27d) (0.79 g, yield 100%) that was used directly in the next step.

Step 5: Synthesis of ethyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (27e)

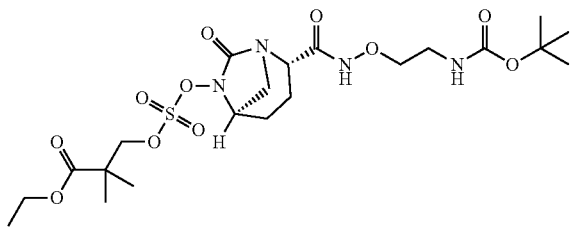 [SMILES: CCOC(=O)C(C)(C)COS(=O)(=O)ON1C(=O)N2C[C@H]1CC[C@H]2C(=O)NOCCNC(=O)OC(C)(C)C]

tert-Butyl (2-(((2S,5R)-6-hydroxy-7-oxo-1,6-diazabicyclo[3.2.1]octane-2-carboxamido)oxy)ethyl)carbamate (27d) (0.79 g, 2.30 mmol) was dissolved in THF (14 mL) and 1,3-dimethyltetrahydropyrimidin-2(1H)-one (6 mL), and the resulting solution was cooled to −78° C. under a nitrogen atmosphere. A solution of NaHMDS in THF (1M, 3.45 mL, 3.45 mmol) was added dropwise, and the mixture was stirred at −78° C. for 10 min. A solution of ethyl 3-((chlorosulfonyl)oxy)-2,2-dimethylpropanoate (3a) (675 mg, 2.76 mmol) in THF (2 mL) was then added to the reaction mixture via a syringe. After 10 min at −78° C., the reaction mixture was allowed to warm to room temperature and stirred overnight. The reaction mixture was diluted with EtOAc and washed with saturated NaHCO₃, water, and brine. The organic layer was dried with anhydrous Na₂SO₄, filtered, and concentrated under vacuum to give a crude residue. The residue was purified by silica gel column chromatography using EtOAc/hexane (1:1 to 3:1) as eluent to give the product (27e) as an off-white foam (0.68 g, yield 54%). ¹H NMR (300 MHz, CDCl₃): δ 9.60 (br, s, 1H), 5.27 (br, t, 1H), 4.58-4.73 (dd, 2H, J=9.3 Hz), 3.02-4.22 (m, 10H), 1.62-2.40 (m, 4H), 1.44 (t, 9H), 1.26-1.28 (m, 9H). MS (ESI) C₂₁H₃₆N₄O₁₁S=553 (M+1)⁺.

Step 6: Synthesis of ethyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate (27)

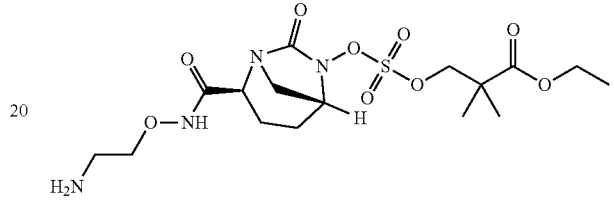

To a mixture of ethyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (27e) (340 mg, 0.62 mmol) in DCM (4 mL) was added trifluoroacetic acid (4 mL) at −10° C. The reaction mixture was stirred at −10° C. for 30 min. LC/MS analysis indicated that the starting material was completely consumed. The mixture was concentrated under vacuum to give a crude residue. The residue was purified by prep-HPLC on a C18 column eluting with MeCN/H₂O containing 0.1% TFA (5-80%) to give the title compound (27) as an off-white foam (243 mg, yield 72%). ¹H NMR (300 MHz, CDCl₃): δ 8.10 (br s, 3H), 4.52-4.67 (dd, 2H, J=9.3 Hz), 3.12-4.21 (m, 10H), 1.93-2.23 (m, 4H), 1.19-1.29 (m, 9H). ¹³C NMR (75 MHz, CDCl₃): δ 174.7, 169.5, 167.6, 80.8, 73.0, 61.7, 60.7, 60.2, 46.5, 43.1, 38.5, 22.3, 21.9, 20.6, 18.5, 14.3. ¹⁹F NMR (282 MHz, CDCl₃): δ −75.6. MS (ESI) C₁₆H₂₈N₄O₉S=453 (M+1)⁺.

Analytical HPLC was performed using an Agilent 1200 system with a Phenomenex® C18 column (150×4.6 mm i.d.). The mobile phase was a linear gradient of MeCN and water (0.1% TFA, 5% MeCN to 100% MeCN in 15 min). The flow rate was maintained at 1 mL/min and the eluent was monitored with UV detector at 220 nm and at 254 nm. HPLC retention time: 7.10 min.

Example 28

Synthesis of 2-methoxyethyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate (28)

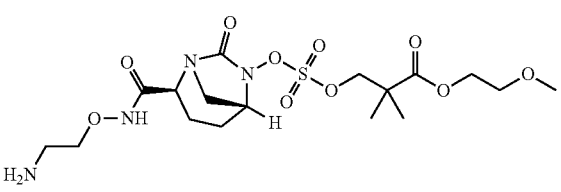 [SMILES: COCCOC(=O)C(C)(C)COS(=O)(=O)ON1C(=O)N2C[C@H]1CC[C@H]2C(=O)NOCCN]

Step 1: Synthesis of 2-methoxyethyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (28a)

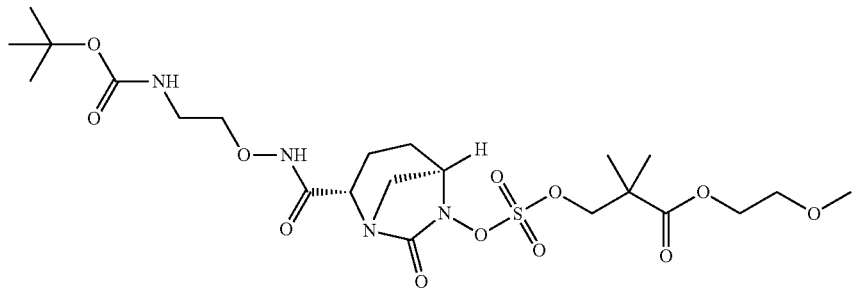 [SMILES: COCCOC(=O)C(C)(C)COS(=O)(=O)ON1C(=O)N2C[C@H]1CC[C@H]2C(=O)NOCCNC(=O)OC(C)(C)C]

tert-butyl (2-(((2S,5R)-6-hydroxy-7-oxo-1,6-diazabicyclo[3.2.1]octane-2-carboxamido)oxy)ethyl)carbamate (27d) (0.79 g, 2.30 mmol) was dissolved in THF (14 mL) and 1,3-dimethyltetrahydropyrimidin-2(1H)-one (6 mL), and the resulting solution was cooled to −78° C. under a nitrogen atmosphere. A solution of NaHMDS in THF (1M, 2.76 mL, 2.76 mmol) was added dropwise, and the mixture was stirred at −78° C. for 10 min. A solution of 2-methoxyethyl 3-((chlorosulfonyl)oxy)-2,2-dimethylpropanoate (15b) (758 mg, 2.76 mmol) in THF (2 mL) was then added to the reaction mixture via a syringe. After 10 min at −78° C., the reaction mixture was allowed to warm to room temperature and stirred overnight. The reaction mixture was diluted with EtOAc and washed with saturated NaHCO$_3$, water, and brine. The organic layer was dried with anhydrous Na$_2$SO$_4$, filtered, and concentrated under vacuum to give a crude residue. The residue was purified by silica gel column chromatography using EtOAc/hexane (1:1 to 3:1) as eluent to give the product (28a) as a white foam (0.65 g, yield 49%). $^1$H NMR (300 MHz, CDCl$_3$): δ 9.60 (br, s, 1H), 5.30 (br, t, 1H), 4.60-4.72 (dd, 2H, J=8.7 Hz), 3.02-4.22 (m, 15H), 1.62-2.40 (m, 4H), 1.45 (t, 9H), 1.21-1.30 (m, 6H). MS (ESI) C$_{22}$H$_{38}$N$_4$O$_{12}$S=583 (M+1)$^+$.

Step 2: Synthesis of 2-methoxyethyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate (28)

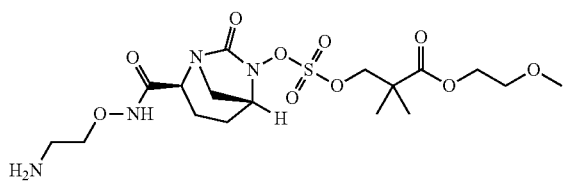 [SMILES: COCCOC(=O)C(C)(C)COS(=O)(=O)ON1C(=O)N2C[C@H]1CC[C@H]2C(=O)NOCCN]

To a mixture of 2-methoxyethyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (28a) (0.33 g, 0.57 mmol) in DCM (4 mL) was added trifluoroacetic acid (4 mL) at −10° C. The reaction was stirred at −10° C. for 30 min. LC/MS analysis indicated that the stating material was completely consumed. The mixture was concentrated under vacuum to give a crude residue. The residue was purified by prep-HPLC on a C18 column eluting using MeCN/H$_2$O containing 0.1% TFA (5-80%) to give the title compound (28) as off-white foam (128 mg, yield 39%). $^1$H NMR (300 MHz, CDCl$_3$): δ 8.10 (br s, 3H), 4.53-4.68 (dd, 2H, J=8.7 Hz), 3.11-4.21 (m, 15H), 1.96-2.23 (m, 4H), 1.28 (s, 6H). $^{13}$C NMR (75 MHz, CDCl$_3$): δ 174.6, 169.5, 167.6, 80.6, 72.9, 70.6, 64.5, 60.6, 60.1, 59.2, 46.5, 43.2, 38.4, 22.2, 21.9, 20.5, 18.5. $^{19}$F NMR (282 MHz, CDCl$_3$): δ 75.6. MS (ESI) C$_{17}$H$_{30}$N$_4$O$_{10}$S=483 (M+1)$^+$. HPLC retention time (MeCN/H$_2$O in 0.1% TFA): 6.59 min.

Example 29

Synthesis of (5-methyl-2-oxo-1,3-dioxol-4-yl)methyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (29)

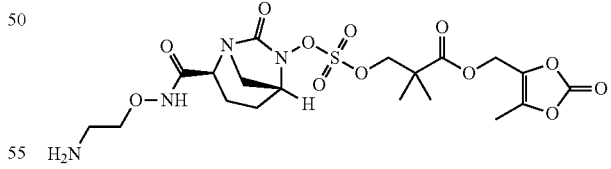

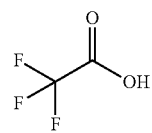

Step 1: Synthesis of (5-methyl-2-oxo-1,3-dioxol-4-yl)methyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (29a)

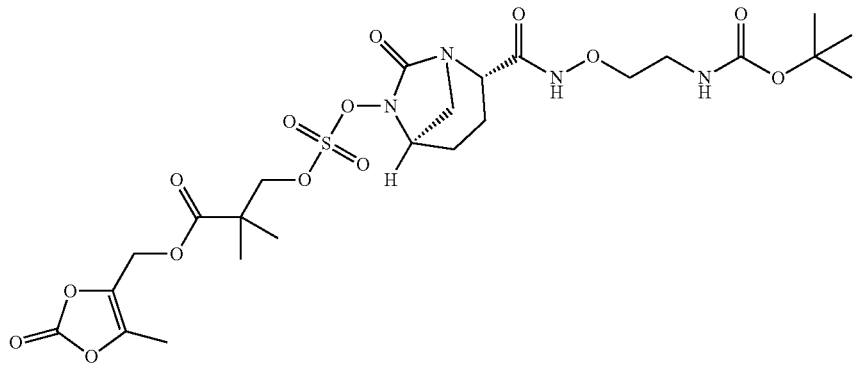 [SMILES: Cc1oc(=O)oc1COC(=O)C(C)(C)COS(=O)(=O)ON1C(=O)N2C[C@H]1CC[C@H]2C(=O)NOCCNC(=O)OC(C)(C)C]

tert-Butyl (2-(((2S,5R)-6-hydroxy-7-oxo-1,6-diazabicyclo[3.2.1]octane-2-carboxamido)oxy)ethyl)carbamate (27d) (0.80 g, 2.32 mmol) was dissolved in THF (23 mL) and 1,3-dimethyltetrahydropyrimidin-2(1H)-one (3.3 mL), and the resulting solution was cooled to −78° C. under an atmosphere of nitrogen. A solution of NaHMDS in THF (1M, 2.32 mL, 2.32 mmol) was added dropwise, and the mixture was stirred at −78° C. for 10 min. A solution of (5-methyl-2-oxo-1,3-dioxol-4-yl)methyl 3-((chlorosulfonyl)oxy)-2,2-dimethylpropanoate (25b) (916 mg, 2.8 mmol) in THF (2 mL) was then added to the reaction mixture via a syringe. After 10 min at −78° C., the reaction mixture was allowed to warm to room temperature and stirred overnight. The reaction mixture was diluted with EtOAc and washed with water, and brine. The organic layer was dried with anhydrous $Na_2SO_4$, filtered, and concentrated under vacuum to give a crude residue. The residue was purified by silica gel column chromatography using EtOAc/hexane (0-99%) as eluent to give the product (29a) as off-white foam (399.8 mg, yield 27%). $^1$H NMR (300 MHz, chloroform-d) δ 9.75 (s, 1H), 5.37 (s, 1H), 5.30 (d, J=0.7 Hz, 2H), 5.00-4.76 (m, 2H), 4.46 (d, J=9.3 Hz, 1H), 4.16-4.00 (m, 2H), 3.94 (s, 4H), 3.42 (s, 2H), 3.38-3.26 (m, 4H), 3.03 (d, J=12.2 Hz, 2H), 2.19 (s, 6H), 2.16 (d, J=5.5 Hz, 2H), 2.02 (d, J=14.0 Hz, 3H), 1.92 (s, 2H), 1.56 (m, 1H), 1.48-1.41 (m, 9H), 1.41-1.20 (m, 6H). MS (ESI) $C_{24}H_{36}N_4O_{14}S$: 637 (M+1)$^+$.

Step 2: Synthesis of (5-methyl-2-oxo-1,3-dioxol-4-yl)methyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (29)

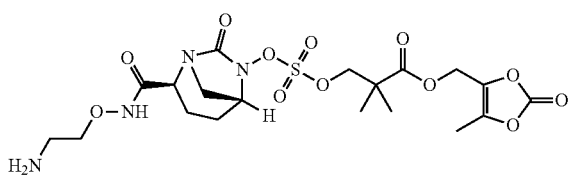

-continued

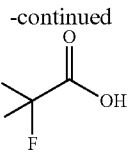

To a mixture of (5-methyl-2-oxo-1,3-dioxol-4-yl)methyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (29a) (0.33 g, 0.52 mmol) in DCM (3 mL) was added trifluoroacetic acid (0.3 mL) at −10° C. The reaction was stirred at −10° C. for 4 h. LC/MS analysis indicated that the stating material was completely consumed. The mixture was concentrated under vacuum to give a crude residue. The residue was purified by prep-HPLC on C18 column eluting using MeCN/$H_2O$ containing 0.1% TFA (0-80%) to give the title compound (29) as off-white foam (9.1 mg, yield 3.2%). $^1$H NMR (300 MHz, MeCN-$d_3$): δ 7.61 (s, 1H), 4.97-4.83 (m, 3H), 4.74-4.60 (m, 1H), 4.55 (d, J=9.3 Hz, 1H), 4.24-4.00 (m, 2H), 3.94-3.83 (m, 1H), 3.73-3.62 (m, 2H), 3.29 (d, J=12.3 Hz, 2H), 3.19 (s, 3H), 2.15 (dq, J=1.3, 0.6 Hz, 3H), 1.93 (s, 1H), 1.39-1.07 (m, 8H). $^{19}$F NMR (282 MHz, MeCN-$d_3$): δ 76.1, −76.3. MS (ESI) $C_{19}H_{28}N_4O_{12}S$: 537 (M+1)$^+$ Example 30

Synthesis of hexyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA Salt (30)

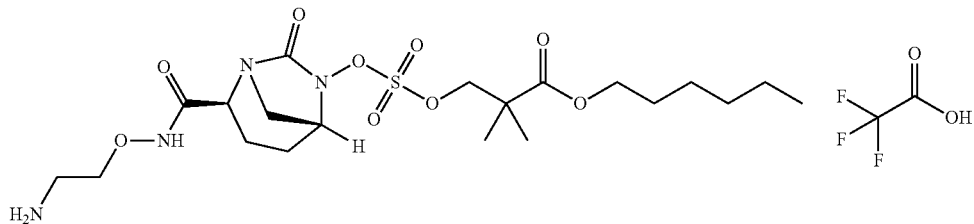

Step 1: Synthesis of hexyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (30a)

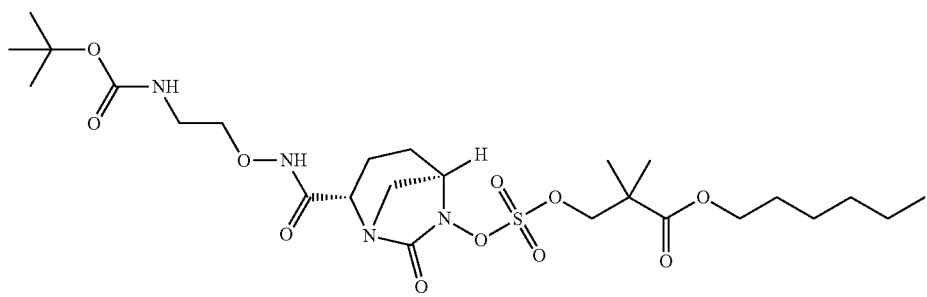 [SMILES: CCCCCCOC(=O)C(C)(C)COS(=O)(=O)ON1C(=O)N2C[C@H]1CC[C@H]2C(=O)NOCCNC(=O)OC(C)(C)C]

tert-Butyl (2-(((2S,5R)-6-hydroxy-7-oxo-1,6-diazabicyclo[3.2.1]octane-2-carboxamido)oxy)ethyl)carbamate (27d) (0.51 g, 1.48 mmol) was dissolved in THF (18 mL) and 1,3-dimethyltetrahydropyrimidin-2(1H)-one (2.8 mL), and the resulting solution was cooled to −78° C. under a nitrogen atmosphere. A solution of NaHMDS in THF (1M, 1.9 mL, 1.9 mmol) was added dropwise, and the mixture was stirred at −78° C. for 10 min. A solution of hexyl 3-((chlorosulfonyl)oxy)-2,2-dimethylpropanoate (730 mg, 2.42 mmol) in THF (2 mL) was then added to the reaction mixture via a syringe. After 10 min at −78° C., the reaction mixture was allowed to warm to room temperature and stirred overnight. The reaction mixture was diluted with EtOAc and washed with water, and brine. The organic layer was dried with anhydrous $Na_2SO_4$, filtered, and concentrated under vacuum to give a crude residue. The residue was purified by silica gel column chromatography using EtOAc/hexane (0-99%) as eluent to give the product (30a) as off-white foam (194.3 mg, yield 22%). $^1$H NMR (300 MHz, $CDCl_3$): δ 9.54 (s, 1H), 5.26 (s, 1H), 4.60 (d, J=9.0 Hz, 2H), 4.21-4.02 (m, 7H), 3.46 (d, J=16.3 Hz, 1H), 3.31 (s, 2H), 3.03 (d, J=12.0 Hz, 1H), 2.39 (dd, J=14.9, 6.3 Hz, 1H), 2.19 (s, 1H), 2.08-1.89 (m, 2H), 1.65-1.55 (m, 2H), 1.45 (s, 10H), 1.35-1.19 (m, 10H), 0.94-0.79 (m, 3H). MS (ESI) $C_{25}H_{44}N_4O_{11}S$: 607 (M−1)$^+$.

Step 2: Synthesis of hexyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (30)

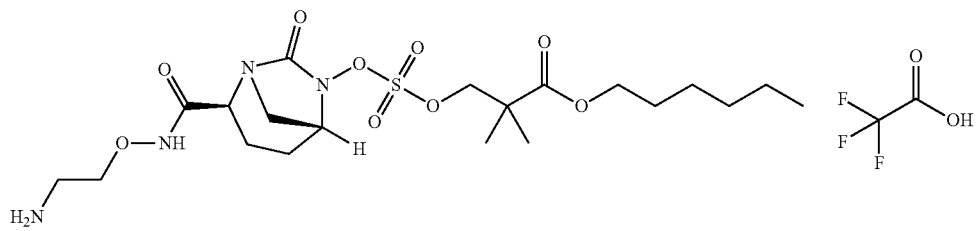

To a solution of hexyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (30a) (144.3 mg, 0.237 mmol) in DCM (3 mL) was added trifluoroacetic acid (0.15 mL) at 0° C. The reaction was stirred at 0° C. for 1 h. LC/MS analysis indicated that the stating material was completely consumed. The mixture was concentrated under vacuum to give a crude residue. The residue was purified by prep-HPLC on a C18 column eluting using MeCN/H$_2$O containing 0.1% TFA (0-80%) to give the title compound (30) as a brown oil (68.1 mg, yield 56%). $^1$H NMR (300 MHz, CDCl$_3$): δ 7.80-7.73 (m, 2H), 6.94 (s, 1H), 4.57 (dt, J=28.2, 14.1 Hz, 2H), 4.22 (s, 1H), 4.08 (ddt, J=17.3, 13.2, 8.0 Hz, 6H), 3.96 (s, 2H), 3.28 (d, J=10.2 Hz, 2H), 2.10 (s, 1H), 1.93 (s, 1H), 1.62 (m, 2H), 1.28 (ddd, J=12.8, 6.5, 3.7 Hz, 12H), 1.19 (s, 2H), 0.94-0.82 (m, 3H). $^{13}$C NMR (75 MHz, CDCl$_3$): δ 176.6, 174.3, 169.2, 167.3, 161.6, 118.2, 114.3, 80.4, 73.7, 72.6, 65.5, 65.3, 60.3, 59.9, 46.3, 42.9, 42.8, 38.4, 31.4, 28.4, 28.3, 25.5, 25.5, 22.5, 22.1, 22.0, 21.6, 20.3, 18.2, 14.0. $^{19}$F NMR (282 MHz, CDCl$_3$): δ −75.8. MS (ESI) C$_{20}$H$_{36}$N$_4$O$_9$S: 509 (M+1)$^+$. HPLC retention time (MeCN/H$_2$O in 0.1% TFA): 8.96 min.

Example 31

Synthesis of heptyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (31)

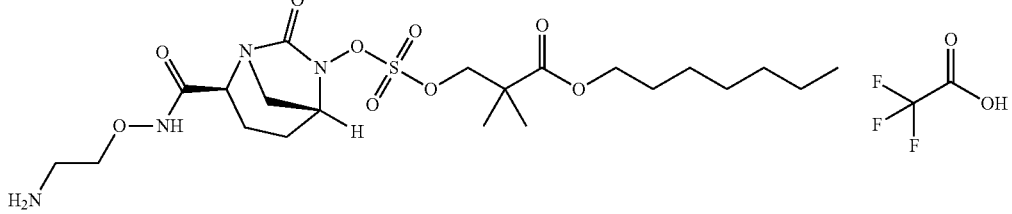

Step 1: Synthesis of heptyl 3-(((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)-2,2-dimethylpropanoate (31a)

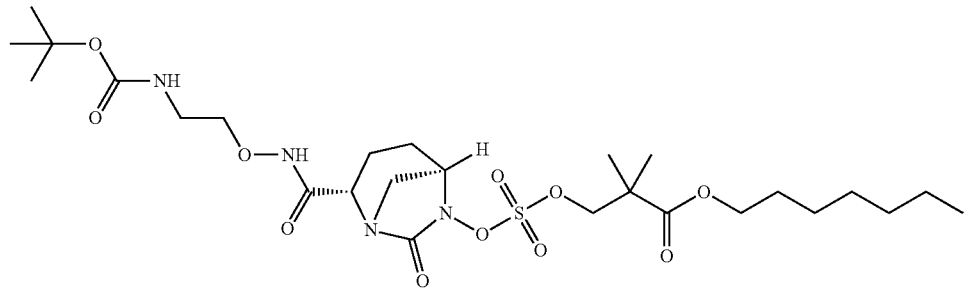

A method similar to that of Step 1 of Example 30 was used to obtain 274.0 mg of the title compound (31a) (44% yield) as off white solid. $^1$H NMR (300 MHz, CDCl$_3$): δ 9.75 (s, 1H), 5.37 (t, J=6.2 Hz, 1H), 4.72-4.52 (m, 2H), 4.09 (dddd, J=18.6, 10.4, 3.8, 2.1 Hz, 3H), 3.91 (t, J=4.8 Hz, 2H), 3.51-3.19 (m, 3H), 3.05 (d, J=12.1 Hz, 1H), 2.43-2.29 (m, 1H), 2.21-2.07 (m, 1H), 2.06-1.77 (m, 3H), 1.62 (t, J=6.9 Hz, 2H), 1.40 (s, 9H), 1.40-1.17 (m, 16H), 0.92-0.81 (m, 3H). MS (ESI) C$_{26}$H$_{46}$N$_4$O$_{11}$S: 523 (M+1−Boc)$^+$.

Step 2: Synthesis of heptyl 3-(((((2S,5R)-2-((2-aminoethoxy)carbamoyl)-7-oxo-1,6-diazabicyclo[3.2.1]octan-6-yl)oxy)sulfonyl)oxy)-2,2-dimethylpropanoate TFA salt (31)

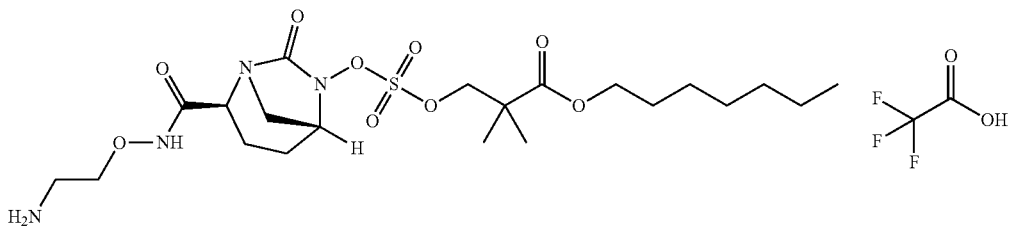

A method similar to that of Step 2 of Example 30 was used to prepare the title compound (31) (214.5 mg, 93%) as a brown oil. $^1$H NMR (300 MHz, CDCl$_3$): δ 10.61 (s, 1H), 8.02 (s, 3H), 4.63 (d, J=8.7 Hz, 1H), 4.53 (d, J=8.9 Hz, 1H), 4.17 (d, J=13.3 Hz, 3H), 4.12-3.97 (m, 4H), 3.95 (s, 1H), 3.26 (s, 3H), 3.18-3.08 (m, 1H), 2.22 (s, 1H), 2.10 (s, 1H), 1.61 (q, J=7.0 Hz, 2H), 1.25 (m, 12H), 1.18 (s, 2H), 0.87 (m, 3H). $^{13}$C NMR (75 MHz, CDCl$_3$): δ 176.5, 174.3, 169.1, 167.3, 80.3, 73.7, 72.6, 65.5, 65.3, 60.3, 59.9, 46.3, 42.9, 42.8, 38.3, 31.7, 31.7, 28.9, 28.9, 28.4, 25.8, 25.8, 22.6, 22.1, 22.0, 22.0, 21.6, 20.3, 18.3, 14.0. $^{19}$F NMR (282 MHz, CDCl$_3$): δ −75.71. MS (ESI) C$_{21}$H$_{38}$N$_4$O$_9$S: 523 (M+1)$^+$. HPLC retention time (MeCN/H$_2$O in 0.1% TFA): 9.37 min.

Example 32

Synthesis of ethyl 1-((((((2S,5R)-2-((2-aminoethoxy)carbamoyl)-7-oxo-1,6-diazabicyclo[3.2.1]octan-6-yl)oxy)sulfonyl)oxy)methyl)cyclohexanecarboxylate TFA salt (32)

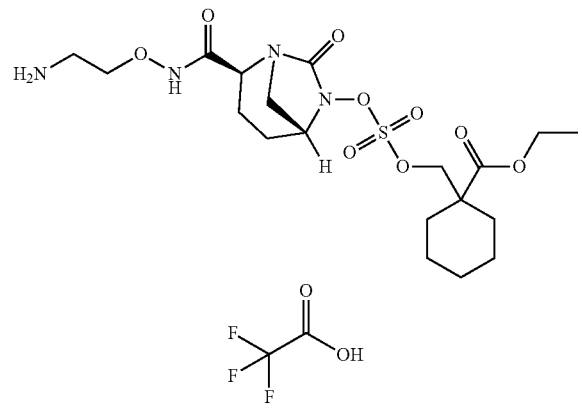

Step 1: Synthesis of ethyl 1-((((((2S,5R)-2-((2-((tert-butoxycarbonyl)amino)ethoxy)carbamoyl)-7-oxo-1,6-diazabicyclo[3.2.1]octan-6-yl)oxy)sulfonyl)oxy)methyl)cyclohexanecarboxylate (32a)

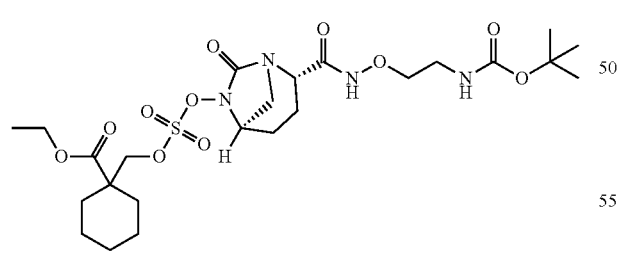

A method similar to that of Step 1 of Example 30 was applied for the coupling between tert-butyl (2-(((2S,5R)-6-hydroxy-7-oxo-1,6-diazabicyclo[3.2.1]octane-2-carboxamido)oxy)ethyl)carbamate and ethyl 1-(((chlorosulfonyl)oxy)methyl)cyclohexanecarboxylate (27d) to give 122.2 mg of the title compound (32a) (14% yield for 3 steps as) off white solid. $^1$H NMR (300 MHz, CDCl$_3$): δ 9.92 (d, J=5.6 Hz, 1H), 5.46 (d, J=5.7 Hz, 1H), 4.68 (d, J=9.2 Hz, 1H), 4.52 (d, J=9.2 Hz, 1H), 4.24-3.98 (m, 5H), 3.88 (t, J=4.8 Hz, 2H), 3.37 (d, J=6.7 Hz, 1H), 3.25 (dt, J=10.1, 5.1 Hz, 2H), 3.04 (d, J=12.1 Hz, 1H), 2.30 (t, J=6.8 Hz, 1H), 2.16-1.80 (m, 6H), 1.52 (d, J=9.3 Hz, 3H), 1.4 (s, 9H), 1.34 (m, 2H), 1.22 (td, J=7.2, 5.0 Hz, 3H). MS (ESI) C$_{24}$H$_{40}$N$_4$O$_{11}$S: 593 (M+1)$^+$.

Step 2: Synthesis of ethyl 1-((((((2S,5R)-2-((2-aminoethoxy)carbamoyl)-7-oxo-1,6-diazabicyclo[3.2.1]octan-6-yl)oxy)sulfonyl)oxy)methyl)cyclohexanecarboxylate TFA salt (32)

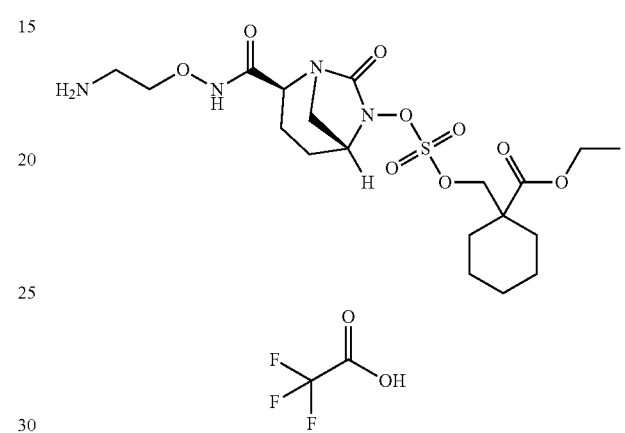

A method similar to that of Step 2 of Example 30 was applied to obtain 91.4 mg of the title compound (32) (90% yield) as off white solid. $^1$H NMR (300 MHz, CDCl$_3$): δ 10.74 (s, 1H), 7.98 (s, 3H), 4.65 (d, J=9.2 Hz, 1H), 4.50 (d, J=9.1 Hz, 1H), 4.26-4.04 (m, 3H), 4.13 (s, 3H), 3.95 (s, 1H), 3.26 (d, J=9.9 Hz, 3H), 3.14 (d, J=11.6 Hz, 1H), 2.02 (s, 4H), 1.92 (s, 3H), 1.50-1.22 (m, 8H), 1.22 (d, J=7.5 Hz, 2H). $^{13}$C NMR (75 MHz, CDCl$_3$): δ 175.6, 173.5, 169.2, 167.3, 118.5, 114.6, 80.3, 73.6, 72.6, 61.3, 61.1, 60.3, 60.0, 47.2, 47.1, 46.2, 38.2, 30.6, 30.2, 30.1, 25.5, 25.3, 22.4, 22.1, 22.0, 20.3, 18.3, 14.1. $^{19}$F NMR (282 MHz, CDCl$_3$): δ −75.7. MS (ESI) C$_{19}$H$_{32}$N$_4$O$_9$S: 493 (M+1)$^+$. HPLC retention time (MeCN/H$_2$O in 0.1% TFA): 8.05 min.

Example 33

Synthesis of (2S,5R)-2-((2-aminoethoxy)carbamoyl)-7-oxo-1,6-diazabicyclo[3.2.1]octan-6-yl hydrogen sulfate (33)

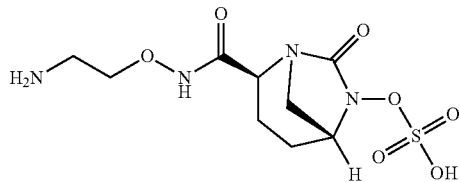 [SMILES: NCCONC(=O)[C@@H]1CC[C@@H]2CN1C(=O)N2OS(=O)(=O)O]

Step 1: Synthesis of tetrabutylammonium (2S,5R)-2-((2-((tert-butoxycarbonyl)amino)ethoxy)carbamoyl)-7-oxo-1,6-diazabicyclo[3.2.1]octan-6-yl sulfate (33a)

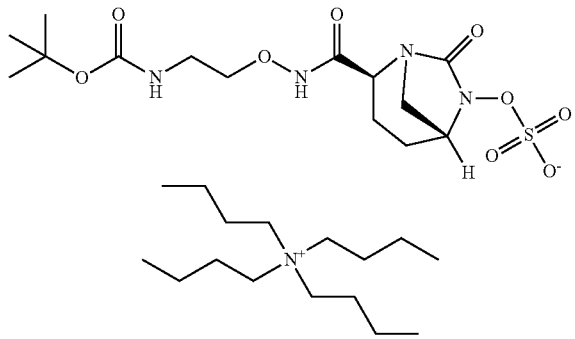

To a solution of tert-butyl (2-(((2S,5R)-6-hydroxy-7-oxo-1,6-diazabicyclo[3.2.1]octane-2-carboxamido)oxy)ethyl)carbamate (27d) (0.79 g, 2.30 mmol) in pyridine (35 mL) was added pyridine-sulfur trioxide complex (1.46 g, 9.2 mmol). The reaction was stirred at room temperature for 64 h. Additional pyridine-sulfur trioxide complex (1.46 g, 9.2 mmol) was added and the reaction was stirred at 35° C. for 16 h. The mixture was concentrated under vacuum to give a crude residue. To a solution of above product in DCM (30 mL) was added 0.5 N aqueous dipotassium hydrogen phosphate (7.4 mL) at 0° C. After stirred at 0° C. for 10 min, tetrabutyl ammonium hydrogen sulfate (0.86 g, 2.53 mmol) was added. The resulting solution was stirred at room temperature for 30 min. After the organic layer was separated, the aqueous layer was extracted three times with DCM. The combined extracted organic layers were dried with anhydrous $Na_2SO_4$, filtered, and concentrated under vacuum to give a residue. The residue was purified by silica gel column chromatography using 10% MeOH in DCM as eluent to give the product (33a) as an off-white solid (0.51 g, yield 33%). MS (ESI) $C_{14}H_{24}N_4O_9S=423$ (M−1)⁺.

Step 2: Synthesis of (2S,5R)-2-((2-aminoethoxy)carbamoyl)-7-oxo-1,6-diazabicyclo[3.2.1]octan-6-yl hydrogen sulfate (33)

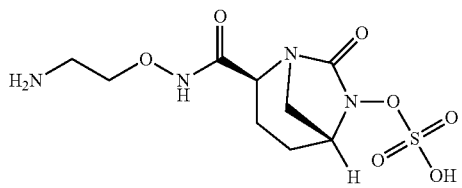 [SMILES: NCCONC(=O)[C@@H]1CC[C@@H]2CN1C(=O)N2OS(=O)(=O)O]

To a solution of tetrabutylammonium (2S,5R)-2-((2-((tert-butoxycarbonyl)amino)ethoxy)carbamoyl)-7-oxo-1,6-diazabicyclo[3.2.1]octan-6-yl sulfate (33a) (0.51 g, 0.77 mmol) in DCM (10 mL) at −10° C. was added TFA (10 mL). LC/MS analysis indicated that the reaction was complete after 1 h. The mixture was concentrated under vacuum to give a crude residue. The residue was stirred with diethyl ether to provide a yellow precipitate. The solid was filtered, and washed with acetone. The residue was dissolved in water and acetonitrile (1:1) and lyophilized to provide a yellow solid. The residue was washed with acetone again. The residue was dissolved in water and acetonitrile (1:1) and lyophilized to provide the title compound (33) as a yellow solid (68 mg, yield 27%). ¹H NMR (300 MHz, DMSO-d₆): δ 7.84 (br s, 3H), 3.82-4.00 (m, 3H), 2.92-3.33 (m, 5H), 2.00 (m, 1H), 1.87 (m, 1H), 1.68 (m, 2H). ¹³C NMR (75 MHz, DMSO-d₆): 169.1, 166.5, 72.8, 58.6, 58.3, 47.7, 38.2, 21.3, 19.0. MS (ESI) $C_9H_{16}N_4O_7S=323$ (M−1)⁺. HPLC retention time (MeCN/H₂O in 0.1% TFA): 1.52 min.

Example 34

Synthesis of (2S,5R)-2-carbamoyl-7-oxo-1,6-diazabicyclo[3.2.1]octan-6-yl 1H-imidazole-1-sulfonate (34)

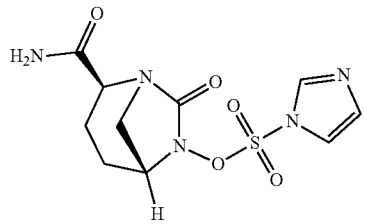 [SMILES: NC(=O)[C@@H]1CC[C@@H]2CN1C(=O)N2OS(=O)(=O)n1ccnc1]

(2S,5R)-6-Hydroxy-7-oxo-1,6-diazabicyclo[3.2.1]octane-2-carboxamide (1) (741 mg, 4.0 mmol) was dissolved in tetrahydrofuran (36 mL) and 1,3-dimethyltetrahydropyrimidin-2(1H)-one (2 mL), and the resulting solution was cooled to −78° C. A solution of NaHMDS, 1.0M in THF (4.4 mL, 4.4 mmol) was added dropwise to the cooled solution and stirred for 10 min. 1-((1H-Imidazol-1-yl)sulfonyl)-3-methyl-1H-imidazol-3-ium trifluoromethanesulfonate (prepared according to *Org. Lett.* 2013, 15, 18-21 & *J. Org. Chem.* 2003, 68, 115-119) (2.90 g, 8.0 mmol) was added quickly to the reaction mixture. After 10 min, the reaction mixture was warmed to 0° C. (reaction monitored by TLC using 70% EtOAc/hexanes). The mixture was stirred for 1 h at room temperature, then diluted with EtOAc (50 mL) and quenched with saturated aqueous NaHCO₃ (50 mL). The organic and aqueous layers were separated, and the organic layer washed with saturated aqueous NaHCO₃ (50 mL), H₂O (3×50 mL), and brine (50 mL), and then dried (Na₂SO₄), and concentrated under vacuum to leave a crude residue. The residue was purified by column chromatography on silica gel using EtOAc/hexanes (1:9 to 1:0) as eluent to give the product (34) (0.393 g, 31%) as a solid. LC-MS: m/z=316.0 [M+H]⁺. ¹H NMR (300 MHz, 1,4-dioxane-ds): δ 8.15 (s, 1H), 7.58 (ft, J=1.5 Hz, 1H), 7.15 (s, 1H), 6.92 (s, 1H), 6.48 (s, 1H), 3.95 (d, J=6.3 Hz, 1H), 3.70 (s, 1H), 3.08 (s, 2H), 2.23-2.17 (m, 1H), 2.04-1.97 (m, 1H), 1.88-1.74 (m, 2H). ¹³C NMR (75 MHz, 1,4-dioxane-ds): δ 171.4, 167.6, 139.2, 132.0, 119.9, 62.9, 61.8, 46.9, 21.5, 18.7.

Example 35

Synthesis of ethyl 5-(((((2S,5R)-2-carbamoyl-7-oxo-1,6-diazabicyclo[3.2.1]octan-6-yl)oxy)sulfonyl)oxy)-4,4-dimethylpentanoate (35)

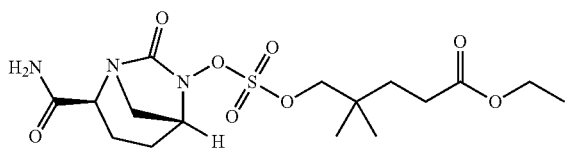 [SMILES: CCOC(=O)CCC(C)(C)COS(=O)(=O)ON1C(=O)N2C[C@H]1CC[C@H]2C(N)=O]

Step 1: Synthesis of ethyl 5-hydroxy-4,4-dimethylpentanoate (35a)

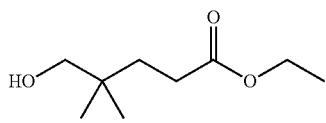

To a suspension of sodium 5-ethoxy-2,2-dimethyl-5-oxopentanoate (3.77 g, 17.9 mmol) in a mixture of tetrahydrofuran (39 mL) and DMF (13 mL) was added a solution of isopropyl chloroformate, 1.0M in toluene (27.0 mL, 27.0 mmol) at 0° C. The mixture was stirred at 0° C. for 10 min, and then allowed to warm to room temperature, and stirred for 2 h. The solution was cooled to 0° C. and sodium borohydride (1.21 g, 35.9 mmol) was added. The mixture was stirred for 20 min then methanol (6.5 mL) was added to the solution. After 10 min of stirring, ethyl acetate (25 mL) modified with a few drops of triethylamine and a saturated aqueous solution of NH$_4$Cl (25 mL) were added. The layers were separated, and the aqueous layer was extracted with EtOAc (2×40 mL). The combined organic layers were washed with brine, dried (MgSO$_4$), filtered and the filtrate was concentrated under vacuum. The residue was purified by column chromatography on silica gel using EtOAc/hexanes modified with 0.1% TEA (5:95 to 4:6) to give the product (35a) (2.01 g, 64% crude) as a colorless oil. One drop of triethylamine was added to the product to suppress lactonization.

Step 2: Synthesis of ethyl 5-((chlorosulfonyl)oxy)-4,4-dimethylpentanoate (35b)

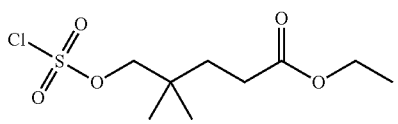 [SMILES: CCOC(=O)CCC(C)(C)COS(=O)(=O)Cl]

A solution of sulfuryl chloride (0.64 mL, 8.7 mmol) in Et$_2$O (10 mL) was cooled to −78° C. under an atmosphere of nitrogen. A solution of ethyl 5-hydroxy-4,4-dimethylpentanoate (35a) (0.76 g, 4.4 mmol) and pyridine (0.39 mL, 4.8 mmol) in Et$_2$O (10 mL) was added dropwise to the sulfuryl chloride solution over the course of 10 min. The syringe was rinsed with Et$_2$O (3×1 mL) and this was also added to the mixture. The mixture was stirred at −78° C. for 1.5 h, additional pyridine (0.9 equiv.) was added, and the mixture was filtered through a pad of Celite®. The filtrate was concentrated under vacuum to give the product (35b) (0.897 g) as a colorless oil. This was used in the next step without further purification.

Step 3: Synthesis of ethyl 5-(((((2S,5R)-2-carbamoyl-7-oxo-1,6-diazabicyclo[3.2.1]octan-6-yl)oxy)sulfonyl)oxy)-4,4-dimethylpentanoate (35)

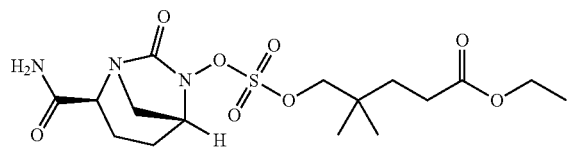 [SMILES: CCOC(=O)CCC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (278 mg, 1.5 mmol) was dissolved in THF (14 mL) and HMPA (0.6 mL), and the resulting solution was cooled to −78° C. under a nitrogen atmosphere. A solution of ethyl 5-((chlorosulfonyl)oxy)-4,4-dimethylpentanoate (35b) (0.45 g, 1.6 mmol) in THF (3 mL) was cooled to −78° C. and quickly added to the mixture. The flask containing the sulfating reagent was rinsed with THF (1 mL), while the flask temperature was maintained at −78° C., and this was added quickly to the reaction mixture. After stirring for 15 min, the mixture was warmed to room temperature and stirred for 45 min. The mixture was diluted with EtOAc (30 mL) and the reaction quenched with saturated aqueous NaHCO$_3$ (30 mL). The organic and aqueous layers were partitioned, and the organic layer was washed with water (3×30 mL), and brine (30 mL), dried (MgSO$_4$), and the solvent removed under vacuum. The residue was purified by column chromatography on silica gel using EtOAc/hexanes (3:7 to 4:1) to give the product (35) (157 mg, 25%) as a solid. LC-MS: m/z=422.2 [M+H]$^+$. $^1$H NMR (300 MHz, CDCl$_3$): δ 5.52 (s, 1H), 5.83 (s, 1H), 4.49 (d, J=9.3 Hz, 1H), 4.21-4.08 (m, 4H), 4.03 (d, J=6.9 Hz, 1H), 3.34-3.30 (m, 1H), 3.02 (d, J=12.3 Hz, 1H), 2.43-2.38 (m, 1H), 2.32-2.26 (m, 2H), 2.17-2.11 (m, 1H), 1.99-1.82 (m, 2H), 1.72-1.66 (m, 3H), 1.25 (t, J=7.1 Hz, 3H), 0.98 (s, 6H). $^{13}$C NMR (75 MHz, CDCl$_3$): δ173.5, 171.1, 167.1, 83.4, 62.0, 60.6, 60.3, 47.2, 34.2, 33.3, 29.3, 23.6, 23.3, 20.8, 17.6, 14.3.

Example 36

Synthesis of hexyl 5-(((((2S,5R)-2-carbamoyl-7-oxo-1,6-diazabicyclo[3.2.1]octan-6-yl)oxy)sulfonyl)oxy)-4,4-dimethylpentanoate (36)

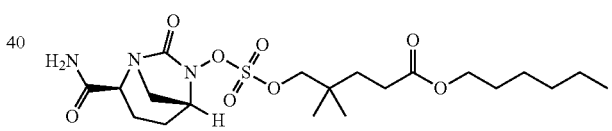

Step 1: Synthesis of sodium-5-(hexyloxy)-2,2-dimethyl-5-oxopentanoate (36a)

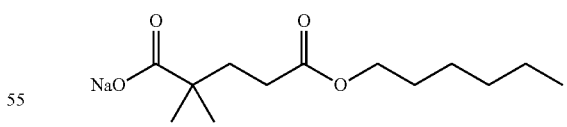

To a solution of 2,2-dimethylglutaric anhydride (5.0 g, 35.2 mmol) in 1-hexanol (50 mL) was added a solution of sodium hexan-1-olate (5.4 g, 43.5 mmol) in 1-hexanol. After 20 h of stirring, the solvent was evaporated and the resulting solid was suspended in diethyl ether (80 mL). The mixture was filtered and the solid was washed with diethyl ether (2×40 mL). The solid was dried under high vacuum to afford the product (36a) (3.84 g, 41%) as a solid. $^1$H NMR (300 MHz, D$_2$O): δ 4.14 (t, J=6.5 Hz, 2H), 2.38-2.33 (m, 2H), 1.82-1.77 (m, 2H), 1.75-1.63 (m, 2H), 1.43-1.28 (m, 6H), 1.12 (s, 6H), 0.92-0.88 (m, 3H). The spectrum revealed that the product was contaminated with a small amount of an unidentified substance.

Step 2: Synthesis of hexyl 5-hydroxy-4,4-dimethylpentanoate (36b)

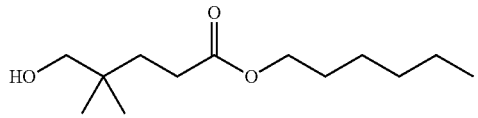 [SMILES: CCCCCCOC(=O)CCC(C)(C)CO]

To a suspension of sodium 5-(hexyloxy)-2,2-dimethyl-5-oxopentanoate (36a) (3.84 g, 14.4 mmol) in a mixture of THF (31 mL) and DMF (10 mL) was added isopropyl chloroformate, 1.0M in toluene (21.6 mL, 21.6 mmol) at 0° C. and the mixture was stirred for 10 min. After 3.3 h of stirring at room temperature, the solution was cooled to 0° C. and sodium borohydride (0.98 g, 28.8 mmol) was added. The mixture was stirred for 20 min and MeOH (5.2 mL) was added to the solution (reaction monitored by TLC using 2:8 ethyl acetate/hexanes as eluent). After 15 min, a few drops of triethylamine were added. After another 15 min of stirring, ethyl acetate (25 mL) and a solution of saturated aqueous $NH_4Cl$ was added (25 mL). The organic and aqueous layers were separated, and the aqueous layer was extracted with EtOAc (2×40 mL). The combined organic layers were washed with brine, dried ($MgSO_4$), and filtered, and the filtrate was concentrated in vacuo. The residue was purified by column chromatography on silica gel using EtOAc/hexanes modified with 0.1% $Et_3N$ (5:95 to 3:7) to give the product (36b) (2.16 g, 65%) as a colorless oil. One drop of $Et_3N$ was added to suppress lactonization.

Step 3: Synthesis of hexyl 5-((chlorosulfonyl)oxy)-4,4-dimethylpentanoate (36c)

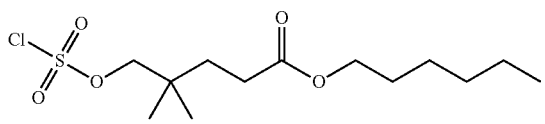 [SMILES: CCCCCCOC(=O)CCC(C)(C)COS(=O)(=O)Cl]

A solution of sulfuryl chloride (0.38 mL, 5.2 mmol) in $Et_2O$ (8.5 mL) was cooled to −78° C. under a nitrogen atmosphere. A solution of hexyl 5-hydroxy-4,4-dimethylpentanoate (36b) (0.60 g, 2.6 mmol) and pyridine (0.42 mL, 5.2 mmol) in $Et_2O$ (8.5 mL) was added dropwise to the sulfuryl chloride solution over the course of 10 min. The syringe was rinsed with $Et_2O$ (3×1 mL) and the rinse was also added to the mixture. The mixture was stirred for 4.5 h (reaction monitored by TLC using 2:8 EtOAc/hexanes as eluent). The solids were filtered off and the solvent was concentrated in vacuo to give the product (36c) as a colorless oil with a quantitative yield. To this was added 3 mL of THF and the solution was stored at −78° C. This was used in the next step without further purification.

Step 4: Synthesis of hexyl 5-(((((2S,5R)-2-carbamoyl-7-oxo-1,6-diazabicyclo[3.2.1]octan-6-yl)oxy)sulfonyl)oxy)-4,4-dimethylpentanoate (36)

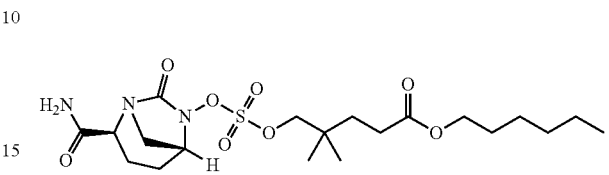

(2S,5R)-6-hydroxy-7-oxo-1,6-diazabicyclo[3.2.1]octane-2-carboxamide (1) (370 mg, 2.0 mmol) was dissolved in tetrahydrofuran (19 mL) and HMPA (0.8 mL), and the resulting solution was cooled to −78° C. under an atmosphere. A solution of NaHMDS, 1.0 M in THF (2.2 mL, 2.2 mmol) was added dropwise to the cooled solution and stirred for 10 min. A solution of hexyl 5-((chlorosulfonyl)oxy)-4,4-dimethylpentanoate (36c) (0.72 g, 2.2 mmol) in THF (3 mL) was cooled to −78° C. and quickly added to the reaction mixture. The flask containing the sulfating reagent was rinsed with THF (3×1 mL), while the flask temperature was maintained at −78° C., and the rinse was quickly added to the reaction mixture. After stirring for 10 min the mixture was warmed to room temperature and stirred overnight. The reaction was then quenched with saturated $NaHCO_3$ (40 mL) and extracted with EtOAc (40 mL). The organic layer was concentrated, and the oily residue partitioned between $H_2O$ (40 mL) and EtOAc (40 mL). The organic layer was washed with brine, dried ($MgSO_4$), filtered and concentrated under vacuum. The residue was purified by column chromatography on silica gel using EtOAc/hexanes as eluent (1:9 to 8:2) to give the product (36) (421 mg, 44%) as a solid. LC-MS: m/z=478.0 [M+H]$^+$. $^1$H NMR (300 MHz, CDCl$_3$): δ 6.48 (s, 1H), 5.59 (s, 1H), 4.51 (d, J=8.7 Hz, 1H), 4.22-4.18 (m, 2H), 4.08-4.04 (m, 3H), 3.36-3.32 (m, 1H), 3.02 (d, J=12.6 Hz, 1H), 2.47-2.41 (m, 1H), 2.33-2.28 (m, 2H), 2.18-2.13 (m, 1H), 2.01-1.79 (m, 2H), 1.72-1.59 (m, 4H), 1.35-1.31 (m, 6H), 0.99 (s, 6H), 0.91-0.87 (m, 3H). $^{13}$C NMR (75 MHz, CDCl$_3$): δ 173.6, 170.9, 167.1, 83.5, 64.9, 62.0, 60.2, 47.3, 34.3, 33.3, 31.6, 29.3, 28.7, 25.7, 23.6, 23.3, 22.7, 20.9, 17.6, 14.1.

Example 37

Synthesis of heptyl 5-(((((2S,5R)-2-carbamoyl-7-oxo-1,6-diazabicyclo[3.2.1]octan-6-yl)oxy)sulfonyl)oxy)-4,4-dimethylpentanoate (37)

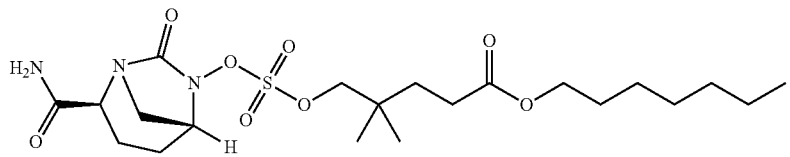 [SMILES: CCCCCCCOC(=O)CCC(C)(C)COS(=O)(=O)ON1C(=O)N2C[C@H]1CC[C@H]2C(N)=O]

Step 1: Synthesis of sodium 5-(heptyloxy)-2,2-dimethyl-5-oxopentanoate (37a)

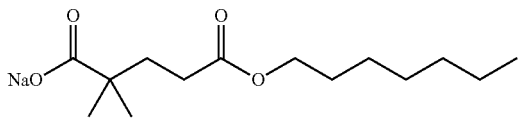

To a solution of 2,2-dimethylglutaric anhydride (5.0 g, 35.2 mmol) in 1-heptanol (40 mL) was added a solution of sodium heptan-1-olate (6.01 g, 43.5 mmol) in 1-heptanol (30 mL). After stirring overnight the solvent was evaporated and the resulting solid was suspended in Et$_2$O (80 mL). The mixture was filtered and the solid was washed with Et$_2$O (2×40 mL). The solid was dried under high vacuum to afford the product (37a) (7.89 g, 80%) as a solid. $^1$H NMR (300 MHz, D$_2$O): δ 4.14 (t, J=6.5 Hz, 2H), 2.36-2.32 (m, 2H), 1.82-1.77 (m, 2H), 1.74-1.63 (m, 2H), 1.40-1.31 (m, 8H), 1.11 (s, 6H), 0.92-0.87 (m, 3H). The spectrum revealed that the product was contaminated with a small amount of an unidentified substance.

Step 2: Synthesis of heptyl 5-hydroxy-4,4-dimethylpentanoate (37b)

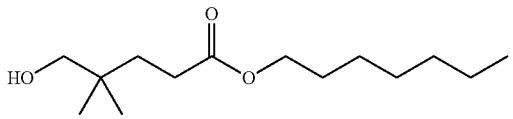 [SMILES: CCCCCCCOC(=O)CCC(C)(C)CO]

To a suspension of sodium 5-(heptyloxy)-2,2-dimethyl-5-oxopentanoate (37a) (7.89 g, 28.1 mmol) in a mixture of THF (61 mL) and DMF (20 mL) was added isopropyl chloroformate, 1.0M in toluene (42.2 mL, 42.2 mmol) at 0° C. and the mixture was stirred for 10 min. After 4 h of stirring at room temperature, the suspension was cooled to 0° C. and sodium borohydride (1.9 g, 56.3 mmol) was added. The mixture was stirred for 20 min and then MeOH (10 mL) was added to the solution (reaction monitored by TLC using 2:8 ethyl acetate/hexanes). After 30 min of stirring, EtOAc (50 mL), a few drops of Et$_3$N, and a saturated aqueous solution of NH$_4$Cl were added (50 mL). The aqueous and organic layers were separated, and the aqueous layer was extracted with EtOAc (2×80 mL). The combined organic layers were washed with brine (80 mL), and the filtrate was concentrated in vacuo. The residual solution was washed with H$_2$O (3×100 mL), brine (100 mL), and dried (Na$_2$SO$_4$), and concentrated. During all extractions, several drops of Et$_3$N were added to the organic layer to suppress lactonization. The residue was purified by column chromatography on silica gel using EtOAc/hexanes modified with 0.1% Et$_3$N (0:1 to 3:7) as eluent to give the product (37b) (3.35 g, 49% crude) as a colorless oil.

Step 3: Synthesis of heptyl 5-((chlorosulfonyl)oxy)-4,4-dimethylpentanoate (37c)

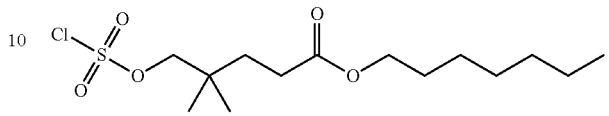

A solution of sulfuryl chloride (0.60 mL, 8.2 mmol) in Et$_2$O (13 mL) was cooled to −78° C. under a nitrogen atmosphere. A solution of heptyl 5-hydroxy-4,4-dimethylpentanoate (37b) (1.0 g, 4.1 mmol) and pyridine (0.66 mL, 8.2 mmol) in Et$_2$O (13 mL) was added dropwise to the sulfuryl chloride solution over the course of 10 min. The syringe was rinsed with diethyl ether (3×1 mL) and this was also added to the mixture. The mixture was stirred for 4.5 h (reaction monitored by TLC using 2:8 ethyl acetate/hexanes as eluent). The solids were filtered-off, and the filtrate concentrated in vacuo to give the product (37c) (1.13 g) as a colorless oil. To this was added 3 mL of THF and the solution stored at −78° C. This was used in the next step without further purification.

Step 4: Synthesis of heptyl 5-(((((2S,5R)-2-carbamoyl-7-oxo-1,6-diazabicyclo[3.2.1]octan-6-yl)oxy)sulfonyl)oxy)-4,4-dimethylpentanoate (37)

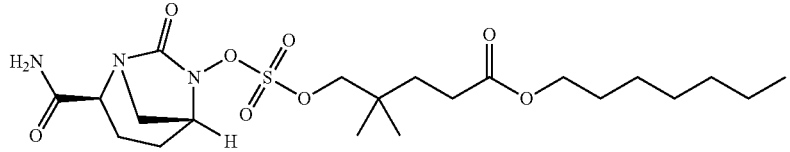 [SMILES: CCCCCCCOC(=O)CCC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.56 g, 3.0 mmol) was dissolved in THF (28 mL) and HMPA (1.2 mL), and the resulting solution was cooled to −78° C. under an atmosphere of nitrogen. A solution of NaHMDS, 1.0 M in THF (3.3 mL, 3.3 mmol) was added dropwise to the cooled solution and stirred for 10 min. A solution of heptyl 5-((chlorosulfonyl)oxy)-4,4-dimethylpentanoate (37c) (1.13 g, 3.3 mmol) was dissolved in THF (3 mL, with the temperature maintained at −78° C.) and quickly added to the reaction mixture. The flask containing the sulfating reagent was rinsed with THF (3×1 mL), while the flask temperature was maintained at −78° C., and this was also added quickly to the reaction mixture. After stirring for 10 min, the mixture was warmed to room temperature and stirred overnight. The mixture was quenched with a saturated aqueous solution of sodium bicarbonate (60 mL) and extracted with EtOAc (60 mL).

The organic layer was concentrated, and the oily residue diluted with EtOAc (60 mL) and washed with water (2×60 mL). The organic layer was washed with brine, dried (MgSO$_4$), and concentrated under vacuum. The residue was purified by column chromatography on silica gel EtOAc/hexanes (1:9 to 8:2) as eluent to give the product (37) (473 mg, 32%) as a solid. LC-MS: m/z=492.0 [M+H]$^+$. $^1$H NMR (300 MHz, CDCl$_3$): δ 6.48 (s, 1H), 5.62 (s, 1H), 4.51 (d, J=9.3 Hz, 1H), 4.22-4.18 (m, 2H), 4.08-4.04 (m, 3H), 3.36-3.31 (m, 1H), 3.02 (d, J=12.6 Hz, 1H), 2.47-2.41 (m, 1H), 2.33-2.28 (m, 2H), 2.18-2.13 (m, 1H), 2.01-1.80 (m, 2H), 1.72-1.60 (m, 4H), 1.31-1.28 (m, 8H), 0.99 (s, 6H), 0.91-0.86 (m, 3H). $^{13}$C NMR (75 MHz, CDCl$_3$): δ 173.6, 170.9, 167.1, 83.4, 64.9, 62.0, 60.2, 47.2, 34.2, 33.3, 31.8, 29.2, 29.0, 28.7, 26.0, 23.6, 23.3, 22.7, 20.8, 17.6, 14.2.

Example 38

Synthesis of 2-methoxyethyl 5-(((((2S,5R)-2-carbamoyl-7-oxo-1,6-diazabicyclo[3.2.1]octan-6-yl)oxy)sulfonyl)oxy)-4,4-dimethylpentanoate (38)

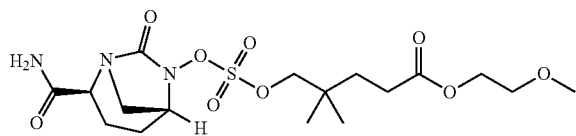 [SMILES: COCCOC(=O)CCC(C)(C)COS(=O)(=O)ON1C(=O)N2C[C@H]1CC[C@H]2C(N)=O]

Step 1: Synthesis of sodium 5-(2-methoxyethoxy)-2,2-dimethyl-5-oxopentanoate (38a)

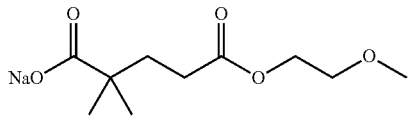

To a solution of 2,2-dimethylglutaric anhydride (5.0 g, 35.2 mmol) in 2-methoxyethanol (30 mL) was added a solution sodium 2-methoxyethanolate (4.27 g, 43.5 mmol) in 2-methoxyethanol (30 mL). After 20 h of stirring, the solvent was evaporated and the resulting solid was suspended in Et$_2$O (80 mL). The mixture was filtered and the solid was washed with Et$_2$O (2×40 mL). The solid was dried under high vacuum to afford the product (38a) (6.44 g, 76%) as a solid. $^1$H NMR (300 MHz, D$_2$O): δ 4.30-4.27 (m, 2H), 3.75-3.72 (m, 2H), 3.42 (s, 3H), 2.41-2.36 (m, 2H), 1.83-1.78 (m, 2H), 1.12 (s, 6H). The spectrum revealed that the product was contaminated with a small amount of an unidentified substance.

Step 2: Synthesis of 2-methoxyethyl 5-hydroxy-4,4-dimethylpentanoate (38b)

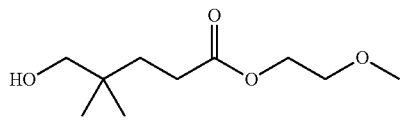

To a suspension of sodium 5-(2-methoxyethoxy)-2,2-dimethyl-5-oxopentanoate (38a) (6.44 g, 26.8 mmol) in a mixture of THF (58 mL) and DMF (19 mL) was added isopropyl chloroformate, 1.0M in toluene (40.2 mL, 40.2 mmol) at 0° C. and stirred for 10 min. After 4 h of stirring at room temperature, the mixture was stored at −78° C. overnight. The suspension was cooled to 0° C. and sodium borohydride (1.81 g, 53.6 mmol) was added. The mixture was stirred for 20 min and then MeOH (9.6 mL) was added to the solution (reaction monitored by TLC using 3:7 EtOAc/hexanes as eluent). After 30 min of stirring, EtOAc (50 mL) with a few drops of Et$_3$N followed by a saturated aqueous solution of NH$_4$Cl (50 mL) were added. The layers were separated and the aqueous layer was extracted with EtOAc (2×80 mL). The combined organic layers were washed with brine, dried (MgSO$_4$), filtered, and the filtrate was concentrated in vacuo. The residue was purified by column chromatography on silica gel to give the product (38b) (2.54 g, 46% crude).

Step 3: Synthesis of 2-methoxyethyl 5-((chlorosulfonyl)oxy)-4,4-dimethylpentanoate (38c)

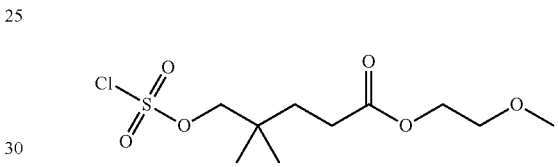

A solution of sulfuryl chloride (0.36 mL, 4.9 mmol) in Et$_2$O (8 mL) was cooled to −78° C. under a nitrogen atmosphere. A solution of 2-methoxyethyl 5-hydroxy-4,4-dimethylpentanoate (38b) (0.50 g, 2.4 mmol) and pyridine (0.40 mL, 4.9 mmol) in Et$_2$O (8 mL) was added dropwise to the sulfuryl chloride solution over the course of 10 min. The syringe was rinsed with Et$_2$O (3×1 mL) and the rinse was also added to the mixture. The mixture was stirred for 4.5 h (reaction monitored by TLC using 2:8 EtOAc/hexanes as eluent). The solids were filtered-off and the filtrate concentrated in vacuo to give the product (38c) (0.60 g, 2.0 mmol) as a colorless oil. To this was added 3 mL of THF and the solution was stored at −78° C. This was used in the next step without further purification.

Step 4: Synthesis of 2-methoxyethyl 5-(((((2S,5R)-2-carbamoyl-7-oxo-1,6-diazabicyclo[3.2.1]octan-6-yl)oxy)sulfonyl)oxy)-4,4-dimethylpentanoate (38)

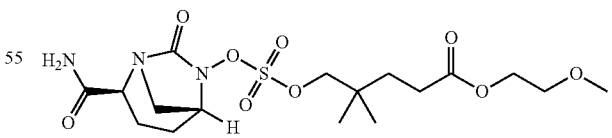

(2S,5R)-6-hydroxy-7-oxo-1,6-diazabicyclo[3.2.1]octane-2-carboxamide (1) (370 mg, 2.0 mmol) was dissolved in THF (19 mL) and HMPA (0.8 mL), and the resulting solution was cooled to −78° C. under an atmosphere of nitrogen. A 1.0 M solution of NaHMDS in THF (2.2 mL, 2.2 mmol) was added dropwise to the cooled solution and stirred for 10 min. 2-Methoxyethyl 5-((chlorosulfonyl)oxy)-4,4-dimethylpentanoate (38c) (0.60 g, 2.0 mmol) dissolved in THF (3 mL, its temperature maintained at −78° C.) was quickly added to the reaction mixture. The flask containing the sulfating reagent was rinsed with THF (3×1 mL), while the flask temperature was maintained at −78° C., and the rinse was quickly added to the reaction mixture. After stirring for 10 min, the mixture was warmed to room temperature and stirred overnight. The reaction was quenched with a saturated solution of aqueous sodium bicarbonate (40 mL) and extracted with EtOAc (40 mL). The organic layer was concentrated, and the oily residue partitioned between H$_2$O (40 mL) and EtOAc (40 mL). The organic layer was washed with brine, dried (MgSO$_4$), and concentrated under vacuum. The residue was purified by column chromatography on silica gel using EtOAc/hexanes (1:9 to 8:2) as eluent to give the product (38) (164 mg, 18%) as a solid. LC-MS: 452.0 [M+H]$^+$. $^1$H NMR (300 MHz, CDCl$_3$): δ 6.53 (s, 1H), 5.62 (s, 1H), 4.51 (d, J=9.3 Hz, 1H), 4.24-4.18 (m, 4H), 4.05-4.03 (m, 1H), 3.61-3.58 (m, 2H), 3.39-3.32 (m, 4H), 3.01 (d, J=11.7 Hz, 1H), 2.47-2.33 (m, 3H), 2.18-2.13 (m, 1H), 2.00-1.82 (m, 2H), 1.73-1.68 (m, 2H), 0.99 (s, 6H). $^{13}$C NMR (75 MHz, CDCl$_3$): δ 173.6, 171.0, 167.1, 83.4, 70.6, 63.7, 62.0, 60.2, 59.1, 47.2, 34.2, 33.2, 29.1, 23.6, 23.3, 20.8, 17.6.

Example 39

Synthesis of 5-(((((2S,5R)-2-carbamoyl-7-oxo-1,6-diazabicyclo[3.2.1]octan-6-yl)oxy)sulfonyl)oxy)-2,2,4,4-tetramethylpentyl propionate (39)

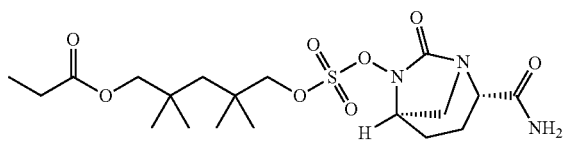 [SMILES: CCC(=O)OCC(C)(C)CC(C)(C)COS(=O)(=O)ON1C(=O)N2C[C@H]1CC[C@H]2C(N)=O]

Step 1: Synthesis of 5,5-dimethyltetrahydro-2H-pyran-2-one (39a)

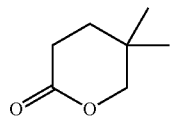

To a solution of ethyl 5-hydroxy-4,4-dimethylpentanoate (35a) (26.5 g, 152.1 mmol) in dichloromethane (683 mL) was added trifluoroacetic acid (1.75 mL, 22.8 mmol). The mixture was stirred at room temperature for 3 d. The reaction was quenched with a saturated aqueous sodium bicarbonate solution (150 mL), stirred rapidly for 30 min, and the layers were separated. The organic layer was washed with brine (150 mL), dried (Na$_2$SO$_4$), and concentrated under vacuum. The residue was purified by column chromatography on silica gel flash using EtOAc/hexanes (0:1 to 45:55) as eluent to give the product (39a) (8.79 g, 45%) as a colorless oil. The product was used in the next step without further purification and was contaminated with small amounts of unidentified byproducts. $^1$H NMR (300 MHz, CDCl$_3$): δ 3.97 (s, 2H), 2.56 (t, J=7.4 Hz, 2H), 1.69 (t, J=7.4 Hz, 2H), 1.05 (s, 6H).

Step 2: Synthesis of 3,3,5,5-tetramethyltetrahydro-2H-pyran-2-one (39b)

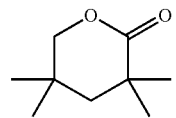

5,5-Dimethyltetrahydro-2H-pyran-2-one (39a) (8.79 g, 68.6 mmol) was dissolved in anhydrous DMF (150 mL) and the resulting solution was cooled to 0° C. under an inert atmosphere of argon. Sodium hydride, 60% in mineral oil (8.23 g, 205.7 mmol) was added in one portion and the mixture stirred for 20 min. This was followed by the drop-wise addition of MeI (17.1 mL, 274.3 mmol). The resulting solution was stirred at 0° C. for 20 min and then at room temperature for 3 d. The mixture was diluted with EtOAc (350 mL) and then quenched at 0° C. via the careful dropwise addition of a saturated aqueous solution of NH$_4$Cl (100 mL). The aqueous and organic layers were separated, and the aqueous layer was extracted with EtOAc (350 mL). The combined organic layers were washed with H$_2$O (6×300 mL), brine (300 mL), dried (Na$_2$SO$_4$), and concentrated under vacuum. The residue was purified by column chromatography on silica using EtOAc/hexanes (1:9) as eluent to give the product (39b) (3.42 g, 32%). The product was used in the next step without further purification and was contaminated with small amounts of various unidentified byproducts. $^1$H NMR (300 MHz, CDCl$_3$): δ 4.01 (s, 2H), 1.62 (s, 2H), 1.30 (s, 6H), 1.02 (s, 6H).

Step 3: Synthesis of 2,2,4,4-tetramethylpentane-1,5-diol (39c)

A necked round bottom flask containing a stirring slurry of 95% LiAlH$_4$ (0.87 g, 21.6 mmol) in Et$_2$O (126 mL) was cooled to 0° C. under an atmosphere of argon. To this slurry was added a solution of 3,3,5,5-tetramethyltetrahydro-2H-pyran-2-one (39b) (2.94 g, 18.8 mmol) in Et$_2$O (50 mL) under an inert atmosphere of argon. This was warmed to room temperature and stirred overnight. The mixture was cautiously quenched with H$_2$O (80 mL) then 3 M NaOH (120 mL) and stirred for 30 min. The mixture was filtered through a pad of Celite®, and the pad was rinsed thoroughly with Et$_2$O. The aqueous and organic layers were separated, and the aqueous layer was extracted with Et$_2$O (3×100 mL). The combined organic layers were concentrated under vacuum and the residue was purified by column chromatography on silica gel using EtOAc/hexanes (2:8 to 6:4) as eluent to give the product (39c) (2.59 g, 86%) as a solid. $^1$H NMR (300 MHz, CDCl$_3$): δ 3.41 (s, 4H), 2.55 (s, 2H), 1.34 (s, 2H), 0.95 (s, 12H)

Step 4: Synthesis of 5-hydroxy-2,2,4,4-tetramethylpentyl propionate (39d)

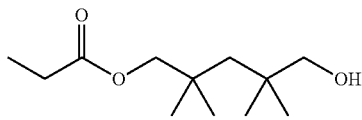

To a stirring solution of 2,2,4,4-tetramethylpentane-1,5-diol (39c) (0.48 g, 3.0 mmol) and pyridine (0.24 mL, 3.0 mmol) in DCM (20 mL) was added propionyl chloride (0.26 mL, 3.0 mmol) dropwise over the course of 30 min at ca. 0° C. (ice bath). The reaction mixture was stirred overnight at room temperature. The mixture was diluted with $H_2O$ (20 mL), and the layers were separated. The aqueous layer was extracted with DCM (2×20 mL), and the combined organic layers were washed with brine (20 mL), dried ($Na_2SO_4$), and concentrated under vacuum. The residue was purified by column chromatography on silica gel EtOAc/hexanes (5:95 to 6:4) as eluent to give the product (39d) (411 mg, 63%). $^1$H NMR (300 MHz, $CDCl_3$): δ 3.85 (s, 2H), 3.32 (s, 2H), 2.37 (q, J=7.7 Hz, 2H), 1.50 (s, 1H), 1.36 (s, 2H), 1.16 (t, J=7.5 Hz, 3H), 1.03 (s, 6H), 0.99 (s 6H).

Step 5: Synthesis of 5-((chlorosulfonyl)oxy)-2,2,4,4-tetramethylpentyl propionate (39e)

A solution of sulfuryl chloride (0.136 mL, 1.9 mmol) in $Et_2O$ (6.4 mL) was cooled to −78° C. under an atmosphere of argon. A solution of 5-hydroxy-2,2,4,4-tetramethylpentyl propionate (39d) (404 mg, 1.9 mmol) and pyridine (0.15 mL, 1.9 mmol) in $Et_2O$ (6.4 mL) was added dropwise to the sulfuryl chloride solution over the course of 10 min. The mixture was warmed to room temperature and stirred for 70 min. The solids were filtered to give a solution of the product (39e) in $Et_2O$ as the filtrate. The yield was assumed quantitative, and the mixture was used in the next step without further purification.

Step 6: Synthesis of 5-(((((2S,5R)-2-carbamoyl-7-oxo-1,6-diazabicyclo[3.2.1]octan-6-yl)oxy)sulfonyl)oxy)-2,2,4,4-tetramethylpentyl propionate (39)

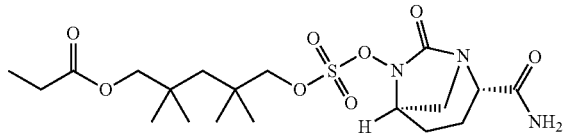 [SMILES: CCC(=O)OCC(C)(C)CC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (346 mg, 1.9 mmol) was dissolved in THF (21.8 mL) and 1,3-dimethyltetrahydropyrimidin-2(1H)-one (1.0 mL), and the resulting solution was cooled to −78° C. under an atmosphere of argon. A solution of NaHMDS, 1.0 M in THF (1.9 mL, 1.9 mmol) was added dropwise to the cooled solution and stirred for 90 min. A solution of 5-((chlorosulfonyl)oxy)-2,2,4,4-tetramethylpentyl propionate (39e) (0.59 g, 1.9 mmol) in $Et_2O$ (ca. 20 mL) was added to the reaction mixture (cannula). After stirring for 10 min the mixture was warmed to room temperature and stirred for 4 h. The reaction was then quenched with a saturated aqueous solution of sodium bicarbonate (40 mL) and extracted with EtOAc (40 mL). The organic layer was washed with $H_2O$ (3×40 mL), brine (40 mL), dried ($Na_2SO_4$), and concentrated under vacuum. The residue was purified by silica gel flash column chromatography using EtOAc/hexanes (1:9 to 8:2) as eluent to give the product (39) (254 mg, 29%) as a solid. LC-MS: m/z=464.1 [M+H]$^+$. $^1$H NMR (300 MHz, $CDCl_3$): δ 6.53 (s, 1H), 5.64 (s, 1H), 4.53 (d, J=9 Hz, 1H), 4.23 (d, J=9 Hz, 1H), 4.18 (m, 1H) 4.06-4.04 (m, 1H), 3.80 (s, 2H), 3.36-3.32 (m, 1H), 3.01 (d, J=12.3 Hz, 1H), 2.47-2.33 (m, 3H), 2.19-2.13 (m, 1H), 2.01-1.79 (m, 2H), 1.43 (s, 2H), 1.16 (t, J=7.7 Hz, 3H), 1.09 (s, 6H), 1.03 (s, 6H). $^{13}$C NMR (75 MHz, $CDCl_3$): δ 174.6, 171.1, 167.1, 84.9, 73.3, 61.9, 60.2, 47.2, 46.2, 36.0, 35.3, 27.8, 26.6, 26.3, 25.9, 25.3, 20.8, 17.5, 9.3.

Example 40

Synthesis of 5-(((((2S,5R)-2-carbamoyl-7-oxo-1,6-diazabicyclo[3.2.1]octan-6-yl)oxy)sulfonyl)oxy)-2,2,4,4-tetramethylpentyl benzoate (40)

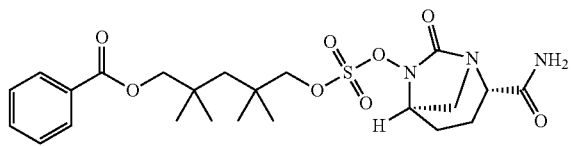 [SMILES: CC(C)(COC(=O)c1ccccc1)CC(C)(C)COS(=O)(=O)ON1C(=O)N2C[C@H]1CC[C@H]2C(N)=O]

Step 1: Synthesis of 5-hydroxy-2,2,4,4-tetramethylpentyl benzoate (40a)

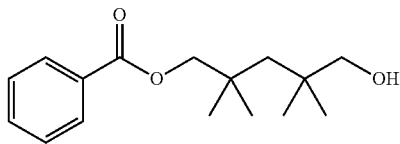 [SMILES: CC(C)(CO)CC(C)(C)COC(=O)c1ccccc1]

To a stirred solution of 2,2,4,4-tetramethylpentane-1,5-diol (39c) (0.48 g, 3.0 mmol) and pyridine (0.24 mL, 3.0 mmol) in DCM (20 mL) was added benzoyl chloride (0.37 mL, 3.0 mmol) dropwise over the course of 30 min at ca. 0° C. (ice bath) under an atmosphere of argon. The reaction mixture was stirred overnight at room temperature. The mixture was diluted with $H_2O$ (20 mL), and the layers were separated. The aqueous layer was extracted with DCM (2×20 mL), and the combined organic layers were washed with brine (20 mL), dried ($Na_2SO_4$), and concentrated under vacuum. The residue was purified by column chromatography on silica gel using EtOAc/hexanes (5:95 to 1:1) as eluent to give the product (40a) (548 mg, 69%) as an oil. $^1$H NMR (300 MHz, $CDCl_3$): δ 8.06 (d, J=8.4 Hz, 2H), 7.59-

7.55 (m, 1H), 7.48-7.43 (m, 2H), 4.09 (s, 2H), 3.35 (s, 2H), 1.48 (s, 2H), 1.13 (s, 6H), 1.02 (s, 6H).

Step 2: Synthesis of 5-((chlorosulfonyl)oxy)-2,2,4,4-tetramethylpentyl benzoate (40b)

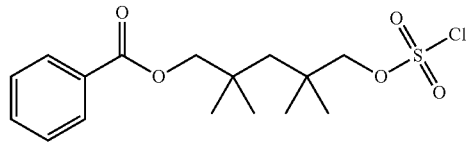 [SMILES: CC(C)(COC(=O)c1ccccc1)CC(C)(C)COS(=O)(=O)Cl]

A solution of sulfuryl chloride (0.15 mL, 2.0 mmol) in Et$_2$O (8.5 mL) was cooled to −78° C. under an atmosphere of argon. A solution of 5-hydroxy-2,2,4,4-tetramethylpentyl benzoate (40a) (541 mg, 2.0 mmol) and pyridine (0.17 mL, 2.0 mmol) in Et$_2$O (8.5 mL) was added dropwise to the sulfuryl chloride solution over the course of 10 min. The mixture was stirred at 0° C. for 20 min, then at room temperature for 90 min. The mixture was filtered and the filtrate used to provide a solution of the product (40b) in Et$_2$O (ca. 20 mL). The yield was assumed quantitative and the product was used in the next step without further purification.

Step 3: Synthesis of 5-(((((2S,5R)-2-carbamoyl-7-oxo-1,6-diazabicyclo[3.2.1]octan-6-yl)oxy)sulfonyl)oxy)-2,2,4,4-tetramethylpentyl benzoate (40)

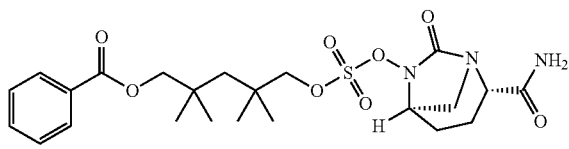 [SMILES: CC(C)(COC(=O)c1ccccc1)CC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (370 mg, 2.0 mmol) was dissolved in THF (23 mL) and 1,3-dimethyltetrahydropyrimidin-2 (1H)-one (1.5 mL), and the resulting solution was cooled to −78° C. under an atmosphere of argon. A solution of NaHMDS, 1.0M in THF (2.0 mL, 2.0 mmol) was added dropwise to the cooled solution and stirred for 90 min. A solution of 5-((chlorosulfonyl)oxy)-2,2,4,4-tetramethylpentyl benzoate (40b) (0.73 g, 2.0 mmol, 1.0 equiv.) dissolved in Et$_2$O (ca. 20 mL) was added to the reaction mixture (cannula). After stirring for 10 min the mixture was warmed to room temperature and stirred for 4 h. The mixture was quenched with a saturated aqueous solution of sodium bicarbonate (40 mL) and extracted with EtOAc (40 mL). The organic layer was washed with H$_2$O (3×40 mL), brine (40 mL), dried (Na$_2$SO$_4$), and concentrated under vacuum. The residue was purified by column chromatography on silica gel using EtOAc/hexanes (1:9 to 8:2) as eluent to give the product (40) (282 mg, 27%) as a solid. LC-MS: m/z=512.15 [M+H]$^+$. $^1$H NMR (300 MHz, CDCl$_3$): δ 8.06 (d, J=7.8 Hz, 2H), 7.59-7.55 (m, 1H), 7.49-7.43 (m, 2H), 6.49 (s, 1H), 5.70 (s, 1H), 4.57 (d, J=9 Hz, 1H), 4.26 (d, J=8.7 Hz, 1H), 4.17 (s, 1H), 4.10-4.01 (m, 3H), 3.29-3.25 (m, 1H), 2.98 (d, J=11.7 Hz, 1H), 2.45-2.35 (m, 1H), 2.17-2.11 (m, 1H), 1.99-1.77 (m, 2H), 1.56 (s, 2H), 1.14- 1.13 (m, 12H). $^{13}$C NMR (75 MHz, CDCl$_3$): δ 171.0, 167.0, 166.6, 133.1, 130.4, 129.7, 128.6, 85.0, 73.9, 61.9, 60.2, 47.2, 46.2, 36.1, 35.7, 26.7, 26.4, 25.9, 25.4, 20.8, 17.5.

Example 41

Synthesis of 5-(((((2S,5R)-2-carbamoyl-7-oxo-1,6-diazabicyclo[3.2.1]octan-6-yl)oxy)sulfonyl)oxy)-2,2,4,4-tetramethylpentyl 2,6-dimethylbenzoate (41)

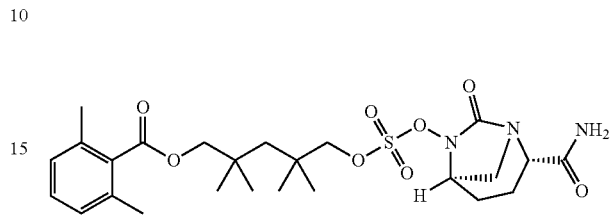

Step 1: Synthesis of 5-hydroxy-2,2,4,4-tetramethylpentyl 2,6-dimethylbenzoate (41a)

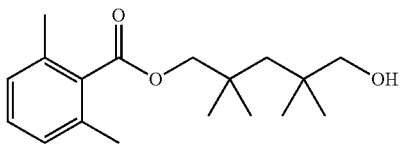 [SMILES: Cc1cccc(C)c1C(=O)OCC(C)(C)CC(C)(C)CO]

To a stirred solution of 2,2,4,4-tetramethylpentane-1,5-diol (39c) (0.48 g, 3.0 mmol) and pyridine (0.24 mL, 3.0 mmol) in DCM (20 mL) was added 2,6-dimethylbenzoyl chloride (0.45 mL, 3.0 mmol) dropwise over the course of 30 min at 0° C. (ice bath) under an atmosphere of argon. The reaction mixture was stirred overnight at room temperature. The mixture was diluted with H$_2$O (20 mL), and the layers were separated. The aqueous layer was extracted with DCM (2×20 mL), and the combined organic layers were washed with brine (20 mL), dried (Na$_2$SO$_4$), and concentrated under vacuum. The residue was purified by column chromatography on silica gel using EtOAc/hexanes (5:95 to 1:1) as eluent to give the product (41a) (462 mg, 53%) as an oil. $^1$H NMR (300 MHz, CDCl$_3$): δ 7.22-7.17 (m, 1H), 7.04 (d, J=7.5 Hz, 2H), 4.10 (s, 2H), 3.32 (s, 2H), 2.33 (s, 6H), 1.41 (s, 2H), 1.10 (s, 6H), 1.00 (s, 6H).

Step 2: Synthesis of 5-((chlorosulfonyl)oxy)-2,2,4,4-tetramethylpentyl 2,6-dimethylbenzoate (41b)

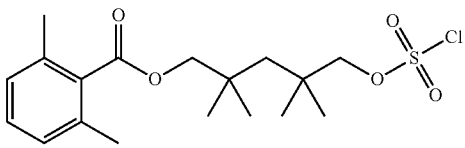 [SMILES: Cc1cccc(C)c1C(=O)OCC(C)(C)CC(C)(C)COS(=O)(=O)Cl]

A solution of sulfuryl chloride (0.11 mL, 1.5 mmol) in Et$_2$O (7 mL) was cooled to −78° C. under an atmosphere of argon. A solution of 5-hydroxy-2,2,4,4-tetramethylpentyl 2,6-dimethylbenzoate (41a) (453 mg, 1.5 mmol) and pyridine (0.13 mL, 1.5 mmol) in Et$_2$O (7 mL) was added dropwise to the sulfuryl chloride solution over the course of 10 min. The mixture was stirred in an ice bath for 20 min, then at room temperature for 90 min. The mixture was filtered and the filtrate stored to give a solution of the product (41b) in Et$_2$O (ca. 20 mL). The yield assumed quantitative. This mixture was used in the next step without further purification (a small quantity was concentrated under vacuum and the NMR taken of the residue). $^1$H NMR (300 MHz, CDCl$_3$): δ 7.21 (t, J=7.7 Hz, 1H), 7.05 (d, J=7.2 Hz, 2H), 4.20 (s, 2H), 4.07 (s, 2H), 2.32 (s, 6H), 1.50 (s, 2H), 1.14 (s, 6H), 1.12 (s, 6H).

Step 3: Synthesis of 5-(((((2S,5R)-2-carbamoyl-7-oxo-1,6-diazabicyclo[3.2.1]octan-6-yl)oxy)sulfonyl) oxy)-2,2,4,4-tetramethylpentyl 2,6-dimethylbenzoate (41)

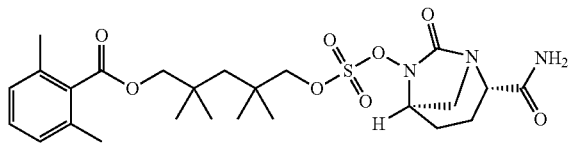 [SMILES: Cc1cccc(C)c1C(=O)OCC(C)(C)CC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (286 mg, 1.5 mmol) was dissolved in THF (18 mL) and 1,3-dimethyltetrahydropyrimidin-2 (1H)-one (2.3 mL) and the resulting solution was cooled to −78° C. under an atmosphere of argon. A solution of NaHMDS, 1.0 M in THF (1.5 mL, 1.5 mmol) was added dropwise to the cooled solution and stirred for 90 min. A solution of 5-((chlorosulfonyl)oxy)-2,2,4,4-tetramethylpentyl 2,6-dimethylbenzoate (41b) (0.61 g, 1.5 mmol) in Et$_2$O (ca. 20 mL) was added to the reaction mixture (cannula). After stirring for 10 min the mixture was warmed to room temperature, stirred for 4 h. The mixture was quenched with a saturated aqueous solution of sodium bicarbonate (40 mL) and extracted with EtOAc (40 mL). The organic layer was washed with H$_2$O (3×40 mL), brine (40 mL), dried (Na$_2$SO$_4$), and concentrated under vacuum. The residue was purified by column chromatography on silica gel using EtOAc/hexanes (1:9 to 8:2) as eluent to give the product (41) (490 mg, 58%) as a solid. LC-MS: m/z=540.07 [M+H]$^+$. $^1$H NMR (300 MHz, CDCl$_3$): δ 7.20 (t, J=7.7 Hz, 1H), 7.04 (d, J=7.5 Hz, 2H), 6.50 (s, 1H), 5.63 (s, 1H), 4.54 (d, J=8.7 Hz, 1H), 4.23 (d, J=8.7 Hz, 1H), 4.17 (s, 1H), 4.06-4.03 (m, 3H), 3.34-3.29 (m, 1H), 3.00 (d, J=11.7 Hz, 1H), 2.47-2.40 (m, 1H), 2.32 (s, 6H), 2.18-2.14 (m, 1H), 2.00-1.78 (m, 2H), 1.49 (s, 2H), 1.11 (s, 12H). $^{13}$C NMR (75 MHz, CDCl$_3$): δ 170.9, 170.4, 167.0, 135.0, 134.2, 129.4, 127.7, 84.9, 74.5, 62.0, 60.2, 47.2, 46.2, 36.1, 35.4, 26.5, 26.4, 26.0, 25.3, 20.8, 20.0, 17.5.

Example 42

Synthesis of (2S,5R)-2-carbamoyl-7-oxo-1,6-diazabicyclo[3.2.1]octan-6-yl ((3-methyl-2-oxotetrahydrofuran-3-yl)methyl) sulfate (42)

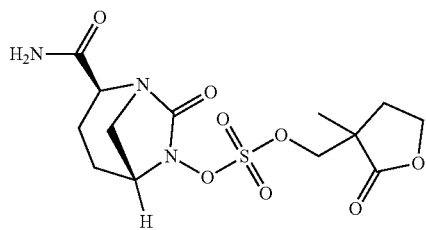 [SMILES: CC1(COS(=O)(=O)ON2C(=O)N3C[C@H]2CC[C@H]3C(N)=O)CCOC1=O]

Step 1: Synthesis of (3-methyl-2-oxotetrahydrofuran-3-yl)methyl sulfochloridate (42a)

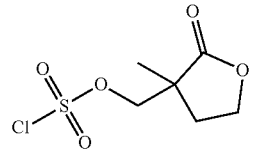

Pyridine (0.28 mL, 3.5 mmol) was added to a stirred mixture of 3-(hydroxymethyl)-3-methyldihydrofuran-2 (3H)-one (prepared according to Synlett 2010, 2625-2627) (0.30 g, 2.3 mmol) and Et$_2$O (8 mL) under an atmosphere of argon. The solution was cooled to −78° C. and sulfuryl chloride (0.28 mL, 3.5 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (42a) as an oil, that was used directly in the next step without further purification (yield assumed quantitative).

Step 2: Synthesis of (2S,5R)-2-carbamoyl-7-oxo-1, 6-diazabicyclo[3.2.1]octan-6-yl ((3-methyl-2-oxotetrahydrofuran-3-yl)methyl) sulfate (42)

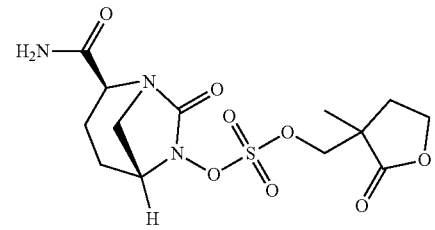 [SMILES: CC1(COS(=O)(=O)ON2C(=O)N3C[C@H]2CC[C@H]3C(N)=O)CCOC1=O]

To a stirred mixture of (2S,5R)-6-hydroxy-7-oxo-1,6-diazabicyclo[3.2.1]octane-2-carboxamide (1) (0.24 g, 1.3 mmol) in THF (20 mL) under an atmosphere of argon was added several drops of 1,3-dimethyltetrahydropyrimidin-2 (1H)-one. The mixture was cooled to −78° C. and stirred for 10 min, then a solution of NaHMDS, 1.0M in THF (1.4 mL, 1.4 mmol) was added dropwise. The mixture was stirred at −78° C. for 8 min, then (3-methyl-2-oxotetrahydrofuran-3-yl)methyl sulfochloridate (42a) (0.30 g, 1.3 mmol) in THF (30 mL) was added at −78° C. The mixture was stirred at −78° C. for 10 min, then allowed to warm to room temperature and stirred overnight. The mixture was diluted with EtOAc and saturated sodium bicarbonate solution. The aqueous and organic layers were separated, and the organic layer was washed with water, dried (Na$_2$SO$_4$), and concentrated under vacuum. The residue was purified by column chromatography on silica gel using EtOAc/hexanes (0:1 to 1:0) as eluent to give a solid (150 mg). NMR indicated a trace impurity, which was removed by trituration with EtOAc to give the product (42) (35 mg) as a solid. LC/MS: m/z=378.0 [M+H]$^+$. $^1$H NMR (300 MHz, d$_6$-DMSO): δ 7.53 (s, 1H), 7.38 (s, 1H), 4.68-4.64 (m, 1H), 4.54 (d, J=9.3 Hz, 1H), 4.32-4.27 (m, 2H), 4.09 (s, 1H), 3.89 (d, J=6.0 Hz, 1H), 3.21-3.13 (m, 2H), 2.38-2.28 (m, 1H), 2.13-2.00 (m, 2H), 1.91-1.66 (m, 3H), 1.21 (s, 3H). $^{13}$C NMR (75 MHz, d$_6$-DMSO): δ 178.3, 171.0, 168.7, 77.9, 65.6, 61.7, 61.2, 46.3, 43.2, 31.2, 20.8, 19.1, 18.9.

(2S,5R)-2-Carbamoyl-7-oxo-1,6-diazabicyclo[3.2.1]octan-6-yl ((3-methyl-2-oxotetrahydrofuran-3-yl)methyl) sulfate (42) was separated into its (S) and (R) isomers, (2S,5R)-2-carbamoyl-7-oxo-1,6-diazabicyclo[3.2.1]octan-6-yl (((S)-3-methyl-2-oxotetrahydrofuran-3-yl)methyl) sulfate (42(S) and (2S,5R)-2-carbamoyl-7-oxo-1,6-diazabicyclo[3.2.1]octan-6-yl (((R)-3-methyl-2-oxotetrahydrofuran-3-yl)methyl) sulfate (42(R):

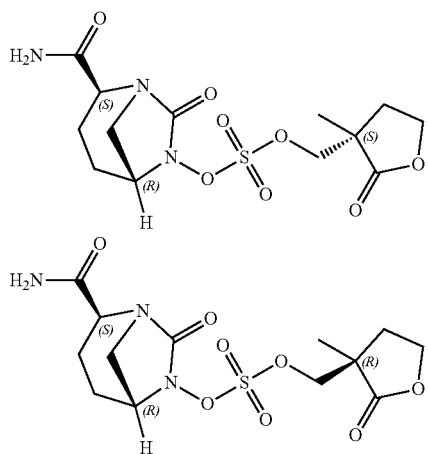

Example 43

Synthesis of 3-(((((2S,5R)-2-carbamoyl-7-oxo-1,6-diazabicyclo[3.2.1]octan-6-yl)oxy)sulfonyl)oxy)-2,2-dimethylpropyl pivalate (43)

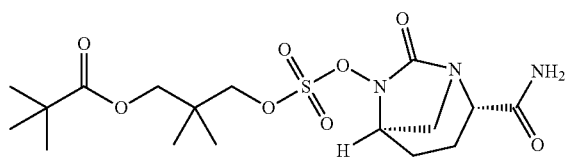 [SMILES: CC(C)(COC(=O)C(C)(C)C)COS(=O)(=O)ON1C(=O)N2C[C@H]1CC[C@H]2C(N)=O]

Step 1: Synthesis of 3-hydroxy-2,2-dimethylpropyl pivalate (43a)

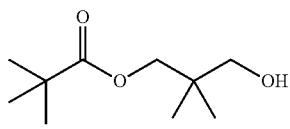

To a stirred solution of 2,2-dimethylpropane-1,3-diol (5.07 g, 48.7 mmol) in DCM (50 mL) at 0° C. under an atmosphere of argon was added trimethylacetyl chloride (2.0 mL, 16.2 mmol), pyridine (2.63 mL, 32.5 mmol) and N,N-4-dimethylaminopyridine (0.4 g, 3.2 mmol). The mixture was allowed to warm to room temperature and stirred at room temperature overnight. The mixture was cooled to 0° C. and the reaction was quenched with the addition of 1N HCl (50 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 1:5) as eluent to give the product (43a) as an oil. $^1$H NMR (300 MHz, CDCl$_3$): δ 3.92 (s, 2H), 3.27 (s, 2H), 1.22 (s, 9H), 0.92 (s, 6H).

Step 2: Synthesis of 3-((chlorosulfonyl)oxy)-2,2-dimethylpropyl pivalate (43b)

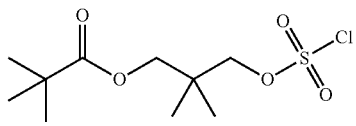 [SMILES: CC(C)(COC(=O)C(C)(C)C)COS(=O)(=O)Cl]

Pyridine (0.75 mL, 9.3 mmol) was added to a stirred mixture of 3-hydroxy-2,2-dimethylpropyl pivalate (43a) (1.17 g, 6.2 mmol) and Et$_2$O (20 mL) under an atmosphere of argon. The solution was cooled to −78° C. and sulfuryl chloride (0.75 mL, 9.3 mmol) in Et$_2$O (8 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (43b) as an oil, that was used directly in the next step without further purification (yield assumed quantitative).

Step 3: Reaction to Produce 3-(((((2S,5R)-2-carbamoyl-7-oxo-1,6-diazabicyclo[3.2.1]octan-6-yl)oxy)sulfonyl)oxy)-2,2-dimethylpropyl pivalate (43)

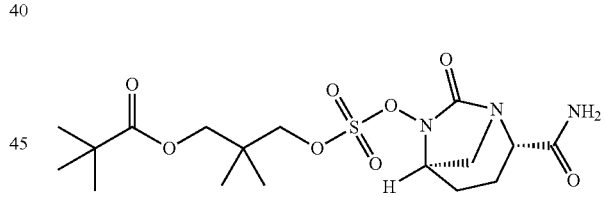

To a stirred mixture of (2S,5R)-6-hydroxy-7-oxo-1,6-diazabicyclo[3.2.1]octane-2-carboxamide (1) (1.1 g, 5.9 mmol) in THF (20 mL) under an atmosphere of argon was added several drops of 1,3-dimethyltetrahydropyrimidin-2(1H)-one. The mixture was cooled to −78° C. and stirred for 10 min, then a solution of NaHMDS, 1.0M in THF (6.5 mL, 6.5 mmol) was added dropwise. The mixture was stirred at −78° C. for 8 min, then 3-((chlorosulfonyl)oxy)-2,2-dimethylpropyl pivalate (43b) (1.7 g, 5.9 mmol) in THF (30 mL) was added at −78° C. The mixture was stirred at −78° C. for 10 min, then allowed to warm to room temperature and stirred overnight. The mixture was diluted with EtOAc and saturated sodium bicarbonate solution. The aqueous and organic layers were separated, and the organic layer was washed with water, dried (Na$_2$SO$_4$), and concentrated under vacuum. The residue was purified by column chromatography on silica gel using EtOAc/hexanes (0:1 to 1:0) as eluent to give the product (43) (654 mg) as a solid. LC/MS: m/z=436.0 [M+H]$^+$. $^1$H NMR (300 MHz, CDCl$_3$): δ 6.48 (s, 1H), 5.58 (s, 1H), 4.60 (d, J=8.7 Hz, 1H), 4.36 (d, J=9.0 Hz, 1H), 4.17 (s, 1H), 4.04 (d, J=6.3 Hz, 1H), 3.95-3.84 (q, 2H), 3.35-3.31 (m, 1H), 3.02 (d, J=12.3 Hz, 1H), 2.50-2.41 (m, 1H), 2.20-2.05 (m, 1H), 1.99-1.78 (m, 2H), 1.22 (s, 9H), 1.04 (s, 6H). $^{13}$C NMR (75 MHz, CDCl$_3$): δ 178.2, 171.1, 167.1, 80.6, 68.4, 62.0, 60.2, 47.2, 39.1, 35.6, 27.3, 21.3, 21.3, 20.8, 17.6.

Example 44

Synthesis of 3-(((((2S,5R)-2-carbamoyl-7-oxo-1,6-diazabicyclo[3.2.1]octan-6-yl)oxy)sulfonyl)oxy)-2,2-dimethylpropyl 3-chloro-2,6-dimethoxybenzoate (44)

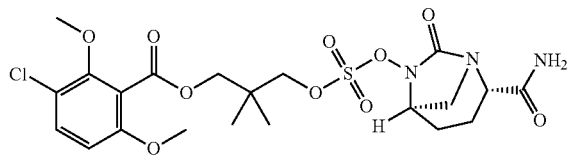 [SMILES: COc1ccc(Cl)c(OC)c1C(=O)OCC(C)(C)COS(=O)(=O)ON1C(=O)N2C[C@H]1CC[C@H]2C(N)=O]

Step 1: Synthesis of 3-hydroxy-2,2-dimethylpropyl 2,6-dimethoxybenzoate (44a)

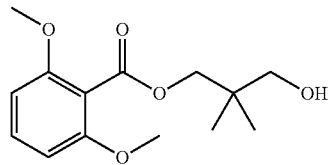 [SMILES: COc1cccc(OC)c1C(=O)OCC(C)(C)CO]

To a stirred solution of 2,2-dimethylpropane-1,3-diol (3.89 g, 37.4 mmol) in DCM (40 mL) at 0° C. under an atmosphere of argon was added 2,6-dimethoxybenzoyl chloride (80% purity; 3.13 g, 12.5 mmol), pyridine (2.02 mL, 24.9 mmol), and N,N-4-dimethylaminopyridine (0.3 g, 2.5 mmol). The mixture was allowed to warm to room temperature and stirred at room temperature overnight. The mixture was cooled to 0° C. and the reaction was quenched by the addition of 1N HCl (50 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 1:5) as eluent to give the product (44a) as an oil. $^1$H NMR (300 MHz, CDCl$_3$): δ 7.19 (t, J=5.0 Hz, 1H), 6.48 (d, J=8.1 Hz, 2H), 4.09 (s, 2H), 3.71 (s, 6H), 3.33 (s, 2H), 0.89 (s, 6H).

Step 2: Synthesis of 3-((chlorosulfonyl)oxy)-2,2-dimethylpropyl 3-chloro-2,6-dimethoxybenzoate (44b)

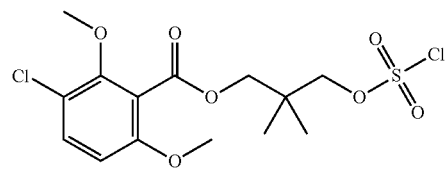 [SMILES: COc1ccc(Cl)c(OC)c1C(=O)OCC(C)(C)COS(=O)(=O)Cl]

Pyridine (0.16 mL, 2.0 mmol) was added to a stirred mixture of 3-hydroxy-2,2-dimethylpropyl 2,6-dimethoxybenzoate (44a) (0.35 g, 1.3 mmol) and Et$_2$O (10 mL) under an atmosphere of argon. The solution was cooled to −78° C. and sulfuryl chloride (0.16 mL, 2.0 mmol) in Et$_2$O (8 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (44b) as an oil, that was used directly in the next step without further purification (yield assumed quantitative). $^1$H NMR (300 MHz, CDCl$_3$): δ 7.36 (d, J=8.7 Hz, 1H), 6.66 (d, J=8.7 Hz, 1H), 4.35 (s, 2H), 4.21 (s, 2H), 3.89 (s, 3H), 3.81 (s, 3H), 1.13 (s, 6H).

Step 3: Synthesis of 3-(((((2S,5R)-2-carbamoyl-7-oxo-1,6-diazabicyclo[3.2.1]octan-6-yl)oxy)sulfonyl)oxy)-2,2-dimethylpropyl 3-chloro-2,6-dimethoxybenzoate (44)

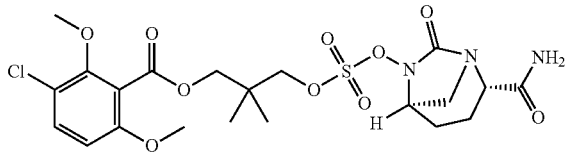 [SMILES: COc1ccc(Cl)c(OC)c1C(=O)OCC(C)(C)COS(=O)(=O)ON1C(=O)N2C[C@H]1CC[C@H]2C(N)=O]

To a stirred mixture of (2S,5R)-6-hydroxy-7-oxo-1,6-diazabicyclo[3.2.1]octane-2-carboxamide (1) (237 mg, 1.3 mmol) in THF (15 mL) under an atmosphere of argon was added several drops of 1,3-dimethyltetrahydropyrimidin-2(1H)-one. The mixture was cooled to −78° C. and stirred for 10 min, then a solution of NaHMDS, 1.0M in THF (1.4 mL, 1.4 mmol) was added dropwise. The mixture was stirred at −78° C. for 8 min, then 3-((chlorosulfonyl)oxy)-2,2-dimethylpropyl 3-chloro-2,6-dimethoxybenzoate (44b) (0.47 g, 1.2 mmol) in THF (8 mL) was added at −78° C. The mixture was stirred at −78° C. for 10 min, then allowed to warm to room temperature and stirred overnight. The mixture was diluted with EtOAc and saturated sodium bicarbonate solution. The aqueous and organic layers were separated, and the organic layer was washed with water, dried (Na$_2$SO$_4$), and concentrated under vacuum. The residue was purified by column chromatography on silica gel using EtOAc/hexanes (0:1 to 1:0) as eluent to give the product (44) as a solid. LC/MS: m/z=550.0 [M+H]$^+$. $^1$H NMR (300 MHz, CDCl$_3$): δ 7.36-7.32 (dd, J=1.2 Hz, 1.2 Hz, 1H), 6.65 (d, J=8.1 Hz, 1H), 6.51 (s, 1H), 5.82 (s, 1H), 4.55 (d, J=8.7 Hz, 1H), 4.38 (d, J=9.0 Hz, 1H), 4.25-4.07 (m, 3H), 4.01 (d, J=6.6 Hz, 1H), 3.88 (s, 3H), 3.81 (s, 3H), 3.27 (d, J=11.7 Hz, 1H), 2.98 (d, J=11.7 Hz, 1H), 2.41-2.37 (m, 1H), 2.14-2.10 (m, 1H), 1.94-1.74 (m, 2H), 1.08 (s, 6H). $^{13}$C NMR (75 MHz, CDCl$_3$): δ 171.1, 167.1, 165.2, 156.1, 153.7, 131.7, 119.8, 119.5, 107.9, 80.4, 69.3, 62.2, 62.0, 60.2, 56.3, 47.1, 35.7, 21.3, 21.2, 20.8, 17.5.

Example 45

Synthesis of 4-(((((2S,5R)-2-carbamoyl-7-oxo-1,6-diazabicyclo[3.2.1]octan-6-yl)oxy)sulfonyl)oxy)-2,2,3,3-tetramethylbutyl 2,6-dimethylbenzoate (45)

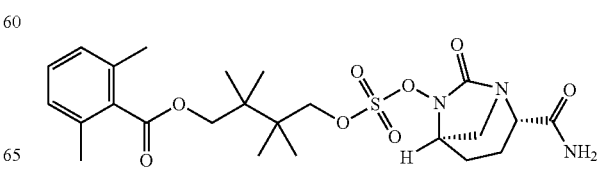

Step 1: Synthesis of 2,2,3,3-tetramethylbutane-1,4-diol (45a)

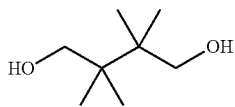

A solution of 3,3,4,4-tetramethyldihydrofuran-2(3H)-one (prepared according to U.S. Pat. No. 3,658,849) (1.0 g, 7.0 mmol) in Et$_2$O (28 mL) was added to a stirring slurry of LiAlH$_4$ (95%; 0.32 g, 8.1 mmol) in Et$_2$O (28 mL) at 0° C. under an atmosphere of argon. The mixture was warmed to room temperature and stirred overnight. Sodium sulfate decahydrate was slowly added until effervescence in the flask ceased. The solid was filtered through a pad of Celite®, and the pad was washed with EtOAc. The filtrate was concentrated under vacuum, and the residue was purified by column chromatography on silica gel using EtOAc/hexanes (0:1 to 7:3) as eluent to give the product (45a) (0.7 g) as a solid. $^1$H NMR (300 MHz, CDCl$_3$): δ 3.41 (s, 4H), 0.88 (s, 12H).

Step 2: Synthesis of 4-hydroxy-2,2,3,3-tetramethylbutyl 2,6-dimethylbenzoate (45b)

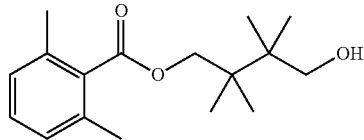 [SMILES: Cc1cccc(C)c1C(=O)OCC(C)(C)C(C)(C)CO]

To a stirred solution of 2,2,3,3-tetramethylbutane-1,4-diol (45a) (0.71 g, 4.9 mmol) in DCM (15 mL) at 0° C. under an atmosphere of argon was added 2,6-dimethylbenzoyl chloride (0.2 mL, 1.6 mmol), pyridine (0.26 mL, 3.2 mmol) and N,N-4-dimethylaminopyridine (0.04 g, 0.3 mmol). The mixture was allowed to warm to room temperature and stirred at room temperature overnight. The mixture was cooled to 0° C. and the reaction was quenched by the addition of 1N HCl (15 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 3:2) as eluent to give the product (45b) as an oil (266 mg). $^1$H NMR (300 MHz, CDCl$_3$): δ 7.18 (t, J=8.4 Hz, 1H), 7.02 (d, J=6.9 Hz, 2H), 4.25 (s, 2H), 3.51 (s, 2H), 2.31 (s, 6H), 0.98 (s, 6H), 0.93 (s, 6H).

Step 3: Synthesis of 4-((chlorosulfonyl)oxy)-2,2,3,3-tetramethylbutyl 2,6-dimethylbenzoate (45c)

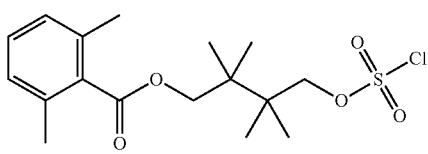 [SMILES: Cc1cccc(C)c1C(=O)OCC(C)(C)C(C)(C)COS(=O)(=O)Cl]

Pyridine (0.11 mL, 1.3 mmol) was added to a stirred mixture of 4-hydroxy-2,2,3,3-tetramethylbutyl 2,6-dimethylbenzoate (45b) (0.26 g, 0.9 mmol) and Et$_2$O (10 mL) under an atmosphere of argon. The solution was cooled to −78° C. and sulfuryl chloride (0.11 mL, 1.3 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (45c) as an oil, that was used directly in the next step without further purification (yield assumed quantitative).

Step 3: Synthesis of 4-(((((2S,5R)-2-carbamoyl-7-oxo-1,6-diazabicyclo[3.2.1]octan-6-yl)oxy)sulfonyl)oxy)-2,2,3,3-tetramethylbutyl 2,6-dimethylbenzoate (45)

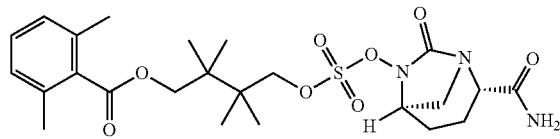 [SMILES: Cc1cccc(C)c1C(=O)OCC(C)(C)C(C)(C)COS(=O)(=O)ON1C(=O)N2C[C@H]1CC[C@H]2C(N)=O]

To a stirred mixture of (2S,5R)-6-hydroxy-7-oxo-1,6-diazabicyclo[3.2.1]octane-2-carboxamide (1) (255 mg, 1.4 mmol) in THF (10 mL) under an atmosphere of argon was added several drops of 1,3-dimethyltetrahydropyrimidin-2 (1H)-one. The mixture was cooled to −78° C. and stirred for 10 min, then a solution of NaHMDS, 1.0M in THF (1.5 mL, 1.5 mmol) was added dropwise. The mixture was stirred at −78° C. for 8 min, then 4-((chlorosulfonyl)oxy)-2,2,3,3-tetramethylbutyl 2,6-dimethylbenzoate (45c) (0.52 g, 1.4 mmol) in THF (5 mL) was added at −78° C. The mixture was stirred at −78° C. for 10 min, and then allowed to warm to room temperature and stirred for 1 h. The mixture was diluted with EtOAc and saturated sodium bicarbonate solution. The aqueous and organic layers were separated, and the organic layer was washed with water, dried (Na$_2$SO$_4$), and concentrated under vacuum. The residue was purified by column chromatography on silica gel using EtOAc/hexanes (0:1 to 1:0) as eluent to give the product (45) as a solid. LC/MS: m/z=526.16 [M+H]$^+$. $^1$H NMR (300 MHz, CDCl$_3$): δ 7.19 (t, J=7.7 Hz, 1H), 7.03 (d, J=6.9 Hz, 2H), 6.47 (s, 1H), 5.58 (s, 1H), 4.76 (d, J=9.3 Hz, 1H), 4.40 (d, J=9.6 Hz, 1H), 4.20-4.16 (m, 3H), 4.04 (d, J=6.3 Hz, 1H), 3.33 (d, J=12.3 Hz, 1H), 2.99 (d, J=12.3 Hz, 1H), 2.45-2.40 (m, 1H), 2.32 (s, 6H), 2.17-2.13 (m, 1H), 2.04-1.83 (m, 2H), 1.05-1.03 (m, 12H). $^{13}$C NMR (75 MHz, CDCl$_3$): δ 170.9, 170.4, 167.1, 134.9, 134.2, 129.4, 127.6, 82.1, 70.8, 62.0, 60.2, 47.3, 39.1, 38.5, 21.0, 20.9, 20.8, 20.5, 20.3, 20.0, 17.5.

Example 46

Synthesis of 4-(((((2S,5R)-2-carbamoyl-7-oxo-1,6-diazabicyclo[3.2.1]octan-6-yl)oxy)sulfonyl)oxy)-2,2,3,3-tetramethylbutyl benzoate (46)

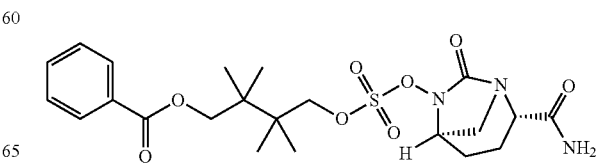

Step 1: Synthesis of 4-hydroxy-2,2,3,3-tetramethylbutyl benzoate (46a)

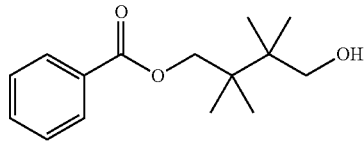 [SMILES: CC(C)(CO)C(C)(C)COC(=O)c1ccccc1]

To a stirred solution of 2,2,3,3-tetramethylbutane-1,4-diol (45a) (0.74 g, 5.0 mmol) in DCM (15 mL) at 0° C. under an atmosphere of argon was added benzoyl chloride (0.25 mL, 2.0 mmol), pyridine (0.33 mL, 4.0 mmol) and N,N-4-dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), then extracted with DCM (twice). The combined organic layers were washed with sat. sodium bicarbonate and brine, then dried ($Na_2SO_4$), and concentrated under vacuum. The residue was purified by column chromatography on silica gel using EtOAc/hexanes (0:1 to 3:2) as eluent to give the product (46a) as an oil. $^1$H NMR (300 MHz, $CDCl_3$): δ 8.05 (d, J=7.2 Hz, 2H), 7.58 (t, J=7.4 Hz, 1H), 7.46 (t, J=7.4 Hz, 2H), 4.27 (s, 2H), 3.59 (s, 2H), 1.05 (s, 6H), 0.99 (s, 6H).

Step 2: Synthesis of 4-((chlorosulfonyl)oxy)-2,2,3,3-tetramethylbutyl benzoate (46b)

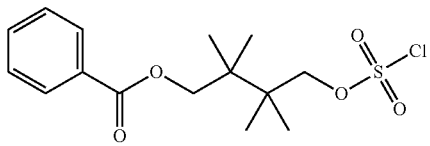 [SMILES: CC(C)(COC(=O)c1ccccc1)C(C)(C)COS(=O)(=O)Cl]

Pyridine (0.29 mL, 3.6 mmol) was added to a stirred mixture of 4-hydroxy-2,2,3,3-tetramethylbutyl benzoate (46a) (0.70 g, 2.8 mmol) and $Et_2O$ (10 mL) under an atmosphere of argon. The solution was cooled to −78° C. and sulfuryl chloride (0.29 mL, 3.6 mmol) in $Et_2O$ (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (46b) as an oil, that was used directly in the next step without further purification (yield assumed quantitative).

Step 3: Synthesis of 4-(((((2S,5R)-2-carbamoyl-7-oxo-1,6-diazabicyclo[3.2.1]octan-6-yl)oxy)sulfonyl)oxy)-2,2,3,3-tetramethylbutyl benzoate (46)

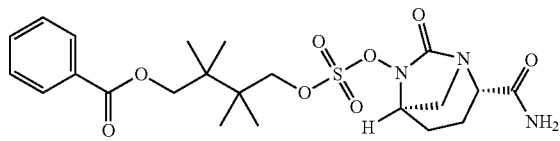 [SMILES: CC(C)(COC(=O)c1ccccc1)C(C)(C)COS(=O)(=O)ON1C(=O)N2C[C@H]1CC[C@H]2C(N)=O]

To a stirred mixture of (2S,5R)-6-hydroxy-7-oxo-1,6-diazabicyclo[3.2.1]octane-2-carboxamide (1) (0.52 g, 2.8 mmol) in THF (10 mL) under an atmosphere of argon was added several drops of 1,3-dimethyltetrahydropyrimidin-2 (1H)-one. The mixture was cooled to −78° C. and stirred for 10 min, then a solution of NaHMDS, 1.0M in THF (3.1 mL, 3.1 mmol), was added dropwise. The mixture was stirred at −78° C. for 8 min, and then 4-((chlorosulfonyl)oxy)-2,2,3,3-tetramethylbutyl benzoate (46b) (0.98 g, 2.8 mmol) in THF (5 mL) was added at −78° C. The mixture was stirred at −78° C. for 10 min, and then allowed to warm to room temperature and stirred for 1 h. The mixture was diluted with EtOAc and saturated sodium bicarbonate solution. The aqueous and organic layers were separated, and the organic layer was washed with water, dried ($Na_2SO_4$), and concentrated under vacuum. The residue was purified by column chromatography on silica gel using EtOAc/hexanes (0:1 to 1:0) as eluent to give the product (46) as a solid. LC/MS: m/z=498.10 [M+H]$^+$. $^1$H NMR (300 MHz, $CDCl_3$): δ 8.05 (d, J=7.2 Hz, 2H), 7.57 (t, J=7.4 Hz, 1H), 7.45 (t, J=7.4 Hz, 2H), 6.47 (s, 1H), 5.61 (s, 1H), 4.87 (d, J=9.0 Hz, 1H), 4.52 (d, J=9.3 Hz, 1H), 4.22-4.17 (m, 3H), 4.01 (d, J=6.3 Hz, 1H), 3.35-3.31 (m, 1H), 2.99 (d, J=14.7 Hz, 1H), 2.43-2.39 (m, 1H), 2.17-2.12 (m, 1H), 1.92-1.81 (m, 2H), 1.10-1.06 (m, 12H). $^{13}$C NMR (75 MHz, $CDCl_3$): δ 170.9, 167.1, 166.6, 133.1, 130.3, 129.7, 128.6, 82.4, 70.5, 62.0, 60.2, 47.3, 39.2, 38.8, 21.1, 21.0, 20.8, 20.5, 20.3, 17.5.

Example 47

Synthesis of 4-(((((2S,5R)-2-carbamoyl-7-oxo-1,6-diazabicyclo[3.2.1]octan-6-yl)oxy)sulfonyl)oxy)-2,2,3,3-tetramethylbutyl propionate (47)

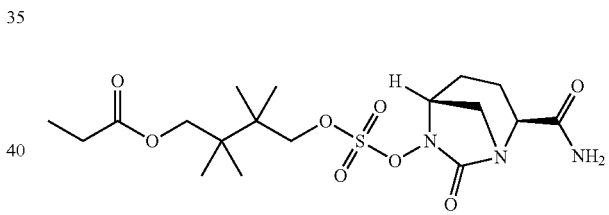

Step 1: Synthesis of 4-hydroxy-2,2,3,3-tetramethylbutyl propionate (47a)

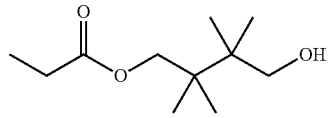

To a stirred solution of 2,2,3,3-tetramethylbutane-1,4-diol (45a) (0.59 g, 4.0 mmol) in DCM (15 mL) at 0° C. under an atmosphere of argon was added propionyl chloride (0.25 mL, 3.1 mmol), pyridine (0.33 mL, 4.0 mmol) and N,N-4-dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), and then extracted with DCM (twice). The combined organic layers were washed with sat. sodium bicarbonate and brine, then dried ($Na_2SO_4$), and concentrated under vacuum. The residue was purified by column chromatography on silica gel using EtOAc/hexanes (0:1 to 3:2) as eluent to give di-acylated material, followed by the product (47a) (300 mg) as an oil. $^1$H NMR (300 MHz, CDCl$_3$): δ 3.99 (s, 2H), 3.49 (s, 2H), 2.38-2.31 (q, 2H), 1.15 (t, J=7.8 Hz, 3H), 0.91 (d, J=4.8 Hz, 12H).

Step 2: Synthesis of 4-((chlorosulfonyl)oxy)-2,2,3,3-tetramethylbutyl propionate (47b)

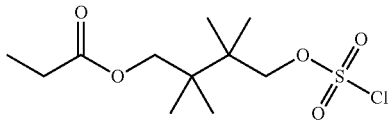 [SMILES: CCC(=O)OCC(C)(C)C(C)(C)COS(=O)(=O)Cl]

Pyridine (0.16 mL, 1.9 mmol) was added to a stirred mixture of 4-hydroxy-2,2,3,3-tetramethylbutyl propionate (47a) (0.30 g, 1.5 mmol) and Et$_2$O (10 mL) under an atmosphere of argon. The solution was cooled to −78° C. and sulfuryl chloride (0.16 mL, 1.9 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (47b) as an oil, that was used directly in the next step without further purification (yield assumed quantitative).

Step 3: Synthesis of 4-(((((2S,5R)-2-carbamoyl-7-oxo-1,6-diazabicyclo[3.2.1]octan-6-yl)oxy)sulfonyl)oxy)-2,2,3,3-tetramethylbutyl propionate (47)

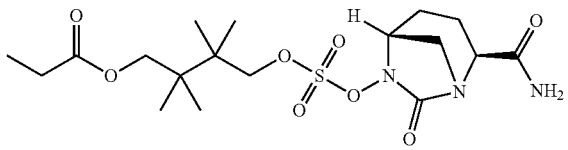 [SMILES: CCC(=O)OCC(C)(C)C(C)(C)COS(=O)(=O)ON1C(=O)N2C[C@H]1CC[C@H]2C(N)=O]

To a stirred mixture of (2S,5R)-6-hydroxy-7-oxo-1,6-diazabicyclo[3.2.1]octane-2-carboxamide 91 (271 mg, 1.5 mmol) in THF (10 mL) under an atmosphere of argon was added several drops of 1,3-dimethyltetrahydropyrimidin-2 (1H)-one. The mixture was cooled to −78° C. and stirred for 10 min, then a solution of NaHMDS, 1.0M in THF (1.6 mL, 1.6 mmol) was added dropwise. The mixture was stirred at −78° C. for 8 min, then 4-((chlorosulfonyl)oxy)-2,2,3,3-tetramethylbutyl propionate (47b) (0.44 g, 1.5 mmol) in THF (5 mL) was added at −78° C. The mixture was stirred at −78° C. for 10 min, then allowed to warm to room temperature and stirred for 1 h. The mixture was diluted with EtOAc and saturated sodium bicarbonate solution. The aqueous and organic layers were separated, and the organic layer was washed with water, dried (Na$_2$SO$_4$), and concentrated under vacuum. The residue was purified by column chromatography on silica gel using EtOAc/hexanes (0:1 to 1:0) as eluent to give the product (47) (300 mg) as a solid. LC/MS: m/z=450.09 [M+H]$^+$. $^1$H NMR (300 MHz, CDCl$_3$): δ 6.49 (s, 1H), 5.62 (s, 1H), 4.77 (d, J=8.7 Hz, 1H), 4.45 (d, J=9.3 Hz, 1H), 4.19 (s, 1H), 4.05 (d, J=6.3 Hz, 1H), 3.95 (s, 2H), 3.35 (d, J=12.0 Hz, 1H), 3.01 (d, J=12.3 Hz, 1H), 2.46-2.34 (m, 3H), 2.19-2.15 (m, 1H), 1.92-1.83 (m, 2H), 1.16 (t, J=7.7 Hz, 3H), 1.01 (d, J=9.3 Hz, 6H), 0.96 (s, 6H). $^{13}$C NMR (75 MHz, CDCl$_3$): δ 174.5, 171.0, 167.1, 82.5, 70.0, 62.0, 60.2, 47.3, 39.1, 38.4, 27.8, 21.0, 20.9, 20.8, 20.4, 20.2, 17.5, 9.3.

Example 48

Synthesis of (2S,5R)-2-carbamoyl-7-oxo-1,6-diazabicyclo[3.2.1]octan-6-yl ((3-methyl-2-oxotetrahydro-2H-pyran-3-yl)methyl) sulfate (48)

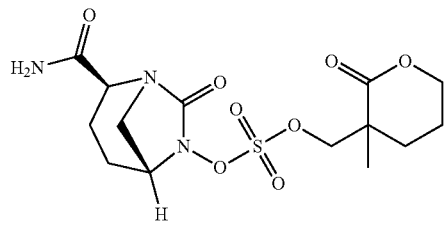 [SMILES: CC1(COS(=O)(=O)ON2C(=O)N3C[C@H]2CC[C@H]3C(N)=O)CCCOC1=O]

Step 1: Synthesis of 3-((benzyloxy)methyl)-3-methyltetrahydro-2H-pyran-2-one (48a)

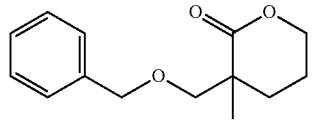 [SMILES: CC1(COCc2ccccc2)CCCOC1=O]

δ-Valerolactone (5.23 g, 52.2 mmol) was dissolved in a mixture of THF (120 mL) and HMPA (9.2 mL) under an atmosphere of argon. The reaction mixture was cooled to −78° C. and stirred for 10 min. A solution of lithium diisopropylamide, 2.0 M in THF (28.7 mL, 57.5 mmol) was added dropwise over 5 min. The reaction was stirred at −78° C. for 30 min and then neat MeI (3.3 mL, 52.8 mmol) was added to the reaction over 5 min. The mixture was stirred at −78° C. for 30 min then removed from the cooling bath and allowed to warm to 0° C. and stirred for 30 min (note: the mixture gradually became yellow during this time). The mixture was re-cooled to −78° C. and stirred for 10 min, and then an additional amount of lithium diisopropylamide, 2.0 M in THF (28.7 mL, 57.5 mmol) was added over 5 min. The reaction was stirred at −78° C. for 30 min, then neat benzyl chloromethyl ether (70%; 10.5 mL, 52.8 mmol) was added over 5 min. The mixture was left to warm to room temperature and stirred for 16 h. The solvent was then removed under vacuum and the residue was partitioned between saturated ammonium chloride (200 mL) and EtOAc (200 mL). The aqueous layer was extracted with EtOAc (2×100 mL) and the combined organic layers were washed with brine (2×100 mL), dried (Na$_2$SO$_4$), filtered, and concentrated under vacuum (19 g). The residue was dry-loaded onto silica gel and purified by column chromatography on silica gel (120 g cartridge) using EtOAc/hexanes as eluent to give the product contaminated with an impurity (6.9 g). The residue was re-purified by column chromatography on silica gel using DCM/hexanes (0:1 to 4:1) as eluent to give the product (48a) (1.76 g) as a liquid. $^1$H NMR (300 MHz, CDCl$_3$): δ 7.29-7.37 (m, 5H), 4.61 (dd, J=21.0, 12.3 Hz, 2H), 4.32-4.38 (m, 2H), 3.26-3.81 (dd, J=15.8, 8.1 Hz, 2H), 2.21-2.30 (m, 1H), 1.87-1.94 (m, 2H), 1.59-1.66 (m, 1H), 1.23 (s, 3H).

Step 2: Synthesis of 3-(hydroxymethyl)-3-methyl-tetrahydro-2H-pyran-2-one (48b)

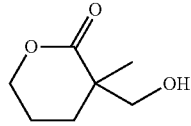

3-((Benzyloxy)methyl)-3-methyltetrahydro-2H-pyran-2-one (48a) (0.52 g, 2.2 mmol) was dissolved in 2-propanol (25 mL) and the solution was degassed and back-flushed with argon. (Note: do not use MeOH as solvent, as it may ring-open the lactone during hydrogenation). Palladium on carbon, 10% (0.26 g, 0.2 mmol), was added to the mixture and the system was sealed. The reaction was degassed and back-flushed with hydrogen (3 times) and stirred under an atmosphere of hydrogen for 2 h. The suspension was filtered through a pad of Celite®, and the filter cake washed with fresh 2-propanol (2×50 mL). The filtrate was concentrated under vacuum, and the product (48b) was used without further purification. $^1$H NMR (300 MHz, CDCl$_3$): δ 4.27-4.45 (m, 2H), 3.67 (d, J=11.4 Hz, 1H), 3.52 (d, J=11.1 Hz, 1H), 1.84-2.03 (m, 2H), 1.58-1.64 (m, 1H), 1.29 (s, 3H).

Step 3: Synthesis of (3-methyl-2-oxotetrahydro-2H-pyran-3-yl)methyl sulfochloridate (48c)

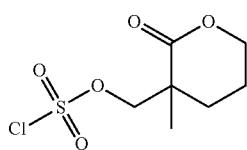

A solution of 3-(hydroxymethyl)-3-methyltetrahydro-2H-pyran-2-one (48b) (0.32 g, 2.2 mmol) and pyridine (0.21 mL, 2.6 mmol) in Et$_2$O (10 mL) was cooled to −78° C. under an atmosphere of argon. Neat sulfuryl chloride (0.21 mL, 2.6 mmol) was added dropwise to the above solution via a syringe. The mixture was stirred at −78° C. for 10 min, then the flask was warmed to room temperature and stirred for 1 h (monitored by TLC EtOAc/hexanes, 3:7). A precipitate formed to give a thick suspension. The suspension was filtered through a 0.45 μM Teflon® filter, and the filter cake rinsed with fresh Et$_2$O (2×5 mL). An aliquot (0.5 mL) was taken and concentrated, and an NMR was obtained for the mixture. The remaining solution containing the product (48c) was used directly in the next step. $^1$H NMR (300 MHz, CDCl$_3$): δ 4.87 (d, J=9.3 Hz, 1H), 4.25-4.50 (m, 2H), 4.32 (d, J=8.7 Hz, 1H), 2.00-2.20 (m, 2H), 1.75-2.00 (m, 2H), 1.39 (s, 3H).

Step 4: Synthesis of (2S,5R)-2-carbamoyl-7-oxo-1,6-diazabicyclo[3.2.1]octan-6-yl ((3-methyl-2-oxotetrahydro-2H-pyran-3-yl)methyl) sulfate (48)

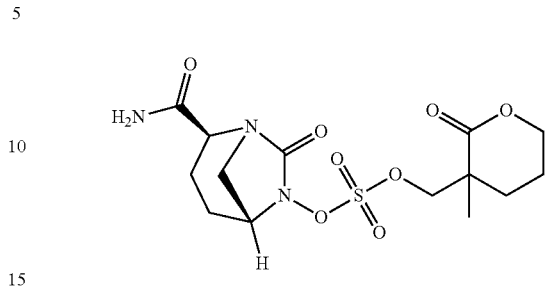

(2S,5R)-6-Hydroxy-7-oxo-1,6-diazabicyclo[3.2.1]octane-2-carboxamide (1) (0.39 g, 2.1 mmol) was dissolved in THF (18 mL) and 1,3-dimethyltetrahydropyrimidin-2(1H)-one (0.65 mL), and the resulting solution was cooled to −78° C. under an atmosphere of argon. NaHMDS, 1.0 M in THF (2.3 mL, 2.3 mmol) was added dropwise to the cooled solution and stirred for 1 h. A solution of (3-methyl-2-oxotetrahydro-2H-pyran-3-yl)methyl sulfochloridate (48c) (0.51 g, 2.1 mmol) in Et$_2$O (from the previous reaction) was added quickly to the reaction mixture. The mixture was allowed to warm to room temperature and stirred overnight. Brine (100 mL) and EtOAc (100 mL) were added to the reaction mixture and the aqueous and organic layers were separated. The aqueous layer was extracted with EtOAc (2×100 mL), and the combined organic layers were washed with brine (3×100 mL), dried (Na$_2$SO$_4$), and concentrated under vacuum. The residue was dry-loaded onto silica gel (8 g) and purified by column chromatography on silica gel using with EtOAc/hexanes (1:4 to 1:0) as eluent to give the desired product (48) (0.21 g) as a solid. LC-MS: m/z=392 [M+H]$^+$. $^1$H NMR (300 MHz, CDCl$_3$): δ 6.55 (br. d, J=9.3 Hz, 1H), 5.77 (br. s, 1H), 4.83-5.03 (m, 1H), 4.56 (m, 0.5H), 4.33-4.45 (m, 2.5H), 4.17 (m, 1H), 4.06 (m, 1H), 3.35 (d, J=9.3 Hz, 1H), 3.04 (m, 1H), 2.38-2.44 (m, 1H), 1.68-2.20 (m, 7H), 1.36 (d, J=7.2 Hz, 3H). $^{13}$C NMR (75 MHz, CDCl$_3$): δ 172.8, 172.5, 171.2, 171.0, 167.3, 167.1, 80.4, 79.9, 76.7, 70.8, 70.8, 62.0, 60.3, 60.2, 47.2, 47.1, 43.1, 43.0, 29.8, 29.6, 22.9, 22.9, 20.9 20.8, 20.17. (Note: there are several signals that are split due to chirality in the lactone product).

Example 49

Synthesis of 2-(3-(((((2S,5R)-2-carbamoyl-7-oxo-1,6-diazabicyclo[3.2.1]octan-6-yl)oxy)sulfonyl)oxy)-2,2-dimethylpropyl)phenyl acetate (49)

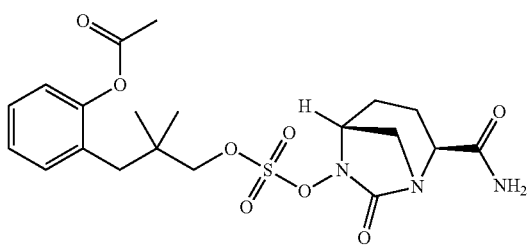 [SMILES: CC(=O)Oc1ccccc1CC(C)(C)COS(=O)(=O)ON1C(=O)N2C[C@H]1CC[C@H]2C(N)=O]

Step 1: Synthesis of ethyl 3-(2-methoxyphenyl)-2,2-dimethylpropanoate (49a)

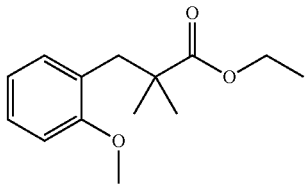 [SMILES: CCOC(=O)C(C)(C)Cc1ccccc1OC]

A stirred solution of lithium diisopropylamide, 2.0 M in THF (26.6 mL, 53.2 mmol) was diluted with THF (100 mL) was cooled to −78° C. under an atmosphere of argon, and stirred for 5 min. Neat ethyl isobutyrate (6.68 mL, 49.7 mmol) was added dropwise over 15 min, and the mixture allowed to stir at −78° C. for 1 h. A solution of 1-(bromomethyl)-2-methoxybenzene (prepared according to *J. Am. Chem. Soc.* 2013, 135, 11951) (12.0 g, 59.7 mmol) in THF (100 mL) was added dropwise over 30 min. The mixture was allowed to warm to room temperature and stirred for 20 h. The reaction was quenched with brine (100 mL) and extracted with Et$_2$O (4×100 mL). The combined organic layers were dried (MgSO$_4$), filtered, and concentrated under vacuum. The crude residue was purified by column chromatography on silica gel (120 g column) using EtOAc/hexanes (0:1 to 5:95) as eluent to give the product (49a) as a liquid (8.06 g, 68%). $^1$H NMR (300 MHz, CDCl$_3$): δ 7.18 (dt, J=1.8, 8.1 Hz, 1H), 7.06 (dd, J=1.5, 8.1 Hz, 1H), 6.82-6.87 (m, 2H), 4.12 (q, J=6.9 Hz, 2H), 3.77 (s, 3H), 2.92 (s, 2H), 1.26 (t, J=6.9 Hz, 3H), 1.15 (s, 6H).

Step 2: Synthesis of 3,3-dimethylchroman-2-one (49b)

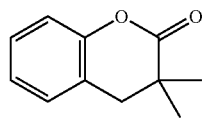

Ethyl 3-(2-methoxyphenyl)-2,2-dimethylpropanoate (49a) (8.1 g, 34.2 mmol) was dissolved in DCM (200 mL) and cooled to 0° C. under an atmosphere of argon. A solution of BBr$_3$ (3.6 mL, 37.7 mmol) in DCM (100 mL) was added dropwise to the cold solution. The mixture was warmed to room temperature and stirred overnight (a solid formed during the reaction). The colored suspension was cooled in an ice water bath and water (150 mL) was added to the mixture. The organic and aqueous layers were separated, and the aqueous layer was extracted with DCM (3×75 mL). The combined organic layers were dried (MgSO$_4$; note: the solution became darker), filtered, and concentrated under vacuum to give the product (49b) (4.85 g, 80%) as an oil. This material was used without further purification. $^1$H NMR (300 MHz, CDCl$_3$): δ 7.01-7.25 (m, 3H), 2.85 (s, 2H), 1.29 (s, 6H).

Step 3: Synthesis of 2-(3-hydroxy-2,2-dimethylpropyl)phenol (49c)

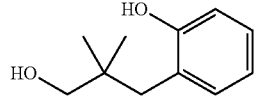

LiAlH$_4$ (1.94 g, 51.1 mmol) was suspended in Et$_2$O (52.5 mL) under an atmosphere of argon and the mixture was cooled to 0° C. in an ice water bath. A solution of 3,3-dimethylchroman-2-one (49b) (4.85 g, 27.5 mmol) in Et$_2$O (50 mL) and added dropwise to the suspension over 30 min. The mixture was warmed to room temperature and stirred for 20 h. The mixture was cooled in an ice water bath and water (2 mL), 15% aqueous sodium hydroxide (2 mL), and water (6 mL), were sequentially added by slow addition. The mixture was warmed to room temperature and stirred for 15 min. Anhydrous MgSO$_4$ was added to the suspension and the mixture stirred for 15 min. The mixture was filtered, and the filter cake washed with Et$_2$O (3×50 mL). The filtrate was concentrated under vacuum to give the product (49c) (4.34 g, 88%) as a solid. This material was used without further purification. $^1$H NMR (300 MHz, CDCl$_3$): δ 7.15 (dt, J=8.1, 1.5 Hz, 1H), 7.04 (dd, J=7.5, 1.8 Hz, 1H), 6.82-7.01 (m, 2H), 3.22 (s, 2H), 2.61 (s, 2H), 0.98 (s, 6H).

Step 4: Synthesis of 2-(3-((tert-butyldimethylsilyl)oxy)-2,2-dimethylpropyl)phenol (49d)

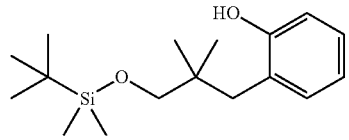 [SMILES: CC(C)(CO[Si](C)(C)C(C)(C)C)Cc1ccccc1O]

A solution of 2-(3-hydroxy-2,2-dimethylpropyl)phenol (49c) (4.0 g, 22.2 mmol) and imidazole (3.8 g, 56.0 mmol) was dissolved in DMF (50 mL) and tert-butyldimethylsilyl chloride (4.0 g, 26.6 mmol) was added to the solution and stirred for 2 h. The solvent was removed under high vacuum and the residue was purified by column chromatography on silica gel (40 g cartridge) with hexanes (5:95 to 2:3) as eluent to give the product (49d) as an oil (7.34 g, >100%). The compound was approximately 90% pure and was used directly in the next step without further purification. $^1$H NMR (300 MHz, CDCl$_3$): δ 7.11 (dt, J=7.5, 1.8 Hz, 1H), 7.10 (dd, J=7.5, 1.8 Hz, 1H), 6.90 (dd, J=8.1, 1.5 Hz, 1H), 6.79 (dt, J=6.9, 0.9 Hz, 1H), 3.17 (s, 2H), 2.57 (s, 2H), 0.97 (s, 9H), 0.92 (s, 6H), 0.13 (s, 6H).

Step 5: Synthesis of 2-(3-((tert-butyldimethylsilyl)oxy)-2,2-dimethylpropyl)phenyl acetate (49e)

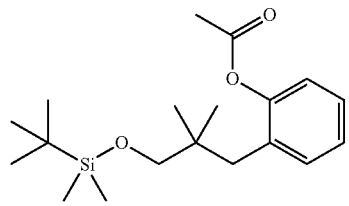 [SMILES: CC(=O)Oc1ccccc1CC(C)(C)CO[Si](C)(C)C(C)(C)C]

A solution of 2-(3-((tert-butyldimethylsilyl)oxy)-2,2-dimethylpropyl)phenol (49d) (ca. 90% purity; 2.5 g, 7.6 mmol) and Et₃N (2.3 g, 22.9 mmol) in THF (90 mL) was cooled to 0° C. in an ice bath under an atmosphere of argon. Acetyl chloride (0.65 mL, 9.2 mmol) was added dropwise to the mixture, and after complete addition the ice bath was removed. The reaction was allowed to warm to room temperature and stirred for 2 h. The suspension was filtered and the solid washed with fresh THF (2×20 mL). The filtrate was concentrated under vacuum and the residue dry-loaded onto silica gel, then purified by column chromatography on silica gel (40 g cartridge) using 0-8% EtOAc/hexanes (0:1 to 8:92) as eluent to give the product (49e) (2.16 g, 84%) as an oil. ¹H NMR (300 MHz, CDCl₃): δ 7.11-7.27 (m, 3H), 7.04 (d, J=7.5 Hz, 1H), 3.25 (s, 2H), 2.51 (s, 2H), 2.30 (s, 3H), 0.93 (s, 9H), 0.81 (s, 6H), 0.06 (s, 6H).

Step 6: Synthesis of 2-(3-hydroxy-2,2-dimethylpropyl)phenyl acetate and 3-(2-hydroxyphenyl)-2,2-dimethylpropyl acetate (49f)

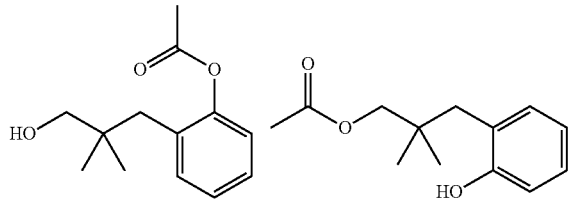

Pyridine hydrofluoride (70%, 1.3 mL, 10.4 mmol) was added to a stirred solution of 2-(3-((tert-butyldimethylsilyl)oxy)-2,2-dimethylpropyl)phenyl acetate (49e) (0.70 g, 2.1 mmol) and pyridine (2.5 mL, 31.2 mmol) in THF (25 mL) at room temperature under an atmosphere of argon, and the mixture was stirred for 24 h. The solvent was removed under vacuum (bath temperature set to 25° C.), and the residue was dissolved in EtOAc (100 mL), washed with brine (3×75 mL), dried (Na₂SO₄), filtered, and concentrated under vacuum to give a mixture of the desired alcohol and 3-(2-hydroxyphenyl)-2,2-dimethylpropyl acetate in a 65:35. NMR analysis showed the presence of both esters of the product (49f). This material was used directly in the next step without further purification. ¹H NMR (300 MHz, CDCl₃) of desired product: δ 6.8-7.26 (m, 4H), 3.79 (s, 2H), 3.27 (s, 2H), 2.62 (s, 2H), 2.53 (s, 2H), 2.33 (s, 3H), 2.13 (s, 3H), 0.974 (s, 6H), 0.90 (s, 6H).

Step 7: Synthesis of 2-(3-((chlorosulfonyl)oxy)-2,2-dimethylpropyl)phenyl acetate (49 g)

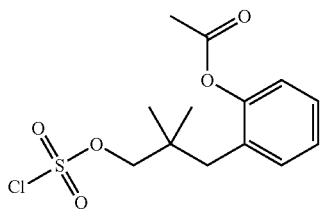 [SMILES: CC(=O)Oc1ccccc1CC(C)(C)COS(=O)(=O)Cl]

A solution of sulfuryl chloride (172 µL, 2.1 mmol) in Et₂O (6.8 mL) was cooled to −78° C. under an atmosphere of argon. A solution of 2-(3-hydroxy-2,2-dimethylpropyl)phenyl acetate (49f) (0.43 g, 1.9 mmol) and pyridine (172 µL, 2.1 mmol) in Et₂O (2.0 mL) was added dropwise to the sulfuryl chloride solution via cannula. The mixture was stirred at −78° C. for 10 min, then the flask was warmed to room temperature and stirred for 1.5 h (monitored by TLC 30% EtOAc/hexanes). The suspension was filtered through a 0.45 µm PTFE syringe filter, and the syringe filter was rinsed with fresh Et₂O (10 mL) to provide the product (49 g). The filtrate was used immediately in the next step without further purification. The yield was assumed to be quantitative.

Step 8: Synthesis of 2-(3-(((((2S,5R)-2-carbamoyl-7-oxo-1,6-diazabicyclo[3.2.1]octan-6-yl)oxy)sulfonyl)oxy)-2,2-dimethylpropyl)phenyl acetate (49)

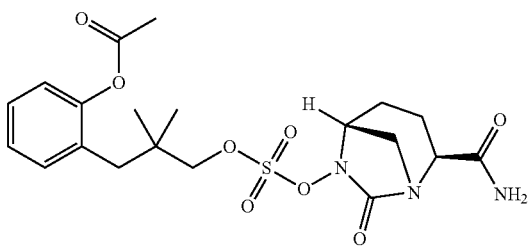 [SMILES: CC(=O)Oc1ccccc1CC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.44 g, 2.4 mmol) was dissolved in THF (22 mL) and 1,3-dimethyltetrahydropyrimidin-2(1H)-one (0.8 mL), and the resulting solution was cooled to −78° C. under an atmosphere of argon. A solution of NaHMDS, 1.0 M in THF (2.1 mL, 2.1 mmol) was added dropwise to the cooled solution and stirred for 10 min. A solution of 2-(3-((chlorosulfonyl)oxy)-2,2-dimethylpropyl)phenyl acetate (49 g) (0.62 g, 1.9 mmol) in Et₂O from the previous reaction was quickly added to the reaction mixture. After 10 min, the reaction mixture was warmed to room temperature and stirred overnight. Brine (100 mL) was added to the reaction mixture and the aqueous and organic layers were separated. The aqueous layer was extracted with EtOAc (2×200 mL) and the combined organic layers were washed with brine (3×75 mL), dried (Na₂SO₄), filtered, and concentrated under vacuum. The residue was dissolved in DMF (6 mL) and filtered through a 0.45 µm frit, and then purified by preparative HPLC with 20-90% MeCN/water (no modifier) as eluent to give the product (49) (0.18 g, 20%) as a solid. LC-MS: m/z=470 [M+H]⁺. ¹H NMR (300 MHz, CDCl₃): δ 7.23-7.29 (m, 1H), 7.18-7.20 (m, 2H), 7.08 (d, J=7.5 Hz, 1H), 6.52 (br. s, 1H), 5.78 (br. s, 1H), 4.55 (d, J=7.5 Hz, 1H), 4.19-4.22 (m, 2H), 4.05 (br. d, J=7.2 Hz, 1H), 3.30 (br. d, J=11.7 Hz, 1H), 2.99 (d, J=11.7 Hz, 1H), 2.51-2.62 (m, 2H), 2.39-2.44 (m, 1H), 2.34 (s, 3H), 2.10-2.19 (m, 1H), 1.84-2.00 (m, 2H), 0.98 (d, J=3.0 Hz, 6H). ¹³C NMR (75 MHz, CDCl₃): δ 171.1, 169.6, 167.1, 149.6, 132.8, 129.1, 128.0, 125.8, 122.7, 83.4, 62.0, 60.3, 47.2, 38.1, 36.3, 23.7, 21.3, 20.8, 17.6.

177

Example 50

Synthesis of 2-(3-(((((2S,5R)-2-carbamoyl-7-oxo-1,6-diazabicyclo[3.2.1]octan-6-yl)oxy)sulfonyl)oxy)-2,2-dimethylpropyl)phenyl pivalate (50)

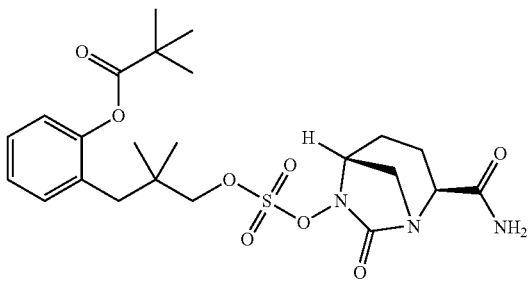 [SMILES: CC(C)(COS(=O)(=O)ON1C(=O)N2C[C@H]1CC[C@H]2C(N)=O)Cc1ccccc1OC(=O)C(C)(C)C]

Step 1: Synthesis of 2-(3-((tert-butyldimethylsilyl)oxy)-2,2-dimethylpropyl)phenyl pivalate (50a)

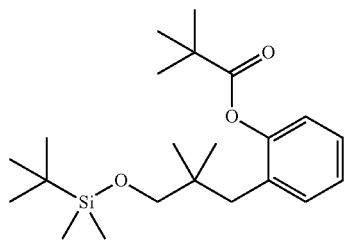 [SMILES: CC(C)(CO[Si](C)(C)C(C)(C)C)Cc1ccccc1OC(=O)C(C)(C)C]

2-(3-((tert-Butyldimethylsilyl)oxy)-2,2-dimethylpropyl)phenol (0.9 g, 3.1 mmol) and N,N-4-dimethylaminopyridine (0.93 g, 7.6 mmol) were dissolved in THF (50 mL) under an atmosphere of argon. Trimethylacetyl chloride (0.45 mL, 3.7 mmol) was added dropwise to the mixture at room temperature to immediately form a white solid, and the addition was continued until a suspension was formed. The reaction was stirred at room temperature for 2 h, and then filtered and the filter cake washed with THF (10 mL). The filtrate was dry-loaded on to silica gel (15 g) and purified by column chromatography on silica gel using EtOAc/hexanes (0:1 to 6:94) as eluent to give the product (50a) contaminated with ca. 3% of starting material by NMR analysis. This material was used without further purification. $^1$H NMR (300 MHz, CDCl$_3$): δ 7.27 (dd, J=7.2, 2.1 Hz, 1H), 7.21 (dt, J=7.5, 1.8 Hz, 1H), 7.15 (dt, J=7.8, 1.8 Hz, 1H), 6.97 (dd, J=8.1, 1.8 Hz, 1H), 3.25 (s, 2H), 2.49 (s, 2H), 1.38 (s, 9H), 0.92 (s, 9H), 0.82 (s, 6H), 0.05 (s 6H).

Step 2: Synthesis of 2-(3-hydroxy-2,2-dimethylpropyl)phenyl pivalate (50b)

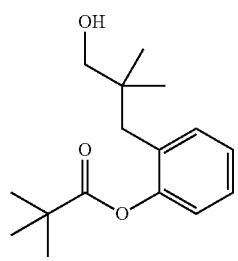 [SMILES: CC(C)(CO)Cc1ccccc1OC(=O)C(C)(C)C]

178

Pyridine hydrofluoride (70%, 1.3 mL, 10.4 mmol) was added to a stirred solution of 2-(3-((tert-butyldimethylsilyl)oxy)-2,2-dimethylpropyl)phenyl pivalate (50a) (0.70 g, 1.8 mmol) and pyridine (2.5 mL, 31.2 mmol) in THF (25 mL) at room temperature under an atmosphere of argon, and the mixture was stirred for 24 h. The solvent was removed under vacuum (bath temperature set to 25° C.), and the residue was dissolved in EtOAc (100 mL) and washed with brine (3×75 mL), dried (Na$_2$SO$_4$), filtered, and concentrated under vacuum to give the desired product (50b) as an oil. This material was used directly in the next step without further purification. $^1$H NMR (300 MHz, CDCl$_3$): δ 7.12-7.26 (m, 3H), 6.98 (m, 1H), 3.31 (s, 2H), 2.51 (s, 2H), 1.39 (s, 9H), 0.89 (s, 9H).

Step 3: Synthesis of 2-(3-((chlorosulfonyl)oxy)-2,2-dimethylpropyl)phenyl pivalate (50c)

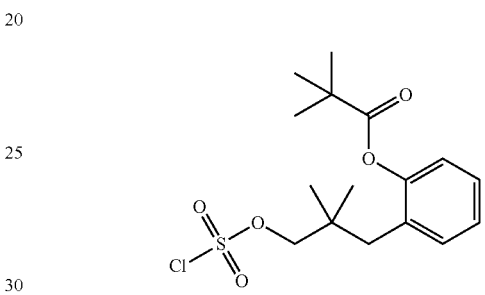

A solution of sulfuryl chloride (173 µL, 2.1 mmol) in Et$_2$O (7.5 mL) was cooled to −78° C. under an argon atmosphere. A solution of 2-(3-hydroxy-2,2-dimethylpropyl)phenyl pivalate (50b) (0.47 g, 1.8 mmol) and pyridine (173 µL, 2.1 mmol) in Et$_2$O (2.2 mL) was added dropwise to the sulfuryl chloride solution via cannula. The mixture was stirred at −78° C. for 10 min, and then the flask was warmed to room temperature and stirred for 1.5 h (monitored by TLC 30% EtOAc/hexanes). The suspension was filtered through a 0.45-µm PTFE syringe filter, and the syringe filter was rinsed with fresh Et$_2$O to provide the product (50c). The filtrate was used immediately in the next step without further purification. The yield was assumed to be quantitative.

Step 4: Synthesis of 2-(3-(((((2S,5R)-2-carbamoyl-7-oxo-1,6-diazabicyclo[3.2.1]octan-6-yl)oxy)sulfonyl)oxy)-2,2-dimethylpropyl)phenyl pivalate (50)

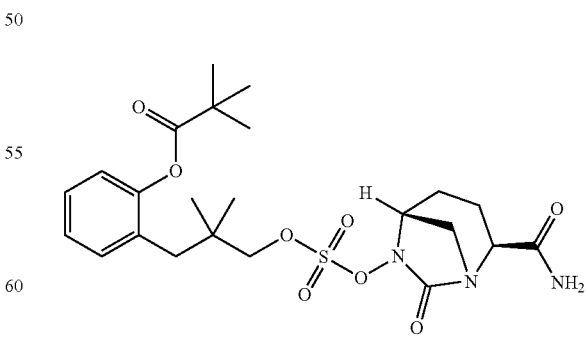

(2S,5R)-6-Hydroxy-7-oxo-1,6-diazabicyclo[3.2.1]octane-2-carboxamide (1) (0.41 g, 2.2 mmol) was dissolved in THF (23 mL) and 1,3-dimethyltetrahydropyrimidin-2(1H)-one (0.8 mL), and the resulting solution was cooled to −78°

C. under an atmosphere of argon. A solution of NaHMDS, 1.0 M in THF (2.2 mL, 2.2 mmol) was added dropwise to the cooled solution and the solution stirred for 10 min. A solution of 2-(3-((chlorosulfonyl)oxy)-2,2-dimethylpropyl)phenyl pivalate (50c) (0.65 g, 1.8 mmol) in Et$_2$O from the previous reaction was added quickly to the reaction mixture. After 10 min, the reaction mixture was warmed to room temperature and stirred overnight. Brine (100 mL) was added to the reaction mixture and the aqueous and organic layers were separated. The aqueous layer was extracted with EtOAc (2×200 mL) and the combined organic layers were washed with brine (3×75 mL), dried (Na$_2$SO$_4$), filtered, and concentrated under vacuum. The residue was dissolved in DMF (6 mL) and filtered through a 0.45-μm frit, and then purified by preparative HPLC to give the product (50) (0.21 g, 23%) as a solid. LC-MS: m/z=512 [M+H]$^+$. $^1$H NMR (300 MHz, CDCl$_3$): δ 7.12-7.28 (m, 3H), 6.99 (d, J=7.5 Hz, 1H), 6.50 (br. s, 1H), 5.78 (br. s, 1H), 4.57 (d, J=9.3 Hz, 1H), 4.26 (d, J=8.7 Hz, 1H), 4.17 (br. s, 1H), 4.04 (d, J=6.3 Hz, 1H), 3.28 (br. d, J=11.7 Hz, 1H), 3.03 (d, J=11.7 Hz, 1H), 2.52-2.62 (m, 2H), 2.39-2.50 (m, 1H), 2.10-2.20 (m, 1H), 1.78-1.98 (m, 2H), 1.38 (s, 9H), 0.97 (d, J=4.2 Hz, 6H). $^{13}$C NMR (75 MHz, CDCl$_3$): δ 177.2, 171.1, 167.0, 150.1, 132.5, 129.2, 127.9, 125.6, 122.6, 83.7, 61.9, 60.2, 47.2, 39.3, 37.5, 36.2, 27.4, 23.5, 20.8, 17.6.

Example 51

Synthesis of S-(4-(((((2S,5R)-2-carbamoyl-7-oxo-1,6-diazabicyclo[3.2.1]octan-6-yl)oxy)sulfonyl)oxy)-3,3-dimethylbutyl) ethanethioate (51)

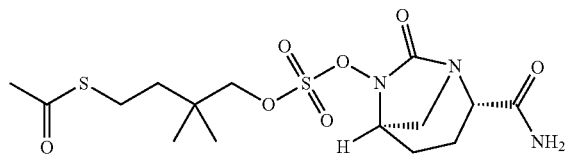 [SMILES: CC(=O)SCCC(C)(C)COS(=O)(=O)ON1C(=O)N2C[C@H]1CC[C@H]2C(N)=O]

Step 1: Synthesis of S-(4-((chlorosulfonyl)oxy)-3,3-dimethylbutyl) ethanethioate (51a)

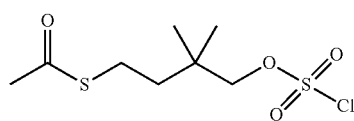

A solution of freshly distilled sulfuryl chloride (271 μL, 3.7 mmol) in Et$_2$O (5 mL) was cooled to −78° C. under an atmosphere of argon. A solution of S-(4-hydroxy-3,3-dimethylbutyl) ethanethioate (prepared according to *Chem. Commun.* 2011, 47, 2038) (500 mg, 2.8 mmol) and pyridine (267 μL, 3.3 mmol) in Et$_2$O (3 mL) was added dropwise to the sulfuryl chloride solution over the course of 5 min. The flask was rinsed with diethyl ether (2×5 mL) and the rinse was also added to the reaction mixture. The mixture was stirred at −78° C. for 1 h and allowed to warm to room temperature and stirred at room temperature for another 20 min. The precipitate was filtered (quickly) and the filter cake rinsed with Et$_2$O (12 mL). The filtrate was concentrated under vacuum at room temperature to afford the title compound (51a) as an oil which was used immediately for the next step without further purification.

Step 2: Synthesis of S-(4-(((((2S,5R)-2-carbamoyl-7-oxo-1,6-diazabicyclo[3.2.1]octan-6-yl)oxy)sulfonyl)oxy)-3,3-dimethylbutyl) ethanethioate (51)

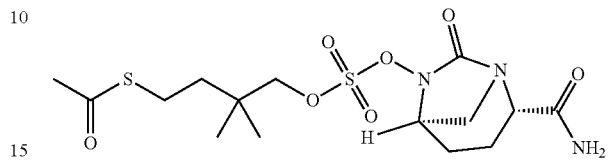

(2S,5R)-6-Hydroxy-7-oxo-1,6-diazabicyclo[3.2.1]octane-2-carboxamide (1) (430 mg, 2.3 mmol) was dissolved in pyridine (8 mL) and cooled to 0° C. under an atmosphere of argon. A solution of S-(4-((chlorosulfonyl)oxy)-3,3-dimethylbutyl) ethanethioate (51a) (0.75 g, 2.7 mmol) in THF (4 mL) was added to the reaction mixture at 0° C. The resulting mixture was stirred for 1 h and the solvents were removed under high vacuum at room temperature. The residue was purified by column chromatography on silica gel using EtOAc/hexanes (0:1 to 9:1) as eluent to afford the product (50) as a solid. LCMS: m/z=424.2 [M+1]+. $^1$H NMR (300 MHz, CDCl$_3$): δ 6.47 (br. s, 1H), 5.61 (br. s, 1H), 4.53 (d, J=8.7 Hz, 1H), 4.24 (d, J=9.0 Hz, 1H), 4.17 (br. s, 1H), 4.05-4.03 (m, 1H), 3.39-3.30 (m, 1H), 3.01 (d, J=9.0 Hz, 1H), 2.85-2.80 (m, 2H), 2.48-2.40 (m, 1H), 2.32 (s, 3H), 2.20-2.18 (m, 1H), 2.01-1.80 (m, 2H), 1.03 (s, 6H). $^{13}$C NMR (75 MHz, CDCl$_3$): δ 195.4, 170.9, 166.9, 83.1, 61.8, 60.0, 47.1, 38.4, 34.8, 30.5, 23.9, 23.4, 23.2, 20.6, 17.4.

Example 52

Synthesis of S-(5-(((((2S,5R)-2-carbamoyl-7-oxo-1,6-diazabicyclo[3.2.1]octan-6-yl)oxy)sulfonyl)oxy)-4,4-dimethylpentyl) ethanethioate (52)

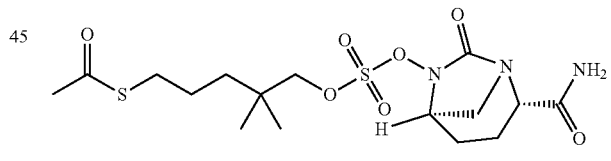

Step 1: Synthesis of 5-bromo-2,2-dimethylpentan-1-ol (52a)

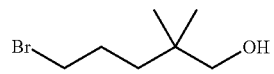

DCM (18 mL) was added to LiBH$_4$ (0.66 g, 30.4 mmol) followed by dropwise addition of anhydrous MeOH (1.2 ml, 30.4 mmol) over 20 min under an atmosphere of argon. After the H$_2$ effervescence had ceased, a solution of ethyl 5-bromo-2,2-dimethylpentanoate (prepared according to PCT Application Publication No. 2011046771) (4.5 g, 19.0 mmol) in DCM (10 mL) was added dropwise over 20 min.

The reaction mixture was heated to reflux for 16 h, cooled to room temperature, and carefully hydrolyzed with a saturated NH$_4$Cl solution (30 mL). The suspension was extracted with DCM (3×50 mL). The combined organic layers were washed with 1N HCl (26 mL) and brine (40 mL), dried, and concentrated under vacuum to give the product (52a) (3.61 g, 97%) as an oil. $^1$H NMR (300 MHz, CDCl$_3$): δ 3.39 (t, J=6.9 Hz, 2H), 3.24 (s, 2H), 1.90-1.76 (m, 2H), 1.48 (br. s, 1H), 1.41-1.36 (m, 2H), 0.88 (s, 6H).

Step 2: Synthesis of
S-(5-hydroxy-4,4-dimethylpentyl) ethanethioate
(52b)

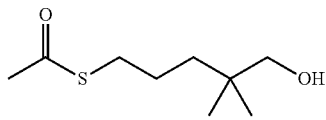

A solution of 5-bromo-2,2-dimethylpentan-1-ol (52a) (2.0 g, 10.3 mmol) and potassium thioacetate (2.34 g, 20.5 mmol) in acetone (22 mL) was stirred under an inert atmosphere at room temperature for 23 h. After removing the solvents under vacuum at room temperature, the residue was purified by column chromatography on silica gel column using EtOAc/hexanes (0:1 to 2:3) as eluent to give the product (52b) (1.2 g, 61%) as an oil. $^1$H NMR (300 MHz, CDCl$_3$): δ 3.31 (s, 2H), 2.85 (t, J=7.8 Hz, 2H), 2.32 (s, 3H), 1.62-1.48 (m, 2H), 1.32-1.21 (m, 2H), 0.86 (s, 6H).

Step 3: Synthesis of S-(5-((chlorosulfonyl)oxy)-4,4-dimethylpentyl) ethanethioate (52c)

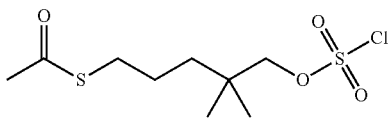 [SMILES: CC(=O)SCCCC(C)(C)COS(=O)(=O)Cl]

A solution of freshly distilled sulfuryl chloride (379 μL, 5.2 mmol) in Et$_2$O (8 mL) was cooled to −78° C. under an atmosphere of argon. A solution of S-(5-hydroxy-4,4-dimethylpentyl) ethanethioate (52b) (700 mg, 3.6 mmol) and pyridine (374 μL, 4.6 mmol) in Et$_2$O (4 mL) was added dropwise to the sulfuryl chloride solution over the course of 5 min. The mixture was stirred at −78° C. for 1 h, and then allowed to warm to room temperature. The precipitate was filtered (quickly) and the filter cake rinsed with Et$_2$O (10 mL). The filtrate was concentrated under vacuum at room temperature to afford the title compound (52c) as an oil which was used immediately for the next step without further purification.

Step 4: Synthesis of S-(5-(((((2S,5R)-2-carbamoyl-7-oxo-1,6-diazabicyclo[3.2.1]octan-6-yl)oxy)sulfonyl)oxy)-4,4-dimethylpentyl) ethanethioate (52)

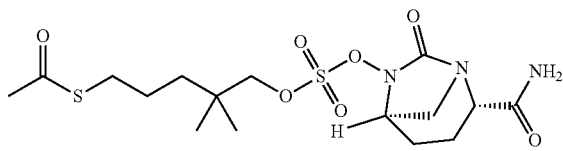 [SMILES: CC(=O)SCCCC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (600 mg, 3.2 mmol) was dissolved in pyridine (9 mL) and cooled to 0° C. under an atmosphere of argon. A solution of S-(5-((chlorosulfonyl)oxy)-4,4-dimethylpentyl) ethanethioate (52c) (857 mg, 3.0 mmol) in THF (5 mL) was added to the reaction mixture at 0° C. The resulting mixture was stirred for 1 h and the solvents were removed under high vacuum at room temperature. The residue was purified by column chromatography on silica gel using EtOAc/hexanes (0:1 to 9:1) as eluent to afford the product (52) (70 mg, 5%) as a solid. LC-MS: m/z=438.2 [MH]$^+$. $^1$H NMR (300 MHz, CDCl$_3$): δ 6.48 (br. s, 1H), 5.56 (br. s, 1H), 4.49 (d, J=9.0 Hz, 1H), 4.19 (d, J=9.6 Hz, 1H), 4.17 (br. s, 1H), 4.05-4.03 (m, 1H), 3.38-3.30 (m, 1H), 3.01 (d, J=9.0 Hz, 1H), 2.85 (t, J=6.9 Hz, 2H), 2.46-2.40 (m, 1H), 2.32 (s, 3H), 2.21-2.18 (m, 1H), 1.98-1.82 (m, 2H), 1.40-1.33 (m, 2H), 0.97 (s, 3H), 0.96 (s, 3H). $^{13}$C NMR (75 MHz, CDCl$_3$): δ 175.7, 170.8, 166.9, 83.6, 61.8, 60.0, 47.1, 37.4, 34.3, 30.6, 29.4, 23.9, 23.6, 23.4, 20.6, 17.4.

Example 53

Synthesis of S-(3-(((((2S,5R)-2-carbamoyl-7-oxo-1,6-diazabicyclo[3.2.1]octan-6-yl)oxy)sulfonyl)oxy)-2,2-dimethylpropyl) ethanethioate (53)

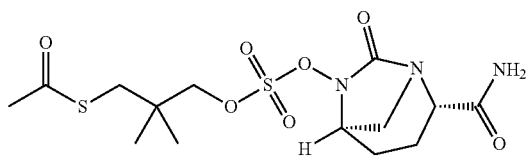 [SMILES: CC(=O)SCC(C)(C)COS(=O)(=O)ON1C(=O)N2C[C@H]1CC[C@H]2C(N)=O]

Step 1: Synthesis of
S-(3-hydroxy-2,2-dimethylpropyl) ethanethioate
(53a)

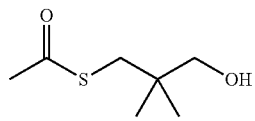

Potassium thioacetate (4.1 g, 35.8 mmol) was dissolved in DMF (20 mL) under an atmosphere of argon. 3-Hydroxy-2,2-dimethylpropyl 4-methylbenzenesulfonate (prepared according to PCT Application Publication No. 2012165648) (4.2 g, 16.3 mmol) was added, and the mixture was stirred at 80° C. for 2.5 h. After cooling, brine (100 mL) was added, and the mixture was extracted with Et$_2$O (3×100 mL). The combined organic layers were washed with brine (5×50 mL), dried (Na$_2$SO$_4$), filtered, and concentrated under vacuum (residual DMF was removed by high vacuum). The residue was purified by column chromatography on silica gel using EtOAc/hexanes (0:1 to 15:85) as eluent to provide the product (53a) (1.06 g, 40%) as an oil. $^1$H NMR (300 MHz, CDCl$_3$): δ 3.23 (br. s, 2H), 2.89 (s, 2H), 2.62 (br. s, 1H), 2.37 (s, 3H), 0.94 (s, 6H).

Step 2: Synthesis of S-(3-((chlorosulfonyl)oxy)-2,2-dimethylpropyl) ethanethioate (53b)

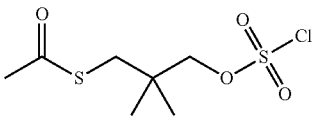

A solution of freshly distilled sulfuryl chloride (283 μL, 3.9 mmol) in Et$_2$O (4 mL) was cooled to −78° C. under an argon atmosphere. A solution of S-(3-hydroxy-2,2-dimethylpropyl) ethanethioate (53a) (520 mg, 3.1 mmol) and pyridine (327 μL, 4.0 mmol) in Et$_2$O (6 mL) was added dropwise to the sulfuryl chloride solution over the course of 5 min. The mixture was stirred at −78° C. for 1 h, then allowed to warm to room temperature. The precipitate was filtered (quickly) and the filter cake rinsed with Et$_2$O (10 mL). The filtrate was concentrated under vacuum at room temperature to afford the title compound (53b) as an oil which was used immediately for the next step without further purification.

Step 3: Synthesis of S-(3-(((((2S,5R)-2-carbamoyl-7-oxo-1,6-diazabicyclo[3.2.1]octan-6-yl)oxy)sulfonyl)oxy)-2,2-dimethylpropyl) ethanethioate (53)

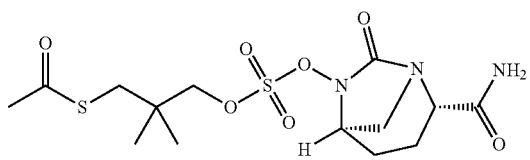 [SMILES: CC(=O)SCC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (600 mg, 3.2 mmol) was dissolved in pyridine (10 mL) and cooled to 0° C. under an atmosphere of argon. A solution of S-(5-((chlorosulfonyl)oxy)-4,4-dimethylpentyl) ethanethioate (53b) (800 mg, 3.1 mmol) in THF (6 mL) was added to the reaction mixture at 0° C. The resulting mixture was stirred for 2 h and the solvents were removed under high vacuum at room temperature. The residue was purified by column chromatography on silica gel using EtOAc/hexanes (0:1 to 7:3) as eluent to afford the product (53) (90 mg, 7%) as a solid. LCMS: m/z=410.1 [M+H]$^+$. $^1$H NMR (300 MHz, CDCl$_3$): δ 6.47 (br. s, 1H), 5.56 (br. s, 1H), 4.51 (d, J=9.3 Hz, 1H), 4.25 (d, J=9.6 Hz, 1H), 4.17 (br. s, 1H), 4.06-4.03 (m, 1H), 3.36-3.24 (m, 1H), 3.06-2.88 (m, 2H), 2.51-2.41 (m, 1H), 2.36 (s, 3H), 2.21-2.08 (m, 1H), 1.98-1.82 (m, 2H), 1.36-1.22 (m, 1H), 1.04 (s, 3H), 1.02 (s, 3H). $^{13}$C NMR (75 MHz, CDCl$_3$): δ 194.7, 170.8, 166.9, 81.9, 61.8, 60.1, 47.1, 36.7, 35.6, 30.6, 23.2, 22.9, 20.6, 17.4.

Example 54

Synthesis of 3-(((((2S,5R)-2-carbamoyl-7-oxo-1,6-diazabicyclo[3.2.1]octan-6-yl)oxy)sulfonyl)oxy)-2,2-dimethylpropyl 2,6-dimethylbenzoate (54)

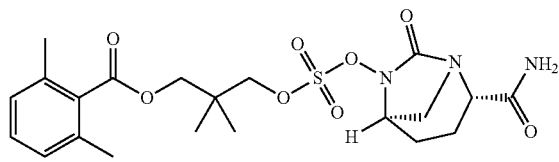 [SMILES: Cc1cccc(C)c1C(=O)OCC(C)(C)COS(=O)(=O)ON1C(=O)N2C[C@H]1CC[C@H]2C(N)=O]

Step 1: Synthesis of 3-hydroxy-2,2-dimethylpropyl 2,6-dimethylbenzoate (54a)

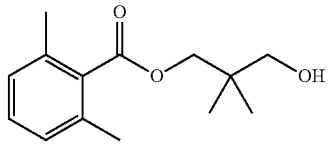 [SMILES: Cc1cccc(C)c1C(=O)OCC(C)(C)CO]

To a stirred solution of 2,2-dimethylpropane-1,3-diol (2.5 g, 24.3 mmol) in DCM (60 mL) at ca. 0° C. (ice bath) under an atmosphere of argon, was added 2,6-dimethylbenzoyl chloride (1.2 mL, 8.1 mmol), pyridine (1.1 mL, 13.7 mmol), and N,N-4-dimethylaminopyridine (99 mg, 0.8 mmol). The reaction mixture was allowed to gradually warm to room temperature and the mixture was stirred overnight. The reaction was quenched by the addition of 1N HCl, and the mixture was extracted with DCM (twice). The combined organic extracts were washed with a saturated aqueous solution of NaHCO$_3$ and brine, dried (MgSO$_4$), filtered and concentrated under vacuum. The residue was purified by column chromatography on silica gel using EtOAc/hexanes (1:9 to 2:3) as eluent to give the product (54a) (1.5 g, 78%) as an oil. $^1$H NMR (300 MHz, CDCl$_3$): δ 7.21 (m, 1H), 7.04 (m, 2H), 4.18 (s, 2H), 3.41 (s, 2H), 2.32 (s, 6H), 2.20 (br. s, 1H), 0.99 (s, 6H).

Step 2: Synthesis of 3-((chlorosulfonyl)oxy)-2,2-dimethylpropyl 2,6-dimethylbenzoate (54b)

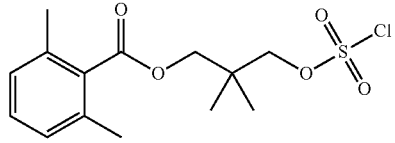 [SMILES: Cc1cccc(C)c1C(=O)OCC(C)(C)COS(=O)(=O)Cl]

A solution of freshly distilled sulfuryl chloride (0.25 mL, 3.9 mmol) in Et$_2$O (6 mL) was cooled to −78° C. under an argon atmosphere. A solution of 3-hydroxy-2,2-dimethylpropyl 2,6-dimethylbenzoate (54a) (500 mg, 2.1 mmol) and pyridine (0.26 mL, 3.3 mmol) in Et$_2$O (6 mL) was added dropwise to the sulfuryl chloride solution over the course of 5 min. The mixture was stirred at −78° C. for 1 h, and then allowed to warm to room temperature. The precipitate was filtered (quickly) and the filter cake rinsed with Et$_2$O (12 mL). The filtrate was concentrated under vacuum at room temperature to afford the title compound (54b) as an oil, which was used immediately in the next step without further purification.

Step 3: Synthesis of 3-(((((2S,5R)-2-carbamoyl-7-oxo-1,6-diazabicyclo[3.2.1]octan-6-yl)oxy)sulfonyl)oxy)-2,2-dimethylpropyl 2,6-dimethylbenzoate (54)

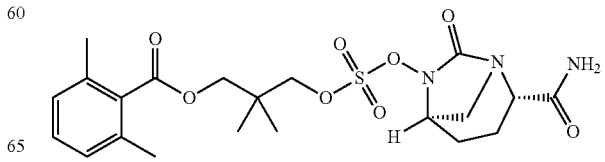

(2S,5R)-6-Hydroxy-7-oxo-1,6-diazabicyclo[3.2.1]octane-2-carboxamide (1) (420 mg, 2.3 mmol) was dissolved in THF (12 mL) and 1,3-dimethyltetrahydropyrimidin-2(1H)-one (0.7 mL), and the resulting solution was cooled to −78° C. under an argon atmosphere. A solution of NaHMDS, 1.0 M in THF (2.3 mL, 2.3 mmol) was added dropwise to the cooled solution and stirred for 10 min. A solution of 3-((chlorosulfonyl)oxy)-2,2-dimethylpropyl 2,6-dimethylbenzoate (54b) (660 mg, 2.0 mmol) in THF (8 mL) was added quickly to the reaction mixture. After stirring at −78° C. for 10 min, the mixture was allowed to warm to room temperature and stirred for 2 h. EtOAc (400 mL), and saturated aqueous NaHCO$_3$ (40 mL) and water (40 mL) were added. The organic layer was separated and washed with saturated aqueous NaHCO$_3$ (60 mL), H$_2$O (3×50 mL), brine (60 mL), and then dried (Na$_2$SO$_4$), and concentrated under vacuum. The residue was purified by column chromatography on silica gel using EtOAc/hexanes (0:1 to 7:3) as eluent to give the product (180 mg, 19%) as a solid. LC-MS: m/z=484.01 [M+H]$^+$. $^1$HNMR (300 MHz, CDCl$_3$): δ 7.19 (m, 1H), 7.04 (m, 2H), 6.47 (s, 1H), 5.55 (s, 1H), 4.58 (d, J=9.3 Hz, 1H), 4.39 (d, J=9.0 Hz, 1H), 4.22 (d, J=11.1 Hz, 1H), 4.16 (m, 1H), 4.11 (d, J=11.1 Hz, 1H), 4.04-4.02 (m, 1H), 3.33-3.29 (m, 1H), 3.01-2.98 (m, 1H), 2.45-2.40 (m, 1H), 2.32 (s, 6H), 2.20-2.08 (m, 1H), 1.93-1.76 (m, 2H), 1.10 (s, 6H). $^{13}$C NMR (75 MHz, CDCl$_3$): δ 170.8, 169.9, 166.9, 134.9, 133.6, 129.4, 127.5, 80.2, 69.1, 61.8, 60.1, 47.1, 35.2, 21.4, 21.3, 20.7, 19.8, 17.4.

Example 55

Synthesis of 3-(((((2S,5R)-2-carbamoyl-7-oxo-1,6-diazabicyclo[3.2.1]octan-6-yl)oxy)sulfonyl)oxy)-2,2-dimethylpropyl adamantane-1-carboxylate (55)

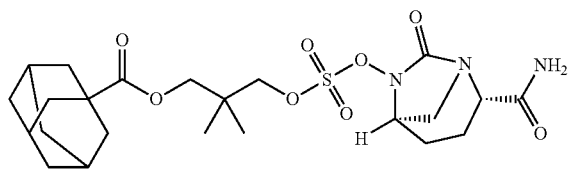 [SMILES: CC(C)(COC(=O)C12CC3CC(CC(C3)C1)C2)COS(=O)(=O)ON1C(=O)N2C[C@H]1CC[C@H]2C(N)=O]

Step 1: Synthesis of 3-hydroxy-2,2-dimethylpropyl (3r,5r,7r)-adamantane-1-carboxylate (55a)

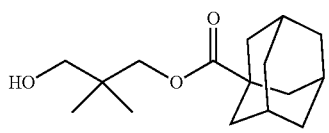 [SMILES: CC(C)(CO)COC(=O)C12CC3CC(CC(C3)C1)C2]

To a stirred solution of 2,2-dimethylpropane-1,3-diol (2.5 g, 24.3 mmol) in DCM (60 mL) at ca. 0° C. (ice bath) under an argon atmosphere, was added 1-adamantane-carbonyl chloride (1.36 g, 6.9 mmol), pyridine (1.1 mL, 13.7 mmol), and N,N-4-dimethylaminopyridine (99 mg, 0.8 mmol). The reaction mixture was allowed to gradually warm to room temperature and the mixture was stirred overnight. The reaction was quenched by the addition of 1N HCl, and the mixture was extracted with DCM (twice). The combined organic extracts were washed with a saturated aqueous solution of NaHCO$_3$ and brine, dried (MgSO$_4$), filtered, and concentrated under vacuum to give the product (55a) (1.82 g, 100%) as an oil. $^1$H NMR (300 MHz, CDCl$_3$): δ 3.91 (s, 2H), 3.25 (s, 2H), 2.01 (br. s, 3H), 1.89 (br. s, 6H), 1.71 (br. s, 7H), 0.91 (s, 6H).

Step 2: Synthesis of 3-((chlorosulfonyl)oxy)-2,2-dimethylpropyl (3r,5r,7r)-adamantane-1-carboxylate (55b)

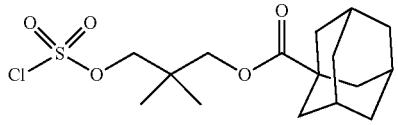 [SMILES: CC(C)(COC(=O)C12CC3CC(CC(C3)C1)C2)COS(=O)(=O)Cl]

A solution of freshly distilled sulfuryl chloride (266 μL, 3.3 mmol) in Et$_2$O (4 mL) was cooled to −78° C. under an argon atmosphere. A solution of 3-hydroxy-2,2-dimethyl-propyl-adamantane-1-carboxylate (55a) (600 mg, 2.2 mmol) and pyridine (0.28 mL, 3.5 mmol) in Et$_2$O (4 mL) was added dropwise to the sulfuryl chloride solution over the course of 5 min. The flask was rinsed with Et$_2$O (5 mL), and the rinse was also added to the reaction mixture. The mixture was stirred at −78° C. for 1 h, and then allowed to warm to room temperature. The precipitate was filtered (quickly) and the filter cake rinsed with Et$_2$O (12 mL). The filtrate was concentrated under vacuum at room temperature to afford the title compound (55b) as an oil, which was used immediately in the next step without further purification.

Step 3: Synthesis of 3-(((((2S,5R)-2-carbamoyl-7-oxo-1,6-diazabicyclo[3.2.1]octan-6-yl)oxy)sulfonyl)oxy)-2,2-dimethylpropyl adamantane-1-carboxylate (55)

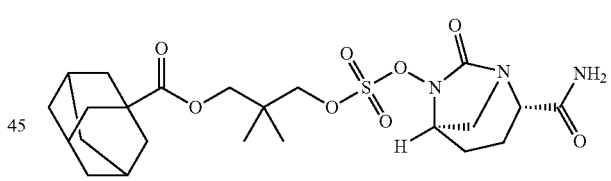

(2S,5R)-6-Hydroxy-7-oxo-1,6-diazabicyclo[3.2.1]octane-2-carboxamide (1) (442 mg, 2.4 mmol) was dissolved in THF (14 mL) and 1,3-dimethyltetrahydropyrimidin-2(1H)-one (0.8 mL), and the resulting solution was cooled to −78° C. under an argon atmosphere. A solution of NaHMDS, 1.0 M in THF (2.6 mL, 2.6 mmol) was added dropwise to the cooled solution and stirred for 10 min. A solution of 3-((chlorosulfonyl)oxy)-2,2-dimethylpropyl-adamantane-1-carboxylate (55b) (750 mg, 2.1 mmol) in THF (8 mL) was quickly added to the reaction mixture. After stirring at −78° C. for 10 min, the mixture was allowed to warm to room temperature and stirred for 2 h. EtOAc (400 mL) and saturated aqueous NaHCO$_3$ (40 mL) and H$_2$O (40 mL) were added. The organic layer was separated and washed with saturated aqueous NaHCO$_3$ (60 mL), H$_2$O (3×50 mL), brine (60 mL), then dried (Na$_2$SO$_4$), and concentrated under vacuum. The residue was purified by column chromatography on silica gel using EtOAc/hexanes (0:1 to 7:3) as eluent to give the product (55) (180 mg, 17%) as a solid. LC-MS:

m/z=514.12 [M+H]⁺. ¹H NMR (300 MHz, CDCl₃): δ 6.48 (s, 1H), 5.55 (s, 1H), 4.58 (d, J=8.7 Hz, 1H), 4.36 (d, J=9.3 Hz, 1H), 4.17 (m, 1H), 4.05 (d, J=6.9 Hz, 1H), 3.93 (d, J=11.1 Hz, 1H), 3.84 (d, J=11.1 Hz, 1H), 3.34-3.32 (m, 1H), 3.03-2.99 (m, 1H), 2.49-2.41 (m, 1H), 2.20-2.14 (m, 1H), 2.04 (br. s, 3H), 1.91-1.8 (m, 8H), 1.87 (br. s, 6H), 1.03 (s, 7H). ¹³C NMR (75 MHz, CDCl₃): δ 178.0, 171.7, 167.7, 81.3, 68.7, 62.6, 60.8, 47.8, 41.6, 39.5, 37.2, 36.2, 28.6, 22.0, 21.9, 21.4, 18.1.

Example 56

Synthesis of diethyl 2-((((((2S,5R)-2-carbamoyl-7-oxo-1,6-diazabicyclo[3.2.1]octan-6-yl)oxy)sulfonyl)oxy)methyl)-2-methylmalonate (56)

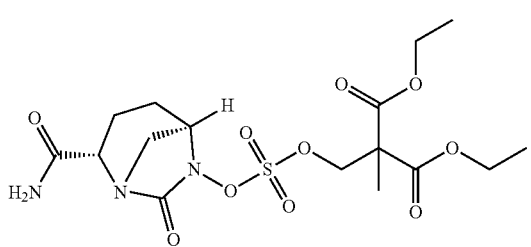 [SMILES: CCOC(=O)C(C)(COS(=O)(=O)ON1C(=O)N2C[C@H]1CC[C@H]2C(N)=O)C(=O)OCC]

Step 1: Synthesis of diethyl 2-(hydroxymethyl)-2-methylmalonate (56a)

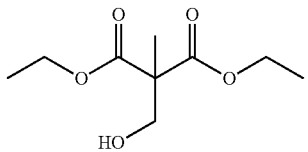

To a suspension of paraformaldehyde (1.3 g, 43.3 mmol) and K₂CO₃ (11 g, 79 mmol) in EtOH (150 mL) was added diethyl 2-methylmalonate (4.5 mL, 26.3 mmol). The mixture was stirred at room temperature for 17 h, then filtered through a pad of Celite®, and the filter cake washed with EtOH (2×30 mL). The filtrate was concentrated under vacuum and the residue was purified by column chromatography on silica gel using EtOAc/hexanes (0:1 to 3:2) as eluent to afford the product (56a) (4.0 g, 74%) as an oil. ¹H NMR (300 MHz, CDCl₃): δ 4.22 (q, J=6.9 Hz, 4H), 3.83 (d, J=6.9 Hz, 2H), 2.90 (t, J=7.8 Hz, 1H), 1.42 (s, 3H), 1.26 (t, J=6.9 Hz, 6H).

Step 2: Synthesis of diethyl 2-(((chlorosulfonyl)oxy)methyl)-2-methylmalonate (56b)

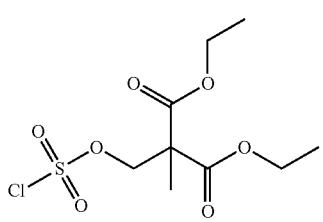 [SMILES: CCOC(=O)C(C)(COS(=O)(=O)Cl)C(=O)OCC]

A solution of freshly distilled sulfuryl chloride (248 μL, 3.0 mmol) in Et₂O (8 mL) was cooled to −78° C. under an atmosphere of argon. A solution of diethyl 2-(hydroxymethyl)-2-methylmalonate (56a) (500 mg, 2.4 mmol) and pyridine (0.26 mL, 3.2 mmol) in Et₂O (4 mL) was added dropwise to the sulfuryl chloride solution over the course of 5 min. The flask was rinsed with Et₂O (5 mL), and the rinse was also added to the reaction mixture. The mixture was stirred at −78° C. for 1 h, and then allowed to warm to room temperature. The precipitate was filtered (quickly) and the filter cake rinsed with Et₂O (12 mL). The filtrate was concentrated under vacuum at room temperature to afford the title compound (56b) as an oil which was used immediately in the next step without further purification.

Step 3: Synthesis of diethyl 2-((((((2S,5R)-2-carbamoyl-7-oxo-1,6-diazabicyclo[3.2.1]octan-6-yl)oxy)sulfonyl)oxy)methyl)-2-methylmalonate (56)

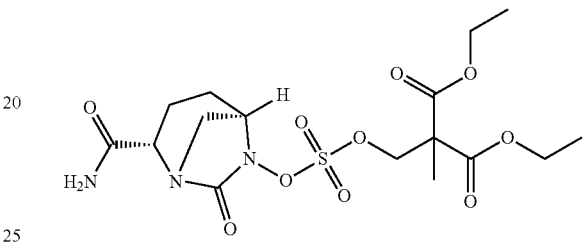

(2S,5R)-6-Hydroxy-7-oxo-1,6-diazabicyclo[3.2.1]octane-2-carboxamide (1) (390 mg, 2.1 mmol) was dissolved in THF (10 mL) and 1,3-dimethyltetrahydropyrimidin-2 (1H)-one (0.8 mL), and the resulting solution was cooled to −78° C. under an argon atmosphere. A solution of NaHMDS, 1.0 M in THF (2.2 mL, 2.2 mmol) was added dropwise to the cooled solution and stirred for 10 min. A solution of diethyl 2-(((chlorosulfonyl)oxy)methyl)-2-methylmalonate (56b) (638 mg, 2.1 mmol) in THF (8 mL) was quickly added to the reaction mixture. After stirring at −78° C. for 10 min, the mixture was allowed to warm to room temperature and stirred for 2 h. EtOAc (400 mL) and saturated aqueous NaHCO₃ (40 mL) and H₂O (40 mL) were added. The organic layer was separated and washed with saturated aqueous NaHCO₃ (60 mL), H₂O (3×50 mL), brine (60 mL), then dried (Na₂SO₄), and concentrated under vacuum. The residue was purified by column chromatography on silica gel using EtOAc/hexanes (0:1 to 9:1) as eluent to give the product (56) (166 mg, 17%) as a solid. LC-MS: m/z=452.03 [M+H]⁺. ¹H NMR (300 MHz, CDCl₃): δ 6.49 (s, 1H), 5.58 (s, 1H), 5.02 (d, J=8.7 Hz, 1H), 4.93 (d, J=9.3 Hz, 1H), 4.24 (q, J=7.2 Hz, 4H), 4.17 (m, 1H), 4.05 (d, J=6.9 Hz, 1H), 3.35 (m, 1H), 3.01 (d, J=11.1 Hz, 1H), 2.49-2.41 (m, 1H), 2.20-2.14 (m, 1H), 1.98-1.81 (m, 2H), 1.56 (s, 3H), 1.28 (t, J=7.2 Hz, 6H). ¹³C NMR (75 MHz, CDCl₃): δ 171.1, 168.6, 168.5, 167.1, 76.5, 62.3, 61.9, 60.2, 53.9, 47.1, 20.8, 17.8, 17.5, 14.0.

Example 57

Synthesis of propyl 3-(((((2S,5R)-2-carbamoyl-7-oxo-1,6-diazabicyclo[3.2.1]octan-6-yl)oxy)sulfonyl)oxy)-2,2-dimethylpropanoate (57)

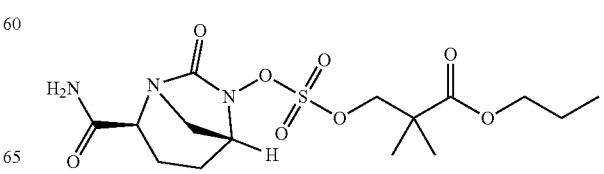

Step 1: Synthesis of propyl 3-hydroxy-2,2-dimethylpropanoate (57a)

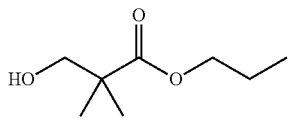

A mixture of 3-hydroxy-2,2-dimethylpropanoic acid (1.15 g, 9.7 mmol) was charged and 1-propanol (15 mL) and conc. $H_2SO_4$ (70 µL, 1.3 mmol) in a 20 mL-microwave vial was stirred at room temperature and then heated in a microwave at 80° C. for 2 h, and stirred at room temperature overnight. When the desired product was identified by TLC (EtOAc/hexanes; 3:7) the mixture was concentrated under vacuum (40° C.) and diluted with EtOAc (80 mL) and $H_2O$ (30 mL). The organic layer was washed with $H_2O$ (twice), and brine, then dried ($Na_2SO_4$), filtered, and concentrated to give the product (57a) (1.18 g, 76%) as an oil. The material was used next step directly without purification. $^1$H NMR (300 MHz, $CDCl_3$): δ 4.07 (t, J=6.6 Hz, 2H), 3.55 (s, 2H), 2.42 (br. s, 1H), 1.70-1.61 (m, 2H), 1.19 (s, 6H), 0.95 (t, J=7.5 Hz, 3H).

Step 2: Synthesis of propyl 3-((chlorosulfonyl)oxy)-2,2-dimethylpropanoate (57b)

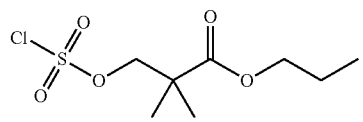

A solution of freshly distilled sulfuryl chloride (194 µL, 2.7 mmol) in $Et_2O$ (1.0 mL) was cooled to −78° C. under an atmosphere of argon. A solution of propyl 3-hydroxy-2,2-dimethylpropanoate (57a) (0.42 g, 2.6 mmol) and pyridine (215 µL, 2.7 mmol) in $Et_2O$ was added dropwise to the sulfuryl chloride solution over the course of 5 min. The flask was rinsed with $Et_2O$ (3×1 mL), and the rinse was added to the reaction mixture. The mixture was stirred at −78° C. for 5 min and then allowed to warm to room temperature and stirred for 1 h. The mixture was filtered and the filtrate was concentrated under vacuum to afford the title compound (57b) (0.56 g, 83%) as an oil, which was used immediately in the next step without further purification. $^1$H NMR (300 MHz, $CDCl_3$): δ 4.50 (s, 2H), 4.10 (t, J=6.6 Hz, 2H), 1.72-1.64 (m, 2H), 1.32 (s, 6H), 0.95 (t, J=7.2 Hz, 3H).

Step 3: Synthesis of propyl 3-(((((2S,5R)-2-carbamoyl-7-oxo-1,6-diazabicyclo[3.2.1]octan-6-yl)oxy)sulfonyl)oxy)-2,2-dimethylpropanoate (57)

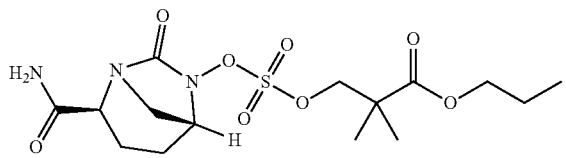 [SMILES: CCCOC(=O)C(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.22 g, 1.2 mmol) was dissolved in THF (5.5 mL) and HMPA (1.0 mL), and the resulting stirred solution was cooled to −78° C. under an atmosphere of argon. A solution of NaHMDS, 1.0 M in THF (1.5 mL, 1.5 mmol) was added to the mixture, and then a solution of propyl 3-((chlorosulfonyl)oxy)-2,2-dimethylpropanoate (57b) (0.40 g, 1.5 mmol) in THF (2×1 mL) was quickly added to the reaction mixture. After 10 min stirring at −78° C., the mixture was allowed to warm to room temperature and stirred for 1 h. The mixture was quenched with $H_2O$ and diluted with EtOAc (40 mL). The aqueous and organic layers were separated and the organic layer was washed with brine, dried ($Na_2SO_4$), and concentrated under vacuum. The residue was purified by column chromatography on silica gel using EtOAc/hexanes (3:7 to 1:0) as eluent to give the desired product (57) (190 mg, 39%) as a solid. LCMS: m/z=408.1 [M+H]$^+$. $^1$H NMR (300 MHz, $CDCl_3$): δ 6.47 (br. s, 1H), 5.57 (br. s, 1H), 4.66 (dd, J=9.0, 35.1 Hz, 2H), 4.17-4.04 (m, 4H), 3.32 (d, J=12.3 Hz, 1H), 3.02 (d, J=10.8 Hz, 1H), 2.46-2.41 (m, 1H), 2.14-2.13 (m, 1H), 1.99-1.83 (m, 2H), 1.71-1.66 (m, 2H), 1.29 (s, 3H), 1.28 (s, 3H), 0.95 (t, J=7.6 Hz, 3H). $^{13}$C NMR (75 MHz, $CDCl_3$): δ174.1, 170.9, 166.8, 80.3, 66.8, 61.8, 60.1, 47.1, 42.9, 22.1, 21.9, 21.6, 20.7, 17.4, 10.3.

Example (58)

Synthesis of butyl 3-(((((2S,5R)-2-carbamoyl-7-oxo-1,6-diazabicyclo[3.2.1]octan-6-yl)oxy)sulfonyl)oxy)-2,2-dimethylpropanoate (58)

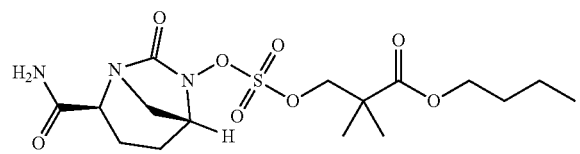 [SMILES: CCCCOC(=O)C(C)(C)COS(=O)(=O)ON1C(=O)N2C[C@H]1CC[C@H]2C(N)=O]

Step 1: Synthesis of butyl 3-hydroxy-2,2-dimethylpropanoate (58a)

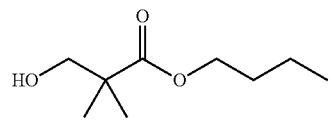

A mixture of 3-hydroxy-2,2-dimethylpropanoic acid (1.15 g, 9.7 mmol) was charged and 1-butanol (15 mL) and conc. $H_2SO_4$ (70 µL, 1.3 mmol) in a 20 mL-microwave vial was stirred at room temperature then heated in a microwave at 80° C. for 2 h, then stirred at room temperature overnight. When the desired product was identified by TLC (EtOAc/hexanes; 3:7) the mixture was concentrated under vacuum (40° C.; co-evaporated with toluene×3) and diluted with EtOAc (80 mL) and $H_2O$ (30 mL). The organic layer was washed with $H_2O$ (twice), and brine, then dried ($Na_2SO_4$), filtered and concentrated to give the product (58a) (1.24 g, 81%) as an oil. The material was used next step directly without purification. $^1$H NMR (300 MHz, $CDCl_3$): δ 4.11 (t, J=6.5 Hz, 2H), 3.55 (s, 2H), 2.42 (br. s, 1H), 1.65-1.58 (m, 2H), 1.43-1.35 (m, 2H), 1.19 (s, 6H), 0.94 (t, J=7.5 Hz, 3H).

Step 2: Synthesis of butyl 3-((chlorosulfonyl)oxy)-2,2-dimethylpropanoate (58b)

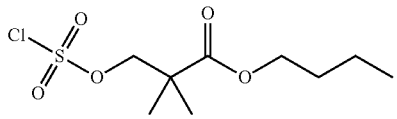 [SMILES: CCCCOC(=O)C(C)(C)COS(=O)(=O)Cl]

A solution of freshly distilled sulfuryl chloride (198 µL, 2.7 mmol) in Et$_2$O (1.0 mL) was cooled to −78° C. under an atmosphere of argon. A solution of propyl 3-hydroxy-2,2-dimethylpropanoate (58a) (0.47 g, 2.7 mmol) and pyridine (219 µL, 2.7 mmol) in Et$_2$O was added dropwise to the sulfuryl chloride solution over the course of 5 min. The flask was rinsed with Et$_2$O (3×1 mL), which was added to the reaction mixture. The mixture was stirred at −78° C. for 5 min and then allowed to warm to room temperature and stirred for 1 h. The mixture was filtered, and the filtrate was concentrated under vacuum to afford the title compound (58b) (0.52 g, 72%) as an oil, which was used immediately in the next step without further purification. $^1$H NMR (300 MHz, CDCl$_3$): δ 4.50 (s, 2H), 4.14 (t, J=6.8 Hz, 2H), 1.66-1.59 (m, 2H), 1.43-1.35 (m, 2H), 1.32 (s, 6H), 0.94 (t, J=7.4 Hz, 3H).

Step 3: Synthesis of butyl 3-(((((2S,5R)-2-carbamoyl-7-oxo-1,6-diazabicyclo[3.2.1]octan-6-yl)oxy)sulfonyl)oxy)-2,2-dimethylpropanoate (58)

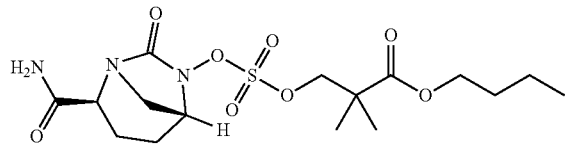 [SMILES: CCCCOC(=O)C(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.22 g, 1.2 mmol) was dissolved in THF (5 mL) and HMPA (1 mL), and the resulting stirred solution was cooled to −78° C. under an argon atmosphere. A solution of NaHMDS, 1.0 M in THF (1.5 mL, 1.5 mmol) was added, and the mixture stirred for 10 min. A solution of butyl 3-((chlorosulfonyl)oxy)-2,2-dimethylpropanoate (58b) (0.41 g, 1.5 mmol) in THF (5×1 mL) was quickly added to the reaction mixture. After 10 min stirring at −78° C., the mixture was allowed to warm to room temperature and stirred for 1 h. The mixture was quenched with H$_2$O and diluted with EtOAc (40 mL). The aqueous and organic layers were separated, and the organic layer was washed with brine, dried (Na$_2$SO$_4$), and concentrated under vacuum. The residue was dissolved in DMF and purified by preparative HPLC to give the desired product (58) (70 mg, 14%) as a solid. LCMS: m/z=422.2 [M+H]$^+$. $^1$H NMR (300 MHz, CDCl$_3$): δ 6.47 (br. s, 1H), 5.67 (br. s, 1H), 4.65 (dd, J=34.8, 9.0 Hz, 2H), 4.16-4.04 (m, 4H), 3.32 (d, J=11.7 Hz, 1H), 3.02 (d, J=12.3 Hz, 1H), 2.47-2.40 (m, 1H), 2.18-2.13 (m, 1H), 2.01-1.80 (m, 2H), 1.67-1.58 (m, 3H), 1.45-1.32 (m, 2H), 1.28 (s, 3H), 1.27 (s, 3H), 0.94 (t, J=7.4 Hz, 3H). $^{13}$C NMR (75 MHz, CDCl$_3$): δ 174.1, 170.8, 166.8, 80.3, 65.1, 61.8, 60.1, 47.1, 42.8, 30.5, 22.1, 21.6, 20.7, 19.0, 17.4, 13.6.

Example 59

Synthesis of (5-methyl-2-oxo-1,3-dioxol-4-yl)methyl 3-(((((2S,5R)-2-carbamoyl-7-oxo-1,6-diazabicyclo[3.2.1]octan-6-yl)oxy)sulfonyl)oxy)-2,2-dimethylpropanoate (59)

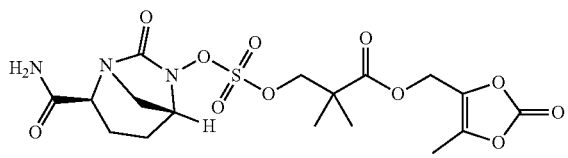 [SMILES: Cc1oc(=O)oc1COC(=O)C(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.22 g, 1.2 mmol) was dissolved in THF (10 mL) and HMPA (0.5 mL), and the resulting stirred solution was cooled to −78° C. under an atmosphere of argon. A solution of NaHMDS, 1.0 M in THF (1.3 mL, 1.3 mmol) was added to the mixture, and the mixture stirred for 10 min. A solution of (5-methyl-2-oxo-1,3-dioxol-4-yl)methyl 3-((chlorosulfonyl)oxy)-2,2-dimethylpropanoate (0.42 g, 1.3 mmol) in THF (5×1 mL) was quickly added to the reaction mixture. After 10 min stirring at −78° C., the mixture was allowed to warm to room temperature and stirred for 1 h. The mixture was cooled to 0° C. and quenched with H$_2$O and diluted with EtOAc (40 mL). The aqueous and organic layers were separated, and the organic layer was washed with brine, dried (Na$_2$SO$_4$), and concentrated under vacuum. The residue was purified by preparative HPLC to give the desired product (59) (189 mg, 34%) as a solid. LCMS: m/z=478.1 [M+H]$^+$. $^1$H NMR (300 MHz, CDCl$_3$): δ 6.68 (br. s, 1H), 5.74 (br. s, 1H), 4.95-4.79 (m, 3H), 4.50 (d, J=9.3 Hz, 1H), 4.14 (br. s, 1H), 4.03 (d, J=7.2 Hz, 1H), 3.32 (d, J=12.3 Hz, 1H), 3.02 (d, J=12.3 Hz, 1H), 2.45-2.39 (m, 1H), 2.17-2.09 (m, 4H), 1.98-1.79 (m, 2H), 1.30 (s, 3H), 1.29 (s, 3H). $^{13}$C NMR (75 MHz, CDCl$_3$): δ 177.6, 171.0, 167.0, 152.2, 140.5, 133.2, 80.0, 61.8, 60.2, 54.4, 47.0, 43.0, 21.8, 21.7, 20.7, 17.5, 9.3.

Example 60

Synthesis of 4-(((((2S,5R)-2-carbamoyl-7-oxo-1,6-diazabicyclo[3.2.1]octan-6-yl)oxy)sulfonyl)oxy)-3,3-dimethylbutyl pivalate (60)

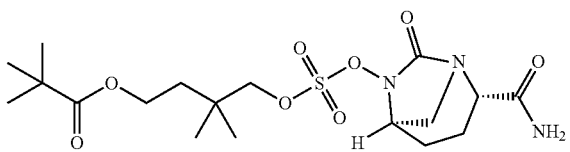 [SMILES: CC(C)(CCOC(=O)C(C)(C)C)COS(=O)(=O)ON1C(=O)N2C[C@H]1CC[C@H]2C(N)=O]

Step 1: Synthesis of 4-hydroxy-3,3-dimethylbutyl pivalate (60a)

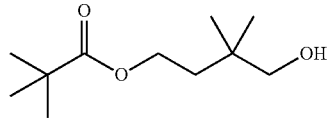

To a stirred solution of 2,2-dimethylbutane-1,4-diol (0.86 g, 7.3 mmol) in DCM (9 mL) at ca. 0° C. (ice bath) under an argon atmosphere, was added trimethylacetyl chloride (0.89 mL, 7.3 mmol), Et$_3$N (1.17 mL, 14.5 mmol), and N,N-4-dimethylaminopyridine (catalytic amount). The reaction mixture was allowed to gradually warm to room temperature and the mixture was stirred overnight. The mixture was quenched by the addition of 1N HCl (50 mL). The organic and aqueous layers were partitioned and the aqueous layer was extracted with DCM (twice). The combined organic layers were washed with saturated NaHCO$_3$ and brine, then dried (Na$_2$SO$_4$), and concentrated under vacuum. The residue was purified by column chromatography on silica gel using EtOAc/hexanes (0:1 to 3:7) as eluent to give the desired product (60a) (0.42 g, 28%). $^1$H NMR (300 MHz, CDCl$_3$): δ 4.13 (t, J=7.1 Hz, 2H), 3.35 (s, 2H), 1.61 (q, J=6.9 Hz, 2H), 1.19 (s, 9H), 0.93 (s, 6H).

Step 2: Synthesis of 4-((chlorosulfonyl)oxy)-3,3-dimethylbutyl pivalate (60b)

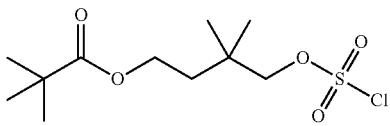 [SMILES: CC(C)(CCOC(=O)C(C)(C)C)COS(=O)(=O)Cl]

A solution of freshly distilled sulfuryl chloride (153 µL, 2.1 mmol) in Et$_2$O (4.5 mL) was cooled to −78° C. under an argon atmosphere. A solution of 4-hydroxy-3,3-dimethylbutyl pivalate (60a) (0.42 g, 2.1 mmol) and pyridine (203 µL, 2.5 mmol) in Et$_2$O (3 mL) was added dropwise to the sulfuryl chloride solution over the course of 60 min. The mixture was allowed to warm to room temperature and stirred for 30 min. The mixture was filtered, and the filtrate was concentrated under vacuum to afford the title compound (60b) as an oil, which was used immediately in the next step without further purification. $^1$H NMR (300 MHz, CDCl$_3$): δ 4.23 (s, 2H), 4.13 (t, J=6.8 Hz, 2H), 1.71 (t, J=6.6 Hz, 2H), 1.19 (s, 9H), 1.08 (s, 6H).

Step 3: Synthesis of 4-(((((2S,5R)-2-carbamoyl-7-oxo-1,6-diazabicyclo[3.2.1]octan-6-yl)oxy)sulfonyl)oxy)-3,3-dimethylbutyl pivalate (60)

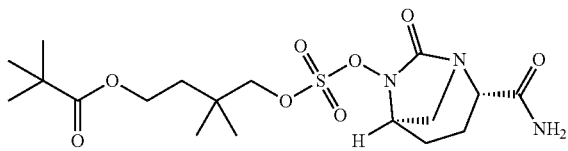 [SMILES: CC(C)(CCOC(=O)C(C)(C)C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.41 g, 2.2 mmol) was dissolved in THF (18.5 mL) and HMPA (0.9 mL), and the resulting stirred solution was cooled to −78° C. under an atmosphere of argon. A solution of NaHMDS, 1.0 M in THF (2.2 mL, 2.2 mmol) was added to the mixture, and the mixture stirred for 10 min. A solution of 4-((chlorosulfonyl)oxy)-3,3-dimethylbutyl pivalate (60b) (0.73 g, 2.4 mmol) in THF (20 mL) was quickly added to the reaction mixture. After 10 min stirring at −78° C., the mixture was allowed to warm to room temperature and stirred for 16 h. The mixture was quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel using EtOAc/hexanes (0:1 to 1:0) as eluent to give the product (60) (176 mg) as a solid. LCMS: m/z=450.15 [M+H]$^+$. $^1$H NMR (300 MHz, CDCl$_3$): δ 6.49 (br. s, 1H), 5.59 (br. s, 1H), 4.55 (d, J=9.3 Hz, 1H), 4.26-4.04 (m, 5H), 3.34 (d, J=11.7 Hz, 1H), 3.02 (d, J=12.3 Hz, 1H), 2.45-2.41 (m, 1H), 2.19-2.15 (m, 1H), 2.01-1.85 (m, 2H), 1.69 (t, J=6.8 Hz, 2H), 1.19 (s, 9H), 1.05 (s, 6H). $^{13}$C NMR (75 MHz, CDCl$_3$): δ178.6, 171.0, 167.0, 83.8, 61.9, 60.8, 60.2, 47.2, 38.7, 36.9, 34.0, 27.2, 24.0, 23.7, 20.8, 17.5.

Example 61

Synthesis of ethyl 2-((((((2S,5R)-2-carbamoyl-7-oxo-1,6-diazabicyclo[3.2.1]octan-6-yl)oxy)sulfonyl)oxy)methyl)-2-ethylbutanoate (61)

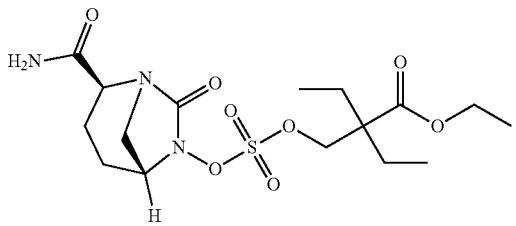 [SMILES: CCOC(=O)C(CC)(CC)COS(=O)(=O)ON1C(=O)N2C[C@H]1CC[C@H]2C(N)=O]

Step 1: Synthesis of ethyl 2-(((chlorosulfonyl)oxy)methyl)-2-ethylbutanoate (61a)

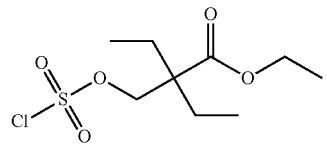 [SMILES: CCOC(=O)C(CC)(CC)COS(=O)(=O)Cl]

A solution of freshly distilled sulfuryl chloride (126 µL, 1.7 mmol) in Et$_2$O (3.2 mL) was cooled to −78° C. under an argon atmosphere. A solution of ethyl 2-ethyl-2-(hydroxymethyl)butanoate (ex-enamine) (0.30 g, 1.7 mmol) and pyridine (153 µL, 1.9 mmol) in Et$_2$O (2.1 mL) was added dropwise to the sulfuryl chloride solution over the course of 60 min. The mixture was allowed to warm to room temperature and stirred for 30 min. The mixture was re-cooled to −78° C. and sulfuryl chloride (20 µL) was added, and the reaction allowed to warm to room temperature and stirred for a further 30 min. Et$_2$O (5 mL) was added and the mixture stirred for 5 min, then filtered, and the filtrate was concentrated under vacuum to afford the title compound (61a), which was used immediately in the next step without further purification. $^1$H NMR (300 MHz, CDCl$_3$): δ 4.62 (s, 2H), 4.21 (q, J=7.3 Hz, 2H), 1.78-1.58 (m, 4H), 1.28 (t, J=7.1 Hz, 3H), 0.88 (t, J=7.7 Hz, 6H).

Step 2: Synthesis of ethyl 2-((((((2S,5R)-2-carbamoyl-7-oxo-1,6-diazabicyclo[3.2.1]octan-6-yl)oxy)sulfonyl)oxy)methyl)-2-ethylbutanoate (61)

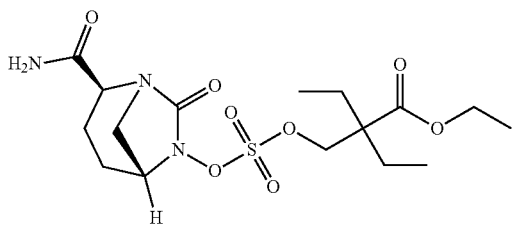 [SMILES: CCOC(=O)C(CC)(CC)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.25 g, 1.4 mmol) was dissolved in THF (11.2 mL) and HMPA (0.6 mL), and the resulting stirred solution was cooled to −78° C. under an atmosphere of argon. A solution of NaHMDS, 1.0 M in THF (1.4 mL, 1.4 mmol) was added to the mixture, and the mixture stirred for 10 min. A solution of ethyl 2-(((chlorosulfonyl)oxy)methyl)-2-ethylbutanoate (61a) (0.41 g, 1.5 mmol) in THF (20 mL) was quickly added to the reaction mixture. After 10 min stirring at −78° C., the mixture was allowed to warm to room temperature and stirred for 16 h. The mixture was quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel to give the product (61) (162 mg, 29%) as a solid. LCMS: m/z=422.03 [M+H]$^+$. $^1$H NMR (300 MHz, CDCl$_3$): δ 6.50 (br. s, 1H), 5.66 (br. s, 1H), 4.87 (d, J=9.9 Hz, 1H), 4.70 (d, J=9.9 Hz, 1H), 4.22-4.14 (m, 3H), 4.06 (d, J=7.2 Hz, 1H), 3.33 (d, J=11.7 Hz, 1H), 3.02 (d, J=12.3H, 1H), 2.47-2.41 (m, 1H), 2.22-2.12 (m, 1H), 2.01-1.60 (m, 6H), 1.27 (t, J=7.1 Hz, 3H), 0.92-0.83 (m, 6H). $^{13}$C NMR (75 MHz, CDCl$_3$): δ 173.3, 171.1, 167.1, 75.2, 62.0, 61.1, 60.2, 50.6, 47.2, 26.2, 25.8, 20.9, 17.5, 14.3, 8.4, 8.3.

Example 62

Synthesis of 4-(((((2S,5R)-2-carbamoyl-7-oxo-1,6-diazabicyclo[3.2.1]octan-6-yl)oxy)sulfonyl)oxy)-3,3-dimethylbutyl 2,6-dimethylbenzoate (62)

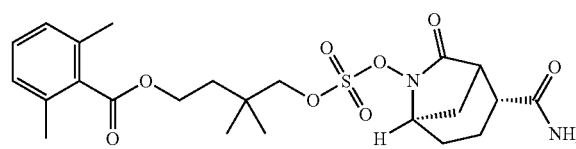

Step 1: Synthesis of 4-hydroxy-3,3-dimethylbutyl 2,6-dimethylbenzoate (62a)

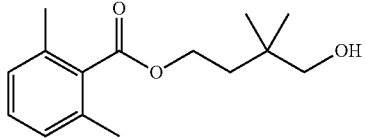 [SMILES: Cc1cccc(C)c1C(=O)OCCC(C)(C)CO]

To a stirred solution of 2,2-dimethylbutane-1,4-diol (0.84 g, 7.1 mmol) in DCM (9 mL) at ca. 0° C. (ice bath) under an argon atmosphere, was added 2,6-dimethylbenzoyl chloride (1.0 g, 5.9 mmol), pyridine (0.96 mL, 11.9 mmol), and N,N-4-dimethylaminopyridine (catalytic amount). The reaction mixture was allowed to gradually warm to room temperature and the mixture was stirred overnight. The mixture was quenched by the addition of 1N HCl (50 mL). The organic and aqueous layers were partitioned and the aqueous layer was extracted with DCM (twice). The combined organic layers were washed with saturated NaHCO$_3$, and then dried (Na$_2$SO$_4$), and concentrated under vacuum. The residue was purified by column chromatography on silica gel using EtOAc/hexanes (0:1 to 3:7) as eluent to give the desired product (62a) (0.42 g, 28%). $^1$H NMR (300 MHz, CDCl$_3$): δ 7.18 (t, J=7.6 Hz, 1H), 7.04-7.01 (m, 2H), 4.41 (t, J=7.6 Hz, 2H), 3.37 (s, 2H), 2.31 (s, 6H), 1.76 (t, J=7.5 Hz, 2H), 0.97 (s, 6H).

Step 2: Synthesis of 4-((chlorosulfonyl)oxy)-3,3-dimethylbutyl 2,6-dimethylbenzoate (62b)

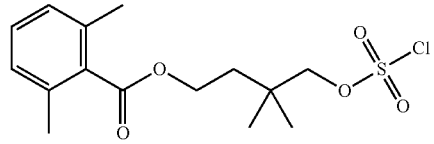 [SMILES: Cc1cccc(C)c1C(=O)OCCC(C)(C)COS(=O)(=O)Cl]

A solution of freshly distilled sulfuryl chloride (122 μL, 1.7 mmol) in Et$_2$O (1.0 mL) was cooled to −78° C. under an atmosphere of argon. A solution of 4-hydroxy-3,3-dimethylbutyl 2,6-dimethylbenzoate (62a) (0.42 g, 1.7 mmol) and pyridine (136 μL, 1.7 mmol) in Et$_2$O (1.5 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (62b) as an oil, which was used immediately in the next step without further purification (not pure). $^1$H NMR (300 MHz, CDCl$_3$): δ 7.19 (t, J=7.7 Hz, 1H), 7.03 (d, J=7.5 Hz, 2H), 4.41 (t, J=7.4 Hz, 2H), 4.23 (s, 2H), 2.31 (s, 6H), 1.84 (t, J=6.9 Hz, 2H), 1.11 (s, 6H).

Step 3: Synthesis of 4-(((((2S,5R)-2-carbamoyl-7-oxo-1,6-diazabicyclo[3.2.1]octan-6-yl)oxy)sulfonyl)oxy)-3,3-dimethylbutyl 2,6-dimethylbenzoate (62)

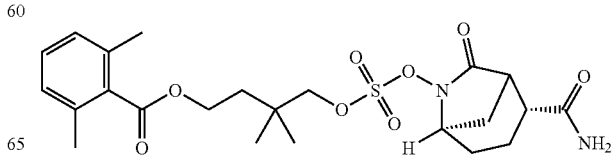

(2S,5R)-6-Hydroxy-7-oxo-1,6-diazabicyclo[3.2.1]octane-2-carboxamide (1) (0.22 g, 1.2 mmol) was dissolved in THF (10 mL) and HMPA (0.5 mL), and the resulting stirred solution was cooled to −78° C. under an atmosphere of argon. A solution of NaHMDS, 1.0 M in THF (1.2 mL, 1.2 mmol) was added to the mixture, and the mixture stirred for 10 min. A solution of 4-((chlorosulfonyl)oxy)-3,3-dimethylbutyl 2,6-dimethylbenzoate (62b) (0.42 g, 1.2 mmol) in Et$_2$O (20 mL) was quickly added to the reaction mixture. After 10 min stirring at −78° C., the mixture was allowed to warm to room temperature and stirred for 1 h. The mixture was cooled to 0° C. and quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel using EtOAc/hexanes (0:1 to 7:3) as eluent to give the product (62) (192 mg, 32%) as a solid. LCMS: m/z=498.08 [M+H]$^+$. $^1$H NMR (300 MHz, CDCl$_3$): δ 7.18 (t, J=7.5 Hz, 1H), 7.02 (d, J=7.5 Hz, 2H), 6.48 (br. s, 1H), 5.63 (br. s, 1H), 4.57 (d, J=9.0 Hz, 1H), 4.40 (t, J=7.5 Hz, 2H), 4.25 (d, J=8.7 Hz, 1H), 4.17 (br. s, 1H), 4.04 (d, J=6.3 Hz, 1H), 3.32 (d, J=12.3 Hz, 1H), 3.00 (d, J=12.3 Hz, 1H), 2.47-2.40 (m, 1H), 2.31 (s, 6H), 2.18-2.14 (m, 1H), 1.97-1.80 (m, 4H), 1.08 (s, 6H). $^{13}$C NMR (75 MHz, CDCl$_3$): δ 170.9, 170.0, 167.1, 134.8, 133.8, 129.4, 127.6, 83.4, 61.9, 61.3, 60.1, 47.1, 36.7, 33.9, 23.9, 23.6, 20.7, 19.8, 17.4.

Example 63

Synthesis of 4-(((((2S,5R)-2-carbamoyl-7-oxo-1,6-diazabicyclo[3.2.1]octan-6-yl)oxy)sulfonyl)oxy)-3,3-dimethylbutyl adamantane-1-carboxylate (63)

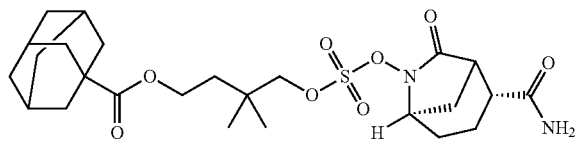 [SMILES: CC(C)(CCOC(=O)C12CC3CC(CC(C3)C1)C2)COS(=O)(=O)ON1C(=O)C2C[C@H]1CC[C@H]2C(N)=O]

Step 1: Synthesis of 4-hydroxy-3,3-dimethylbutyl adamantane-1-carboxylate (63a)

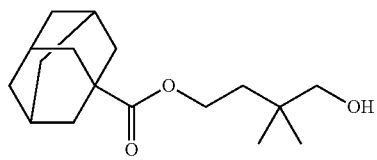 [SMILES: CC(C)(CO)CCOC(=O)C12CC3CC(CC(C3)C1)C2]

To a stirred solution of 2,2-dimethylbutane-1,4-diol (0.72 g, 6.1 mmol) in DCM (20 mL) at ca. 0° C. (ice bath) under an atmosphere of argon, was added 1-adamantane-carbonyl chloride (1.1 g, 10.1 mmol), pyridine (0.82 mL, 10.1 mmol), and N,N-4-dimethylaminopyridine (0.03 g, 0.3 mmol). The reaction mixture was allowed to gradually warm to room temperature and the mixture was stirred overnight. The mixture was quenched by the addition of 1N HCl. The organic and aqueous layers were partitioned, and the aqueous layer was extracted with DCM (twice). The combined organic layers were washed with saturated NaHCO$_3$ and brine, and then dried (MgSO$_4$), and concentrated under vacuum. The residue was purified by column chromatography on silica gel using EtOAc/hexanes (0:1 to 1:1) as eluent to give the desired product (63a) (0.49 g, 35%). $^1$H NMR (300 MHz, CDCl$_3$): δ 4.14-4.09 (m, 2H), 3.34 (s, 2H), 2.00 (m, 3H), 1.90-1.86 (m, 6H), 1.75-1.59 (m, 6H), 1.59 (t, J=7.1 Hz, 2H), 0.92 (s, 6H).

Step 2: Synthesis of 4-((chlorosulfonyl)oxy)-3,3-dimethylbutyl adamantane-1-carboxylate (63b)

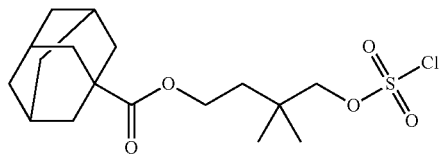 [SMILES: CC(C)(CCOC(=O)C12CC3CC(CC(C3)C1)C2)COS(=O)(=O)Cl]

A solution of freshly distilled sulfuryl chloride (127 μL, 1.7 mmol) in Et$_2$O (1.2 mL) was cooled to −78° C. under an atmosphere of argon. A solution of 4-hydroxy-3,3-dimethylbutyl adamantane-1-carboxylate (63a) (0.48 g, 1.7 mmol) and pyridine (141 μL, 1.7 mmol) in Et$_2$O (1.7 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min and then allowed to warm to room temperature and stirred for 1 h. The mixture was filtered, and the filtrate was concentrated under vacuum to afford the title compound (63b) as an oil, which was used immediately in the next step without further purification (not pure). H NMR (300 MHz, CDCl$_3$): δ 4.25 (s, 2H), 4.13 (t, J=6.8 Hz, 2H), 2.01 (m, 3H), 1.90-1.85 (m, 6H), 1.73-1.69 (m, 8H), 1.08 (s, 6H).

Step 3: Synthesis of 4-(((((2S,5R)-2-carbamoyl-7-oxo-1,6-diazabicyclo[3.2.1]octan-6-yl)oxy)sulfonyl)oxy)-3,3-dimethylbutyl adamantane-1-carboxylate (63)

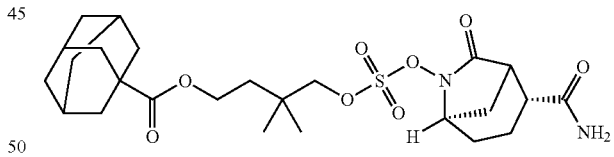

(2S,5R)-6-Hydroxy-7-oxo-1,6-diazabicyclo[3.2.1]octane-2-carboxamide (1) (0.22 g, 1.2 mmol) was dissolved in THF (10 mL) and HMPA (0.5 mL), and the resulting stirred solution was cooled to −78° C. under an atmosphere of argon. A solution of NaHMDS, 1.0 M in THF (1.2 mL, 1.2 mmol) was added to the mixture, and the mixture stirred for 10 min. A solution of 4-((chlorosulfonyl)oxy)-3,3-dimethylbutyl adamantane-1-carboxylate (63b) (0.66 g, 1.7 mmol) in Et$_2$O (20 mL) was added quickly to the reaction mixture. After 10 min stirring at −78° C., the mixture was allowed to warm to room temperature and stirred for 1 h. The mixture was cooled to 0° C. and quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel using EtOAc/hexanes (0:1 to 7:3) as eluent to give a solid, which was triturated with hexanes to give the product (63) (230 mg, 36%) as a solid. LCMS: m/z=528.17 [M+H]$^+$. $^1$H NMR (300 MHz, CDCl$_3$): δ 7.18 (t, J=7.5 Hz, 1H), 7.02 (d, J=7.5 Hz, 2H), 6.48 (br. s, 1H), 5.63 (br. s, 1H), 4.57 (d, J=9.0 Hz, 1H), 4.40 (t, J=7.5 Hz, 2H), 4.25 (d, J=8.7 Hz, 1H), 4.17 (br. s, 1H), 4.04 (d, J=6.3 Hz, 1H), 3.32 (d, J=12.3 Hz, 1H), 3.00 (d, J=12.3 Hz, 1H), 2.47-2.40 (m, 1H), 2.31 (s, 6H), 2.18-2.14 (m, 1H), 1.97-1.80 (m, 4H), 1.08 (s, 6H). $^{13}$C NMR (75 MHz, CDCl$_3$): δ 177.8, 171.0, 167.1, 83.9, 62.0, 60.7, 60.2, 47.2, 40.7, 39.0, 39.0, 37.0, 36.6, 34.1, 28.0, 24.0, 23.8, 20.8, 17.5.

Example 64

Synthesis of 4-(((((2S,5R)-2-carbamoyl-7-oxo-1,6-diazabicyclo[3.2.1]octan-6-yl)oxy)sulfonyl)oxy)-3,3-dimethylbutyl 2,6-dimethoxybenzoate (64)

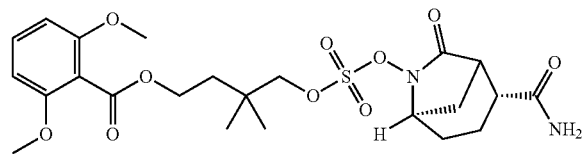 [SMILES: COc1cccc(OC)c1C(=O)OCCC(C)(C)COS(=O)(=O)ON1C(=O)C2C[C@H]1CC[C@H]2C(N)=O]

Step 1: Synthesis of 4-hydroxy-3,3-dimethylbutyl 2,6-dimethoxybenzoate (64a)

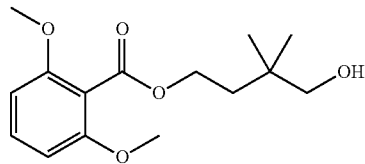 [SMILES: COc1cccc(OC)c1C(=O)OCCC(C)(C)CO]

To a stirred solution of 2,2-dimethylbutane-1,4-diol (1.85 g, 15.7 mmol) in DCM (28 mL) at ca. 0° C. (ice bath) under an atmosphere of argon, was added 2,6-dimethoxybenzoyl chloride (80%; 3.93 g, 15.7 mmol), Et$_3$N (2.5 mL, 31.3 mmol), and N,N-4-dimethylaminopyridine (catalytic amount). The reaction mixture was allowed to gradually warm to room temperature and the mixture was stirred overnight. The mixture was concentrated under vacuum and suspended in EtOAc, and then filtered and the filter cake washed with EtOAc. The filtrate was concentrated under vacuum and the residue purified by column chromatography on silica gel using EtOAc/hexanes (0:1 to 2:3) as eluent to give the desired product (64a) (ca. 80% purity; 0.92 g). $^1$H NMR (300 MHz, CDCl$_3$): δ 7.29-7.26 (m, 1H), 6.57-6.53 (m, 3H), 4.43-4.39 (m, 2H), 3.83 (s, 6H), 3.36 (s, 2H), 1.74 (t, J=6.5 Hz, 2H), 0.95 (s, 6H).

Step 2: Synthesis of 4-((chlorosulfonyl)oxy)-3,3-dimethylbutyl 2,6-dimethoxybenzoate (64b)

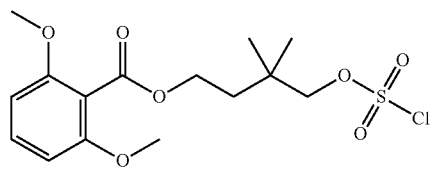 [SMILES: COc1cccc(OC)c1C(=O)OCCC(C)(C)COS(=O)(=O)Cl]

A solution of freshly distilled sulfuryl chloride (0.2 mL, 2.7 mmol) in Et$_2$O (1.9 mL) was cooled to −78° C. under an argon atmosphere. A solution of 4-hydroxy-3,3-dimethylbutyl 2,6-dimethoxybenzoate (64a) (ca. 80% purity; 0.97 g, 2.7 mmol) and pyridine (222 µL, 2.7 mmol) in Et$_2$O (2.7 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (64b) as an oil, which was used immediately in the next step without further purification (not pure).

Step 3: Synthesis of 4-(((((2S,5R)-2-carbamoyl-7-oxo-1,6-diazabicyclo[3.2.1]octan-6-yl)oxy)sulfonyl)oxy)-3,3-dimethylbutyl 2,6-dimethoxybenzoate (64)

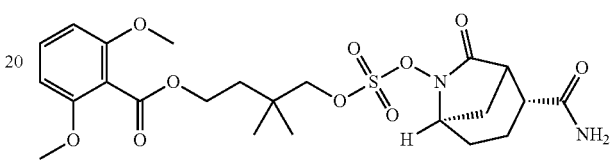

(2S,5R)-6-Hydroxy-7-oxo-1,6-diazabicyclo[3.2.1]octane-2-carboxamide (1) (0.21 g, 1.1 mmol) was dissolved in THF (9.4 mL) and HMPA (0.5 mL), and the resulting stirred solution was cooled to −78° C. under an argon atmosphere. A solution of NaHMDS, 1.0 M in THF (1.1 mL, 1.1 mmol) was added to the mixture, and the mixture stirred for 10 min. A solution of 4-((chlorosulfonyl)oxy)-3,3-dimethylbutyl 2,6-dimethoxybenzoate (64b) (0.65 g, 1.7 mmol) in Et$_2$O (20 mL) was quickly added to the reaction mixture. After 10 min stirring at −78° C., the mixture was allowed to warm to room temperature and stirred for 1 h. The mixture was cooled to 0° C. and quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel using EtOAc/hexanes (0:1 to 1:0) as eluent to give the product (64) (100 mg, 17%) as a solid. LCMS: m/z=530.01 [M+H]$^+$. $^1$H NMR (300 MHz, CDCl$_3$): δ 7.31-7.25 (m, 1H), 6.54 (d, J=9.0 Hz, 2H), 6.50 (br. s, 1H), 5.58 (br. s, 1H), 4.54 (d, J=8.7 Hz, 1H), 4.40 (t, J=6.8 Hz, 2H), 4.28 (d, J=8.7 Hz, 1H), 4.16 (br. s, 1H), 4.03 (d, J=6.9 Hz, 1H), 3.81 (s, 6H), 3.33 (d, J=11.7 Hz, 1H), 2.99 (d, J=7.2 Hz, 1H), 2.44-2.39 (m, 1H), 2.21-2.13 (m, 1H), 1.93-1.79 (m, 4H), 1.07 (s, 6H). $^{13}$C NMR (75 MHz, CDCl$_3$): δ171.0, 167.1, 166.7, 157.3, 131.2, 113.1, 103.9, 84.0, 62.0, 61.8, 60.2, 56.0, 47.2, 36.6, 34.1, 23.8, 23.6, 20.8, 17.5.

Example 65

Synthesis of 5-(((((2S,5R)-2-carbamoyl-7-oxo-1,6-diazabicyclo[3.2.1]octan-6-yl)oxy)sulfonyl)oxy)-4,4-dimethylpentyl benzoate (65)

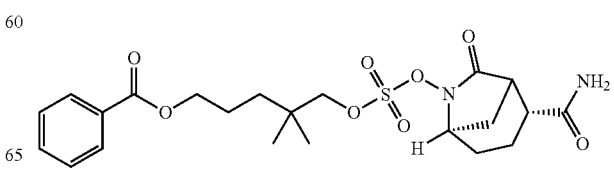

Step 1: Synthesis of 5-hydroxy-4,4-dimethylpentyl benzoate (65a)

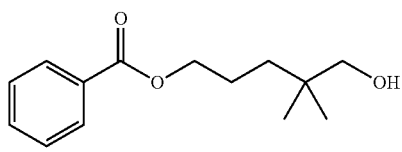 [SMILES: CC(C)(CO)CCCOC(=O)c1ccccc1]

To a stirred solution of 2,2-dimethylpentane-1,5-diol (*J. Org. Chem.* 2010, 75, 1892-1897; PCT International Publication No. WO 2002092606) (1.55 g, 11.7 mmol) in DCM (20 mL) at ca. 0° C. (ice bath) under an argon atmosphere, was added benzoyl chloride (1.5 mL, 12.9 mmol). The reaction mixture was stirred at room temperature for 2.5 h and concentrated under vacuum. EtOAc was added to the residue and the mixture was stirred. The filtrate was concentrated under the residue purified by column chromatography on silica gel using EtOAc/hexanes (0:1 to 1:4) as eluent to give the product (65a) (1.38 g, 50%) as an oil. $^1$H NMR (300 MHz, CDCl$_3$): δ 8.04 (d, J=6.9 Hz, 2H), 7.56 (t, J=7.5 Hz, 1H), 7.44 (t, J=7.5 Hz, 2H), 4.31 (t, J=6.8 Hz, 2H), 3.36 (s, 2H), 1.81-1.71 (m, 2H), 1.42-1.36 (m, 2H), 0.92 (s, 6H).

Step 2: Synthesis of 5-((chlorosulfonyl)oxy)-4,4-dimethylpentyl benzoate (65b)

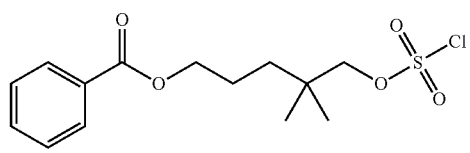 [SMILES: CC(C)(CCCOC(=O)c1ccccc1)COS(=O)(=O)Cl]

A solution of freshly distilled sulfuryl chloride (0.2 mL, 2.7 mmol) in Et$_2$O (1.9 mL) was cooled to −78° C. under an argon atmosphere. A solution of 4-hydroxy-3,3-dimethylpentyl benzoate (65a) (0.76 g, 3.2 mmol) and pyridine (218 µL, 2.7 mmol) in Et$_2$O (2.7 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (65b) as an oil, which was used immediately in the next step without further purification (not pure). $^1$H NMR (300 MHz, CDCl$_3$): δ 8.04 (d, J=7.5 Hz, 2H), 7.57-7.55 (m, 1H), 7.48-7.33 (m, 1H), 4.35-4.29 (m, 2H), 4.23 (s, 2H), 1.81-1.74 (m, 2H), 1.53-1.21 (m, 2H), 1.06 (s, 6H).

Step 3: Synthesis of 5-(((((2S,5R)-2-carbamoyl-7-oxo-1,6-diazabicyclo[3.2.1]octan-6-yl)oxy)sulfonyl)oxy)-4,4-dimethylpentyl benzoate (65)

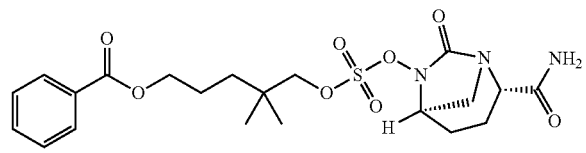 [SMILES: CC(C)(CCCOC(=O)c1ccccc1)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.21 g, 1.1 mmol) was dissolved in THF (9.4 mL) and HMPA (0.5 mL), and the resulting stirred solution was cooled to −78° C. under an argon atmosphere. A solution of NaHMDS, 1.0 M in THF (1.1 mL, 1.1 mmol) was added to the mixture, and the mixture stirred for 10 min. A solution of 5-((chlorosulfonyl)oxy)-4,4-dimethylpentyl benzoate (65b) (0.42 g, 1.2 mmol) in Et$_2$O (20 mL) was quickly added to the reaction mixture. After 10 min stirring at −78° C., the mixture was allowed to warm to room temperature and stirred for 1 h. The mixture was cooled to 0° C. and quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel using EtOAc/hexanes (0:1 to 7:3) as eluent to give the product (65) (160 mg, 29%) as a solid. LCMS: m/z=484.10 [M+H]$^+$. $^1$H NMR (300 MHz, CDCl$_3$): δ 8.04 (d, J=7.5 Hz, 2H), 7.57-7.54 (m, 1H), 7.47-7.42 (m, 2H), 6.43 (br. s, 1H), 5.51 (br. s, 1H), 4.56 (d, J=9.0 Hz, 1H), 4.32-4.17 (m, 4H), 4.02 (d, J=7.2 Hz, 1H), 3.28 (d, J=12.3 Hz, 1H), 2.97 (d, J=12.3 Hz, 1H), 2.44-2.40 (m, 1H), 2.20-2.14 (m, 1H), 1.94-1.72 (m, 4H), 1.51-1.45 (m, 2H), 1.02 (s, 6H). $^{13}$C NMR (75 MHz, CDCl$_3$): δ 171.0, 167.1, 166.8, 133.1, 130.4, 129.7, 128.5, 83.6, 65.3, 61.9, 60.2, 47.2, 34.8, 34.3, 23.9, 23.6, 23.3, 20.8, 17.5.

Example 66

Synthesis of 5-(((((2S,5R)-2-carbamoyl-7-oxo-1,6-diazabicyclo[3.2.1]octan-6-yl)oxy)sulfonyl)oxy)-4,4-dimethylpentyl 2,6-dimethoxybenzoate (66)

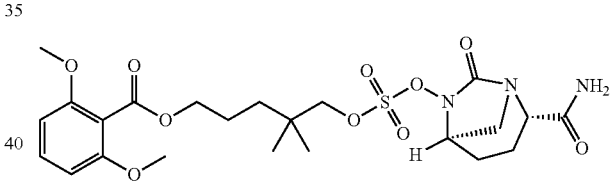

Step 1: Synthesis of 5-hydroxy-4,4-dimethylpentyl 2,6-dimethoxybenzoate (66a)

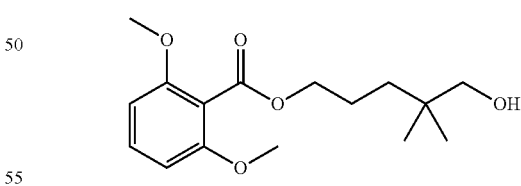

To a stirred solution of 2,2-dimethylpentane-1,5-diol (1.5 g, 11.3 mmol) in pyridine (8.3 mL) at 0° C. under an argon atmosphere was added 2,6-dimethoxybenzoyl chloride (80%; 1.4 g, 5.6 mmol) in one portion. The reaction mixture was allowed to warm to room temperature and for 3 h. The reaction mixture was concentrated to dryness and EtOAc was added. The mixture was filtered and the filtrate was concentrated under vacuum. The residue was purified by column chromatography on silica gel using EtOAc/hexanes (0:1 to 3:7) as eluent to give the product (66a) (0.65 g, 39%) as an oil. $^1$H NMR (300 MHz, CDCl$_3$): δ 7.31-7.26 (m, 2H), 6.55 (d, J=8.1 Hz, 2H), 4.33 (t, J=6.2 Hz, 2H), 3.82 (s, 6H), 3.33 (s, 2H), 1.77-1.67 (m, 2H), 1.41-1.35 (m, 2H), 0.92 (s, 6H).

Step 2: Synthesis of
5-((chlorosulfonyl)oxy)-4,4-dimethylpentyl
2,6-dimethoxybenzoate (66b)

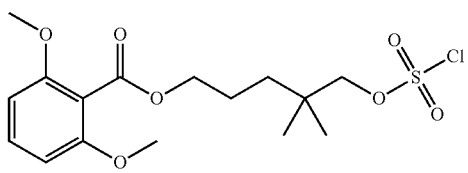 [SMILES: COc1cccc(OC)c1C(=O)OCCCC(C)(C)COS(=O)(=O)Cl]

A solution of freshly distilled sulfuryl chloride (0.16 mL, 2.2 mmol) in Et$_2$O was cooled to –78° C. under an atmosphere of argon. A solution of 5-hydroxy-4,4-dimethylpentyl 2,6-dimethoxybenzoate (66a) (0.65 g, 2.2 mmol) and pyridine (177 µL, 2.2 mmol) in Et$_2$O was added dropwise to the sulfuryl chloride solution over the course of 15 min. The flask was rinsed with Et$_2$O (2×20 mL), and the rinse was added to the reaction mixture. The mixture was stirred at –78° C. for 10 min and then allowed to warm to room temperature and stirred for 1 h. The mixture was filtered, and the filtrate was concentrated under vacuum to afford the title compound (66b) as an oil, which was used immediately in the next step without further purification (not pure). $^1$H NMR (300 MHz, CDCl$_3$): δ 7.32-7.26 (m, 1H), 6.56 (d, J=8.7 Hz, 2H), 4.34 (t, J=6.2 Hz, 2H), 4.21 (s, 2H), 3.81 (s, 6H), 1.77-1.71 (m, 2H), 1.52-1.46 (m, 2H), 1.03 (s, 6H).

Step 3: Synthesis of 5-(((((2S,5R)-2-carbamoyl-7-oxo-1,6-diazabicyclo[3.2.1]octan-6-yl)oxy)sulfonyl)oxy)-4,4-dimethylpentyl 2,6-dimethoxybenzoate (66)

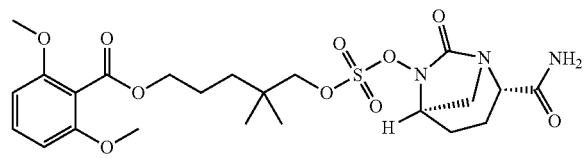 [SMILES: COc1cccc(OC)c1C(=O)OCCCC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.21 g, 1.1 mmol) was dissolved in THF (9.4 mL) and HMPA (0.5 mL), and the resulting stirred solution was cooled to –78° C. under an atmosphere of argon. A solution of NaHMDS, 1.0 M in THF (1.1 mL, 1.1 mmol) was added to the mixture, and the mixture stirred for 10 min. A solution of 5-((chlorosulfonyl)oxy)-4,4-dimethylpentyl 2,6-dimethoxybenzoate (66b) (0.49 g, 1.2 mmol) in Et$_2$O (20 mL) was quickly added to the reaction mixture. After 10 min stirring at –78° C., the mixture was allowed to warm to room temperature and stirred for 1 h. The mixture was cooled to 0° C. and quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel using EtOAc/hexanes (0:1 to 1:0) as eluent to give the product (66) (115 mg, 18%) as a solid. LCMS: m/z=544.17 [M+H]$^+$ & 589.11 [M+HCOOH]$^+$. $^1$H NMR (300 MHz, CDCl$_3$): δ 7.31-7.25 (m, 1H), 6.55 (d, J=8.7 Hz, 2H), 6.51 (br. s, 1H), 5.51 (br. s, 1H), 4.53 (d, J=9.0 Hz, 1H), 4.33 (t, J=6.2 Hz, 2H), 4.23-4.16 (m, 2H), 4.03 (d, J=7.5 Hz, 1H), 3.82 (s, 6H), 3.31 (d, J=12.3 Hz, 1H), 2.98 (d, J=11.7 Hz, 1H), 2.42-2.39 (m, 1H), 2.20-2.18 (m, 1H), 2.00-1.68 (m, 4H), 1.49-1.44 (m, 2H), 1.00 (s, 6H). $^{13}$C NMR (75 MHz, CDCl$_3$): δ 171.0, 167.0, 166.7, 157.4, 131.2, 110.1, 104.1, 83.9, 65.6, 62.0, 60.2, 56.1, 47.2, 34.7, 34.3, 23.8, 23.6, 23.4, 20.8, 17.6.

Example 67

Synthesis of 5-(((((2S,5R)-2-carbamoyl-7-oxo-1,6-diazabicyclo[3.2.1]octan-6-yl)oxy)sulfonyl)oxy)-4,4-dimethylpentyl 2,6-dimethylbenzoate (67)

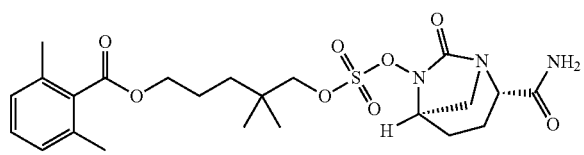 [SMILES: Cc1cccc(C)c1C(=O)OCCCC(C)(C)COS(=O)(=O)ON1C(=O)N2C[C@H]1CC[C@H]2C(N)=O]

Step 1: Synthesis of 5-hydroxy-3,3-dimethylpentyl 2,6-dimethylbenzoate (67a)

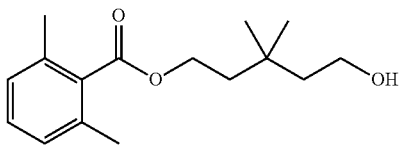 [SMILES: Cc1cccc(C)c1C(=O)OCCC(C)(C)CCO]

To a stirred solution of 2,2-dimethylpentane-1,5-diol (1.1 g, 8.3 mmol) in pyridine (8.3 mL) at 0° C. under an argon atmosphere was added 2,6-dimethylbenzoyl chloride in one portion. The reaction mixture was allowed to warm to room temperature for 3 h. The reaction was concentrated to dryness and EtOAc was added. The mixture was filtered and the filtrate was concentrated under vacuum. The residue was purified by column chromatography on silica gel using EtOAc/hexanes (0:1 to 1:4) as eluent to give the product (67a) (0.44 g, 25%) as an oil. $^1$H NMR (300 MHz, CDCl$_3$): δ 7.18 (t, J=7.7 Hz, 1H), 7.03 (d, J=7.5 Hz, 2H), 4.32 (t, J=6.3 Hz, 2H), 3.34 (s, 2H), 2.32 (s, 6H), 1.78-1.68 (m, 2H), 1.40-1.34 (m, 2H), 0.90 (s, 6H).

Step 2: Synthesis of
5-((chlorosulfonyl)oxy)-4,4-dimethylpentyl
2,6-dimethylbenzoate (67b)

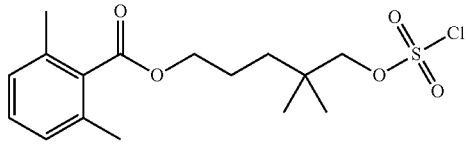 [SMILES: Cc1cccc(C)c1C(=O)OCCCC(C)(C)COS(=O)(=O)Cl]

A solution of freshly distilled sulfuryl chloride (122 µL, 1.7 mmol) in Et$_2$O was cooled to –78° C. under an atmosphere of argon. A solution of 5-hydroxy-4,4-dimethylpentyl 2,6-dimethylbenzoate (67a) (0.44 g, 1.7 mmol) and pyridine (135 μL, 1.7 mmol) in Et$_2$O was added dropwise to the sulfuryl chloride solution over the course of 15 min. The flask was rinsed with Et$_2$O (2×20 mL), and the rinse was added to the reaction mixture. The mixture was stirred at −78° C. for 10 min and then allowed to warm to room temperature and stirred for 1 h. The mixture was filtered, and the filtrate was concentrated under vacuum to afford the title compound (67b), which was used immediately in the next step without further purification. $^1$H NMR (300 MHz, CDCl$_3$): δ 7.19 (t, J=7.5 Hz, 1H), 7.03 (d, J=7.5 Hz, 2H), 4.33 (t, J=6.2 Hz, 2H), 4.20 (s, 2H), 2.32 (s, 6H), 1.81-1.71 (m, 2H), 1.51-1.45 (m, 2H), 1.04 (s, 6H).

Step 3: Synthesis of 5-(((((2S,5R)-2-carbamoyl-7-oxo-1,6-diazabicyclo[3.2.1]octan-6-yl)oxy)sulfonyl)oxy)-4,4-dimethylpentyl 2,6-dimethylbenzoate (67)

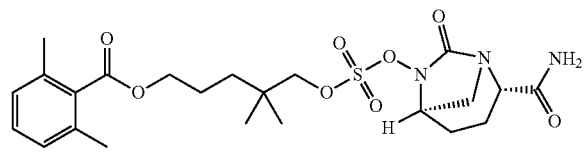

(2S,5R)-6-Hydroxy-7-oxo-1,6-diazabicyclo[3.2.1]octane-2-carboxamide (1) (0.21 g, 1.1 mmol) was dissolved in THF (9.4 mL) and HMPA (0.5 mL), and the resulting stirred solution was cooled to −78° C. under an argon atmosphere. A solution of NaHMDS, 1.0 M in THF (1.1 mL, 1.1 mmol) was added to the mixture, and the mixture stirred for 10 min. A solution of 5-((chlorosulfonyl)oxy)-4,4-dimethylpentyl 2,6-dimethylbenzoate (67b) (0.49 g, 1.4 mmol) in Et$_2$O (20 mL) was quickly added to the reaction mixture. After 10 min stirring at −78° C., the mixture was allowed to warm to room temperature and stirred for 1 h. The mixture was cooled to 0° C. and quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel using EtOAc/hexanes (0:1 to 7:3) as eluent to give the product (67) (200 mg, 32%) as a solid. LCMS: m/z=512.18 [M+H]$^+$. $^1$H NMR (300 MHz, CDCl$_3$): δ 7.19 (t, J=7.5 Hz, 1H), 7.03 (d, J=7.5 Hz, 2H), 6.45 (br. s, 1H), 5.52 (br. s, 1H), 4.54 (d, J=9.3 Hz, 1H), 4.31 (t, J=7.4 Hz, 2H), 4.23-4.17 (m, 2H), 4.03 (d, J=7.2 Hz, 1H), 3.31 (d, J=11.7 Hz, 1H), 2.99 (d, J=12.3 Hz, 1H), 2.45-2.40 (m, 1H), 2.32 (s, 6H), 2.18-2.14 (m, 1H), 1.98-1.70 (m, 4H), 1.48-1.42 (m, 2H), 1.00 (s, 6H). $^{13}$C NMR (75 MHz, CDCl$_3$): δ 170.9, 170.2, 167.1, 135.0, 134.1, 129.4, 127.7, 83.6, 65.4, 62.0, 60.2, 47.2, 34.9, 34.3, 23.7, 23.6, 23.3, 20.8, 19.9, 17.5.

Example 68

Synthesis of 5-(((((2S,5R)-2-carbamoyl-7-oxo-1,6-diazabicyclo[3.2.1]octan-6-yl)oxy)sulfonyl)oxy)-4,4-dimethylpentyl 2-methylbenzoate (68)

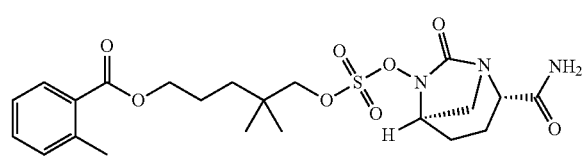

Step 1: Synthesis of 4-hydroxy-3,3-dimethylbutyl 2-methylbenzoate (68a)

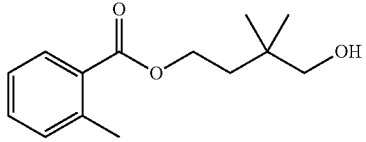 [SMILES: Cc1ccccc1C(=O)OCCC(C)(C)CO]

To a stirred solution of 2,2-dimethylbutane-1,4-diol (0.80 g, 6.8 mmol) in pyridine (5 mL) at ca. 0° C. (ice bath) under an argon atmosphere, was added toluoyl chloride (0.89 mL, 6.8 mmol) dropwise. The reaction mixture was allowed to gradually warm to room temperature and the mixture was stirred for 4 h. The mixture was concentrated under vacuum and suspended in EtOAc, and then filtered and the filter cake washed with EtOAc. The filtrate was concentrated under vacuum and the residue purified by column chromatography on silica gel using EtOAc/hexanes (0:1 to 3:7) as eluent to give the desired product (68a) (0.7 g, 44%). $^1$H NMR (300 MHz, CDCl$_3$): δ 7.88 (d, J=8.4 Hz, 1H), 7.40 (t, J=7.1 Hz, 1H), 7.26-7.24 (m, 2H), 4.38 (t, J=7.3 Hz, 2H), 3.41 (s, 3H), 2.60 (s, 3H), 1.78 (t, J=7.5 Hz, 2H), 0.98 (s, 6H).

Step 2: Synthesis of 4-((chlorosulfonyl)oxy)-3,3-dimethylbutyl 2-methylbenzoate (68b)

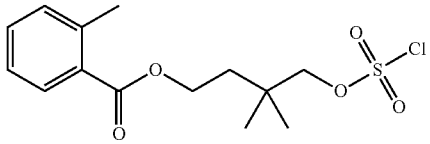 [SMILES: Cc1ccccc1C(=O)OCCC(C)(C)COS(=O)(=O)Cl]

A solution of freshly distilled sulfuryl chloride (96 μL, 1.3 mmol) in Et$_2$O (0.8 mL) was cooled to −78° C. under an atmosphere of argon. A solution of 4-hydroxy-3,3-dimethylbutyl 2-methylbenzoate (68a) (0.31 g, 1.3 mmol) and pyridine (106 μL, 1.3 mmol) in Et$_2$O (1.1 mL) was added dropwise to the sulfuryl chloride solution over the course of 15 min. The flask was rinsed with Et$_2$O (2×20 mL), which was added to the reaction mixture. The mixture was stirred at −78° C. for 10 min then allowed to warm to room temperature and stirred for 30 min. The mixture was filtered, and the product (68b) was used immediately in the next step without further purification. $^1$H NMR (300 MHz, CDCl$_3$): δ 7.89 (d, J=8.1 Hz, 1H), 7.41-7.39 (m, 1H), 7.26-7.25 (m, 2H), 4.41-4.35 (m, 2H), 4.28 (s, 2H), 2.61 (s, 3H), 1.87 (t, J=7.2 Hz, 2H), 1.13 (s, 6H).

Step 3: Synthesis of 5-(((((2S,5R)-2-carbamoyl-7-oxo-1,6-diazabicyclo[3.2.1]octan-6-yl)oxy)sulfonyl)oxy)-4,4-dimethylpentyl 2-methylbenzoate (68)

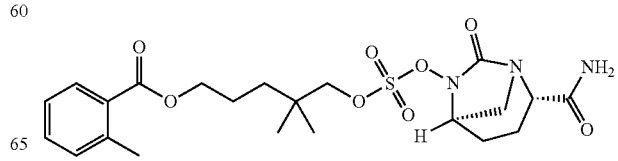

(2S,5R)-6-Hydroxy-7-oxo-1,6-diazabicyclo[3.2.1]octane-2-carboxamide (1) (0.22 g, 1.2 mmol) was dissolved in THF (10 mL) and HMPA (0.5 mL), and the resulting stirred solution was cooled to −78° C. under an atmosphere of argon. A solution of NaHMDS, 1.0 M in THF (1.2 mL, 1.2 mmol) was added to the mixture, and the mixture stirred for 10 min. A solution of 4-((chlorosulfonyl)oxy)-3,3-dimethylbutyl 2-methylbenzoate (68b) (0.42 g, 1.3 mmol) in Et₂O (20 mL) was quickly added to the reaction mixture. After 10 min stirring at −78° C., the mixture was allowed to warm to room temperature and stirred for 1 h. The mixture was cooled to 0° C. and quenched with H₂O and diluted with EtOAc. The aqueous and organic layers were separated, and the organic layer was washed with brine, dried (Na₂SO₄), and concentrated under vacuum. The residue was purified by column chromatography on silica gel using EtOAc/hexanes (0:1 to 7:3) as eluent to give the product (68) (231 mg, 40%) as a solid. LCMS: m/z=484.06 [M+1]⁺. ¹H NMR (300 MHz, CDCl₃): δ 7.90 (d, J=7.5 Hz, 1H), 7.40 (t, J=7.5 Hz, 1H), 7.26-7.24 (m, 2H), 6.44 (br. s, 1H), 5.53 (br. s, 1H), 4.60 (d, J=8.7 Hz, 1H), 4.35 (t, J=7.1 Hz, 2H), 4.28 (d, J=9.0 Hz, 1H), 4.17 (br. s, 1H), 4.03 (d, J=7.2 Hz, 1H), 3.33 (d, J=12.3 Hz, 1H), 2.99 (d, J=11.7 Hz, 1H), 2.60 (s, 3H), 2.47-2.40 (m, 1H), 2.18-2.14 (m, 1H), 1.95-1.82 (m, 4H), 1.10 (s, 6H). ¹³C NMR (75 MHz, CDCl₃): δ 171.0, 167.5, 167.1, 140.5, 132.2, 131.9, 130.7, 129.5, 125.9, 83.7, 62.0, 61.2, 60.2, 47.2, 36.9, 34.0, 24.1, 23.8, 21.9, 20.8, 17.5.

Example 69

Synthesis of 4-(((((2S,5R)-2-carbamoyl-7-oxo-1,6-diazabicyclo[3.2.1]octan-6-yl)oxy)sulfonyl)oxy)-2,2,3,3-tetramethylbutyl 3-chloro-2,6-dimethoxybenzoate (69)

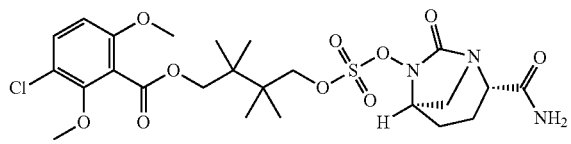 [SMILES: COc1ccc(Cl)c(OC)c1C(=O)OCC(C)(C)C(C)(C)COS(=O)(=O)ON1C(=O)N2C[C@H]1CC[C@H]2C(N)=O]

Step 1: Synthesis of 4-hydroxy-2,2,3,3-tetramethylbutyl 2,6-dimethoxybenzoate (69a)

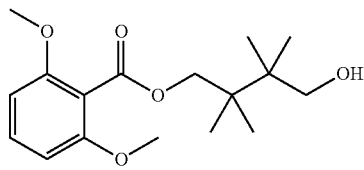 [SMILES: COc1cccc(OC)c1C(=O)OCC(C)(C)C(C)(C)CO]

To a stirred solution of 2,2,3,3-tetramethylbutane-1,4-diol (45a) (0.7 g, 4.8 mmol) in DCM (20 mL) at 0° C. under an atmosphere of argon was added 2,6-dimethoxybenzoyl chloride (80%; 0.55 g, 2.2 mmol), pyridine (0.36 mL, 4.4 mmol) and N,N-4-dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), and then extracted with DCM (twice). The combined organic layers were washed with sat. sodium bicarbonate and brine, then dried (Na₂SO₄), and concentrated under vacuum. The residue was purified by column chromatography on silica gel using EtOAc/hexanes (0:1 to 3:2) as eluent to give the product (69a) as an oil. ¹H NMR (300 MHz, CDCl₃): δ 7.29 (t, J=8.4 Hz, 1H), 6.56 (d, J=8.1 Hz, 2H), 4.24 (s, 2H), 3.81 (s, 6H), 3.49 (s, 2H), 0.98 (s, 6H), 0.92 (s, 6H).

Step 2: Synthesis of 4-((chlorosulfonyl)oxy)-2,2,3,3-tetramethylbutyl 3-chloro-2,6-dimethoxybenzoate (69b)

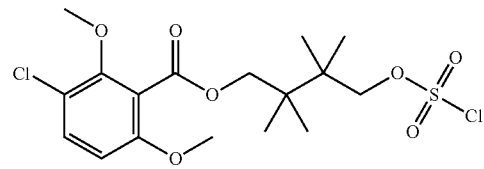 [SMILES: COc1ccc(Cl)c(OC)c1C(=O)OCC(C)(C)C(C)(C)COS(=O)(=O)Cl]

Pyridine (0.15 mL, 1.8 mmol) was added to a stirred mixture of 4-hydroxy-2,2,3,3-tetramethylbutyl propionate (69a) (0.30 g, 1.5 mmol) and Et₂O (10 mL) under an atmosphere of argon. The solution was cooled to −78° C. and sulfuryl chloride (0.15 mL, 1.8 mmol) in Et₂O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the title compound (69b) as an oil, that was used directly in the next step without further purification (yield assumed quantitative).

Step 3: Synthesis of 4-(((((2S,5R)-2-carbamoyl-7-oxo-1,6-diazabicyclo[3.2.1]octan-6-yl)oxy)sulfonyl)oxy)-2,2,3,3-tetramethylbutyl 3-chloro-2,6-dimethoxybenzoate (69)

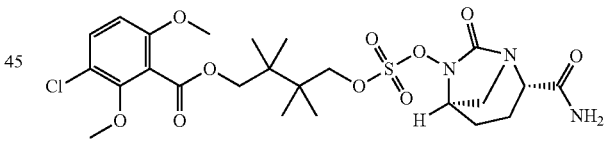

To a stirred mixture of (2S,5R)-6-hydroxy-7-oxo-1,6-diazabicyclo[3.2.1]octane-2-carboxamide (1) (235 mg, 1.3 mmol) in THF (10 mL) under an atmosphere of argon was added several drops of 1,3-dimethyltetrahydropyrimidin-2 (1H)-one. The mixture was cooled to −78° C. and stirred for 10 min, then a solution of NaHMDS, 1.0M in THF (1.4 mL, 1.4 mmol) was added dropwise. The mixture was stirred at −78° C. for 8 min, then 4-((chlorosulfonyl)oxy)-2,2,3,3-tetramethylbutyl 3-chloro-2,6-dimethoxybenzoate (69b) (0.52 g, 1.2 mmol) in THF (5 mL) was added at −78° C. The mixture was stirred at −78° C. for 10 min, then allowed to warm to room temperature and stirred for 1 h. The mixture was diluted with EtOAc and saturated sodium bicarbonate solution. The aqueous and organic layers were separated, and the organic layer was washed with water, dried (Na₂SO₄), and concentrated under vacuum. The residue was purified by column chromatography on silica gel using EtOAc/hexanes (0:1 to 1:0) as eluent to give the product (69)

as a solid. $^1$H NMR (300 MHz, CDCl$_3$): δ 7.33 (d, J=9.0 Hz, 1H), 6.65 (d, J=8.7 Hz, 1H), 6.51 (s, 1H), 5.74 (s, 1H), 4.75 (d, J=9.6 Hz, 1H), 4.44 (d, J=8.7 Hz, 1H), 4.22-4.15 (m, 3H), 4.02 (d, J=6.3 Hz, 1H), 3.88 (s, 3H), 3.81 (s, 3H), 3.31 (d, J=11.7 Hz, 1H), 2.99 (d, J=12.3 Hz, 1H), 2.43-2.39 (m, 1H), 2.16-2.12 (m, 1H), 1.91-1.80 (m, 2H), 1.05-1.01 (m, 12H). $^{13}$C NMR (75 MHz, CDCl$_3$): δ 171.1, 167.1, 165.6, 156.0, 153.6, 131.6, 120.1, 119.5, 107.8, 82.4, 71.2, 62.2, 61.9, 60.2, 56.2, 47.2, 39.0, 38.7, 20.8, 20.7, 20.3, 20.2, 17.5.

Example 70

Synthesis of 2-((((((2S,5R)-2-carbamoyl-7-oxo-1,6-diazabicyclo[3.2.1]octan-6-yl)oxy)sulfonyl)oxy)methyl)-2-methylpropane-1,3-diyl dibenzoate (70)

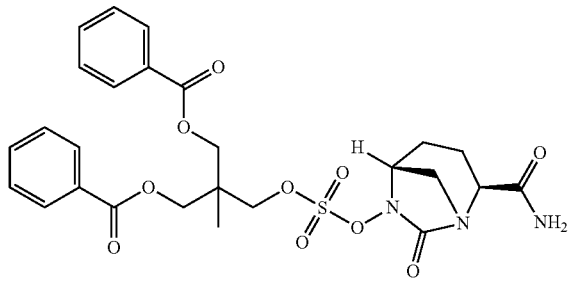 [SMILES: CC(COC(=O)c1ccccc1)(COC(=O)c1ccccc1)COS(=O)(=O)ON1C(=O)N2C[C@H]1CC[C@H]2C(N)=O]

Step 1: Reaction to Produce 2-(hydroxymethyl)-2-methylpropane-1,3-diyl dibenzoate (70a)

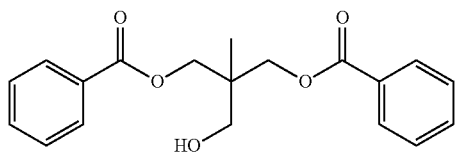 [SMILES: CC(CO)(COC(=O)c1ccccc1)COC(=O)c1ccccc1]

Benzoyl chloride (2.46 mL, 20.0 mmol) was added dropwise to a mixture of 2-(hydroxymethyl)-2-methylpropane-1,3-diol (1.2 g, 10.0 mmol), pyridine (2.02 mL, 25.0 mmol), and N,N-4-dimethylaminopyridine (0.06 g, 0.4 mmol) in DCM (30 mL) at room temperature. After stirring at room temperature overnight, the organic phase was washed with 1 M HCl, water, and brine, dried (MgSO$_4$), and concentrated under vacuum. The residue was purified by column chromatography on silica gel using EtOAc/hexanes (0:1 to 2:3) as eluent to give the product (70a) (1.3 g, 40%) as an oil. $^1$H NMR (300 MHz, CDCl$_3$): δ 8.06-8.02 (m, 4H), 7.62-7.56 (m, 2H), 7.49-7.42 (m, 4H), 4.39 (s, 2H), 4.38 (s, 2H), 3.59 (s, 2H), 1.16 (s, 3H).

Step 2: Synthesis of 2-(((chlorosulfonyl)oxy)methyl)-2-methylpropane-1,3-diyl dibenzoate (70b)

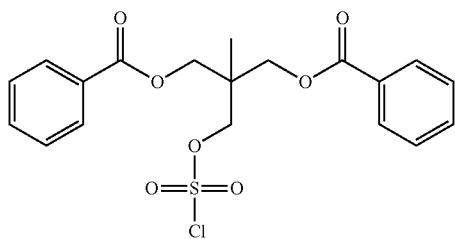 [SMILES: CC(COC(=O)c1ccccc1)(COC(=O)c1ccccc1)COS(=O)(=O)Cl]

A solution of freshly distilled sulfuryl chloride (0.3 mL, 3.7 mmol) in Et$_2$O (5 mL) was cooled to −78° C. under an atmosphere of argon. A solution of 2-(hydroxymethyl)-2-methylpropane-1,3-diyl dibenzoate (70a) (800 mg, 2.4 mmol) and pyridine (0.32 mL, 3.9 mmol) in Et$_2$O (5 mL) was added dropwise to the sulfuryl chloride solution over the course of 5 min. The flask was rinsed with Et$_2$O (3 mL), which was also added to the mixture. The mixture was stirred at −78° C. for 1 h, and then allowed to warm to room temperature. The precipitate was filtered (quickly) and the filter cake rinsed with Et$_2$O (12 mL). The filtrate was concentrated under vacuum at room temperature to afford the title compound (70b) as an oil which was used immediately in the next step without further purification.

Step 3: Synthesis of 2-((((((2S,5R)-2-carbamoyl-7-oxo-1,6-diazabicyclo[3.2.1]octan-6-yl)oxy)sulfonyl)oxy)methyl)-2-methylpropane-1,3-diyl dibenzoate (70)

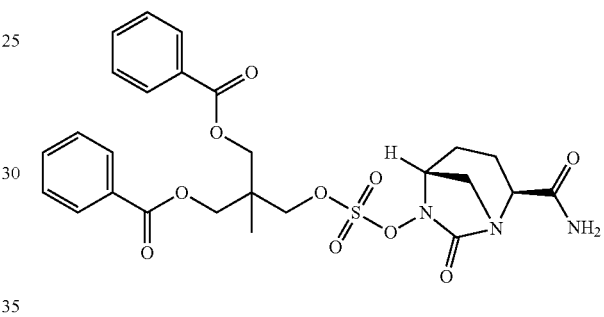

(2S,5R)-6-Hydroxy-7-oxo-1,6-diazabicyclo[3.2.1]octane-2-carboxamide (1) (400 mg, 2.2 mmol) was dissolved in THF (10 mL) and HMPA (1.1 mL), and the resulting solution was cooled to −78° C. under an argon atmosphere. A 1.0 M NaHMDS solution in THF (2.3 mL) was added dropwise to the cooled solution and stirred for 10 min. 2-(((Chlorosulfonyl)oxy)methyl)-2-methylpropane-1,3-diyl dibenzoate (70b) (922 mg, 2.2 mmol) was dissolved in THF (8 mL) and was added quickly to the reaction mixture. After stirring at −78° C. for 10 min, the reaction mixture was allowed to warm to room temperature. After stirring at room temperature for 2 h, EtOAc (400 mL) and saturated aqueous NaHCO$_3$ (40 mL) and H$_2$O (40 mL) were added. The aqueous and organic layers were separated, and the organic layer washed with saturated aqueous NaHCO$_3$ (60 mL), water (3×50 mL), brine (60 mL), then dried (Na$_2$SO$_4$), and concentrated under vacuum. The residue was purified by column chromatography on silica gel using EtOAc/hexanes (0:1 to 1:9) as eluent to give the product (70) (186 mg, 15%) as an oil. LC-MS: m/z=576 [M+H]$^+$. $^1$H NMR (300 MHz, CDCl$_3$): δ 8.06-8.03 (m, 4H), 7.60-7.55 (m, 2H), 7.44-7.26 (m, 4H), 6.41 (s, 1H), 5.49 (s, 1H), 4.97 (d, J=9.3 Hz, 1H), 4.68 (d, J=9.3 Hz, 1H), 4.43-4.39 (m, 4H), 4.13 (m, 1H), 4.01-3.99 (m, 1H), 3.13 (m, 1H), 2.95-2.91 (m, 1H), 2.45-2.40 (m, 1H), 2.20-2.08 (m, 1H), 1.93-1.76 (m, 2H), 1.12 (s, 3H). $^{13}$C NMR (75 MHz, CDCl$_3$): δ 170.8, 167.1, 166.1, 133.3, 129.8, 129.7, 128.5, 77.2, 66.1, 65.9, 61.8, 60.1, 46.9, 39.4, 20.6, 17.4, 16.9.

Example 71

Synthesis of 2-((((((2S,5R)-2-carbamoyl-7-oxo-1,6-diazabicyclo[3.2.1]octan-6-yl)oxy)sulfonyl)oxy)methyl)-2-methylpropane-1,3-diyl diacetate (71)

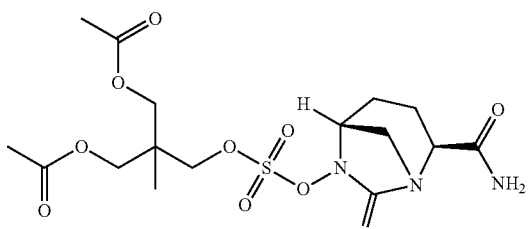

Step 1: Synthesis of 2-(hydroxymethyl)-2-methylpropane-1,3-diyl diacetate (71a)

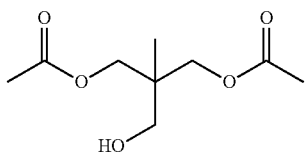

Acetic anhydride (3.46 mL, 36.6 mmol) was added dropwise to a mixture of 2-(hydroxymethyl)-2-methylpropane-1,3-diol (2.2 g, 18.0 mmol), pyridine (12 mL, 25.0 mmol), and N,N-4-dimethylaminopyridine (0.05 g) at room temperature. After stirring at room temperature overnight, the mixture was concentrated under vacuum. The mixture was suspended in EtOAc (100 mL), and $H_2O$ (20 mL) was slowly added at 0° C. The aqueous and organic layers were partitioned, and the organic layer was washed with and brine, dried ($Na_2SO_4$), then concentrated under vacuum. The residue was purified by column chromatography on silica gel using EtOAc/hexanes (0:1 to 3:2) as eluent to give the product (71a) (1.0 g, 26%). $^1H$ NMR (300 MHz, $CDCl_3$): δ 4.02 (s, 4H), 3.41 (s, 2H), 2.08 (s, 6H), 0.96 (s, 3H).

Step 2: Synthesis of 2-(((chlorosulfonyl)oxy)methyl)-2-methylpropane-1,3-diyl diacetate (71b)

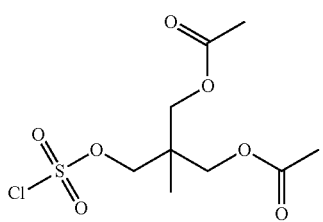 [SMILES: CC(=O)OCC(C)(COC(C)=O)COS(=O)(=O)Cl]

A solution of freshly distilled sulfuryl chloride (0.33 mL, 4.0 mmol) in $Et_2O$ (4 mL) was cooled to −78° C. under an atmosphere of argon. A solution of 2-(hydroxymethyl)-2-methylpropane-1,3-diyl diacetate (71a) (550 mg, 2.7 mmol) and pyridine (0.35 mL, 4.3 mmol) in $Et_2O$ (4 mL) was added dropwise to the sulfuryl chloride solution over the course of 5 min. The flask was rinsed with $Et_2O$ (5 mL), which was also added to the mixture. The mixture was stirred at −78° C. for 1 h, then allowed to warm to room temperature. The precipitate was filtered (quickly) and the filter cake rinsed with $Et_2O$ (12 mL). The filtrate was concentrated under vacuum at room temperature to afford the title compound (71b) as an oil which was used immediately for the next step without further purification.

Step 3: Synthesis of 2-((((((2S,5R)-2-carbamoyl-7-oxo-1,6-diazabicyclo[3.2.1]octan-6-yl)oxy)sulfonyl)oxy)methyl)-2-methylpropane-1,3-diyl diacetate (71)

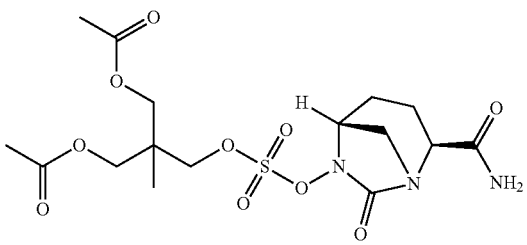 [SMILES: CC(=O)OCC(C)(COC(C)=O)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (430 mg, 2.3 mmol) was dissolved in THF (8 mL) and HMPA (0.8 mL), and the resulting solution was cooled to −78° C. under an atmosphere of argon. NaHMDS, 1.0 M in THF (2.4 mL, 2.4 mmol) was added dropwise to the cooled solution and stirred for 10 min. 2-(((Chlorosulfonyl)oxy)methyl)-2-methylpropane-1,3-diyl diacetate (71b) (703 mg, 2.3 mmol) was dissolved in THF (8 mL) and was added quickly to the reaction mixture. After stirring at −78° C. for 10 min, the reaction mixture was allowed to warm to room temperature. After stirring at room temperature for 2 h, EtOAc (400 mL) and saturated aqueous $NaHCO_3$ (40 mL) and $H_2O$ (40 mL) were added. The aqueous and organic layers were separated, and the organic layer washed with saturated aqueous $NaHCO_3$ (60 mL), $H_2O$ (3×50 mL), brine (60 mL), and then dried ($Na_2SO_4$), and concentrated under vacuum. The residue was purified by column chromatography on silica gel using EtOAc/hexanes (0:1 to 1:9) as eluent to give the product (71) (198 mg, 19%) as an oil. LC-MS: m/z=452 [M+H]$^+$. $^1H$ NMR (300 MHz, $CDCl_3$): δ 6.50 (s, 1H), 5.68 (s, 1H), 4.72 (d, J=9.3 Hz, 1H), 4.46 (d, J=9.3 Hz, 1H), 4.16 (m, 1H), 4.12-4.08 (m, 4H), 3.36-3.32 (m, 1H), 3.04-3.00 (m, 1H), 2.45-2.40 (m, 1H), 2.20-2.12 (m, 1H), 2.09 (s, 6H), 1.91-1.76 (m, 2H), 1.11 (s, 3H). $^{13}C$ NMR (75 MHz, $CDCl_3$): δ 171.1, 170.8, 170.7, 167.1, 76.9, 65.2, 61.9, 60.2, 47.1, 38.8, 20.8, 20.7, 17.5, 16.6.

Example 72

Synthesis of 5-(((((2S,5R)-2-carbamoyl-7-oxo-1,6-diazabicyclo[3.2.1]octan-6-yl)oxy)sulfonyl)oxy)-2,2,4,4-tetramethylpentyl 2,6-dimethoxybenzoate (72)

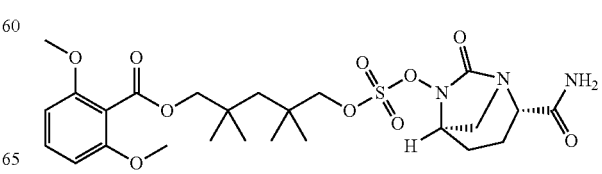

Step 1: Synthesis of 5-hydroxy-2,2,4,4-tetramethylpentyl 2,6-dimethoxybenzoate (72a)

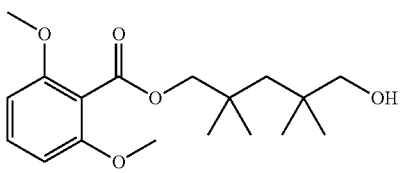 [SMILES: COc1cccc(OC)c1C(=O)OCC(C)(C)CC(C)(C)CO]

To a stirred solution of 2,2,4,4-tetramethylpentane-1,5-diol (39c) (0.64 g, 4.0 mmol) and pyridine (0.32 mL, 4.0 mmol) in DCM (27 mL) was added 2,6-dimethoxybenzoyl chloride (80%; 1.0 g, 4.0 mmol) in DCM (10 mL) dropwise over the course of 30 min at 0° C. (ice bath) under an atmosphere of argon. The reaction mixture was allowed to warm to room temperature and stirred overnight. The mixture was diluted with $H_2O$ (30 mL), and the layers were separated. The aqueous layer was extracted with DCM (2×30 mL), and the combined organic layers were washed with brine (30 mL), dried ($Na_2SO_4$), and concentrated under vacuum. The residue was purified by column chromatography on silica gel using EtOAc/hexanes (0:1 to 2:98) as eluent to give the product (72a) (927 mg, 71%) as an oil. The compound was contaminated, presumably with the diacylated byproduct. The material was used in the next step without further purification.

Step 2: Synthesis of 5-((chlorosulfonyl)oxy)-2,2,4,4-tetramethylpentyl 2,6-dimethoxybenzoate (72b)

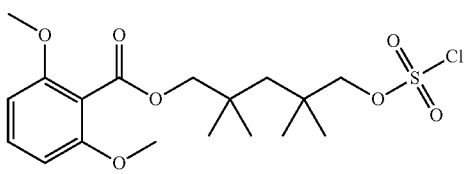 [SMILES: COc1cccc(OC)c1C(=O)OCC(C)(C)CC(C)(C)COS(=O)(=O)Cl]

A solution of sulfuryl chloride (0.21 mL, 2.8 mmol) in $Et_2O$ (13 mL) was cooled to −78° C. under an argon atmosphere. A solution of 5-hydroxy-2,2,4,4-tetramethylpentyl 2,6-dimethoxybenzoate (72a) (921 mg, 2.8 mmol) and pyridine (0.23 mL, 2.8 mmol) in $Et_2O$ (13 mL) was added dropwise to the sulfuryl chloride solution over the course of 10 min. The mixture was stirred at −78° C. for 5 h. The mixture was filtered and the filtrate stored to give a solution of the product (72b) in $Et_2O$ (ca. 20 mL). The yield was assumed to be quantitative. This mixture was used in the next step without further purification.

Step 3: Synthesis of 5-(((((2S,5R)-2-carbamoyl-7-oxo-1,6-diazabicyclo[3.2.1]octan-6-yl)oxy)sulfonyl)oxy)-2,2,4,4-tetramethylpentyl 2,6-dimethoxybenzoate (72)

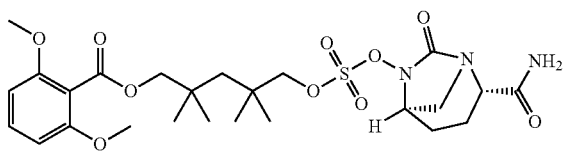 [SMILES: COc1cccc(OC)c1C(=O)OCC(C)(C)CC(C)(C)COS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (525 mg, 2.8 mmol) was dissolved in THF (33 mL) and 1,3-dimethyltetrahydropyrimidin-2(1H)-one (4 mL) and the resulting solution was cooled to −78° C. under an atmosphere of argon. A solution of NaHMDS, 1.0 M in THF (2.8 mL, 2.8 mmol) was added dropwise to the cooled solution and stirred for 90 min. A solution of 5-((chlorosulfonyl)oxy)-2,2,4,4-tetramethylpentyl 2,6-dimethoxybenzoate (72b) (1.2 g, 2.8 mmol) in $Et_2O$ (ca. 20 mL) was added to the reaction mixture (cannula). After stirring for 10 min the mixture was warmed to room temperature, and stirred for 2 h. The mixture was quenched with a saturated aqueous solution of sodium bicarbonate (40 mL) and extracted with EtOAc (40 mL). The organic layer was washed with $H_2O$ (3×40 mL), brine (40 mL), dried ($Na_2SO_4$), and concentrated under vacuum. The residue was purified by column chromatography on silica gel using EtOAc/hexanes (2:3 to 9:1) as eluent to give the product (72) (726 mg, 43%) as a solid. LC-MS: m/z=572.08 [M+H]$^+$. $^1$H NMR (300 MHz, CDCl$_3$): δ 7.32-7.26 (m, 1H), 6.56 (d, J=8.1 Hz, 2H), 6.52 (s, 1H), 5.64 (s, 1H), 4.53 (d, J=8.7 Hz, 1H), 4.24 (d, J=9.0 Hz, 1H), 4.17 (s, 1H), 4.07-4.04 (m, 3H), 3.81 (s, 6H), 3.34-3.30 (m, 1H), 3.00 (d, J=12.3 Hz, 1H), 2.47-2.40 (m, 1H), 2.14 (m, 1H), 2.05-1.84 (m, 2H), 1.48 (s, 2H), 1.11 (s, 6H), 1.10 (s, 6H). $^{13}$C NMR (75 MHz, CDCl$_3$): δ 171.0, 167.0, 166.8, 157.5, 131.1, 113.3, 103.9, 85.2, 74.2, 61.9, 60.2, 56.0, 47.2, 46.1, 36.0, 35.7, 26.4, 26.3, 25.9, 25.2, 20.8, 17.5.

Example 73

Synthesis of ethyl 3-(((((2S,5R)-2-carbamoyl-7-oxo-1,6-diazabicyclo[3.2.1]octan-6-yl)oxy)sulfonyl)oxy)-2,2-dimethylbutanoate (73)

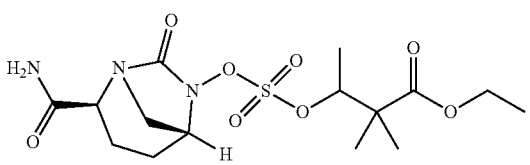 [SMILES: CCOC(=O)C(C)(C)C(C)OS(=O)(=O)ON1C(=O)N2C[C@H]1CC[C@H]2C(N)=O]

Step 1: Synthesis of R/S-ethyl 3-((chlorosulfonyl)oxy)-2,2-dimethylbutanoate (73a)

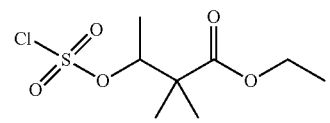

A solution of freshly distilled sulfuryl chloride (148 μL, 2.0 mmol) in $Et_2O$ (0.2 mL) was cooled to −78° C. under an argon atmosphere. A solution of ethyl 3-hydroxy-2,2-dimethylbutanoate (prepared according to *J. Med. Chem.* 1987, 30, 366-374 and *Ad. Synth. Catal.* 2009, 351, 3128-3132) (324 mg, 2.0 mmol) and pyridine (164 μL, 2.0 mmol) in $Et_2O$ (0.2 mL) was added dropwise to the sulfuryl chloride solution over the course of 15 min. The flask was rinsed with $Et_2O$ (2×20 mL), which was added to the reaction mixture. The mixture was stirred at −78° C. for 30 min. The mixture was filtered and the product (73a) was used directly in the next step with an assumed quantitative yield. $^1$H NMR (300 MHz, CDCl$_3$): δ 5.34-5.29 (m, 1H), 4.22-4.14 (m, 2H), 1.55-1.52 (m, 3H), 1.35-1.08 (m, 9H).

Step 2: Synthesis of ethyl 3-(((((2S,5R)-2-carbamoyl-7-oxo-1,6-diazabicyclo[3.2.1]octan-6-yl)oxy)sulfonyl)oxy)-2,2-dimethylbutanoate (73)

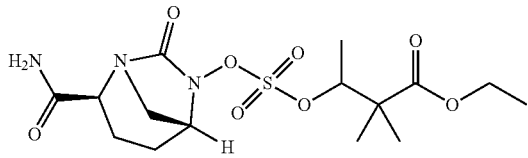 [SMILES: CCOC(=O)C(C)(C)C(C)OS(=O)(=O)ON1C(=O)N2C[C@H]1CC[C@H]2C(N)=O]

(2S,5R)-6-Hydroxy-7-oxo-1,6-diazabicyclo[3.2.1]octane-2-carboxamide (1) (0.22 g, 1.2 mmol) was dissolved in THF (10 mL) and HMPA (0.5 mL), and the resulting stirred solution was cooled to −78° C. under an atmosphere of argon. A solution of NaHMDS, 1.0 M in THF (1.2 mL, 1.2 mmol) was added to the mixture, and the mixture stirred for 10 min. A solution of ethyl 3-((chlorosulfonyl)oxy)-2,2-dimethylbutanoate (73a) (0.51 g, 2.0 mmol) in Et$_2$O (20 mL) was added quickly to the reaction mixture. After 10 min stirring at −78° C., the mixture was allowed to warm to room temperature and stirred for 1 h. The mixture was cooled to 0° C. and quenched with H$_2$O and diluted with EtOAc. The aqueous and organic layers were separated, and the organic layer was washed with brine, dried (Na$_2$SO$_4$), and concentrated under vacuum. The residue was purified by column chromatography on silica gel using EtOAc/hexanes (0:1 to 7:3) as eluent to give the product (73) (70 mg, 15%) as a solid. $^1$H NMR (300 MHz, CDCl$_3$): δ 6.51 (br. s, 1H), 5.66 (br. s, 1H), 5.32 (q, J=6.3 Hz, 1H), 4.21-4.14 (m, 3H), 4.07 (t, J=6.3 Hz, 1H), 3.35-3.31 (m, 1H), 3.04-2.98 (m, 1H), 2.44-2.39 (m, 1H), 2.17-2.09 (m, 1H), 1.95-1.83 (m, 2H), 1.58-1.48 (m, 3H), 1.31-1.20 (m, 9H). $^{13}$C NMR (75 MHz, CDCl$_3$): δ 174.5, 174.4, 171.2, 171.1, 166.8, 166.6, 91.1, 90.6, 62.0, 62.0, 61.5, 61.5, 60.2, 47.2, 47.2, 47.1, 21.2, 20.9, 20.8, 20.8, 20.6, 20.3, 17.5, 17.5, 15.9, 15.5, 14.2 (Note: $^{13}$C NMR showed some duplicated peaks, due to a mixture of diastereomers).

Example 74

Synthesis of (2S,5R)-2-carbamoyl-7-oxo-1,6-diazabicyclo[3.2.1]octan-6-yl ((3,5,5-trimethyl-2-oxotetrahydrofuran-3-yl)methyl) sulfate (74)

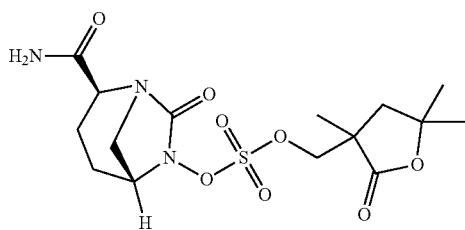 [SMILES: CC1(C)CC(C)(COS(=O)(=O)ON2C(=O)N3C[C@H]2CC[C@H]3C(N)=O)C(=O)O1]

Step 1: Synthesis of 3,5,5-trimethyldihydrofuran-2(3H)-one (74a)

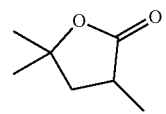

5,5-Dimethyldihydrofuran-2(3H)-one (4.7 g, 41.2 mmol) was dissolved in THF (94 mL) and the mixture was cooled to −78° C. under an atmosphere of argon. A solution of lithium diisopropylamide, 2.0 M solution in THF (22.6 mL, 45.2 mmol) was added dropwise over 10 min. The reaction was stirred at −78° C. for 2 h, and then neat MeI (2.6 mL, 41.6 mmol) was added to the reaction over 5 min. The reaction was stirred at −78° C. for 45 min, and then the mixture was allowed to warm to room temperature and stirred for 16 h. The reaction was quenched with saturated NH$_4$Cl (25 mL) and the mixture concentrated to remove THF. The aqueous residue was diluted with H$_2$O to dissolve solid and then extracted with ethyl acetate (3×40 mL). The combined organic layer was concentrated under vacuum, and the residue was purified by column chromatography on silica gel using EtOAc/hexanes (0:1 to 2:3) as eluent to provide a liquid which solidified on standing. This solid was purified further via Kugelrohr distillation to give the product (74a) (3.2 g) as an oil. $^1$H NMR (300 MHz, CDCl$_3$): δ 2.78-2.87 (m, 1H), 2.33 (dd, J=9.3, 12.3 Hz, 1H), 1.71 (t, J=12.3 Hz, 1H), 1.45 (s, 3H), 1.38 (s, 3H), 1.29 (d, J=6.9 Hz, 3H).

Step 2: Synthesis of 3-((benzyloxy)methyl)-3,5,5-trimethyldihydrofuran-2(3H)-one (74b)

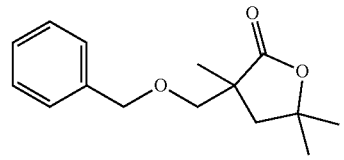 [SMILES: CC1(C)CC(C)(COCc2ccccc2)C(=O)O1]

3,5,5-Trimethyldihydrofuran-2(3H)-one (74a) (3.2 g, 25.0 mmol) was dissolved in THF (60 mL) and the mixture was cooled to −78° C. under an atmosphere of argon. A solution of lithium diisopropylamide, 2.0 M in THF (13.7 mL, 27.5 mmol) was added dropwise over 10 min. The mixture was stirred at −78° C. for 30 min, then neat benzyl chloromethyl ether (90%; 4.2 mL, 27.5 mmol) was added over 5 min. The mixture was allowed to warm to room temperature and was stirred for 16 h. Saturated NH$_4$Cl (10 mL) and H$_2$O (10 mL) was added and the solvent was removed under vacuum. The residue was extracted with EtOAc (2×75 mL) and the combined organic layers were washed with brine (2×75 mL), dried (Na$_2$SO$_4$), filtered and concentrated under vacuum (5.8 g). The residue was purified by column chromatography on silica gel using EtOAc/hexanes (0:1 to 2:3) as eluent to give the product (2.27 g) and impure fractions (1.35 g). The impure fractions were re-purified by column chromatography on silica gel using EtOAc/hexanes (0:1 to 1:4) as eluent to give additional pure product (74b) (1.39 g). The product (3.66 g) was an oil. $^1$H NMR (300 MHz, CDCl$_3$): δ 7.28-7.34 (m, 5H), 4.62 (dd, J=11.7, 35.1 Hz, 2H), 3.61 (d, J=11.7 Hz, 1H), 3.32 (d, J=11.7 Hz, 1H), 2.48 (d, J=12.9 Hz, 1H), 1.89 (d, J=12.9 Hz, 1H), 1.45 (d, J=6.9 Hz, 6H), 1.26 (s, 3H).

Step 3: Synthesis of 3-(hydroxymethyl)-3,5,5-trimethyldihydrofuran-2(3H)-one (74c)

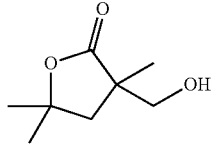

3-((Benzyloxy)methyl)-3,5,5-trimethyldihydrofuran-2(3H)-one (74b) (1.8 g, 7.2 mmol) was dissolved in 2-propanol (60 mL) and the solution was degassed with argon. Solid 10.0% palladium on carbon (0.31 g, 0.3 mmol) was added to the flask. The flask was sealed and vacuum degassed, and then back flushed with hydrogen (3 times). The reaction was stirred for 6 h. The suspension was filtered through Celite® and the filter cake washed with 2-propanol (15 mL). The filtrate was concentrated under vacuum to provide the product (74c) as a crude oil. $^1$H NMR (300 MHz, CDCl$_3$): δ 3.75 (dd, J=6.9, 11.1 Hz, 1H), 3.51 (dd, J=5.7, 11.1 Hz, 1H), 2.33 (d, J=12.9 Hz, 1H), 2.23 (t, J=6 Hz, 1H), 1.94 (d, J=12.9 Hz, 1H), 1.48 (d, J=6.9 Hz, 6H), 1.32 (s, 3H).

Step 4: Synthesis of (3,5,5-trimethyl-2-oxotetrahydrofuran-3-yl)methyl sulfochloridate (74d)

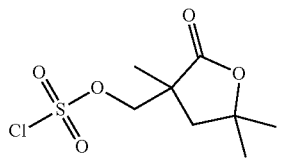

A solution of 3-(hydroxymethyl)-3,5,5-trimethyldihydrofuran-2(3H)-one (74c) (0.50 g, 3.2 mmol) and pyridine (0.28 mL, 3.5 mmol) in Et$_2$O (10 mL) was cooled to –78° C. under an atmosphere of argon. Neat sulfuryl chloride (0.28 mL, 3.5 mmol) was added dropwise to the above solution via syringe. The mixture was stirred at –78° C. for 10 min, then the flask was warmed to room temperature and stirred for 1 h (monitored by TLC 30% EA/hexanes). A precipitate formed to give a thick suspension. The suspension was filtered through a 0.45-μM Teflon® filter and the filter cake rinsed with fresh Et$_2$O (2×5 mL). An aliquot (0.5 mL) was taken and concentrated and an NMR was obtained for the mixture. The remaining solution containing the product (74d) was used directly in the next step. $^1$H NMR (300 MHz, CDCl$_3$): δ 4.60 (d, J=9.3 Hz, 1H), 4.36 (d, J=9.3 Hz, 1H), 2.37 (d, J=14.1 Hz, 1H), 2.09 (d, J=13.5 Hz, 1H), 1.51 (d, J=8.4 Hz, 6H), 1.44 (s, 3H).

Step 5: Synthesis of (2S,5R)-2-carbamoyl-7-oxo-1,6-diazabicyclo[3.2.1]octan-6-yl ((3,5,5-trimethyl-2-oxotetrahydrofuran-3-yl)methyl) sulfate (74)

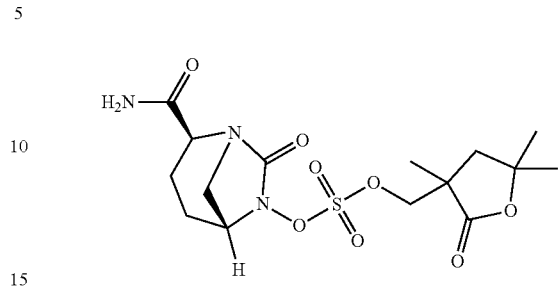

(2S,5R)-6-Hydroxy-7-oxo-1,6-diazabicyclo[3.2.1]octane-2-carboxamide (1) (0.64 g, 3.5 mmol) was dissolved in THF (30 mL) and 1,3-dimethyltetrahydropyrimidin-2(1H)-one (1.4 mL), and the resulting solution was cooled to –78° C. under an argon atmosphere. NaHMDS, 1.0 M solution in THF (3.5 mL, 3.5 mmol) was added dropwise to the cooled solution and the mixture stirred for 1 h. A solution of (3,5,5-trimethyl-2-oxotetrahydrofuran-3-yl)methyl sulfochloridate (74d) (0.81 g, 3.2 mmol) in Et$_2$O from the previous reaction was added quickly to the reaction mixture. The mixture was allowed to warm to room temperature and stirred overnight. Brine (100 mL) and EtOAc (100 mL) were added, and the aqueous and organic layers were separated. The aqueous layer was extracted with EtOAc (2×100 mL) and the combined organic layers were washed with brine (3×100 mL), dried (Na$_2$SO$_4$), and concentrated under vacuum. The residue was purified by column chromatography on silica gel using EtOAc/hexanes (1:4 to 1:0) as eluent to give a solid (0.42 g). The solid was triturated with Et$_2$O (100 mL) for 16 h, filtered and the filter cake washed with fresh Et$_2$O (3×20 mL) to give the product (74) (0.28 g) as a solid. LC-MS: m/z=406 [M+H]$^+$. $^1$H NMR (300 MHz, CDCl$_3$): δ, 6.55 (br. d, J=44.7 Hz, 1H), 5.82 (br. s, 1H), 4.86 (dd, J=9.3, 63.6 Hz, 1H), 4.55 (dd, J=9.3, 46.2 Hz, 1H), 4.03-4.16 (m, 2H), 3.30-3.35 (m, 1H), 3.06 (dd, J=4.8, 12.3 Hz, 1H), 2.38-2.45 (m, 2H), 2.10-2.20 (m, 1H), 1.8-2.04 (m, 3H), 1.48 (s, 3H), 1.477 (d, J=6.6 Hz, 3H), 1.40 (d, J=4.2 Hz, 3H). $^{13}$C NMR (75 MHz, CDCl$_3$): δ 177.3, 177.0, 170.9, 170.8, 167.3, 167.0, 82.0, 81.9, 78.6, 77.8, 61.9, 60.2, 60.2, 47.1, 46.9, 45.8, 45.7, 43.6, 43.2, 30.1, 29.8, 29.7, 22.5, 20.7, 20.7, 17.4 (Note: $^{13}$C NMR showed some duplicated peaks, due to a mixture of diastereomers).

Example 75

Synthesis of ethyl 3-(((((2S,5R)-2-carbamoyl-3-methyl-7-oxo-1,6-diazabicyclo[3.2.1]oct-3-en-6-yl)oxy)sulfonyl)oxy)-2,2-dimethylpropanoate (75)

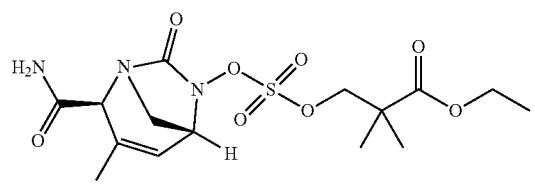 [SMILES: CCOC(=O)C(C)(C)COS(=O)(=O)ON1C(=O)N2C[C@H]1C=C(C)[C@H]2C(N)=O]

(2S,5R)-6-(Benzyloxy)-3-methyl-7-oxo-1,6-diazabicyclo[3.2.1]oct-3-ene-2-carboxamide (1) (3.6 mg, 0.01 mmol)

was dissolved in a mixed solvent (EtOAc/H$_2$O/EtOH: 0.22/ 0.34/0.11 mL), to which was added Et$_3$N (0.25 μL, 0.002 mmol) and Pd/C (dry, 10%; 1.3 mg, 20 mol %) under N$_2$ at room temperature. A hydrogen balloon was placed on the reaction flask to replace nitrogen. The reaction mixture was degassed under vacuum and recharged with hydrogen (3 times). The mixture was stirred at room temperature for 5 h and monitored by LCMS. When the reaction was complete the mixture was diluted with EtOAc (2 mL) and washed with brine. The organic phase was isolated and dried (Na$_2$SO$_4$), filtered and concentrated under vacuum. The residue (4.3 mg, 0.02 mmol) was dissolved in THF (0.4 mL) and cooled to −78° C. NaHMDS (1M in THF; 21.3 μL, 0.02 mmol) was added dropwise. The reaction mixture was stirred at −78° C. for 20 min, and then ethyl 3-((chlorosulfonyl)oxy)-2,2-dimethylpropanoate (7.8 mg, 0.03 mmol) was added. The reaction was stirred at −78° C. for 20 min and then slowly warmed up to room temperature and stirred overnight (the reaction was monitored with LCMS). After the reaction was complete, EtOAc (5 mL) was added and the organic layer washed with saturated NaHCO$_3$, followed by brine. The organic phase was isolated and dried (Na$_2$SO$_4$), and the product (75) concentrated under vacuum. LC/MS: m/z=406 [M+H]$^+$ Example 76

Oral Bioavailability in Rats

A pharmacokinetic (PK) study was performed in three male Sprague-Dawley (SD) rats following intravenous (IV) and oral (PO) administrations of avibactam at 2 mg/kg and test compounds at 10 mg/kg, respectively and avibactam measured in plasma.

Avibactam, was dissolved in phosphate buffered saline (PBS) (pH 7.5) at 0.4 mg/mL for intravenous (IV) injection. Compounds for oral administration were formulated in 10% ethanol/40% polyethylene glycol (PEG) 400/50% water for injection (WFI) (pH 6.5) at 1 mg/mL. The dosing volumes were 5 mL/kg for IV and 10 mL/kg for PO. All aspects of this work including housing, experimentation, and animal disposal were performed in general accordance with the "Guide for the Care and Use of Laboratory Animals: Eighth Edition" (National Academies Press, Washington, D.C., 2011); and Suckow et al., Ed. The Laboratory Rat. 2nd Edition. Academic Press. New York. 2005. Animals had access to standard lab diet and autoclaved tap water ad libitum.

Blood aliquots (300 μL to 400 μL) were collected from jugular vein-catheterized rats into tubes coated with lithium heparin at various times. The tubes were mixed gently and kept on ice and then centrifuged at 2,500 rpm for 15 min at 4° C., within 1 h after collection. For animals in the control groups, blood was collected by cardiac puncture and the plasma was harvested and kept frozen at −70° C. until further analysis. Beaudoin et al., Bioanalytical method validation for the simultaneous determination of ceftazidime and avibactam in rat plasma. *Bioanalysis*. 2016 8:111-22.

Plasma samples were processed using acetonitrile precipitation and analyzed by LC-MS/MS. A plasma calibration curve was generated with aliquots of drug-free plasma were spiked with the test substance at the specified concentration levels. The spiked plasma samples were processed together with the unknown plasma samples using the same procedure. The processed plasma samples were stored at −70° C. until receiving LC-MS/MS analysis, at which time peak areas were recorded, and the concentrations of the test substance in the unknown plasma samples were determined using the respective calibration curve. The reportable linear range of the assay was determined, along with the lower limit of quantitation (LLQ). Plots of plasma concentration of compound versus time are constructed. The pharmacokinetic parameters of compound after IV and PO dosing (AUC$_{last}$, AUC$_{INF}$, T$_{1/2}$, T$_{max}$, and C$_{max}$) are obtained from the non-compartmental analysis (NCA) of the plasma data using WinNonlin. WinNonlin® Certara L.P. Pharsight, St. Louis, Mo.

In these tests, avibactam exhibited an oral bioavailability (% F) of 1.2%, and compounds (3), (4), (10), (11), (12), (13), (14), (15), (16), (17), (18), and (19) exhibited an oral bioavailability (% F) greater than 10%. Also, compounds (36), (37), (42), (53), (57), (58), and (59) exhibited an oral bioavailability (% F) greater than 10%.

In these tests, relebactam exhibited an oral bioavailability (% F) of 1.8%, and compounds (20), (22), (23), and (25) exhibited an oral bioavailability (% F) greater than 5%.

Example 77

Minimum Inhibitory Concentration

Minimum inhibitor concentration (MIC) values of the investigational monobactams and β-lactamase inhibitors were determined by broth microdilution susceptibility testing conducted in accordance with guidelines from the Clinical and Laboratory Standards Institute (Clinical and Laboratory Standards Institute (CLSI). Methods for Dilution Antimicrobial Susceptibility Tests for Bacteria That Grow Aerobically; Approved Standard-Tenth Edition. CLSI document M07-A10. CLSI, 950 West Valley Road, Suite 2500, Wayne, Pa. 19087-1898 USA, 2015; CLSI. Performance Standards for Antimicrobial Susceptibility Testing: Twenty-Sixth Informational Supplement. CLSI document M100-S26, CLSI, 950 West Valley Road, Suite 2500, Wayne, Pa. 19087 USA, 2016) against a panel of bacterial strains expressing characterized β-lactamases that confer resistance to β-lactams. Zasowski et al., The β-Lactams Strike Back: Ceftazidime-Avibactam. *Pharmacotherapy*, 2015 35:755-70; Levasseur et al., In vitro antibacterial activity of the ceftazidime-avibactam combination against enterobacteriaceae, including strains with well-characterized β-lactamases. *Antimicrob Agents Chemother*, 2015 59:1931-4. Compounds were stored as dry powder and stored at −20° C. prior to testing. These compounds and comparator drugs were solubilized in the appropriate solvent on the day of the assay. All drugs were tested using a drug concentration range of 0.001 μg/mL to 64 μg/mL. β-lactamase inhibitors were tested at a constant concentration of 4 μg/mL. Isolates were streaked onto appropriate media and incubated overnight at 35° C. The MIC values were determined using cation-adjusted Mueller Hinton broth (MHBII; BD, Sparks, MD) in accordance with CLSI guidelines in 96-well format plates. MICs were recorded after 18 h incubation at 35° C. The MIC was read and recorded as the lowest concentration of drug that inhibited visible growth of the organism.

Example 78

Oral Bioavailability in Dogs

The oral bioavailability of certain avibactam prodrugs provided by the present disclosure in dogs was evaluated.

Dosing formulations were prepared on the day of dosing. Intravenous formulations were prepared under aseptic conditions, sterile filtered, and brought to room temperature prior to dosing. The intravenous formulation included avibactam at a final concentration of 2.0 mg/mL in PBS at pH 7.5.

The oral dosing formulations had a final concentration of either avibactam or an avibactam prodrug of 2 mg/mL in a solution of 1 mL ethanol, 4 mL PEG400, and 5 mL water for injection, with the pH adjusted to 7 with 1N NaOH.

The formulations were administered to male Beagle dogs weighing from 8 kg to 410 kg. The animals were maintained in accordance with the Guide for the Care and Use of Laboratory Animals, National Research Council, The National Academies Press, Washington, D C, 2011.

The dogs received either an IV bolus dose of 10 mg/kg, or a peroral dose of 20 mg/kg. The dose levels were selected to bridge the gap between primary historical control data and the NHP study (American Veterinary Medial Association. AVMA Guidelines on Euthanasia. 2013) to accurately predict the prodrug activity in humans. Intravenous administration was into the cephalic vein followed by a 0.5 mL flush with sterile saline. Oral administration via to the stomach using an 18-French catheter followed by a 15-mL flush with deionized water. Two dogs were used for each arm of the study.

The plasma concentration of avibactam was measured at intervals following administration. Within 2 minutes of collection, 100 µL of whole blood was transferred to K$_2$EDTA tubes containing 300 µL acetonitrile. Each via with the blood/acetonitrile mixture was vortexed for about 30 seconds and immediately frozen on dry ice and maintained frozen (−55° C. to −85° C.) until analysis. The avibactam concentration was determined using LC/MS/MS.

The area under the concentration vs. time curves (AUC) was calculated using the linear trapezoidal method with linear interpolation. The percent oral bioavailability (% F) of avibactam was determined by comparing the AUC following oral administration with the AUC following IV administration on a dose normalized basis.

Compounds (3), (13), and (15) exhibited an avibactam oral bioavailability in male Beagle dogs of greater than 50% F.

Example 79

Oral Bioavailability in Monkeys

The oral bioavailability of certain avibactam prodrugs provided by the present disclosure in male Cynomolgus monkeys was evaluated.

Dosing formulations were prepared on the day of dosing. Intravenous formulations were prepared under aseptic conditions, sterile filtered, and brought to room temperature prior to dosing. The intravenous formulation included avibactam at a final concentration of 2.0 mg/mL in PBS at pH 7.5.

The oral dosing formulations had a final concentration of either avibactam or an avibactam prodrug of 2 mg/mL in a solution of 1 mL ethanol, 4 mL PEG400, and 5 mL water for injection, with the pH adjusted to 7 with 1N NaOH.

The formulations were administered to male Cynomolgus monkeys weighing from 2 kg to 4 kg. The animals were maintained in accordance with the Guide for the Care and Use of Laboratory Animals, National Research Council, The National Academies Press, Washington, D C, 2011.

The monkeys received either an IV bolus dose of 10 mg/kg, or a peroral dose of 20 mg/kg. The dosing levels were selected to mimic therapeutically effective systemic concentrations in humans. Intravenous administration was into the saphenous vein. Oral administration was via oral intubation via a flexible oral tube. Two monkeys were used for each arm of the study.

The plasma concentration of avibactam was measured at intervals following administration. Within 2 minutes of collection, 100 µL of whole blood was transferred to K2EDTA tubes containing 300 µL acetonitrile. Each via with the blood/acetonitrile mixture was vortexed for about 30 seconds and immediately frozen on dry ice and maintained frozen (−55° C. to −85° C.) until analysis. The avibactam concentration was determined using LC/MS/MS.

The area under the concentration vs. time curves (AUC) was calculated using the linear trapezoidal method with linear interpolation. The percent oral bioavailability (% F) of avibactam was determined by comparing the AUC following oral administration with the AUC following IV administration on a dose normalized basis.

Compounds (3), (13), and (15) exhibited an avibactam oral bioavailability in Cynomolgus monkeys of greater than 50% F.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A compound of Formula (1):

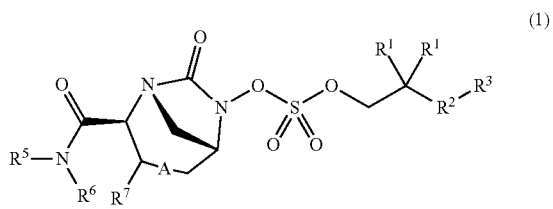

or a pharmaceutically acceptable salt thereof, wherein,
each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;
$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heteerocycloalkyl, substituted $C_{5-6}$ aryl, substituted $C_{5-6}$ heteroaryl, and —CH═C($R^4$)$_2$, wherein,
$R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (=) and $R^7$ is $C_{1-3}$ alkyl.

2. The compound of claim 1, wherein each $R^1$ is independently $C_{1-6}$ alkyl, or each $R^1$ together with the geminal carbon atom to which they are bonded form a $C_{5-6}$ cycloalkyl ring, a substituted $C_{5-6}$ cycloalkyl ring, a $C_{5-6}$ heterocycloalkyl ring, or a substituted $C_{5-6}$ heterocycloalkyl ring.

3. The compound of claim 1, wherein $R^2$ is independently selected from a single bond, $C_{1-2}$ alkanediyl, and substituted $C_{1-2}$ alkanediyl.

4. The compound of claim 1, wherein $R^3$ is —C(O)—O—$R^4$, wherein $R^4$ is selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

5. The compound of claim 1, wherein the compound has the structure of Formula (2a):

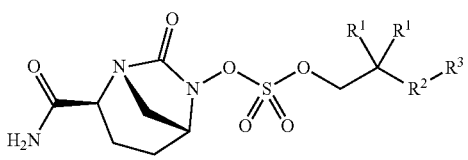

(2a)

or a pharmaceutically acceptable salt thereof.

6. The compound of claim 5, wherein,
each $R^1$ is independently selected from $C_{1-3}$ alkyl, or each $R^1$ together with the geminal carbon atom to which they are bonded form a $C_{3-6}$ cycloalkyl ring, a substituted $C_{3-6}$ cycloalkyl ring, a $C_{3-6}$ heterocycloalkyl ring, or a substituted $C_{3-6}$ heterocycloalkyl ring;
$R^2$ is a single bond;
$R^3$ is —C(O)—O—$R^4$; and
$R^4$ is selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

7. The compound of claim 5, wherein the compound is selected from:

3-(((((2S,5R)-2-carbamoyl-7-oxo-1,6-diazabicyclo[3.2.1]octan-6-yl)oxy)sulfonyl)oxy)-2,2-dimethylpropyl benzoate (2);

ethyl 3-(((((2S,5R)-2-carbamoyl-7-oxo-1,6-diazabicyclo[3.2.1]octan-6-yl)oxy)sulfonyl)oxy)-2,2-dimethylpropanoate (3);

benzyl 3-(((((2S,5R)-2-carbamoyl-7-oxo-1,6-diazabicyclo[3.2.1]octan-6-yl)oxy)sulfonyl)oxy)-2,2-dimethylpropanoate (4);

4-(((((2S,5R)-2-carbamoyl-7-oxo-1,6-diazabicyclo[3.2.1]octan-6-yl)oxy)sulfonyl)oxy)-3,3-dimethylbutyl benzoate (6);

4-(((((2S,5R)-2-carbamoyl-7-oxo-1,6-diazabicyclo[3.2.1]octan-6-yl)oxy)sulfonyl)oxy)-3,3-dimethylbutyl propionate (7);

benzyl (4-(((((2S,5R)-2-carbamoyl-7-oxo-1,6-diazabicyclo[3.2.1]octan-6-yl)oxy)sulfonyl)oxy)-3,3-dimethylbutyl) adipate (8);

6-(4-(((((2S,5R)-2-carbamoyl-7-oxo-1,6-diazabicyclo[3.2.1]octan-6-yl)oxy)sulfonyl)oxy)-3,3-dimethylbutoxy)-6-oxohexanoic acid (9);

methyl 3-(((((2S,5R)-2-carbamoyl-7-oxo-1,6-diazabicyclo[3.2.1]octan-6-yl)oxy)sulfonyl)oxy)-2,2-dimethylpropanoate (10);

isopropyl 3-(((((2S,5R)-2-carbamoyl-7-oxo-1,6-diazabicyclo[3.2.1]octan-6-yl)oxy)sulfonyl)oxy)-2,2-dimethylpropanoate (11);

hexyl 3-(((((2S,5R)-2-carbamoyl-7-oxo-1,6-diazabicyclo[3.2.1]octan-6-yl)oxy)sulfonyl)oxy)-2,2-dimethylpropanoate (12);

heptyl 3-(((((2S,5R)-2-carbamoyl-7-oxo-1,6-diazabicyclo[3.2.1]octan-6-yl)oxy)sulfonyl)oxy)-2,2-dimethylpropanoate (13);

tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14);

2-methoxyethyl 3-(((((2S,5R)-2-carbamoyl-7-oxo-1,6-diazabicyclo[3.2.1]octan-6-yl)oxy)sulfonyl)oxy)-2,2-dimethylpropanoate (15);

oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16);

ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17);

ethyl 1-((((((2S,5R)-2-carbamoyl-7-oxo-1,6-diazabicyclo[3.2.1]octan-6-yl)oxy)sulfonyl)oxy)methyl)cyclopropanecarboxylate (18);

ethyl 1-((((((2S,5R)-2-carbamoyl-7-oxo-1,6-diazabicyclo[3.2.1]octan-6-yl)oxy)sulfonyl)oxy)methyl)cyclobutanecarboxylate (19);

(2S,5R)-2-carbamoyl-7-oxo-1,6-diazabicyclo[3.2.1]octan-6-yl 1H-imidazole-1-sulfonate (34);

ethyl 5-(((((2S,5R)-2-carbamoyl-7-oxo-1,6-diazabicyclo[3.2.1]octan-6-yl)oxy)sulfonyl)oxy)-4,4-dimethylpentanoate (35);

hexyl 5-(((((2S,5R)-2-carbamoyl-7-oxo-1,6-diazabicyclo[3.2.1]octan-6-yl)oxy)sulfonyl)oxy)-4,4-dimethylpentanoate (36);

heptyl 5-(((((2S,5R)-2-carbamoyl-7-oxo-1,6-diazabicyclo[3.2.1]octan-6-yl)oxy)sulfonyl)oxy)-4,4-dimethylpentanoate (37);

2-methoxyethyl 5-(((((2S,5R)-2-carbamoyl-7-oxo-1,6-diazabicyclo[3.2.1]octan-6-yl)oxy)sulfonyl)oxy)-4,4-dimethylpentanoate (38);

5-(((((2S,5R)-2-carbamoyl-7-oxo-1,6-diazabicyclo[3.2.1]
octan-6-yl)oxy)sulfonyl)oxy)-2,2,4,4-tetramethylpen-
tyl propionate (39);
5-(((((2S,5R)-2-carbamoyl-7-oxo-1,6-diazabicyclo[3.2.1]
octan-6-yl)oxy)sulfonyl)oxy)-2,2,4,4-tetramethylpen-
tyl benzoate (40);
5-(((((2S,5R)-2-carbamoyl-7-oxo-1,6-diazabicyclo[3.2.1]
octan-6-yl)oxy)sulfonyl)oxy)-2,2,4,4-tetramethylpen-
tyl 2,6-dimethylbenzoate (41);
(2S,5R)-2-carbamoyl-7-oxo-1,6-diazabicyclo[3.2.1]oc-
tan-6-yl ((3-methyl-2-oxotetrahydrofuran-3-yl)methyl)
sulfate (42);
3-(((((2S,5R)-2-carbamoyl-7-oxo-1,6-diazabicyclo[3.2.1]
octan-6-yl)oxy)sulfonyl)oxy)-2,2-dimethylpropyl
pivalate (43);
3-(((((2S,5R)-2-carbamoyl-7-oxo-1,6-diazabicyclo[3.2.1]
octan-6-yl)oxy)sulfonyl)oxy)-2,2-dimethylpropyl
3-chloro-2,6-dimethoxybenzoate (44);
4-(((((2S,5R)-2-carbamoyl-7-oxo-1,6-diazabicyclo[3.2.1]
octan-6-yl)oxy)sulfonyl)oxy)-2,2,3,3-tetramethylbutyl
2,6-dimethylbenzoate (45);
4-(((((2S,5R)-2-carbamoyl-7-oxo-1,6-diazabicyclo[3.2.1]
octan-6-yl)oxy)sulfonyl)oxy)-2,2,3,3-tetramethylbutyl
benzoate (46);
4-(((((2S,5R)-2-carbamoyl-7-oxo-1,6-diazabicyclo[3.2.1]
octan-6-yl)oxy)sulfonyl)oxy)-2,2,3,3-tetramethylbutyl
propionate (47);
(2S,5R)-2-carbamoyl-7-oxo-1,6-diazabicyclo[3.2.1]oc-
tan-6-yl ((3-methyl-2-oxotetrahydro-2H-pyran-3-yl)
methyl) sulfate (48);
2-(3-(((((2S,5R)-2-carbamoyl-7-oxo-1,6-diazabicyclo
[3.2.1]octan-6-yl)oxy)sulfonyl)oxy)-2,2-dimethylpro-
pyl)phenyl acetate (49);
2-(3-(((((2S,5R)-2-carbamoyl-7-oxo-1,6-diazabicyclo
[3.2.1]octan-6-yl)oxy)sulfonyl)oxy)-2,2-dimethylpro-
pyl)phenyl pivalate (50);
S-(4-(((((2S,5R)-2-carbamoyl-7-oxo-1,6-diazabicyclo
[3.2.1]octan-6-yl)oxy)sulfonyl)oxy)-3,3-dimethylbu-
tyl) ethanethioate (51);
S-(5-(((((2S,5R)-2-carbamoyl-7-oxo-1,6-diazabicyclo
[3.2.1]octan-6-yl)oxy)sulfonyl)oxy)-4,4-dimethylpen-
tyl) ethanethioate (52);
S-(3-(((((2S,5R)-2-carbamoyl-7-oxo-1,6-diazabicyclo
[3.2.1]octan-6-yl)oxy)sulfonyl)oxy)-2,2-dimethylpro-
pyl) ethanethioate (53);
3-(((((2S,5R)-2-carbamoyl-7-oxo-1,6-diazabicyclo[3.2.1]
octan-6-yl)oxy)sulfonyl)oxy)-2,2-dimethylpropyl 2,6-
dimethylbenzoate (54);
3-(((((2S,5R)-2-carbamoyl-7-oxo-1,6-diazabicyclo[3.2.1]
octan-6-yl)oxy)sulfonyl)oxy)-2,2-dimethylpropyl ada-
mantane-1-carboxylate (55);
diethyl 2-((((((2S,5R)-2-carbamoyl-7-oxo-1,6-diazabicy-
clo[3.2.1]octan-6-yl)oxy)sulfonyl)oxy)methyl)-2-
methylmalonate (56);
propyl 3-(((((2S,5R)-2-carbamoyl-7-oxo-1,6-diazabicy-
clo[3.2.1]octan-6-yl)oxy)sulfonyl)oxy)-2,2-dimethyl-
propanoate (57);
butyl 3-(((((2S,5R)-2-carbamoyl-7-oxo-1,6-diazabicyclo
[3.2.1]octan-6-yl)oxy)sulfonyl)oxy)-2,2-dimethylpro-
panoate (58);
(5-methyl-2-oxo-1,3-dioxol-4-yl)methyl 3-(((((2S,5R)-2-
carbamoyl-7-oxo-1,6-diazabicyclo[3.2.1]octan-6-yl)
oxy)sulfonyl)oxy)-2,2-dimethylpropanoate (59);
4-(((((2S,5R)-2-carbamoyl-7-oxo-1,6-diazabicyclo[3.2.1]
octan-6-yl)oxy)sulfonyl)oxy)-3,3-dimethylbutyl piva-
late (60);

ethyl 2-((((((2S,5R)-2-carbamoyl-7-oxo-1,6-diazabicyclo
[3.2.1]octan-6-yl)oxy)sulfonyl)oxy)methyl)-2-ethylbu-
tanoate (61);
4-(((((2S,5R)-2-carbamoyl-7-oxo-1,6-diazabicyclo[3.2.1]
octan-6-yl)oxy)sulfonyl)oxy)-3,3-dimethylbutyl 2,6-
dimethylbenzoate (62);
4-(((((2S,5R)-2-carbamoyl-7-oxo-1,6-diazabicyclo[3.2.1]
octan-6-yl)oxy)sulfonyl)oxy)-3,3-dimethylbutyl ada-
mantane-1-carboxylate (63);
4-(((((2S,5R)-2-carbamoyl-7-oxo-1,6-diazabicyclo[3.2.1]
octan-6-yl)oxy)sulfonyl)oxy)-3,3-dimethylbutyl 2,6-
dimethoxybenzoate (64);
5-(((((2S,5R)-2-carbamoyl-7-oxo-1,6-diazabicyclo[3.2.1]
octan-6-yl)oxy)sulfonyl)oxy)-4,4-dimethylpentyl ben-
zoate (65);
5-(((((2S,5R)-2-carbamoyl-7-oxo-1,6-diazabicyclo[3.2.1]
octan-6-yl)oxy)sulfonyl)oxy)-4,4-dimethylpentyl 2,6-
dimethoxybenzoate (66);
5-(((((2S,5R)-2-carbamoyl-7-oxo-1,6-diazabicyclo[3.2.1]
octan-6-yl)oxy)sulfonyl)oxy)-4,4-dimethylpentyl 2,6-
dimethylbenzoate (67);
5-(((((2S,5R)-2-carbamoyl-7-oxo-1,6-diazabicyclo[3.2.1]
octan-6-yl)oxy)sulfonyl)oxy)-4,4-dimethylpentyl
2-methylbenzoate (68);
4-(((((2S,5R)-2-carbamoyl-7-oxo-1,6-diazabicyclo[3.2.1]
octan-6-yl)oxy)sulfonyl)oxy)-2,2,3,3-tetramethylbutyl
3-chloro-2,6-dimethoxybenzoate (69);
2-((((((2S,5R)-2-carbamoyl-7-oxo-1,6-diazabicyclo
[3.2.1]octan-6-yl)oxy)sulfonyl)oxy)methyl)-2-methyl-
propane-1,3-diyl dibenzoate (70);
2-((((((2S,5R)-2-carbamoyl-7-oxo-1,6-diazabicyclo
[3.2.1]octan-6-yl)oxy)sulfonyl)oxy)methyl)-2-methyl-
propane-1,3-diyl diacetate (71);
5-(((((2S,5R)-2-carbamoyl-7-oxo-1,6-diazabicyclo[3.2.1]
octan-6-yl)oxy)sulfonyl)oxy)-2,2,4,4-tetramethylpen-
tyl 2,6-dimethoxybenzoate (72);
ethyl 3-(((((2S,5R)-2-carbamoyl-7-oxo-1,6-diazabicyclo
[3.2.1]octan-6-yl)oxy)sulfonyl)oxy)-2,2-dimethylbu-
tanoate (73);
(2S,5R)-2-carbamoyl-7-oxo-1,6-diazabicyclo[3.2.1]oc-
tan-6-yl ((3,5,5-trimethyl-2-oxotetrahydrofuran-3-yl)
methyl) sulfate (74);
a pharmaceutically acceptable salt of any of the forego-
ing; and
a combination of any of the foregoing.
8. The compound of claim 5, wherein the compound is
selected from:
ethyl 3-(((((2S,5R)-2-carbamoyl-7-oxo-1,6-diazabicyclo
[3.2.1]octan-6-yl)oxy)sulfonyl)oxy)-2,2-dimethylpro-
panoate (3);
benzyl 3-(((((2S,5R)-2-carbamoyl-7-oxo-1,6-diazabicy-
clo[3.2.1]octan-6-yl)oxy)sulfonyl)oxy)-2,2-dimethyl-
propanoate (4);
methyl 3-(((((2S,5R)-2-carbamoyl-7-oxo-1,6-diazabicy-
clo[3.2.1]octan-6-yl)oxy)sulfonyl)oxy)-2,2-dimethyl-
propanoate (10);
isopropyl 3-(((((2S,5R)-2-carbamoyl-7-oxo-1,6-diazabi-
cyclo[3.2.1]octan-6-yl)oxy)sulfonyl)oxy)-2,2-dimeth-
ylpropanoate (11);
hexyl 3-(((((2S,5R)-2-carbamoyl-7-oxo-1,6-diazabicyclo
[3.2.1]octan-6-yl)oxy)sulfonyl)oxy)-2,2-dimethylpro-
panoate (12);
heptyl 3-(((((2S,5R)-2-carbamoyl-7-oxo-1,6-diazabicy-
clo[3.2.1]octan-6-yl)oxy)sulfonyl)oxy)-2,2-dimethyl-
propanoate (13);

tert-butyl 3-(((((2S,5R)-2-carbamoyl-7-oxo-1,6-diazabicyclo[3.2.1]octan-6-yl)oxy)sulfonyl)oxy)-2,2-dimethylpropanoate (14);
2-methoxyethyl 3-(((((2S,5R)-2-carbamoyl-7-oxo-1,6-diazabicyclo[3.2.1]octan-6-yl)oxy)sulfonyl)oxy)-2,2-dimethylpropanoate (15);
oxetan-3-yl 3-(((((2S,5R)-2-carbamoyl-7-oxo-1,6-diazabicyclo[3.2.1]octan-6-yl)oxy)sulfonyl)oxy)-2,2-dimethylpropanoate (16);
ethyl 1-((((((2S,5R)-2-carbamoyl-7-oxo-1,6-diazabicyclo[3.2.1]octan-6-yl)oxy)sulfonyl)oxy)methyl)cyclohexanecarboxylate (17);
ethyl 1-((((((2S,5R)-2-carbamoyl-7-oxo-1,6-diazabicyclo[3.2.1]octan-6-yl)oxy)sulfonyl)oxy)methyl)cyclopropanecarboxylate (18);
ethyl 1-((((((2S,5R)-2-carbamoyl-7-oxo-1,6-diazabicyclo[3.2.1]octan-6-yl)oxy)sulfonyl)oxy)methyl)cyclobutanecarboxylate (19);
hexyl 5-(((((2S,5R)-2-carbamoyl-7-oxo-1,6-diazabicyclo[3.2.1]octan-6-yl)oxy)sulfonyl)oxy)-4,4-dimethylpentanoate (36);
heptyl 5-(((((2S,5R)-2-carbamoyl-7-oxo-1,6-diazabicyclo[3.2.1]octan-6-yl)oxy)sulfonyl)oxy)-4,4-dimethylpentanoate (37);
(2S,5R)-2-carbamoyl-7-oxo-1,6-diazabicyclo[3.2.1]octan-6-yl ((3-methyl-2-oxotetrahydrofuran-3-yl)methyl) sulfate (42);
S-(3-(((((2S,5R)-2-carbamoyl-7-oxo-1,6-diazabicyclo[3.2.1]octan-6-yl)oxy)sulfonyl)oxy)-2,2-dimethylpropyl) ethanethioate (53);
propyl 3-(((((2S,5R)-2-carbamoyl-7-oxo-1,6-diazabicyclo[3.2.1]octan-6-yl)oxy)sulfonyl)oxy)-2,2-dimethylpropanoate (57);
butyl 3-(((((2S,5R)-2-carbamoyl-7-oxo-1,6-diazabicyclo[3.2.1]octan-6-yl)oxy)sulfonyl)oxy)-2,2-dimethylpropanoate (58);
(5-methyl-2-oxo-1,3-dioxol-4-yl)methyl 3-(((((2S,5R)-2-carbamoyl-7-oxo-1,6-diazabicyclo[3.2.1]octan-6-yl)oxy)sulfonyl)oxy)-2,2-dimethylpropanoate (59);
a pharmaceutically acceptable salt of any of the foregoing; and
a combination of any of the foregoing.

9. The compound of claim 5, wherein,
each $R^1$ is independently selected from $C_{1-3}$ alkyl, or each $R^1$ together with the carbon atom to which they are bonded form a $C_{3-6}$ cycloalkyl ring;
$R^2$ is selected from single bond, methane-diyl, and ethane-diyl; and
$R^3$ is selected from —C(O)—O—$R^4$ and —S—C(O)—$R^4$, wherein $R^4$ is selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

10. The compound of claim 5, wherein,
each $R^1$ is independently selected from $C_{1-3}$ alkyl, or each $R^1$ together with the carbon atom to which they are bonded form a $C_{3-6}$ cycloalkyl ring;
$R^2$ is a single bond; and
$R^3$ is —C(O)—O—$R^4$, where $R^4$ is selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

11. The compound of claim 5, wherein,
each $R^1$ is independently selected from $C_{1-3}$ alkyl, or each $R^1$ together with the carbon atom to which they are bonded form a $C_{3-6}$ cycloalkyl ring;
$R^2$ is —(CH$_2$)$_2$—; and
$R^3$ is —C(O)—O—$R^4$ wherein $R^4$ is selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

12. The compound of claim 5, wherein,
each $R^1$ is selected from $C_{1-3}$ alkyl, or each $R^1$ together with the carbon atom to which they are bonded form a $C_{3-6}$ cycloalkyl ring;
$R^2$ is —CH$_2$—; and
$R^3$ is —S—C(O)—$R^4$, wherein $R^4$ is selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

13. The compound of claim 5, wherein,
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$, heterocycloalkyl ring;
$R^2$ is a single bond; and
R is $C_{1-3}$ alkyl.

14. The compound of claim 5, wherein,
each $R^1$ is independently selected from $C_{1-3}$ alkyl;
$R^2$ is selected from a single bond and methanediyl; and
$R^3$ is selected from —O—C(O)—$R^4$ and —C(O)—O—$R^4$, wherein $R^4$ is selected from $C_{1-8}$ alkyl and substituted phenyl.

15. The compound of claim 5, wherein,
each $R^1$ is independently selected from $C_{1-3}$ alkyl;
$R^2$ is a single bond;
$R^1$ is —CH═C($R^4$)$_2$, wherein each $R^4$ is —C(O)—O—$R^8$; and
each $R^8$ is $C_{1-4}$ alkyl.

16. The compound of claim 5, wherein,
each $R^1$ is independently selected from $C_{1-3}$ alkyl;
$R^2$ is selected from a single bond and methanediyl; and
$R^3$ is substituted phenyl, wherein the one or more substituents is independently selected from —CH$_2$—O—C(O)—$R^4$ and —C(O)—$R^4$, wherein $R^4$ is selected from $C_{1-8}$ alkyl and phenyl.

17. The compound of claim 5, wherein,
each $R^1$ is independently selected from $C_{1-3}$ alkyl;
$R^2$ is selected from —C($R^8$)$_2$— and —CH$_2$—C($R^8$)$_2$—, wherein each $R^8$ is independently selected from $C_{1-3}$ alkyl; and
$R^3$ is selected from —C(O)—O—$R^4$ and —O—C(O)—$R^4$, herein $R^4$ is selected from $C_{1-8}$ alkyl, $C_{1-8}$ heteroalkyl, substituted $C_{1-8}$ alkyl, substituted $C_{1-8}$ heteroalkyl, and 4(yl-methyl)-5-methyl-1,3-dioxol-2-one.

18. The compound of claim 5, wherein,
each $R^1$ together with the carbon atom to which they are bonded form a substituted $C_{5-6}$ heterocyclic ring;
$R^2$ is a single bond; and
$R^3$ is $C_{1-3}$ alkyl.

19. The compound of claim 1, wherein the compound has the structure of Formula (4):

(4)

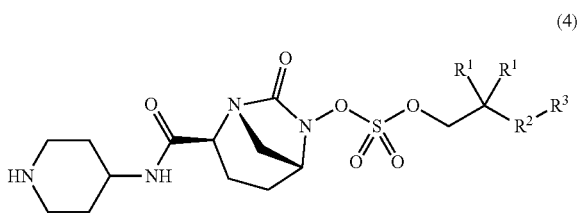

or a pharmaceutically acceptable salt thereof.

20. The compound of claim 19, wherein,
each $R^1$ is independently selected from $C_{1-3}$ alkyl, or each $R^1$ together with the carbon atom to which they are bonded form a $C_{3-6}$ cycloalkyl ring;
$R^2$ is a single bond; and
R is —C(O)—O—$R^4$, wherein $R^4$ is selected from $C_{1-8}$ alkyl, $C_{1-8}$ heteroalkyl, $C_{7-10}$ arylalkyl, $C_{5-8}$ heterocycloalkyl, and substituted $C_{5-10}$ heterocycloalkylalkyl.

21. The compound of claim 19, wherein the compound is selected from:
ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (20);
2-methoxyethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (21);
4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (22);
4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (23);
4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidin-1-ium 2,2,2-trifluoroacetate (24);
(5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (25);
a pharmaceutically acceptable salt of any of the foregoing; and
a combination of any of the foregoing.

22. The compound of claim 1, wherein the compound has the structure of Formula (5):

(5)

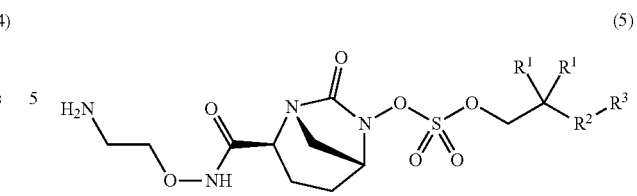

or a pharmaceutically acceptable salt thereof.

23. A pharmaceutical composition comprising the compound of claim 1 and a pharmaceutically acceptable vehicle.

24. The pharmaceutical composition of claim 23, further comprising an antibiotic.

25. The pharmaceutical composition of claim 24, wherein the antibiotic comprises a β-lactam antibiotic.

26. The pharmaceutical composition of claim 23, wherein the pharmaceutical composition is an oral dosage formulation.

27. The pharmaceutical composition of claim 23, wherein the pharmaceutical composition is an oral dosage form.

28. A method of treating a bacterial infection in a patient comprising administering to a patient in need of such treatment a therapeutically effective amount of the compound of claim 1 or a pharmaceutically acceptable salt thereof; and a therapeutically effective amount of a β-lactam antibiotic, wherein bacteria causing the bacterial infection produce a β-lactamase.

29. The method of claim 28, wherein administering comprises orally administering.

30. A method of treating a bacterial infection in a patient comprising administering to a patient in need of such treatment a therapeutically effective amount of the compound of claim 1 or a pharmaceutically acceptable salt thereof, and a therapeutically effective amount of a β-lactam antibiotic, wherein,
the bacterial infection is capable of being treated with a therapeutically effective amount of the β-lactam antibiotic when co-administered with a therapeutically effective amount of a compound having the structure:

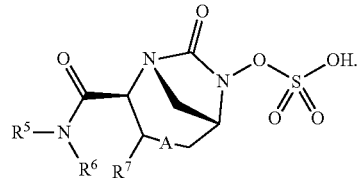

* * * * *

UNITED STATES PATENT AND TRADEMARK OFFICE
CERTIFICATE OF CORRECTION

PATENT NO.         : 10,085,999 B1
APPLICATION NO.    : 15/934497
DATED              : October 2, 2018
INVENTOR(S)        : Eric M. Gordon et al.

Page 1 of 1

It is certified that error appears in the above-identified patent and that said Letters Patent is hereby corrected as shown below:

In the Claims

Column 223, Claim 6, Line 63, that reads "heteerocycloalkyl" should read -- heterocycloalkyl --

Column 228, Claim 15, Line 41, that reads "$R^1$ is" should read -- $R^3$ is --

Column 228, Claim 17, Line 58, that reads "herein $R^4$ is selected" should read -- wherein $R^4$ is selected --

Column 229, Claim 20, Line 18, that reads "R is" should read -- $R^3$ is --

Signed and Sealed this
Twenty-fourth Day of September, 2019

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 10,085,999 B1 |
| APPLICATION NO. | : 15/934497 |
| DATED | : October 2, 2018 |
| INVENTOR(S) | : Eric M. Gordon et al. |

It is certified that error appears in the above-identified patent and that said Letters Patent is hereby corrected as shown below:

In the Claims

Column 224, Claim 7, Line 1 that reads "3-(((((2S,5R)" should read -3-(((((1R,2S,5R)-

Column 224, Claim 7, Line 4 that reads "3-(((((2S,5R)" should read -3-(((((1R,2S,5R)-

Column 224, Claim 7, Line 7 that reads "3-(((((2S,5R)" should read -3-(((((1R,2S,5R)-

Column 224, Claim 7, Line 11 that reads "4-(((((2S,5R)" should read -4-(((((1R,2S,5R)-

Column 224, Claim 7, Line 14 that reads "4-(((((2S,5R)" should read -4-(((((1R,2S,5R)-

Column 224, Claim 7, Line 17 that reads "(4-(((((2S,5R)" should read -(4-(((((1R,2S,5R)-

Column 224, Claim 7, Line 20 that reads "6-(4-(((((2S,5R)" should read -6-(4-(((((1R,2S,5R)-

Column 224, Claim 7, Line 23 that reads "3-(((((2S,5R)" should read -3-(((((1R,2S,5R)-

Column 224, Claim 7, Line 26 that reads "3-(((((2S,5R)" should read -3-(((((1R,2S,5R)-

Column 224, Claim 7, Line 29 that reads "3-(((((2S,5R)" should read -3-(((((1R,2S,5R)-

Column 224, Claim 7, Line 32 that reads "3-(((((2S,5R)" should read -3-(((((1R,2S,5R)-

Column 224, Claim 7, Line 36 that reads "3-(((((2S,5R)" should read -3-(((((1R,2S,5R)-

Column 224, Claim 7, Line 39 that reads "3-(((((2S,5R)" should read -3-(((((1R,2S,5R)-

Column 224, Claim 7, Line 42 that reads "3-(((((2S,5R)" should read -3-(((((1R,2S,5R)-

Signed and Sealed this
Twenty-seventh Day of October, 2020

Andrei Iancu
*Director of the United States Patent and Trademark Office*

Column 224, Claim 7, Line 45 that reads "1-(((((2S,5R)" should read -1-(((((1R,2S,5R)-

Column 224, Claim 7, Line 48 that reads "1-(((((2S,5R)" should read -1-(((((1R,2S,5R)-

Column 224, Claim 7, Line 51 that reads "1-(((((2S,5R)" should read -1-(((((1R,2S,5R)-

Column 224, Claim 7, Line 54 that reads "(2S,5R)" should read -(1R,2S,5R)-

Column 224, Claim 7, Line 56 that reads "5-(((((2S,5R)" should read -5-(((((1R,2S,5R)-

Column 224, Claim 7, Line 59 that reads "5-(((((2S,5R)" should read -5-(((((1R,2S,5R)-

Column 224, Claim 7, Line 62 that reads "5-(((((2S,5R)" should read -5-(((((1R,2S,5R)-

Column 224, Claim 7, Line 65 that reads "5-(((((2S,5R)" should read -5-(((((1R,2S,5R)-

Column 225, Claim 7, Line 1 that reads "5-(((((2S,5R)" should read -5-(((((1R,2S,5R)-

Column 225, Claim 7, Line 4 that reads "5-(((((2S,5R)" should read -5-(((((1R,2S,5R)-

Column 225, Claim 7, Line 7 that reads "5-(((((2S,5R)" should read -5-(((((1R,2S,5R)-

Column 225, Claim 7, Line 10 that reads "(2S,5R)" should read -(1R,2S,5R)-

Column 225, Claim 7, Line 13 that reads "3-(((((2S,5R)" should read -3-(((((1R,2S,5R)-

Column 225, Claim 7, Line 16 that reads "3-(((((2S,5R)" should read -3-(((((1R,2S,5R)-

Column 225, Claim 7, Line 20 that reads "4-(((((2S,5R)" should read -4-(((((1R,2S,5R)-

Column 225, Claim 7, Line 23 that reads "4-(((((2S,5R)" should read -4-(((((1R,2S,5R)-

Column 225, Claim 7, Line 26 that reads "4-(((((2S,5R)" should read -4-(((((1R,2S,5R)-

Column 225, Claim 7, Line 29 that reads "(2S,5R)" should read -(1R,2S,5R)-

Column 225, Claim 7, Line 32 that reads "2-(3-(((((2S,5R)" should read -2-(3(((((1R,2S,5R)-

Column 225, Claim 7, Line 35 that reads "2-(3-(((((2S,5R)" should read -2-(3(((((1R,2S,5R)-

Column 225, Claim 7, Line 38 that reads "S-(4-(((((2S,5R)" should read -S-(4(((((1R,2S,5R)-

Column 225, Claim 7, Line 41 that reads "S-(5-(((((2S,5R)" should read -S-(5(((((1R,2S,5R)-

Column 225, Claim 7, Line 44 that reads "S-(3-(((((2S,5R)" should read -S-(3(((((1R,2S,5R)-

Column 225, Claim 7, Line 47 that reads "3-(((((2S,5R)" should read -3-(((((1R,2S,5R)-

Column 225, Claim 7, Line 50 that reads "3-(((((2S,5R)" should read -3-(((((1R,2S,5R)-

Column 225, Claim 7, Line 53 that reads "2-(((((2S,5R)" should read -2-(((((1R,2S,5R)-

Column 225, Claim 7, Line 56 that reads "3-(((((2S,5R)" should read -3-(((((1R,2S,5R)-

Column 225, Claim 7, Line 59 that reads "3-(((((2S,5R)" should read -3-(((((1R,2S,5R)-

Column 225, Claim 7, Line 62 that reads "3-(((((2S,5R)" should read -3-(((((1R,2S,5R)-

Column 225, Claim 7, Line 65 that reads "4-(((((2S,5R)" should read -4-(((((1R,2S,5R)-

Column 226, Claim 7, Line 1 that reads "2-(((((2S,5R)" should read -2-(((((1R,2S,5R)-

Column 226, Claim 7, Line 4 that reads "4-(((((2S,5R)" should read -4-(((((1R,2S,5R)-

Column 226, Claim 7, Line 7 that reads "4-(((((2S,5R)" should read -4-(((((1R,2S,5R)-

Column 226, Claim 7, Line 10 that reads "4-(((((2S,5R)" should read -4-(((((1R,2S,5R)-

Column 226, Claim 7, Line 13 that reads "5-(((((2S,5R)" should read -5-(((((1R,2S,5R)-

Column 226, Claim 7, Line 17 that reads "5-(((((2S,5R)" should read -5-(((((1R,2S,5R)-

Column 226, Claim 7, Line 20 that reads "5-(((((2S,5R)" should read -5-(((((1R,2S,5R)-

Column 226, Claim 7, Line 23 that reads "5-(((((2S,5R)" should read -5-(((((1R,2S,5R)-

Column 226, Claim 7, Line 26 that reads "4-(((((2S,5R)" should read -4-(((((1R,2S,5R)-

Column 226, Claim 7, Line 29 that reads "2-(((((2S,5R)" should read -2-(((((1R,2S,5R)-

Column 226, Claim 7, Line 32 that reads "2-(((((2S,5R)" should read -2-(((((1R,2S,5R)-

Column 226, Claim 7, Line 35 that reads "5-(((((2S,5R)" should read -5-(((((1R,2S,5R)-

Column 226, Claim 7, Line 39 that reads "3-(((((2S,5R)" should read -3-(((((1R,2S,5R)-

Column 226, Claim 7, Line 42 that reads "(2S,5R)" should read -(1R,2S,5R)-

Column 226, Claim 8, Line 50 that reads "3-(((((2S,5R)" should read -3-(((((1R,2S,5R)-

Column 226, Claim 8, Line 53 that reads "3-(((((2S,5R)" should read -3-(((((1R,2S,5R)-

CERTIFICATE OF CORRECTION (continued)
U.S. Pat. No. 10,085,999 B1

Column 226, Claim 8, Line 56 that reads "3-(((((2S,5R)" should read -3-(((((1R,2S,5R)-

Column 226, Claim 8, Line 59 that reads "3-(((((2S,5R)" should read -3-(((((1R,2S,5R)-

Column 226, Claim 8, Line 62 that reads "3-(((((2S,5R)" should read -3-(((((1R,2S,5R)-

Column 226, Claim 8, Line 65 that reads "3-(((((2S,5R)" should read -3-(((((1R,2S,5R)-

Column 227, Claim 8, Line 1 that reads "3-(((((2S,5R)" should read -3-(((((1R,2S,5R)-

Column 227, Claim 8, Line 4 that reads "3-(((((2S,5R)" should read -3-(((((1R,2S,5R)-

Column 227, Claim 8, Line 7 that reads "3-(((((2S,5R)" should read -3-(((((1R,2S,5R)-

Column 227, Claim 8, Line 10 that reads "1-(((((2S,5R)" should read -1-(((((1R,2S,5R)-

Column 227, Claim 8, Line 13 that reads "1-(((((2S,5R)" should read -1-(((((1R,2S,5R)-

Column 227, Claim 8, Line 16 that reads "1-(((((2S,5R)" should read -1-(((((1R,2S,5R)-

Column 227, Claim 8, Line 20 that reads "5-(((((2S,5R)" should read -5-(((((1R,2S,5R)-

Column 227, Claim 8, Line 23 that reads "5-(((((2S,5R)" should read -5-(((((1R,2S,5R)-

Column 227, Claim 8, Line 26 that reads "(2S,5R)" should read -(1R,2S,5R)-

Column 227, Claim 8, Line 29 that reads "S-(3-(((((2S,5R)" should read -S-(3-(((((1R,2S,5R)-

Column 227, Claim 8, Line 32 that reads "3-(((((2S,5R)" should read -3-(((((1R,2S,5R)-

Column 227, Claim 8, Line 35 that reads "3-(((((2S,5R)" should read -3-(((((1R,2S,5R)-

Column 227, Claim 8, Line 38 that reads "3-(((((2S,5R)" should read -3-(((((1R,2S,5R)-

Column 228, Claim 13, Line 30 that reads "R is $C_{1-3}$ alkyl" should read -$R^3$ is $C_{1-3}$ alkyl- Column 229, Claim 21, Line 23 that reads "3-(((((2S,5R)" should read -3-(((((1R,2S,5R)-

Column 229, Claim 21, Line 26 that reads "3-(((((2S,5R)" should read -3-(((((1R,2S,5R)-

Column 229, Claim 21, Line 29 that reads "4-((2S,5R)" should read -4-((1R,2S,5R)-

Column 229, Claim 21, Line 34 that reads "4-((2S,5R)" should read -4-((1R,2S,5R)-

CERTIFICATE OF CORRECTION (continued)
U.S. Pat. No. 10,085,999 B1

Column 229, Claim 21, Line 38 that reads "4-((2S,5R)" should read -4-((1R,2S,5R)-

Column 229, Claim 21, Line 43 that reads "(((((2S,5R)" should read -(((((1R,2S,5R)-